(12) United States Patent
Yamada et al.

(10) Patent No.: US 8,415,372 B2
(45) Date of Patent: *Apr. 9, 2013

(54) SULFONAMIDE COMPOUND

(75) Inventors: Rintaro Yamada, Tokyo (JP); Minoru Seto, Tokyo (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/526,000

(22) PCT Filed: Feb. 27, 2007

(86) PCT No.: PCT/JP2007/053567
§ 371 (c)(1),
(2), (4) Date: Dec. 15, 2009

(87) PCT Pub. No.: WO2008/105058
PCT Pub. Date: Sep. 4, 2008

(65) Prior Publication Data
US 2010/0093789 A1 Apr. 15, 2010

(51) Int. Cl.
*C07D 401/02* (2006.01)
*A61K 31/47* (2006.01)

(52) U.S. Cl.
USPC .......................................... 514/307; 546/139

(58) Field of Classification Search .................. None
See application file for complete search history.

(56) References Cited

U.S. PATENT DOCUMENTS

| | | | |
|---|---|---|---|
| 4,798,897 A | 1/1989 | Hidaka et al. |
| 5,081,246 A | 1/1992 | Hidaka et al. |
| 5,216,150 A | 6/1993 | Hidaka et al. |
| 5,245,034 A | 9/1993 | Hidaka et al. |
| 5,298,503 A | 3/1994 | Peglion et al. |
| 6,271,224 B1 | 8/2001 | Kapin et al. |
| 6,403,590 B1 | 6/2002 | Hellberg et al. |
| 7,618,984 B2 | 11/2009 | Yamada et al. |
| 7,964,613 B2 | 6/2011 | Matsubara et al. |
| 2004/0102437 A1 | 5/2004 | Takami et al. |
| 2004/0138286 A1 | 7/2004 | Imazakil et al. |
| 2005/0020623 A1 | 1/2005 | Yamada et al. |
| 2005/0096310 A1 | 5/2005 | Yamada et al. |
| 2005/0272751 A1 | 12/2005 | McKerracher et al. |
| 2006/0079688 A1 | 4/2006 | Shibuya et al. |
| 2006/0167043 A1 | 7/2006 | Iwakubo et al. |
| 2006/0223829 A1 | 10/2006 | Aertgeerts et al. |
| 2006/0247266 A1 | 11/2006 | Yamada et al. |
| 2007/0088021 A1 | 4/2007 | Hidaka et al. |
| 2007/0179127 A1 | 8/2007 | Yamada et al. |
| 2008/0021018 A1 | 1/2008 | Ohshima et al. |
| 2009/0048223 A1 | 2/2009 | Matsubara et al. |
| 2009/0156823 A1 | 6/2009 | Kida et al. |

FOREIGN PATENT DOCUMENTS

| | | |
|---|---|---|
| AU | 20675/92 A | 2/1993 |
| CA | 2506464 A1 | 3/2004 |
| CA | 2496797 A1 | 11/2004 |
| CA | 2240271 C | 12/2005 |
| EP | 0 061 673 A1 | 10/1982 |
| EP | 0 287 696 A1 | 10/1988 |
| EP | 0527079 A1 | 2/1993 |
| EP | 0 885 888 A1 | 12/1998 |
| EP | 0 956 865 A1 | 11/1999 |
| EP | 1 074 545 A1 | 2/2001 |
| EP | 1 541 151 A1 | 6/2005 |
| EP | 1 568 382 A1 | 8/2005 |
| EP | 1 878 732 A1 | 4/2006 |
| EP | 1 679 308 A1 | 7/2006 |
| EP | 1902731 A1 | 3/2008 |

(Continued)

OTHER PUBLICATIONS

Australian Office Action dated Jun. 2, 2010, in Australian App. No. 2006285915.
Patini et al., "Bioisoterism: A Rational Approach in Drug Design", Chem. Rev., 1996, vol. 96 pp. 3147-3176.
Decision of Final Rejection dated Nov. 29, 2010 in Korean Application No. 10-2008-7007566.
Extended European Search Report dated Nov. 25, 2010 in EP Application No. 08720915.1.

(Continued)

*Primary Examiner* — Zinna Northington Davis
(74) *Attorney, Agent, or Firm* — Birch, Stewart, Kolasch & Birch, LLP

(57) ABSTRACT

A compound represented by the formula (1) [A represents a nitrogen-containing saturated ring; m represents an integer of 0 to 2; n represents an integer of 1 to 4; $G^1$ represents hydrogen atom, chlorine atom, hydroxyl group, an alkoxy group, or amino group; $G^2$ represents a halogen atom, hydroxyl group, cyano group, carboxy group, an alkyl group, an alkenyl group, and the like; $G^3$ represents hydrogen atom, a halogen atom, hydroxyl group, cyano group, carboxy group, an alkyl group, an alkenyl group, and the like; $G^4$ represents hydroxyl group, or —$N(R^1)(R^2)$ ($R^1$ and $R^2$ represent hydrogen atom, an alkyl group, an aralkyl group, an alkenyl group, an alkynyl group, or a saturated heterocyclic group); $G^5$ is a substituent on a ring-constituting carbon atom of A, and represents hydrogen atom, fluorine atom, or an alkyl group] or a salt thereof, or a derivative thereof that is a prodrug, which potently inhibits Rho kinase.

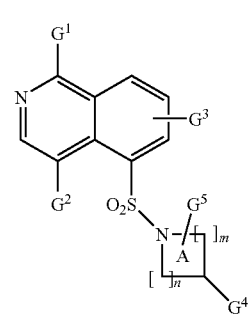

(1)

38 Claims, No Drawings

FOREIGN PATENT DOCUMENTS

| | | |
|---|---|---|
| EP | 1905452 A1 | 4/2008 |
| EP | 1932841 A1 | 6/2008 |
| JP | 57-156463 A | 9/1982 |
| JP | 57-200366 A | 12/1982 |
| JP | 62-111981 A | 5/1987 |
| JP | 02-256666 A | 10/1990 |
| JP | 4-264030 A | 9/1992 |
| JP | 5-208973 A | 8/1993 |
| JP | 06-100540 A | 4/1994 |
| JP | 6-100540 A | 4/1994 |
| JP | 10-87491 A | 4/1998 |
| JP | 10-087491 A | 4/1998 |
| JP | 11-349482 A | 12/1999 |
| JP | 2001-509780 A | 7/2001 |
| JP | 2004-107335 A | 4/2004 |
| JP | 2004-182723 A | 7/2004 |
| JP | 2005-232175 A | 9/2005 |
| JP | 2006-348028 A | 12/2006 |
| JP | 2007-238458 A | 9/2007 |
| WO | WO-93/05014 A1 | 3/1993 |
| WO | WO-97/23222 A1 | 7/1997 |
| WO | WO-97/28130 A1 | 8/1997 |
| WO | WO-98/06433 A1 | 2/1998 |
| WO | WO-99/20620 A1 | 4/1999 |
| WO | WO-99/64011 A1 | 12/1999 |
| WO | WO-01/56988 A1 | 8/2001 |
| WO | WO-02/076976 A2 | 10/2002 |
| WO | WO-02/076977 A2 | 10/2002 |
| WO | WO-02/100833 A1 | 12/2002 |
| WO | WO-2004/009555 A1 | 1/2004 |
| WO | WO-2004/024717 A1 | 3/2004 |
| WO | WO-2004/045644 A1 | 6/2004 |
| WO | WO-2004/076441 A1 | 9/2004 |
| WO | WO-2004/019951 A1 | 11/2004 |
| WO | WO-2004/108724 A1 | 12/2004 |
| WO | WO-2005/011697 A2 | 2/2005 |
| WO | WO-2005/035501 A1 | 4/2005 |
| WO | WO-2005/035503 A1 | 4/2005 |
| WO | WO-2005/035506 A1 | 4/2005 |
| WO | WO-2005/080394 A1 | 9/2005 |
| WO | WO-2006/057397 A1 | 6/2006 |
| WO | WO-2006/115244 A1 | 11/2006 |
| WO | WO-2006/115245 A1 | 11/2006 |
| WO | WO-2006/115247 A1 | 11/2006 |
| WO | WO-2006/137368 A1 | 12/2006 |
| WO | WO-2007/007737 A1 | 1/2007 |
| WO | WO-2007/026664 A1 | 3/2007 |

OTHER PUBLICATIONS

International Preliminary Report on Patentability dated Mar. 13, 2008 in PCT Application No. PCT/JP2006/316913.
International Preliminary Report on Patentability dated Sep. 11, 2009 in PCT Application No. PCT/JP2008/053367.
Official Action dated Feb. 2, 2010 in Canadian Application No. 2621181.
Official Action dated Mar. 22, 2010 in Korean Application No. 10-2008-7007566.
Official Action Action dated Nov. 10, 2010 in Indian Application No. 1251/KOLNP/2008.
Official Action dated Nov. 19, 2010 in Chinese Application No. 200680031607.X.
Official Action dated Oct. 19, 2010 in Mexican Application No. MX/a/2008/002838.
Extended European Search Report, dated Mar. 29, 2011, for European Application No. 06796896.6.
Mexican Office Action, dated Mar. 7, 2011, for Mexican Application No. MX/a/2008/002838.
K. E. Kamm et al., *Annu. Rev. Physiol.* 1989, 51:299-313.
S. Kitani et al., *Biochemical and Biophysical Research Communications*, vol. 183, No. 1, 1992, pp. 48-54.
P. H. Howe et al., *Biochem J.* (1988) 255, 423-429.
M. Barany et al., Biochemistry of Smooth Muscle Contraction, pp. 321-339, 1996.
K. Itoh et al., *Biochimica et Biophysica Acta*, 1136 (1992) 52-56.
M. Tamura et al., *Biochimica et Biophysica Acta*, 1754 (2005) 245-252.
A. Suzuki et al., *Br. J. Pharmacol.* (1993) 109, 703-712.
P. L. Mobley et al., *Experimental Cell Research*, 214, 55-66 (1994).
V. Niggli, *FEBS Letters*, 445 (1999) 69-72.
J. C. Mills et al., *The Journal of Cell Biology*, vol. 140, No. 3, Feb. 9, 1988, 627-636.
J. T. Schmidt et al., *J. Neurobiol.*, 52 (3), pp. 175-188, 2002.
Fukata et al., Trends in Pharmacological Sciences, vol. 22, No. 1, pp. 32-39, Jan. 2001.
Ito et al.; Spine, 32 (19) pp. 2070-2075 (2007).
Uehata et al.; Nature, vol. 389, pp. 990-994 (1997).
Ito et al.; 52$^{nd}$ Meeting of the Orthopedic Research Society, Paper No. 1870 (2006).
Akira Ogata, "Kagaku Jikken Sousahou" 1963, p. 281, 386 (with English translation).
Restriction Requirement of Sep. 8, 2008, in U.S. Appl. No. 11/511,395.
Notice of Allowance/Notice of Allowability issued Mar. 24, 2009, in U.S. Appl. No. 11/511,395.
Notice of Allowance/Notice of Allowability issued Sep. 29, 2009, in U.S. Appl. No. 11/511,395.
Machine generated English translation of JP 11-349482 filed on Dec. 21, 1999, which corresponds to WO99/64011.
Australian Office Action issued in Australian Patent Application No. 2011253822 on Nov. 27, 2012.
Morissette et al., "High-throughout crystallization: polymorphs, salts, co-crystals and solvates of pharmaceutical solids", Advanced Drug Delivery Reviews, vol. 56 (2004) pp. 275-300.

SULFONAMIDE COMPOUND

CONTINUING DATA

This application is a 371 of PCT/JP2007/053567 filed Feb. 27, 2007.

TECHNICAL FIELD

The present invention relates to a novel sulfonamide compound or a salt thereof, or a derivative thereof useful as a prodrug. The present invention also relates to a medicament comprising said novel sulfonamide compound or a salt thereof, or a derivative thereof which is a prodrug as an active ingredient.

BACKGROUND ART

Movements of cells include contraction, migration, release, aggregation and the like, and phosphorylation of the myosin regulatory light chain is important for these cell movements. The myosin regulatory light chain is a subunit having a molecular weight of 20 kDa and constituting myosin, which exists in smooth muscle cells and various non-muscle cells such as neutrophils, platelets and nerve cells of warm-blooded animals (Barany, K., et al., Biochemistry of Smooth Muscle Contraction, pp. 21-35, 1996). Myosin existing in smooth muscle cells and various non-muscle cells such as neutrophils, platelets and nerve cells of warm-blooded animals is constituted by a myosin heavy chain subunit having a molecular weight of about 200 kDa, the myosin regulatory light chain subunit having a molecular weight of about 20 kDa, and a myosin constitutive light chain subunit having a molecular weight of about 17 kDa.

The myosin regulatory light chain is mainly phosphorylated by the myosin light chain kinase to increase the activity of myosin ATPase existing in the myosin heavy chain subunit (Barany, M., et al., Biochemistry of Smooth Muscle Contraction, pp. 321-339, 1996). It is known that the activated myosin having the increased ATPase activity becomes possible to interact with actin and activates movement apparatuses of cytoskeleton to activate cell movements. More specifically, it is known that activation of myosin relates to cell contraction (Kamm, K., et al., Annu. Rev. Physiol., 51, pp. 299-313, 1989). It is also known that activation of myosin relates to change of cell morphology (Schmidt, J. T. et al., J, Neurobiol., 52 (3), pp. 175-188, 2002). It is known that activation of myosin relates to cell migration (Niggli, V., FEBS Lett., 445, pp. 69-72, 1999). Further, it is known that activation of myosin relates to cell release (Kitani, S., et al., Biochem. Biophys. Res. Commun., 183, pp. 48-54, 1992). It is further known that activation of myosin relates to cell aggregation (Itoh, K., et al., Biochim. Biophys. Acta., 1136, pp. 52-56, 1992). It is also known that activation of myosin relates to cell apoptosis (Mills, J. C. et al., J. Cell Biol., Vol. 140, No. 3, pp. 627-636, 1998). Based on these findings, it is considered that an agent which inhibits the phosphorylation of the myosin regulatory light chain suppresses cell contraction, regulates change of cell morphology, suppresses cell migration, suppresses cell release, suppresses cell aggregation and suppresses cell apoptosis.

Cell contraction is deeply involved in diseases relating to contraction of various smooth muscle layers. Examples of such diseases include, for example, hypertension (Samlyo, A. P., et al., Rev. Physiol. Biochem. Pharmacol., Vol. 134, pp. 209-34, 1999), angina pectoris (Shimokawa et al., Cardiovasc. Res., Vol. 43, No. 4, pp. 1029-39, 1999; Satoh, H., et al., Jpn. J. Pharmacol., 79 (suppl.), p. 211, 1999), cerebral vascular spasm (M. Satoh et al., the 57th General Meeting of Japan Neurosurgical Society, Collection of Abstracts, 153, 1998; N. Ono et al., Pharmacol. Ther., Vol. 82, No. 2-3, pp. 123-31, 1991; Shimokawa et al., Cardiovasc. Res., Vol. 43, No. 4, pp. 1029-39, 1999), erectile dysfunction (Andersson, K E. et al., World J. Vrol., 15, pp. 14-20, 1997), bronchial asthma (K. Iidzuka, Allergy, 47, 943, 1998; K. Iidzuka et al., Jpn. J. Respirology Society, 37, 196, 1999) and the like.

Change of cell morphology is deeply involved in diseases relating to morphological change of various cells. Examples of the diseases relating to change of cell morphology include, for example, as those relating to nerve cells of eyes, various nerve dysfunctions such as diabetic retinopathy, and glaucoma (Arakawa, Y., et al., BIO Clinica, 17 (13), pp. 26-28, 2002). Further, cell migration is deeply involved in diseases relating to migration of various cells. Examples of such diseases include, for example, cancer invasion and metastasis (Itoh, K. et al., Nat. Med., Vol. 5, No. 2, pp. 221-5, 1999; Keely, P. et al., Trends Cell Biol., Vol. 8, No. 3, pp. 101-6, 1998), nephritis (Fujimoto, O. et al., Journal of Japanese Society of Internal Medicine, 88 (1), pp. 148-58, 1998) and the like.

Furthermore, it is considered that cell release is deeply involved in various allergies and the like (Keane-Myers A. et al., Curr. Allergy Asthma Rep., 1(6):550-557, 2001), and further, cell aggregation is considered to be deeply involved in thrombosis and the like (Nakai, K. et al., Blood, Vol. 90, No. 10, pp. 3736-42, 1997). Further, it is known that cell apoptosis is involved in neurodegenerative diseases such as Alzheimer's disease, Parkinson's disease and glaucoma, viral diseases, hepatic diseases and the like (Thompson, C. B., Science, Vol. 267, pp. 1456-1462, 1995).

As pathways for regulating phosphorylation of myosin regulatory light chain, two pathways are known, i.e., a pathway based on activation of myosin regulatory light chain kinase induced by elevation of intracellular calcium level, and a pathway based on inactivation of myosin dephosphorylation enzyme resulting from phosphorylation of the enzyme induced by activation of Rho kinase due to activation of low-molecular-weight Rho protein (Fukata, Y., et al., Trends Pharmacol. Sci., 22, pp. 32-39, 2001).

More specifically, it is considered that compounds which inhibit Rho kinase suppress cell contraction, regulate change of cell morphology, suppress cell migration, suppress cell release, suppress cell aggregation, and suppress cell apoptosis, like medicaments which inhibit phosphorylation of myosin regulatory light chain.

Based on these findings, it is considered that a substance which inhibits Rho kinase is useful as an active ingredient of a medicament for prophylactic and/or therapeutic treatment of a disease relating to cell contraction, disease relating to change of cell morphology, disease relating to cell migration, disease relating to cell release, disease relating to cell aggregation, and/or disease relating to cell apoptosis.

As agents inhibiting the phosphorylation of myosin regulatory light chain, isoquinoline derivatives are known. For example, it has been reported that 1-(5-isoquinolinesulfonyl)-2-methylpiperazine (H-7) inhibits the phosphorylation of myosin regulatory light chain of mesenteric artery (Suzuki, A. et al., Br. J. Pharmacol., 109, pp. 703-712, 1993), and there are also known drugs inhibiting the phosphorylation of myosin regulatory light chain of iris smooth muscle (Howe, P. H. et al., Biochem J., 255, pp. 423-429, 1988), and astrocyte (Mobley P. L., et al., Exp. Cell Res., 214, pp. 55-66, 1994). Further, 5-substituted isoquinoline derivatives are also known (International Patent Publication No. 2004/009555). However, the N atom of sulfonamide in these 5-substituted isoquinoline derivatives does not form a ring, and thus they have a structure different from that of the compounds of the present invention. Further, tricyclic compounds are also known (International Patent Publication No. 2004/108724). However, these compounds are tricyclic compounds and do not have sulfonamide, and therefore they are structurally different from the compounds of the present invention.

Further, known Rho kinase inhibitors also include the amide derivatives disclosed in International Patent Publication WO98/06433; isoquinolinesulfonyl derivatives disclosed in International Patent Publication WO97/23222, Uehata, M. et al., Nature, 389, pp 990-994, 1997, and International Patent Publication WO99/64011; heterocyclic amino derivatives disclosed in International Patent Publication WO01/56988; indazole derivatives disclosed in International Patent Publication WO02/100833; quinazoline derivatives disclosed in International Patent Publications WO02/076976 and WO02/076977, and the like. However, any of these compounds are structurally different from the compounds of the present invention.

DISCLOSURE OF THE INVENTION

Object to be Achieved by the Invention

An object of the present invention is to provide a novel substance which potently inhibits Rho kinase. Another object of the present invention is to provide a medicament comprising a substance having the aforementioned characteristic as an active ingredient and useful for prophylactic and/or therapeutic treatment of diseases relating to cell contraction, diseases relating to change of cell morphology, diseases relating to cell migration, diseases relating to cell release, diseases relating to cell aggregation, and diseases relating to cell apoptosis.

Means for Achieving the Object

The inventors of the present invention conducted various researches to achieve the aforementioned objects, namely, they synthesized various sulfonamide compounds represented by the following formula (1) and studied pharmacological actions thereof. As a result, they found that these sulfonamide compounds had an action of strongly inhibiting Rho kinase, and were useful as an active ingredient of a medicament for prophylactic and/or therapeutic treatment of diseases in which Rho kinase is involved, such as diseases relating to cell contraction, diseases relating to change of cell morphology, diseases relating to cell migration, diseases relating to cell release, and diseases relating to cell apoptosis. Further, in order to verify applicability of the aforementioned sulfonamide compounds to specific diseases, they also examined intraocular pressure reducing action of the aforementioned sulfonamide compounds in animals. As a result, they also found that the aforementioned sulfonamide compounds had a superior intraocular pressure reducing action, and were useful also as therapeutic agents of ocular diseases such as glaucoma. The present invention was accomplished on the basis of these findings.

The present invention thus provides the followings.

<1> A compound represented by the following general formula (1) or a salt thereof, or a derivative thereof which is a prodrug:

[Formula 1]

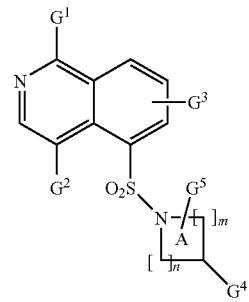

(1)

[in the general formula (1), A represents a nitrogen-containing saturated ring;
m represents an integer of 0, 1, or 2;
n represents an integer of 1, 2, 3, or 4;
$G^1$ represents hydrogen atom, chlorine atom, hydroxyl group, an alkoxy group, or amino group;
$G^2$ represents a halogen atom, hydroxyl group, cyano group, carboxy group, an alkyl group which may be substituted, an alkenyl group which may be substituted, an alkynyl group which may be substituted, an alkoxy group which may be substituted, an alkylthio group which may be substituted, an amino group which may be substituted, an alkylsulfinyl group which may be substituted, an alkylsulfonyl group which may be substituted, or an aryl group which may be substituted;
$G^3$ represents hydrogen atom, a halogen atom, hydroxyl group, cyano group, carboxy group, an alkyl group which may be substituted, an alkenyl group which may be substituted, an alkynyl group which may be substituted, an alkoxy group which may be substituted, an alkylthio group which may be substituted, an amino group which may be substituted, an alkoxycarbonyl group which may be substituted, an acyl group which may be substituted, an acyloxy group which may be substituted, an alkylsulfinyl group which may be substituted, an alkylsulfonyl group which may be substituted, or an aryl group which may be substituted (provided that $G^3$ substitutes at the 3-, 6-, 7-, or 8-position of the isoquinoline ring);
$G^4$ represents hydroxyl group, or —N($R^1$)($R^2$) ($R^1$ and $R^2$ may be the same or different, and independently represent hydrogen atom, an alkyl group which may be substituted, an aralkyl group which may be substituted, an alkenyl group which may be substituted, an alkynyl group which may be substituted, or a saturated heterocyclic group which may be substituted); and
$G^5$ represents a substituent on a ring-constituting carbon atom constituting the nitrogen-containing saturated ring represented by A, and represents hydrogen atom, fluorine atom, or an alkyl group];

<2> The compound or a salt, or a derivative thereof which is a prodrug according to <1>, wherein m is 1;
<3> The compound or a salt, or a derivative thereof which is a prodrug according to <1>, wherein n is 2 or 3;
<4> The compound or a salt, or a derivative thereof which is a prodrug according to <1>, wherein $G^3$ is hydrogen atom;
<5> The compound or a salt, or a derivative thereof which is a prodrug according to <1>, wherein $G^5$ is hydrogen atom; and
<6> The compound or a salt, or a derivative thereof which is a prodrug according to <1>, wherein $G^4$ is —N($R^1$)($R^2$).

From another aspect, the present invention provides a medicament comprising a compound represented by the aforementioned formula (1) or a physiologically acceptable salt thereof, or a derivative thereof which is a prodrug as an active ingredient. This medicament can be used for prophylactic and/or therapeutic treatment of a disease relating to cell contraction, disease relating to change of cell morphology, disease relating to cell migration, disease relating to cell release, disease relating to cell aggregation, and disease relating to cell apoptosis. The present invention also provides a Rho kinase inhibitor containing a compound represented by the aforementioned formula (1) or a physiologically acceptable salt thereof, or a derivative thereof which is a prodrug as an active ingredient.

From another aspect, the present invention provides use of a compound represented by the aforementioned formula (1) or a physiologically acceptable salt thereof, or a derivative thereof which is a prodrug for manufacture of the aforementioned medicament, and a method for prophylactic and/or therapeutic treatment of a disease relating to cell contraction, disease relating to change of cell morphology, disease relating to cell migration, disease relating to cell release, disease relating to cell aggregation, and disease relating to cell apoptosis, which comprises the step of administrating a prophylactically and/or therapeutically effective amount of a substance, for preparation of the aforementioned medicament, which is selected from the group consisting a compound represented by the aforementioned formula (1), a physiologically acceptable salt thereof, and a derivative thereof which is prodrug to a mammal including human.

The present invention further provides a medicament comprising a combination of a substance selected from the group consisting of a compound represented by the aforementioned formula (1), a physiologically acceptable salt thereof, and a derivative thereof which is a prodrug, and a drug for combination use.

A medicament based on the aforementioned combination is useful for prophylactic and/or therapeutic treatment of, for example, disease relating to cell contraction, disease relating to change of cell morphology, disease relating to cell migration, disease relating to cell release, disease relating to cell aggregation, and/or disease relating to cell apoptosis, and it is provided by the present invention.

Best Mode for Carrying Out the Invention

In the specification, unless particularly indicated, examples of the halogen atom include fluorine atom, chlorine atom, bromine atom, and iodine atom.

Examples of the alkyl group include, for example, a straight, branched, or cyclic saturated hydrocarbon group, and a saturated hydrocarbon group consisting a combination thereof, and a lower alkyl group is preferred. In the specification, the term "lower" means that number of carbon atoms constituting a certain functional group is, for example, 1 to 6. As the lower alkyl group, for example, an alkyl group having 1 to 6 carbon atoms is preferred, and an alkyl group having 1 to 3 carbon atoms is particularly preferred. The same shall apply to an alkyl moiety of other substituents having the alkyl moiety (for example, an alkoxy group and the like).

Preferred examples of the alkyl group having 1 to 3 carbon atoms include, for example, methyl group, ethyl group, n-propyl group, isopropyl group, cyclopropyl group and the like, and preferred examples of the alkyl group having 4 to 6 carbon atoms include, for example, n-butyl group, isobutyl group, s-butyl group, t-butyl group, cyclobutyl group, cyclopropylmethyl group, n-pentyl group, cyclopentyl group, cyclopropylethyl group, cyclobutylmethyl group, n-hexyl group, cyclohexyl group, cyclopropylpropyl group, cyclobutylethyl group, cyclopentylmethyl group and the like. As the alkyl group, for example, methyl group, ethyl group, n-propyl group, and isopropyl group are particularly preferred.

Examples of the alkenyl group include, for example, a lower alkenyl group containing one or more double bonds and the like, and a lower alkenyl group containing one double bond is preferred. As the lower alkenyl group, for example, an alkenyl group having 2 to 5 carbon atoms is preferred, and an alkenyl group having 2 to 4 carbon atoms is particularly preferred. Preferred examples of the alkenyl group having 2 to 4 carbon atoms include, for example, vinyl group, allyl group, propenyl group, butylidene group, but-1-enyl group, but-2-enyl group, but-3-enyl group, and the like, and preferred examples of the alkenyl group having 5 carbon atoms include, for example, pentylidene group, pent-1-enyl group, pent-2-enyl group, pent-3-enyl group, pent-4-enyl group, and the like. As the alkenyl group, for example, vinyl group, allyl group, and propenyl group are more preferred, vinyl group, and allyl group are still more preferred, and allyl group is particularly preferred. There is also another embodiment in which vinyl group is particularly preferred.

Examples of the alkynyl group include, for example, a lower alkynyl group containing one or more triple bonds, and the like, and a lower alkynyl group containing one triple bond is preferred. As the lower alkynyl group, for example, an alkynyl group having 2 to 5 carbon atoms is preferred. Specifically, preferred examples include ethynyl group, prop-1-ynyl group, prop-2-ynyl group, but-1-ynyl group, but-2-ynyl group, but-3-ynyl group, pent-1-ynyl group, pent-2-ynyl group, pent-3-ynyl group, pent-4-ynyl group and the like. Ethynyl group, prop-2-ynyl group, and but-3-ynyl group are more preferred, ethynyl group, and prop-1-ynyl group are still more preferred, and ethynyl group is particularly preferred.

Examples of the alkoxy group include, for example, a straight, branched, or cyclic saturated alkyloxy group, and a saturated alkyloxy group consisting a combination thereof, and a lower alkoxy group is preferred. Examples of the lower alkoxy group include, for example, an alkoxy group having 1 to 6 carbon atoms, and an alkoxy group having 1 to 4 carbon atoms is preferred. Preferred examples of the alkoxy group having 1 to 4 carbon atoms include, for example, methoxy group, ethoxy group, n-propoxy group, isopropoxy group, cyclopropoxy group, n-butoxy group, isobutoxy group, s-butoxy group, t-butoxy group, cyclobutoxy group, cyclopropylmethoxy group, and the like, and preferred examples of the alkoxy group having 5 or 6 carbon atoms include, for example, n-pentyloxy group, cyclopentyloxy group, cyclopropylethyloxy group, cyclobutylmethyloxy group, n-hexyloxy group, cyclohexyloxy group, cyclopropylpropyloxy group, cyclobutylethyloxy group, cyclopentylmethyloxy group, and the like.

Examples of the alkylthio group include, for example, a straight, branched, or cyclic saturated alkylthio group, and a saturated alkylthio group consisting a combination thereof, and a lower alkylthio group is preferred. As the lower alkylthio group, for example, an alkylthio group having 1 to 4 carbon atoms is preferred. Specifically, preferred examples include methylthio group, ethylthio group, n-propylthio group, isopropylthio group, cyclopropylthio group, n-butylthio group, isobutylthio group, s-butylthio group, t-butylthio group, cyclobutylthio group, cyclopropylmethylthio group, and the like.

Examples of the amino group include, for example, —NH$_2$ group.

Examples of the alkoxycarbonyl group include, for example, a group consisting of the aforementioned alkoxy group to which carbonyl group is added at the end, and a lower an alkoxycarbonyl group is preferred. Examples of the lower alkoxycarbonyl group include, for example, a group consisting of an alkoxy group having 1 to 6 carbon atoms to which carbonyl group is added at the end, and a group consisting of an alkoxy group having 1 to 4 carbon atoms to which carbonyl group is added at the end is preferred. Specifically, preferred examples include methoxycarbonyl group, ethoxycarbonyl group, n-propoxycarbonyl group, isopropoxycarbonyl group, cyclopropoxycarbonyl group, n-butoxycarbonyl group, isobutoxycarbonyl group, s-butoxycarbonyl group, t-butoxycarbonyl group, cyclobutoxycarbonyl group, cyclopropylmethoxycarbonyl group, and the like.

Preferred examples of the acyl group include, for example, an alkanoyl group and an arylcarbonyl group. An alkanoyl group is preferred, and a lower alkanoyl group is more preferred. Examples of the alkanoyl group include, for example, a straight, branched, or cyclic saturated alkylcarbonyl group, and a saturated alkylcarbonyl group consisting a combination thereof, and the alkyl moiety may contain one or more unsaturated bonds. As the lower alkanoyl group, for example, an acyl group having 2 to 5 carbon atoms is preferred. Specifically, preferred examples include acetyl group, propanoyl group, butanoyl group, 2-methylpropanoyl group, cyclopropylcarbonyl group, pentanoyl group, 3-methylbutanoyl group, 2,2-dimethylpropanoyl group, cyclobutylcarbonyl group, and the like.

Preferred examples of the acyloxy group include, for example, an alkanoyloxy group (alkylcarbonyloxy group) and an arylcarbonyloxy group. An alkanoyloxy group is preferred, and a lower alkanoyloxy group is more preferred. The alkyl moiety of the alkanoyloxy group may contain one or more unsaturated bonds. As the lower alkanoyloxy group, for example, an acyloxy group having 2 to 5 carbon atoms is preferred. Specifically, preferred examples include acetoxy group, propanoyloxy group, butanoyloxy group, 2-methylpropanoyloxy group, cyclopropylcarbonyloxy group, pentanoyloxy group, 3-methylbutanoyloxy group, 2,2-dimethylpropanoyloxy group, cyclobutylcarbonyloxy group, and the like.

Preferred examples of the alkylsulfinyl group include, for example, a lower alkylsulfinyl group. As the lower alkylsulfinyl group, for example, an alkylsulfinyl group having 1 to 4 carbon atoms is preferred. Specifically, preferred examples include methylsulfinyl group, ethylsulfinyl group, n-propylsulfinyl group, isopropylsulfinyl group, cyclopropylsulfinyl group, n-butylsulfinyl group, isobutylsulfinyl group, s-butylsulfinyl group, t-butylsulfinyl group, cyclobutylsulfinyl group, cyclopropylmethylsulfinyl group, and the like.

Preferred examples of the alkylsulfonyl group include, for example, a lower alkylsulfonyl group. As the lower alkylsulfonyl group, for example, an alkylsulfonyl group having 1 to 4 carbon atoms is preferred. Specifically, preferred examples include methylsulfonyl group, ethylsulfonyl group, n-propylsulfonyl group, isopropylsulfonyl group, cyclopropylsulfonyl group, n-butylsulfonyl group, isobutylsulfonyl group, s-butylsulfonyl group, t-butylsulfonyl group, cyclobutylsulfonyl group, cyclopropylmethylsulfonyl group, and the like.

Examples of the aryl ring include, for example, a monocyclic aromatic ring, a condensed polycyclic aromatic ring, and the like. Although the aryl ring may be a hydrocarbon ring, it may contain one ore more, for example, 1 to 3, one or more kinds of heteroatoms selected from the group consisting of nitrogen atom, sulfur atom, and oxygen atom as ring-constituting atoms other than carbon atom.

Examples of the monocyclic aromatic ring include, for example, a monocyclic aromatic hydrocarbon, a monocyclic aromatic heterocyclic ring containing one or more heteroatoms, and the like. Examples include, for example, benzene ring, and a 5- or 6-membered aromatic heterocyclic ring containing one or more heteroatoms. Specifically, preferred examples of the 5- or 6-membered aromatic heterocyclic ring include thiophene, pyridine, furan, thiazole, oxazole, pyrazole, pyrazine, pyrimidine, pyrrole, imidazole, pyridazine, isothiazole, isoxazole, 1,2,4-oxadiazole, 1,3,4-oxadiazole, 1,2,4-thiadiazole, 1,3,4-thiadiazole, furazan, and the like.

Examples of the condensed polycyclic aromatic ring include, for example, a condensed polycyclic aromatic hydrocarbon, a condensed polycyclic aromatic heterocyclic ring containing one or more heteroatoms, and the like. Examples of the condensed polycyclic aromatic hydrocarbon include, for example, a condensed polycyclic aromatic hydrocarbon having 9 to 14 carbon atoms, i.e., bi- or tricyclic aromatic hydrocarbon, and specific preferred examples include, for example, naphthalene, indene, fluorene, anthracene, and the like. Examples of the condensed polycyclic aromatic heterocyclic ring include, for example, a 9- to 14-membered, preferably 9- or 10-membered, condensed polycyclic aromatic heterocyclic ring containing one or more, for example, 1 to 4, heteroatoms, and the like, and preferred specific examples include, for example, benzofuran, benzothiophene, benzimidazole, benzoxazole, benzothiazole, benzisothiazole, naphtho[2,3-b]thiophene, quinoline, isoquinoline, indole, quinoxaline, phenanthoridine, phenothiazine, phenoxazine, phthalazine, naphthylidine, quinazoline, cinnoline, carbazole, β-carboline, acridine, phenazine, phthalimide, thioxanthene, and the like.

Examples of the aryl group include, for example, a monocyclic aromatic group, a condensed polycyclic aromatic group, and the like, and a monovalent residue obtained by removing arbitrary one hydrogen atom from the aryl ring explained above can be exemplified.

Examples of the monocyclic aromatic group include, for example, a monovalent residue obtained by removing arbitrary one hydrogen atom from a monocyclic aromatic ring. Preferred specific examples of the monocyclic aromatic group include, phenyl group, thienyl group (2- or 3-thienyl group), pyridyl group (2-, 3- or 4-pyridyl group), furyl group (2- or 3-furyl group), thiazolyl group (2-, 4- or 5-thiazolyl group), oxazolyl group (2-, 4- or 5-oxazolyl group), pyrazolyl group (1-, 3- or 4-pyrazolyl group), 2-pyrazinyl group, pyrimidinyl group (2-, 4- or 5-pyrimidinyl group), pyrrolyl group (1-, 2- or 3-pyrrolyl group), imidazolyl group (1-, 2- or 4-imidazolyl group), pyridazinyl group (3- or 4-pyridazinyl group), 3-isothiazolyl group, 3-isoxazolyl group, 1,2,4-oxadiazol-5-yl group, 1,2,4-oxadiazol-3-yl group, and the like.

Examples of the condensed polycyclic aromatic group include, for example, a monovalent residue obtained by removing arbitrary one hydrogen atom from a bi- to tetracyclic, preferably, bi- or tricyclic, condensed polycyclic aromatic ring.

Preferred specific examples of the condensed polycyclic aromatic group include, for example, 1-naphthyl group, 2-naphthyl group, 2-indenyl group, 2-anthryl group, quinolyl group (2-, 3-, 4-, 5-, 6-, 7- or 8-quinolyl group), isoquinolyl group (1-, 3-, 4-, 5-, 6-, 7- or 8-isoquinolyl group), indolyl group (1-, 2-, 3-, 4-, 5-, 6- or 7-indolyl group), isoindolyl group (1-, 2-, 4- or 5-isoindolyl group), phthalazinyl group (1-, 5- or 6-phthalazinyl group), quinoxalinyl group (2-, 3- or 5-quinoxalinyl group), benzofuranyl group (2-, 3-, 4-, 5- or 6-benzofuranyl group), benzothiazolyl group (2-, 4-, 5- or 6-benzothiazolyl group), benzimidazolyl group (1-, 2-, 4-, 5- or 6-benzimidazolyl group), fluorenyl group (1-, 2-, 3- or 4-fluorenyl group), thioxanthenyl group, and the like.

The aralkyl group represents, for example, an alkyl group substituted with an aryl group (arylalkyl group). The alkyl moiety of the arylalkyl group is similar to the aforementioned alkyl group, and the aryl moiety of the arylalkyl group is similar to the aforementioned aryl. As the aryl moiety of the arylalkyl, a monocyclic aromatic group is preferred, and examples of the arylalkyl group include, for example, benzyl group, 2-thienylmethyl group, 3-thienylmethyl group, 2-pyridylmethyl group, 3-pyridylmethyl group, 4-pyridylmethyl group, 2-furylmethyl group, 3-furylmethyl group, 2-thiazolylmethyl group, 4-thiazolylmethyl group, 5-thiazolylmethyl group, 2-oxazolylmethyl group, 4-oxazolylmethyl group, 5-oxazolylmethyl group, 1-pyrazolylmethyl group, 3-pyrazolylmethyl group, 4-pyrazolylmethyl group, 2-pyrazinylmethyl group, 2-pyrimidinylmethyl group, 4-pyrimidinylmethyl group, 5-pyrimidinylmethyl group, 1-pyrrolylmethyl group, 2-pyrrolylmethyl group, 3-pyrrolylmethyl group, 1-imidazolylmethyl group, 2-imidazolylmethyl group, 4-imidazolylmethyl group, 3-pyridazinylmethyl group, 4-pyridazinylmethyl group, 3-isothiazolylmethyl group, 3-isoxazolylmethyl group, 1,2,4-oxadiazol-5-ylmethyl group, 1,2,4-oxadiazol-3-ylmethyl group, and the like. Benzyl group, 2-thienylmethyl group, 3-thienylmethyl group, 2-furylmethyl group, 3-furylmethyl group, 2-pyrrolylmethyl group, and 3-pyrrolylmethyl group are preferred, and 2-furylmethyl group is particularly preferred.

Examples of the arylalkyl group include, for example, 2-phenylethyl group, 2-(2-thienyl)ethyl group, 2-(3-thienyl) ethyl group, 2-(2-pyridyl)ethyl group, 2-(3-pyridyl)ethyl group, 2-(4-pyridyl)ethyl group, 2-(2-furyl)ethyl group, 2-(3-furyl)ethyl group, 2-(2-thiazolyl)ethyl group, 2-(4-thiazolyl) ethyl group, 2-(5-thiazolyl)ethyl group, 2-(2-oxazolyl)ethyl group, 2-(4-oxazolyl)ethyl group, 2-(5-oxazolyl)ethyl group, 2-(1-pyrazolyl)ethyl group, 2-(3-pyrazolyl)ethyl group, 2-(4-pyrazolyl)ethyl group, 2-(2-pyrazinyl)ethyl group, 2-(2-pyrimidinyl)ethyl group, 2-(4-pyrimidinyl)ethyl group, 2-(5-pyrimidinyl)ethyl group, 2-(1-pyrrolyl)ethyl group, 2-(2-pyrrolyl)ethyl group, 2-(3-pyrrolyl)ethyl group, 2-(1-imidazolyl)ethyl group, 2-(2-imidazolyl)ethyl group, 2-(4-imidazolyl)ethyl group, 2-(3-pyridazinyl)ethyl group, 2-(4-pyridazinyl)ethyl group, 2-(3-isothiazolyl)ethyl group, 2-(3-isoxazolyl)ethyl group, 2-(1,2,4-oxadiazol-5-yl)ethyl group, 2-(1,2,4-oxadiazol-3-yl)ethyl group, and the like. 2-Phenylethyl group, 2-(2-thienyl)ethyl group, 2-(3-thienyl)ethyl group, 2-(2-furyl)ethyl group, 2-(3-furyl)ethyl group, 2-(2-pyrrolyl)ethyl group, and 2-(3-pyrrolyl)ethyl group are preferred, and 2-(2-furyl)ethyl group is particularly preferred.

Examples of the arylalkyl group include, for example, 1-phenylethyl group, 1-(2-thienyl)ethyl group, 1-(3-thienyl) ethyl group, 1-(2-pyridyl)ethyl group, 1-(3-pyridyl)ethyl group, 1-(4-pyridyl)ethyl group, 1-(2-furyl)ethyl group, 1-(3-furyl)ethyl group, 1-(2-thiazolyl)ethyl group, 1-(4-thiazolyl) ethyl group, 1-(5-thiazolyl)ethyl group, 1-(2-oxazolyl)ethyl group, 1-(4-oxazolyl)ethyl group, 1-(5-oxazolyl)ethyl group, 1-(1-pyrazolyl)ethyl group, 1-(3-pyrazolyl)ethyl group, 1-(4-pyrazolyl)ethyl group, 1-(2-pyrazinyl)ethyl group, 1-(2-pyrimidinyl)ethyl group, 1-(4-pyrimidinyl)ethyl group, 1-(5-pyrimidinyl)ethyl group, 1-(1-pyrrolyl)ethyl group, 1-(2-pyrrolyl)ethyl group, 1-(3-pyrrolyl)ethyl group, 1-(1-imidazolyl)ethyl group, 1-(2-imidazolyl)ethyl group, 1-(4-imidazolyl)ethyl group, 1-(3-pyridazinyl)ethyl group, 1-(4-pyridazinyl)ethyl group, 1-(3-isothiazolyl)ethyl group, 1-(3-isoxazoly)ethyl group, 1-(1,2,4-oxadiazol-5-yl)ethyl group, 1-(1,2,4-oxadiazol-3-yl)ethyl group, and the like. 1-Phenylethyl group, 1-(2-thienyl)ethyl group, 1-(3-thienyl)ethyl group, 1-(2-furyl)ethyl group, 1-(3-furyl)ethyl group, 1-(2-pyrrolyl)ethyl group, and 1-(3-pyrrolyl)ethyl group are preferred, and 1-(2-furyl)ethyl group is particularly preferred.

Examples of the saturated heterocyclic group include, for example, a monocyclic saturated heterocyclic group, and the ring thereof is, for example, a 3- to 7-membered, particularly preferably 5- or 6-membered ring containing one or two, preferably one, heteroatom. Specifically, preferred examples include tetrahydropyranyl group (3- or 4-tetrahydropyranyl group), 3-tetrahydrofuryl group, piperidyl group (3- or 4-piperidyl group), 3-pyrrolidyl group, tetrahydrothiopyranyl group (3- or 4-tetrahydrothiopyranyl group), 3-tetrahydrothiofuryl group, and the like. Tetrahydropyranyl group can be mentioned as a particularly preferred example.

Preferred examples of the substituent of the alkyl group which may be substituted include, for example, hydroxyl group, a halogen atom, carboxy group, cyano group, a saturated heterocyclic group, an acylamino group, an alkylsulfonylamino group, aminocarbonylamino group, an alkylaminocarbonylamino group, an arylaminocarbonylamino group, an alkylsulfonylamino group optionally substituted with one or more halogen atoms, and the like. Hydroxyl group, and a halogen atom are more preferred, hydroxyl group and fluorine atom are still more preferred, and hydroxyl group is particularly preferred. There is also another embodiment in which fluorine atom is particularly preferred.

As the alkyl group which may be substituted, a group selected from the group consisting of the preferred examples mentioned above for the alkyl group, trifluoromethyl group, difluoromethyl group, hydroxymethyl group, and 2-hydroxyethyl group is preferred. Methyl group, ethyl group, n-propyl group, isopropyl group, cyclopropyl group, trifluoromethyl group, difluoromethyl group, hydroxymethyl group, and 2-hydroxyethyl group are more preferred, and methyl group is particularly preferred.

The substituents of the alkenyl group which may be substituted and the alkynyl group which may be substituted are similar to the substituent of the aforementioned alkyl group which may be substituted.

As the alkenyl group which may be substituted, for example, the preferred examples mentioned above for the alkenyl group are preferred, and as the alkynyl group which may be substituted, for example, the preferred examples mentioned above for the alkynyl group are preferred.

The substituent of the alkoxy group which may be substituted is similar to, for example, the substituent of the aforementioned alkyl group which may be substituted, and one or more halogen atoms are particularly preferred.

As the substituted alkoxy group, for example, an alkoxy group optionally substituted with one or more halogen atoms is preferred, and an alkoxy group optionally substituted with one or more halogen atoms and having 1 to 4 carbon atoms is preferred. When the alkoxy group is substituted with two or more halogen atoms, the halogen atoms may be the same or different.

As the alkoxy group which may be substituted, a group selected from the group consisting of, for example, the preferred examples of the alkoxy group having 1 to 4 carbon atoms mentioned above, monofluoromethoxy group, difluoromethoxy group, trifluoromethoxy group, and 2,2,2-trifluoroethoxy group is preferred, and a group selected from the group consisting of the preferred examples of the alkoxy group having 1 to 4 carbon atoms mentioned above, trifluoromethoxy group, and 2,2,2-trifluoroethoxy group is particularly preferred.

Examples of the substituent of the alkylthio group which may be substituted include, for example, a substituent similar to the substituent of the aforementioned alkyl group which may be substituted.

As the alkylthio group which may be substituted, for example, the preferred examples of the aforementioned alkylthio group are preferred.

Preferred examples of the alkoxycarbonyl group which may be substituted include, for example, a group consisting of the aforementioned alkoxy group which may be substituted to which carbonyl group is added at the end.

Examples of the amino group which may be substituted include, for example, —$NH_2$ group, an alkylamino group, a dialkylamino group, an acylamino group, an acyl(alkyl) amino group, an alkylsulfonylamino group, an alkylsulfonyl (alkyl)amino group, an alkylamino group optionally substituted with one or more halogen atoms, an alkylsulfonylamino group optionally substituted with one or more halogen atoms, an alkylsulfonyl(alkyl)amino group optionally substituted with one or more halogen atoms, and the like.

Preferred examples of the alkylamino group include, for example, a lower alkylamino group. As the lower alkylamino group, for example, an alkylamino group having 1 to 4 carbon atoms is preferred. Specifically, preferred examples include methylamino group, ethylamino group, n-propylamino group, isopropylamino group, cyclopropylamino group, n-butylamino group, isobutylamino group, s-butylamino group, t-butylamino group, cyclobutylamino group, cyclopropylmethylamino group, and the like.

Examples of the dialkylamino group include, for example, an amino group substituted with the same or different alkyl groups, and a lower dialkylamino group is usually preferred. As the lower dialkylamino group, for example, an amino group substituted with alkyl groups each having 1 to 4 carbon atoms is preferred. Specifically, preferred examples include dimethylamino group, ethyl(methyl)amino group, diethylamino group, methyl(n-propyl)amino group, isopropyl(methyl)amino group, cyclopropyl(methyl)amino group, n-butyl(methyl)amino group, isobutyl(methyl)amino group, s-butyl(methyl)amino group, t-butyl(methyl)amino group, cyclobutyl(methyl)amino group, cyclopropylmethyl(methyl) amino group, and the like.

Examples of the acylamino group include, for example, an amino group substituted with the aforementioned acyl group, and preferred examples of the acyl group are similar to those mentioned above. Specifically, preferred examples include acetylamino group, propanoylamino group, butanoylamino group, 2-methylpropanoylamino group, cyclopropylcarbonylamino group, pentanoylamino group, 3-methylbutanoylamino group, 2,2-dimethylpropanoylamino group, cyclobutylcarbonylamino group, and the like.

Examples of the acyl(alkyl)amino group include, for example, an amino group simultaneously substituted with one acyl group and one alkyl group, and preferred examples of the acyl group and the alkyl group are similar to those mentioned above. Specifically, preferred examples include acetyl(methyl)amino group, methyl(propanoyl)amino group, butanoyl(methyl)amino group, methyl(2-methylpropanoyl) amino group, cyclopropylcarbonyl(methyl)amino group, methyl(pentanoyl)amino group, methyl(3-methylbutanoyl) amino group, 2,2-dimethylpropanoyl(methyl)amino group, cyclobutylcarbonyl(methyl)amino group, and the like.

Examples of the alkylsulfonylamino group include, for example, an amino group substituted with the aforementioned alkylsulfonyl group, and preferred examples of the alkylsulfonyl group are similar to those mentioned above. Specifically, preferred examples include methylsulfonylamino group, ethylsulfonylamino group, n-propylsulfonylamino group, isopropylsulfonylamino group, cyclopropylsulfonylamino group, n-butylsulfonylamino group, isobutylsulfonylamino group, s-butylsulfonylamino group, t-butylsulfonylamino group, cyclobutylsulfonylamino group, and cyclopropylmethylsulfonylamino group.

Examples of the alkylsulfonyl(alkyl)amino group include, for example, an amino group simultaneously substituted with one alkylsulfonyl group and one alkyl group, and preferred examples of the alkylsulfonyl group and the alkyl group are similar to those mentioned above. Specifically, preferred examples include methyl(methylsulfonyl)amino group, ethylsulfonyl(methyl)amino group, methyl(n-propylsulfonyl) amino group, isopropylsulfonyl(methyl)amino group, cyclopropylsulfonyl(methyl)amino group, n-butylsulfonyl (methyl)amino group, isobutylsulfonyl(methyl)amino group, s-butylsulfonyl(methyl)amino group, t-butylsulfonyl(methyl)amino group, cyclobutylsulfonyl(methyl)amino group, and cyclopropylmethylsulfonyl(methyl)amino group.

Examples of the aminocarbonylamino group include, for example, —$NHCONH_2$ group.

Examples of the alkylaminocarbonylamino group include, for example, an amino group substituted with an alkylaminocarbonyl group, and preferred examples of the alkylamino moiety of the alkylaminocarbonyl group are similar to those of the aforementioned alkylamino group. Specifically, preferred examples include methylaminocarbonylamino group, ethylaminocarbonylamino group, n-propylaminocarbonylamino group, isopropylaminocarbonylamino group, cyclopropylaminocarbonylamino group, n-butylaminocarbonylamino group, isobutylaminocarbonylamino group, s-butylaminocarbonylamino group, t-butylaminocarbonylamino group, cyclobutylaminocarbonylamino group, and cyclopropylmethylaminocarbonylamino group.

Examples of the arylaminocarbonylamino group include, for example, an amino group substituted with an arylaminocarbonyl group, and preferred examples of the aryl moiety of the arylaminocarbonyl group are similar to those of the aforementioned aryl group. Specifically, preferred examples include phenylaminocarbonylamino group, tolylaminocarbonylamino group, xylylaminocarbonylamino group, mesitylaminocarbonylamino group, (1-naphthyl)aminocarbonylamino group, and (2-naphthyl)aminocarbonylamino group.

Examples of the alkylamino group optionally substituted with one or more halogen atoms include, for example, an alkylamino group obtained by replacing one or more of hydrogen atoms of the aforementioned alkylamino group with halogen atoms of arbitrary type, and an alkylamino group optionally substituted with one or more halogen atoms and having 1 to 4 carbon atoms is preferred. When the alkylamino group is substituted with two or more halogen atoms, the halogen atoms may be the same or different. Specifically, preferred examples include chloromethylamino group, dichloromethylamino group, trichloromethylamino group, fluoromethylamino group, difluoromethylamino group, trifluoromethylamino group, fluoroethylamino group, 2,2,2-trifluoroethylamino group, and the like.

Examples of the alkylsulfonylamino group optionally substituted with one or more halogen atoms include, for example, an alkylsulfonylamino group obtained by replacing one or more of hydrogen atoms of the aforementioned alkylsulfonylamino group with halogen atoms of arbitrary type, and an alkylsulfonylamino group optionally substituted with one or more halogen atoms and having 1 to 4 carbon atoms is usually preferred. When the alkylsulfonylamino group is substituted with two or more halogen atoms, the halogen atoms may be the same or different. Specifically, examples include trifluoromethylsulfonylamino group, and the like.

Examples of the alkylsulfonyl(alkyl)amino group optionally substituted with one or more halogen atoms include, for example, an alkylsulfonyl(alkyl)amino group obtained by replacing one or more of hydrogen atoms of the aforementioned alkylsulfonyl(alkyl)amino group with halogen atoms of arbitrary type, and an alkylsulfonyl(alkyl)amino group optionally substituted with one or more halogen atoms and having 1 to 4 carbon atoms is usually preferred. When the alkylsulfonyl(alkyl)amino group is substituted with two or more halogen atoms, the halogen atoms may be the same or different. Specifically, examples include methyl(trifluoromethylsulfonyl)amino group, and the like.

The substituent of the acyl group which may be substituted is similar to, for example, the substituent of the aforementioned alkyl group which may be substituted, and one ore more halogen atoms are particularly preferred.

As the substituted acyl group, for example, an acyl group optionally substituted with one or more halogen atoms is preferred, and an acyl group optionally substituted with one or more halogen atoms and having 2 to 5 carbon atoms is preferred. When the acyl group is substituted with two or more halogen atoms, the halogen atoms may be the same or different. Preferred examples include trifluoroacetyl group, and the like.

As the acyl group which may be substituted, for example, acetyl group, propanoyl group, butanoyl group, 2-methylpropanoyl group, cyclopropylcarbonyl group, pentanoyl group, 3-methylbutanoyl group, 2,2-dimethylpropanoyl group, cyclobutylcarbonyl group, and the like are preferred. However, there is another embodiment in which trifluoroacetyl group is preferred.

As the aralkyl group which may be substituted, for example, the preferred examples of the aforementioned aralkyl group are preferred. There is also another embodiment in which examples in which a carbon atom among the constituent elements forming the aryl ring of the aralkyl group is substituted with an alkyl group, an alkoxy group, amino group, hydroxyl group, or a halogen atom are preferred. Specifically, examples include 4-methylphenylmethyl group, 4-methoxyphenylmethyl group, 4-aminophenylmethyl group, 4-hydroxyphenylmethyl group, 4-fluorophenylmethyl group, 5-methyl-2-furylmethyl group, 4-methyl-2-furylmethyl group, 5-methyl-3-furylmethyl group, 5-methyl-2-pyrrolylmethyl group, 4-methyl-2-pyrrolylmethyl group, 5-methyl-3-pyrrolylmethyl group, 5-methyl-2-thienylmethyl group, 4-methyl-2-thienylmethyl group, 5-methyl-3-thienylmethyl group, and the like. Further, there is another embodiment in which examples in which a nitrogen atom among the constituent elements forming the aryl ring of the aralkyl group is substituted with an alkyl group, or an alkoxy group are preferred. Specifically, examples include 1-methyl-2-pyrrolylmethyl group, 1-ethyl-2-pyrrolylmethyl group, 1-methyl-3-pyrrolylmethyl group, and the like.

As the saturated heterocyclic group which may be substituted, for example, the preferred examples of the aforementioned saturated heterocyclic group are preferred.

In the aforementioned general formula (1), A represents a nitrogen-containing saturated ring. Examples of the nitrogen-containing saturated ring include, for example, a 3- to 8-membered, preferably 4- to 7-membered, monocyclic saturated heterocyclic ring containing one nitrogen atom as a ring-constituting atom. Specifically, azetidine, pyrrolidine, piperidine, homopiperidine, and the like are preferred examples. Further, m represents an integer of 0, 1 or 2, preferably 1 or 2, particularly preferably 1. Furthermore, when m is 1 or 2, n preferably represents an integer of 1, 2 or 3, particularly preferably 2 or 3. Preferred examples of the structure of the ring A include, for example, rings represented by the following formulas (1-a) to (1-c):

[Formula 2]

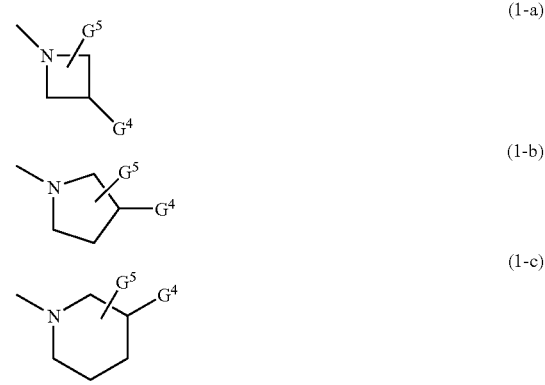

[in the general formulas (1-a) to (1-c), $G^4$ and $G^5$ have the same meanings as those defined above, and the ring-constituting nitrogen atom (N) binds to the $SO_2$ moiety of the compound represented by the general formula (1)], the structure of the formula (1-b), or formula (1-c) is preferred, and the structure of the formula (1-b) is particularly preferred. In the structures of the formula (1-b) and formula (1-c), the carbon atom to which $G^4$ binds becomes asymmetric carbon, and absolute configuration of the carbon atom is preferably S-configuration. There is also another embodiment in which R-configuration is preferred, and there is also another embodiment in which a mixture thereof is preferred.

$G^1$ represents hydrogen atom, chlorine atom, hydroxyl group, an alkoxy group, or amino group. Hydrogen atom, hydroxyl group, and amino group are preferred, and hydrogen atom is particularly preferred. There is also another embodiment in which hydroxyl group is particularly preferred.

$G^2$ represents a halogen atom, hydroxyl group, cyano group, carboxy group, an alkyl group which may be substituted, an alkenyl group which may be substituted, an alkynyl group which may be substituted, an alkoxy group which may be substituted, an alkylthio group which may be substituted, an amino group which may be substituted, an alkylsulfinyl group which may be substituted, an alkylsulfonyl group which may be substituted, or an aryl group which may be substituted.

As $G^2$, for example, a halogen atom, hydroxyl group, an alkyl group which may be substituted, an alkenyl group which may be substituted, an alkynyl group which may be substituted, and an amino group which may be substituted are preferred, and a halogen atom, an alkyl group which may be substituted, an alkenyl group which may be substituted, and an alkynyl group which may be substituted are particularly preferred.

When $G^2$ is a halogen atom, fluorine atom, chlorine atom, and bromine atom are preferred, and fluorine atom is particularly preferred. There is also another embodiment in which chlorine atom is particularly preferred. There is further another embodiment in which bromine atom is particularly preferred.

It is preferred that $G^2$ is hydroxyl group.

When $G^2$ is an alkyl group which may be substituted, a lower alkyl group which may be substituted is preferred. Examples include methyl group, ethyl group, n-propyl group, fluoromethyl group, difluoromethyl group, and trifluoromethyl group, and methyl group is particularly preferred.

When $G^2$ is an alkenyl group which may be substituted, a lower alkenyl group which may be substituted is preferred, and vinyl group is particularly preferred.

When $G^2$ is an alkynyl group which may be substituted, a lower alkynyl group which may be substituted is preferred. Examples include ethynyl group, methylethynyl group, trifluoroethynyl group, and 3-hydroxyprop-1-ynyl group, and ethynyl group is particularly preferred. There is also another embodiment in which 3-hydroxyprop-1-ynyl group is preferred.

When $G^2$ is an amino group which may be substituted, a lower amino group which may be substituted is preferred. Examples include amino group (—$NH_2$ group), methylamino group, and dimethylamino group, and amino group is particularly preferred.

$G^3$ represents hydrogen atom, a halogen atom, hydroxyl group, cyano group, carboxy group, an alkyl group which may be substituted, an alkenyl group which may be substituted, an alkynyl group which may be substituted, an alkoxy group which may be substituted, an alkylthio group which may be substituted, an amino group which may be substituted, an alkoxycarbonyl group which may be substituted, an acyl group which may be substituted, an acyloxy group which may be substituted, an alkylsulfinyl group which may be substituted, an alkylsulfonyl group which may be substituted, or an aryl group which may be substituted, provided that $G^3$ substitutes at the 3-, 6-, 7-, or 8-position of the isoquinoline ring.

$G^3$ preferably substitutes at the 3-, 6-, or 8-position of the isoquinoline ring, particularly preferably at the 3- or 8-position of the isoquinoline ring.

As $G^3$, for example, hydrogen atom, a halogen atom, hydroxyl group, carboxy group, an alkyl group which may be substituted, an alkenyl group which may be substituted, an alkynyl group which may be substituted, an alkoxy group which may be substituted, an alkylthio group which may be substituted, and an amino group which may be substituted are preferred, and hydrogen atom is particularly preferred.

$G^4$ represents hydroxyl group, or —$N(R^1)(R^2)$ ($R^1$ and $R^2$ may be the same or different, and independently represent hydrogen atom, an alkyl group which may be substituted, an aralkyl group which may be substituted, an alkenyl group which may be substituted, an alkynyl group which may be substituted, or a saturated heterocyclic group which may be substituted).

Preferred examples of $G^4$ include, for example, hydroxyl group. There is also another embodiment in which —$N(R^1)(R^2)$ is preferred.

In —$N(R^1)(R^2)$ represented by $G^4$, $R^1$ and $R^2$ may be the same or different, and independently represent hydrogen atom, an alkyl group which may be substituted, an aralkyl group which may be substituted, an alkenyl group which may be substituted, an alkynyl group which may be substituted, or a saturated heterocyclic group which may be substituted.

It is preferred that one of $R^1$ and $R^2$ is hydrogen atom. It is particularly preferred that one of $R^1$ and $R^2$ is hydrogen atom, and the other is hydrogen atom, an alkyl group which may be substituted, an aralkyl group which may be substituted, or a saturated heterocyclic group which may be substituted.

It is preferred that $R^1$ and $R^2$ are both hydrogen atoms. There is also another embodiment in which it is preferred that one of $R^1$ and $R^2$ is hydrogen atom, and the other is an alkyl group which may be substituted. Further, it is also preferred that one of $R^1$ and $R^2$ is hydrogen atom, and the other is methyl group, or ethyl group, and it is particularly preferred that one of $R^1$ and $R^2$ is hydrogen atom, and the other is methyl group. There is also another embodiment in which it is preferred that one of $R^1$ and $R^2$ is hydrogen atom, and the other is an aralkyl group which may be substituted. Further, it is also preferred that one of $R^1$ and $R^2$ is hydrogen atom, and the other is a furylalkyl group, and it is particularly preferred that one of $R^1$ and $R^2$ is hydrogen atom, and the other is 2-furylmethyl group. There is also another embodiment in which it is preferred that one of $R^1$ and $R^2$ is hydrogen atom, and the other is a saturated heterocyclic group which may be substituted. It is also preferred that one of $R^1$ and $R^2$ is hydrogen atom, and the other is tetrahydropyranyl group, and it is particularly preferred that one of $R^1$ and $R^2$ is hydrogen atom, and the other is 4-tetrahydropyranyl group.

$G^5$ is a substituent on a ring-constituting carbon atom constituting the nitrogen-containing saturated ring represented by A, and represents hydrogen atom, fluorine atom, or an alkyl group. $G^5$ preferably substitutes on a carbon atom adjacent to a nitrogen atom constituting the ring. $G^5$ is preferably hydrogen atom, fluorine atom, or a lower alkyl group, particularly preferably hydrogen atom.

Although the combination of the substituents in the compounds represented by the general formula (1) is not particularly limited, examples of the compounds and the like include, for example, (1) the compound wherein m is 1;
(2) the compound wherein n is 2 or 3;
(3) the compound wherein the ring A has a structure of the formula (1-a), formula (1-b), or formula (1-c);
(4) the compound wherein the ring A has a structure of the formula (1-b), or formula (1-c);
(5) the compound wherein the ring A has a structure of the formula (1-b);
(6) the compound wherein $G^3$ is hydrogen atom;
(7) the compound wherein $G^5$ is hydrogen atom;
(8) the compound wherein $G^4$ is —$N(R^1)(R^2)$;
(9) the compound wherein $G^1$ is hydrogen atom, hydroxyl group, or amino group;
(10) the compound wherein $G^1$ is hydrogen atom, or hydroxyl group;
(11) the compound wherein $G^2$ is a halogen atom, hydroxyl group, an alkyl group which may be substituted, an alkenyl group which may be substituted, an alkynyl group which may be substituted, or an amino group which may be substituted;
(12) the compound wherein $G^2$ is a halogen atom, an alkyl group which may be substituted, an alkenyl group which may be substituted, or an alkynyl group which may be substituted;
(13) the compound wherein $G^2$ is a halogen atom;
(14) the compound wherein $G^2$ is an alkyl group which may be substituted;
(15) the compound wherein $G^2$ is an alkenyl group which may be substituted;
(16) the compound wherein $G^2$ is an alkynyl group which may be substituted;
(17) the compound wherein $G^4$ is —$N(R^1)(R^2)$, one of $R^1$ and $R^2$ is hydrogen atom, and the other is hydrogen atom, an alkyl group which may be substituted, an aralkyl group which may be substituted, or a saturated heterocyclic group which may be substituted;
(18) the compound wherein $G^4$ is —$N(R^1)(R^2)$, and $R^1$ and $R^2$ are both hydrogen atoms;

(19) the compound wherein $G^4$ is —$N(R^1)(R^2)$, one of $R^1$ and $R^2$ is hydrogen atom, and the other is an alkyl group which may be substituted;

(20) the compound wherein $G^4$ is —$N(R^1)(R^2)$, one of $R^1$ and $R^2$ is hydrogen atom, and the other is an aralkyl group which may be substituted;

(21) the compound wherein $G^4$ is —$N(R^1)(R^2)$, one of $R^1$ and $R^2$ is hydrogen atom, and the other is a saturated heterocyclic group which may be substituted;

(22) the compound wherein the ring A has a structure of the formula (1-b), or formula (1-c), and $G^3$ and $G^5$ are both hydrogen atoms;

(23) the compound wherein the ring A has a structure of the formula (1-b), or formula (1-c), and $G^1$ is hydrogen atom, or hydroxyl group;

(24) the compound wherein the ring A has a structure of the formula (1-b), or formula (1-c), and $G^2$ is a halogen atom, hydroxyl group, an alkyl group which may be substituted, an alkenyl group which may be substituted, an alkynyl group which may be substituted, or an amino group which may be substituted;

(25) the compound wherein the ring A has a structure of the formula (1-b), or formula (1-c), and $G^2$ is a halogen atom, an alkyl group which may be substituted, an alkenyl group which may be substituted, or an alkynyl group which may be substituted;

(26) the compound wherein the ring A has a structure of the formula (1-b), or formula (1-c), and $G^2$ is a halogen atom;

(27) the compound wherein the ring A has a structure of the formula (1-b), or formula (1-c), and $G^2$ is an alkyl group which may be substituted;

(28) the compound wherein the ring A has a structure of the formula (1-b), or formula (1-c), and $G^2$ is an alkynyl group which may be substituted;

(29) the compound wherein the ring A has a structure of the formula (1-b), or formula (1-c), and $G^4$ is —$N(R^1)(R^2)$;

(30) the compound wherein the ring A has a structure of the formula (1-b), or formula (1-c), $G^4$ is —$N(R^1)(R^2)$, one of $R^1$ and $R^2$ is hydrogen atom, and the other is hydrogen atom, an alkyl group which may be substituted, an aralkyl group which may be substituted, or a saturated heterocyclic group which may be substituted;

(31) the compound wherein the ring A has a structure of the formula (1-b), or formula (1-c), $G^4$ is —$N(R^1)(R^2)$, and $R^1$ and $R^2$ are both hydrogen atoms;

(32) the compound wherein the ring A has a structure of the formula (1-b), or formula (1-c), $G^4$ is —$N(R^1)(R^2)$, one of $R^1$ and $R^2$ is hydrogen atom, and the other is an alkyl group which may be substituted;

(33) the compound wherein the ring A has a structure of the formula (1-b), or formula (1-c), $G^4$ is —$N(R^1)(R^2)$, one of $R^1$ and $R^2$ is hydrogen atom, and the other is an aralkyl group which may be substituted;

(34) the compound wherein the ring A has a structure of the formula (1-b), or formula (1-c), $G^4$ is —$N(R^1)(R^2)$, one of $R^1$ and $R^2$ is hydrogen atom, and the other is a saturated heterocyclic group which may be substituted;

(35) the compound wherein the ring A has a structure of the formula (1-b), or formula (1-c), $G^3$ and $G^5$ are both hydrogen atoms, and $G^4$ is —$N(R^1)(R^2)$;

(36) the compound wherein the ring A has a structure of the formula (1-b), or formula (1-c), $G^1$ is hydrogen atom, or hydroxyl group, and $G^3$ and $G^5$ are both hydrogen atoms;

(37) the compound wherein the ring A has a structure of the formula (1-b), or formula (1-c), $G^2$ is a halogen atom, hydroxyl group, an alkyl group which may be substituted, an alkenyl group which may be substituted, an alkynyl group which may be substituted, or an amino group which may be substituted, and $G^3$ and $G^5$ are both hydrogen atoms;

(38) the compound wherein the ring A has a structure of the formula (1-b), or formula (1-c), $G^2$ is a halogen atom, an alkyl group which may be substituted, an alkenyl group which may be substituted, or an alkynyl group which may be substituted, and $G^3$ and $G^5$ are both hydrogen atoms;

(39) the compound wherein the ring A has a structure of the formula (1-b), or formula (1-c), $G^2$ is a halogen atom, and $G^3$ and $G^5$ are both hydrogen atoms;

(40) the compound wherein the ring A has a structure of the formula (1-b), or formula (1-c), $G^2$ is an alkyl group which may be substituted, and $G^3$ and $G^5$ are both hydrogen atoms;

(41) the compound wherein the ring A has a structure of the formula (1-b), or formula (1-c), $G^2$ is an alkynyl group which may be substituted, and $G^3$ and $G^5$ are both hydrogen atoms;

(42) the compound wherein the ring A has a structure of the formula (1-b), or formula (1-c), $G^1$ is hydrogen atom, or hydroxyl group, $G^2$ is a halogen atom, hydroxyl group, an alkyl group which may be substituted, an alkenyl group which may be substituted, an alkynyl group which may be substituted, or an amino group which may be substituted, and $G^3$ and $G^5$ are both hydrogen atoms;

(43) the compound wherein the ring A has a structure of the formula (1-b), or formula (1-c), $G^1$ is hydrogen atom, or hydroxyl group, $G^2$ is a halogen atom, an alkyl group which may be substituted, an alkenyl group which may be substituted, or an alkynyl group which may be substituted, and $G^3$ and $G^5$ are both hydrogen atoms;

(44) the compound wherein the ring A has a structure of the formula (1-b), or formula (1-c), $G^1$ is hydrogen atom, or hydroxyl group, $G^2$ is a halogen atom, and $G^3$ and $G^5$ are both hydrogen atoms;

(45) the compound wherein the ring A has a structure of the formula (1-b), or formula (1-c), $G^1$ is hydrogen atom, or hydroxyl group, $G^2$ is an alkyl group which may be substituted, and $G^3$ and $G^5$ are both hydrogen atoms;

(46) the compound wherein the ring A has a structure of the formula (1-b), or formula (1-c), $G^1$ is hydrogen atom, or hydroxyl group, $G^2$ is an alkynyl group which may be substituted, and $G^3$ and $G^5$ are both hydrogen atoms;

(47) the compound wherein the ring A has a structure of the formula (1-b), or formula (1-c), $G^3$ and $G^5$ are both hydrogen atoms, $G^4$ is —$N(R^1)(R^2)$, one of $R^1$ and $R^2$ is hydrogen atom, and the other is hydrogen atom, an alkyl group which may be substituted, an aralkyl group which may be substituted, or a saturated heterocyclic group which may be substituted;

(48) the compound wherein the ring A has a structure of the formula (1-b), or formula (1-c), $G^3$ and $G^5$ are both hydrogen atoms, $G^4$ is —$N(R^1)(R^2)$, and $R^1$ and $R^2$ are both hydrogen atoms;

(49) the compound wherein the ring A has a structure of the formula (1-b), or formula (1-c), $G^3$ and $G^5$ are both hydrogen atoms, $G^4$ is —$N(R^1)(R^2)$, one of $R^1$ and $R^2$ is hydrogen atom, and the other is an alkyl group which may be substituted;

(50) the compound wherein the ring A has a structure of the formula (1-b), or formula (1-c), $G^3$ and $G^5$ are both hydrogen atoms, $G^4$ is —$N(R^1)(R^2)$, one of $R^1$ and $R^2$ is hydrogen atom, and the other is an aralkyl group which may be substituted;

(51) the compound wherein the ring A has a structure of the formula (1-b), or formula (1-c), $G^3$ and $G^5$ are both hydrogen atoms, $G^4$ is —$N(R^1)(R^2)$, one of $R^1$ and $R^2$ is hydrogen atom, and the other is a saturated heterocyclic group which may be substituted;

(52) the compound wherein the ring A has a structure of the formula (1-b), or formula (1-c), $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, one of $R^1$ and $R^2$ is hydrogen atom, and the other is hydrogen atom, an alkyl group which may be substituted, an aralkyl group which may be substituted, or a saturated heterocyclic group which may be substituted;

(53) the compound wherein the ring A has a structure of the formula (1-b), or formula (1-c), $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, and $R^1$ and $R^2$ are both hydrogen atoms;

(54) the compound wherein the ring A has a structure of the formula (1-b), or formula (1-c), $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, one of $R^1$ and $R^2$ is hydrogen atom, and the other is an alkyl group which may be substituted;

(55) the compound wherein the ring A has a structure of the formula (1-b), or formula (1-c), $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, one of $R^1$ and $R^2$ is hydrogen atom, and the other is an aralkyl group which may be substituted;

(56) the compound wherein the ring A has a structure of the formula (1-b), or formula (1-c), $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, one of $R^1$ and $R^2$ is hydrogen atom, and the other is a saturated heterocyclic group which may be substituted;

(57) the compound wherein the ring A has a structure of the formula (1-b), and $G^3$ and $G^5$ are both hydrogen atoms;

(58) the compound wherein the ring A has a structure of the formula (1-b), and $G^1$ is hydrogen atom, or hydroxyl group;

(59) the compound wherein the ring A has a structure of the formula (1-b), and $G^2$ is a halogen atom, hydroxyl group, an alkyl group which may be substituted, an alkenyl group which may be substituted, an alkynyl group which may be substituted, or an amino group which may be substituted;

(60) the compound wherein the ring A has a structure of the formula (1-b), and $G^2$ is a halogen atom, an alkyl group which may be substituted, an alkenyl group which may be substituted, or an alkynyl group which may be substituted;

(61) the compound wherein the ring A has a structure of the formula (1-b), and $G^2$ is a halogen atom;

(62) the compound wherein the ring A has a structure of the formula (1-b), and $G^2$ is an alkyl group which may be substituted;

(63) the compound wherein the ring A has a structure of the formula (1-b), and $G^2$ is an alkynyl group which may be substituted;

(64) the compound wherein the ring A has a structure of the formula (1-b), and $G^4$ is $N(R^1)(R^2)$;

(65) the compound wherein the ring A has a structure of the formula (1-b), $G^4$ is —$N(R^1)(R^2)$, one of $R^1$ and $R^2$ is hydrogen atom, and the other is hydrogen atom, an alkyl group which may be substituted, an aralkyl group which may be substituted, or a saturated heterocyclic group which may be substituted;

(66) the compound wherein the ring A has a structure of the formula (1-b), $G^4$ is —$N(R^1)(R^2)$, and $R^1$ and $R^2$ are both hydrogen atoms;

(67) the compound wherein the ring A has a structure of the formula (1-b), $G^4$ is —$N(R^1)(R^2)$, one of $R^1$ and $R^2$ is hydrogen atom, and the other is an alkyl group which may be substituted;

(68) the compound wherein the ring A has a structure of the formula (1-b), $G^4$ is —$N(R^1)(R^2)$, one of $R^1$ and $R^2$ is hydrogen atom, and the other is an aralkyl group which may be substituted;

(69) the compound wherein the ring A has a structure of the formula (1-b), $G^4$ is —$N(R^1)(R^2)$, one of $R^1$ and $R^2$ is hydrogen atom, and the other is a saturated heterocyclic group which may be substituted;

(70) the compound wherein the ring A has a structure of the formula (1-b), $G^3$ and $G^5$ are both hydrogen atoms, and $G^4$ is —$N(R^1)(R^2)$;

(71) the compound wherein the ring A has a structure of the formula (1-b), $G^1$ is hydrogen atom, or hydroxyl group, and $G^3$ and $G^5$ are both hydrogen atoms;

(72) the compound wherein the ring A has a structure of the formula (1-b), $G^2$ is a halogen atom, hydroxyl group, an alkyl group which may be substituted, an alkenyl group which may be substituted, an alkynyl group which may be substituted, or an amino group which may be substituted, and $G^3$ and $G^5$ are both hydrogen atoms;

(73) the compound wherein the ring A has a structure of the formula (1-b), $G^2$ is a halogen atom, an alkyl group which may be substituted, an alkenyl group which may be substituted, or an alkynyl group which may be substituted, and $G^3$ and $G^5$ are both hydrogen atoms;

(74) the compound wherein the ring A has a structure of the formula (1-b), $G^2$ is a halogen atom, and $G^3$ and $G^5$ are both hydrogen atoms;

(75) the compound wherein the ring A has a structure of the formula (1-b), $G^2$ is an alkyl group which may be substituted, and $G^3$ and $G^5$ are both hydrogen atoms;

(76) the compound wherein the ring A has a structure of the formula (1-b), $G^2$ is an alkynyl group which may be substituted, and $G^3$ and $G^5$ are both hydrogen atoms;

(77) the compound wherein the ring A has a structure of the formula (1-b), $G^1$ is hydrogen atom, or hydroxyl group, $G^2$ is a halogen atom, hydroxyl group, an alkyl group which may be substituted, an alkenyl group which may be substituted, an alkynyl group which may be substituted, or an amino group which may be substituted, and $G^3$ and $G^5$ are both hydrogen atoms;

(78) the compound wherein the ring A has a structure of the formula (1-b), $G^1$ is hydrogen atom, or hydroxyl group, $G^2$ is a halogen atom, an alkyl group which may be substituted, an alkenyl group which may be substituted, or an alkynyl group which may be substituted, and $G^3$ and $G^5$ are both hydrogen atoms;

(79) the compound wherein the ring A has a structure of the formula (1-b), $G^1$ is hydrogen atom, or hydroxyl group, $G^2$ is a halogen atom, and $G^3$ and $G^5$ are both hydrogen atoms;

(80) the compound wherein the ring A has a structure of the formula (1-b), $G^1$ is hydrogen atom, or hydroxyl group, $G^2$ is an alkyl group which may be substituted, and $G^3$ and $G^5$ are both hydrogen atoms;

(81) the compound wherein the ring A has a structure of the formula (1-b), $G^1$ is hydrogen atom, or hydroxyl group, $G^2$ is an alkynyl group which may be substituted, and $G^3$ and $G^5$ are both hydrogen atoms;
(82) the compound wherein the ring A has a structure of the formula (1-b), $G^3$ and $G^5$ are both hydrogen atoms, $G^4$ is —$N(R^1)(R^2)$, one of $R^1$ and $R^2$ is hydrogen atom, and the other is hydrogen atom, an alkyl group which may be substituted, an aralkyl group which may be substituted, or a saturated heterocyclic group which may be substituted;
(83) the compound wherein the ring A has a structure of the formula (1-b), $G^3$ and $G^5$ are both hydrogen atoms, $G^4$ is —$N(R^1)(R^2)$, and $R^1$ and $R^2$ are both hydrogen atoms;
(84) the compound wherein the ring A has a structure of the formula (1-b), $G^3$ and $G^5$ are both hydrogen atoms, $G^4$ is —$N(R^1)(R^2)$, one of $R^1$ and $R^2$ is hydrogen atom, and the other is an alkyl group which may be substituted;
(85) the compound wherein the ring A has a structure of the formula (1-b), $G^3$ and $G^5$ are both hydrogen atoms, $G^4$ is —$N(R^1)(R^2)$, one of $R^1$ and $R^2$ is hydrogen atom, and the other is an aralkyl group which may be substituted;
(86) the compound wherein the ring A has a structure of the formula (1-b), $G^3$ and $G^5$ are both hydrogen atoms, $G^4$ is —$N(R^1)(R^2)$, one of $R^1$ and $R^2$ is hydrogen atom, and the other is a saturated heterocyclic group which may be substituted;
(87) the compound wherein the ring A has a structure of the formula (1-b), $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, one of $R^1$ and $R^2$ is hydrogen atom, and the other is hydrogen atom, an alkyl group which may be substituted, an aralkyl group which may be substituted, or a saturated heterocyclic group which may be substituted;
(88) the compound wherein the ring A has a structure of the formula (1-b), $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, and $R^1$ and $R^2$ are both hydrogen atoms;
(89) the compound wherein the ring A has a structure of the formula (1-b), $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, one of $R^1$ and $R^2$ is hydrogen atom, and the other is an alkyl group which may be substituted;
(90) the compound wherein the ring A has a structure of the formula (1-b), $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, one of $R^1$ and $R^2$ is hydrogen atom, and the other is an aralkyl group which may be substituted;
(91) the compound wherein the ring A has a structure of the formula (1-b), $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, one of $R^1$ and $R^2$ is hydrogen atom, and the other is a saturated heterocyclic group which may be substituted;
(92) the compound wherein the ring A has a structure of the formula (1-b), $G^1$ is hydrogen atom, chlorine atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, one of $R^1$ and $R^2$ is hydrogen atom, and the other is hydrogen atom, an alkyl group which may be substituted, an aralkyl group which may be substituted, or a saturated heterocyclic group which may be substituted;
(93) the compound wherein the ring A has a structure of the formula (1-b), $G^1$ is hydrogen atom, chlorine atom, or hydroxyl group, $G^2$ is a halogen atom, $G^3$ and $G^5$ are both hydrogen atoms, $G^4$ is —$N(R^1)(R^2)$, one of $R^1$ and $R^2$ is hydrogen atom, and the other is hydrogen atom, an alkyl group which may be substituted, an aralkyl group which may be substituted, or a saturated heterocyclic group which may be substituted;
(94) the compound wherein the ring A has a structure of the formula (1-b), $G^1$ is hydrogen atom, chlorine atom, or hydroxyl group, $G^2$ is an alkyl group which may be substituted, $G^3$ and $G^5$ are both hydrogen atoms, $G^4$ is —$N(R^1)(R^2)$, one of $R^1$ and $R^2$ is hydrogen atom, and the other is hydrogen atom, an alkyl group which may be substituted, an aralkyl group which may be substituted, or a saturated heterocyclic group which may be substituted;
(95) the compound wherein the ring A has a structure of the formula (1-b), $G^1$ is hydrogen atom, chlorine atom, or hydroxyl group, $G^2$ is an alkenyl group which may be substituted, $G^3$ and $G^5$ are both hydrogen atoms, $G^4$ is —$N(R^1)(R^2)$, one of $R^1$ and $R^2$ is hydrogen atom, and the other is hydrogen atom, an alkyl group which may be substituted, an aralkyl group which may be substituted, or a saturated heterocyclic group which may be substituted;
(96) the compound wherein the ring A has a structure of the formula (1-b), $G^1$ is hydrogen atom, chlorine atom, or hydroxyl group, $G^2$ is an alkynyl group which may be substituted, $G^3$ and $G^5$ are both hydrogen atoms, $G^4$ is —$N(R^1)(R^2)$, one of $R^1$ and $R^2$ is hydrogen atom, and the other is hydrogen atom, an alkyl group which may be substituted, an aralkyl group which may be substituted, or a saturated heterocyclic group which may be substituted;
(97) the compound wherein the ring A has a structure of the formula (1-b), $G^1$ is hydrogen atom, chlorine atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, and $R^1$ and $R^2$ are both hydrogen atoms;
(98) the compound wherein the ring A has a structure of the formula (1-b), $G^1$ is hydrogen atom, chlorine atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, one of $R^1$ and $R^2$ is hydrogen atom, and the other is an alkyl group which may be substituted;
(99) the compound wherein the ring A has a structure of the formula (1-b), $G^1$ is hydrogen atom, chlorine atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, one of $R^1$ and $R^2$ is hydrogen atom, and the other is a lower alkyl group;
(100) the compound wherein the ring A has a structure of the formula (1-b), $G^1$ is hydrogen atom, chlorine atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, one of $R^1$ and $R^2$ is hydrogen atom, and the other is methyl group, or ethyl group;

(101) the compound wherein the ring A has a structure of the formula (1-b), $G^1$ is hydrogen atom, chlorine atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is methyl group;

(102) the compound wherein the ring A has a structure of the formula (1-b), $G^1$ is hydrogen atom, chlorine atom, or hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is an aralkyl group which may be substituted;

(103) the compound wherein the ring A has a structure of the formula (1-b), $G^1$ is hydrogen atom, chlorine atom, or hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is a saturated heterocyclic group which may be substituted;

(104) the compound wherein the ring A has a structure of the formula (1-b), $G^1$ is hydrogen atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(105) the compound wherein the ring A has a structure of the formula (1-b), $G^1$ is hydrogen atom, or hydroxyl group, $G^2$ is a halogen atom, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(106) the compound wherein the ring A has a structure of the formula (1-b), $G^1$ is hydrogen atom, or hydroxyl group, $G^2$ is an alkyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(107) the compound wherein the ring A has a structure of the formula (1-b), $G^1$ is hydrogen atom, or hydroxyl group, $G^2$ is an alkenyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(108) the compound wherein the ring A has a structure of the formula (1-b), $G^1$ is hydrogen atom, or hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(109) the compound wherein the ring A has a structure of the formula (1-b), $G^1$ is hydrogen atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), and $R^1$ and $R^2$ are both hydrogen atoms;

(110) the compound wherein the ring A has a structure of the formula (1-b), $G^1$ is hydrogen atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is an alkyl group which may be substituted;

(111) the compound wherein the ring A has a structure of the formula (1-b), $G^1$ is hydrogen atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is a lower alkyl group;

(112) the compound wherein the ring A has a structure of the formula (1-b), $G^1$ is hydrogen atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is methyl group, or ethyl group;

(113) the compound wherein the ring A has a structure of the formula (1-b), $G^1$ is hydrogen atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is methyl group;

(114) the compound wherein the ring A has a structure of the formula (1-b), $G^1$ is hydrogen atom, or hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is an aralkyl group which may be substituted;

(115) the compound wherein the ring A has a structure of the formula (1-b), $G^1$ is hydrogen atom, or hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is a saturated heterocyclic group which may be substituted;

(116) the compound wherein the ring A has a structure of the formula (1-b), $G^1$ is hydrogen atom, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(117) the compound wherein the ring A has a structure of the formula (1-b), $G^1$ is hydrogen atom, $G^2$ is a halogen atom, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(118) the compound wherein the ring A has a structure of the formula (1-b), $G^1$ is hydrogen atom, $G^2$ is an alkyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(119) the compound wherein the ring A has a structure of the formula (1-b), $G^1$ is hydrogen atom, $G^2$ is an alkenyl group which may be substituted, $G^3$ and $G^5$ are both hydrogen atoms, $G^4$ is —$N(R^1)(R^2)$, one of $R^1$ and $R^2$ is hydrogen atom, and the other is hydrogen atom, an alkyl group which may be substituted, an aralkyl group which may be substituted, or a saturated heterocyclic group which may be substituted;

(120) the compound wherein the ring A has a structure of the formula (1-b), $G^1$ is hydrogen atom, $G^2$ is an alkynyl group which may be substituted, $G^3$ and $G^5$ are both hydrogen atoms, $G^4$ is —$N(R^1)(R^2)$, one of $R^1$ and $R^2$ is hydrogen atom, and the other is hydrogen atom, an alkyl group which may be substituted, an aralkyl group which may be substituted, or a saturated heterocyclic group which may be substituted;

(121) the compound wherein the ring A has a structure of the formula (1-b), $G^1$ is hydrogen atom, $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, and $R^1$ and $R^2$ are both hydrogen atoms;

(122) the compound wherein the ring A has a structure of the formula (1-b), $G^1$ is hydrogen atom, $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, one of $R^1$ and $R^2$ is hydrogen atom, and the other is an alkyl group which may be substituted;

(123) the compound wherein the ring A has a structure of the formula (1-b), $G^1$ is hydrogen atom, $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, one of $R^1$ and $R^2$ is hydrogen atom, and the other is a lower alkyl group;

(124) the compound wherein the ring A has a structure of the formula (1-b), $G^1$ is hydrogen atom, $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, one of $R^1$ and $R^2$ is hydrogen atom, and the other is methyl group, or ethyl group;

(125) the compound wherein the ring A has a structure of the formula (1-b), $G^1$ is hydrogen atom, $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, one of $R^1$ and $R^2$ is hydrogen atom, and the other is methyl group;

(126) the compound wherein the ring A has a structure of the formula (1-b), $G^1$ is hydrogen atom, $G^2$ is an alkynyl group which may be substituted, $G^3$ and $G^5$ are both hydrogen atoms, $G^4$ is —$N(R^1)(R^2)$, one of $R^1$ and $R^2$ is hydrogen atom, and the other is an aralkyl group which may be substituted;

(127) the compound wherein the ring A has a structure of the formula (1-b), $G^1$ is hydrogen atom, $G^2$ is an alkynyl group which may be substituted, $G^3$ and $G^5$ are both hydrogen atoms, $G^4$ is —$N(R^1)(R^2)$, one of $R^1$ and $R^2$ is hydrogen atom, and the other is a saturated heterocyclic group which may be substituted;

(128) the compound wherein the ring A has a structure of the formula (1-b), $G^1$ is hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, one of $R^1$ and $R^2$ is hydrogen atom, and the other is hydrogen atom, an alkyl group which may be substituted, an aralkyl group which may be substituted, or a saturated heterocyclic group which may be substituted;

(129) the compound wherein the ring A has a structure of the formula (1-b), $G^1$ is hydroxyl group, $G^2$ is a halogen atom, $G^3$ and $G^5$ are both hydrogen atoms, $G^4$ is —$N(R^1)(R^2)$, one of $R^1$ and $R^2$ is hydrogen atom, and the other is hydrogen atom, an alkyl group which may be substituted, an aralkyl group which may be substituted, or a saturated heterocyclic group which may be substituted;

(130) the compound wherein the ring A has a structure of the formula (1-b), $G^1$ is hydroxyl group, $G^2$ is an alkyl group which may be substituted, $G^3$ and $G^5$ are both hydrogen atoms, $G^4$ is —$N(R^1)(R^2)$, one of $R^1$ and $R^2$ is hydrogen atom, and the other is hydrogen atom, an alkyl group which may be substituted, an aralkyl group which may be substituted, or a saturated heterocyclic group which may be substituted;

(131) the compound wherein the ring A has a structure of the formula (1-b), $G^1$ is hydroxyl group, $G^2$ is an alkenyl group which may be substituted, $G^3$ and $G^5$ are both hydrogen atoms, $G^4$ is —$N(R^1)(R^2)$, one of $R^1$ and $R^2$ is hydrogen atom, and the other is hydrogen atom, an alkyl group which may be substituted, an aralkyl group which may be substituted, or a saturated heterocyclic group which may be substituted;

(132) the compound wherein the ring A has a structure of the formula (1-b), $G^1$ is hydroxyl group, $G^2$ is an alkynyl group which may be substituted, $G^3$ and $G^5$ are both hydrogen atoms, $G^4$ is —$N(R^1)(R^2)$, one of $R^1$ and $R^2$ is hydrogen atom, and the other is hydrogen atom, an alkyl group which may be substituted, an aralkyl group which may be substituted, or a saturated heterocyclic group which may be substituted;

(133) the compound wherein the ring A has a structure of the formula (1-b), $G^1$ is hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, and $R^1$ and $R^2$ are both hydrogen atoms;

(134) the compound wherein the ring A has a structure of the formula (1-b), $G^1$ is hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, one of $R^1$ and $R^2$ is hydrogen atom, and the other is an alkyl group which may be substituted;

(135) the compound wherein the ring A has a structure of the formula (1-b), $G^1$ is hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, one of $R^1$ and $R^2$ is hydrogen atom, and the other is a lower alkyl group;

(136) the compound wherein the ring A has a structure of the formula (1-b), $G^1$ is hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —$N(R^1)(R^2)$, one of $R^1$ and $R^2$ is hydrogen atom, and the other is methyl group, or ethyl group;

(137) the compound wherein the ring A has a structure of the formula (1-b), $G^1$ is hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is methyl group;

(138) the compound wherein the ring A has a structure of the formula (1-b), $G^1$ is hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is an aralkyl group which may be substituted;

(139) the compound wherein the ring A has a structure of the formula (1-b), $G^1$ is hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is a saturated heterocyclic group which may be substituted;

(140) the compound wherein the ring A has a structure of the formula (1-b), absolute configuration of the carbon atom to which $G^4$ binds is S-configuration, $G^1$ is hydrogen atom, chlorine atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(141) the compound wherein the ring A has a structure of the formula (1-b), absolute configuration of the carbon atom to which $G^4$ binds is S-configuration, $G^1$ is hydrogen atom, chlorine atom, or hydroxyl group, $G^2$ is a halogen atom, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(142) the compound wherein the ring A has a structure of the formula (1-b), absolute configuration of the carbon atom to which $G^4$ binds is S-configuration, $G^1$ is hydrogen atom, chlorine atom, or hydroxyl group, $G^2$ is an alkyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(143) the compound wherein the ring A has a structure of the formula (1-b), absolute configuration of the carbon atom to which $G^4$ binds is S-configuration, $G^1$ is hydrogen atom, chlorine atom, or hydroxyl group, $G^2$ is an alkenyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(144) the compound wherein the ring A has a structure of the formula (1-b), absolute configuration of the carbon atom to which $G^4$ binds is S-configuration, $G^1$ is hydrogen atom, chlorine atom, or hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(145) the compound wherein the ring A has a structure of the formula (1-b), absolute configuration of the carbon atom to which $G^4$ binds is S-configuration, $G^1$ is hydrogen atom, chlorine atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), and $R^1$ and $R^2$ are both hydrogen atoms;

(146) the compound wherein the ring A has a structure of the formula (1-b), absolute configuration of the carbon atom to which $G^4$ binds is S-configuration, $G^1$ is hydrogen atom, chlorine atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is an alkyl group which may be substituted, an aralkyl group which may be substituted, or a saturated heterocyclic group which may be substituted;

(147) the compound wherein the ring A has a structure of the formula (1-b), absolute configuration of the carbon atom to which $G^4$ binds is S-configuration, $G^1$ is hydrogen atom, chlorine atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is an alkyl group which may be substituted;

(148) the compound wherein the ring A has a structure of the formula (1-b), absolute configuration of the carbon atom to which $G^4$ binds is S-configuration, $G^1$ is hydrogen atom, chlorine atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is a lower alkyl group;

(149) the compound wherein the ring A has a structure of the formula (1-b), absolute configuration of the carbon atom to which $G^4$ binds is S-configuration, $G^1$ is hydrogen atom, chlorine atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is methyl group, or ethyl group;

(150) the compound wherein the ring A has a structure of the formula (1-b), absolute configuration of the carbon atom to which $G^4$ binds is S-configuration, $G^1$ is hydrogen atom, chlorine atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is methyl group;

(151) the compound wherein the ring A has a structure of the formula (1-b), absolute configuration of the carbon atom to which $G^4$ binds is S-configuration, $G^1$ is hydrogen atom, chlorine atom, or hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is an aralkyl group which may be substituted;

(152) the compound wherein the ring A has a structure of the formula (1-b), absolute configuration of the carbon atom to which $G^4$ binds is S-configuration, $G^1$ is hydrogen atom, chlorine atom, or hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is a saturated heterocyclic group which may be substituted;

(153) the compound wherein the ring A has a structure of the formula (1-b), absolute configuration of the carbon atom to which $G^4$ binds is S-configuration, $G^1$ is hydrogen atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(154) the compound according to (153) which is the compound of Example 1-1, 1-3, 1-11, 1-14, 1-18, 1-30, 4-1, 7-1, 8-1, 8-3, 8-4, 8-5, 8-6, 8-7, 8-8, 8-12, 8-13, 8-21, 8-26, 9-1, 10-1, 10-7, 11-1, 18-1, 18-3, 18-7, 18-8, 18-31, 19-1, 19-3, 19-4, 19-8, 19-31, 19-40, 21-1, 23-1, 25-1, 29-1, 30-1, 35-1, 36-1, 37-1, or 38-1

(155) the compound wherein the ring A has a structure of the formula (1-b), absolute configuration of the carbon atom to which $G^4$ binds is S-configuration, $G^1$ is hydrogen atom, or hydroxyl group, $G^2$ is a halogen atom, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(156) the compound according to (155) which is the compound of Example 1-1, 1-3, 1-11, 1-14, 1-18, 1-30, 4-1, 7-1, 18-1, 18-3, 18-7, 18-8, 18-31, 19-1, 19-3, 19-4, 19-8, 19-31, 19-40, 21-1, 29-1, 30-1, 35-1, 36-1, 37-1, or 38-1;

(157) the compound wherein the ring A has a structure of the formula (1-b), absolute configuration of the carbon atom to which $G^4$ binds is S-configuration, $G^1$ is hydrogen atom, or hydroxyl group, $G^2$ is an alkyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(158) the compound according to (157) which is the compound of Example 8-1, 8-3, 8-4, 8-5, 8-6, 8-7, 8-8, 8-12, 8-13, 8-21, 8-26, 11-1, 23-1, or 25-1;

(159) the compound wherein the ring A has a structure of the formula (1-b), absolute configuration of the carbon atom to which $G^4$ binds is S-configuration, $G^1$ is hydrogen atom, or hydroxyl group, $G^2$ is an alkenyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(160) the compound wherein the ring A has a structure of the formula (1-b), absolute configuration of the carbon atom to which $G^4$ binds is S-configuration, $G^1$ is hydrogen atom, or hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(161) the compound according to (160) which is the compound of Example 10-1, or 10-7;

(162) the compound wherein the ring A has a structure of the formula (1-b), absolute configuration of the carbon atom to which $G^4$ binds is S-configuration, $G^1$ is hydrogen atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), and $R^1$ and $R^2$ are both hydrogen atoms;

(163) the compound according to (162) which is the compound of Example 1-1, 7-1, 8-1, 9-1, 10-1, 11-1, 18-1, 19-1, 23-1, 25-1, 29-1, or 30-1;

(164) the compound wherein the ring A has a structure of the formula (1-b), absolute configuration of the carbon atom to which $G^4$ binds is S-configuration, $G^1$ is hydrogen atom, chlorine atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is an alkyl group which may be substituted, an aralkyl group which may be substituted, or a saturated heterocyclic group which may be substituted;

(165) the compound according to (164) which is the compound of Example 1-3, 1-11, 1-14, 1-18, 1-30, 4-1, 8-3, 8-4, 8-5, 8-6, 8-7, 8-8, 8-12, 8-13, 8-21, 8-26, 10-7, 18-3, 18-7, 18-8, 18-31, 19-3, 19-4, 19-8, 19-31, 19-40, 35-1, 36-1, or 38-1;

(166) the compound wherein the ring A has a structure of the formula (1-b), absolute configuration of the carbon atom to which $G^4$ binds is S-configuration, $G^1$ is hydrogen atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is an alkyl group which may be substituted;

(167) the compound wherein the ring A has a structure of the formula (1-b), absolute configuration of the carbon atom to which $G^4$ binds is S-configuration, $G^1$ is hydrogen atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is a lower alkyl group;

(168) the compound according to (166) or (167) which is the compound of Example 1-3, 8-3, 8-4, 8-5, 8-26, 18-3, 19-3, 19-4, 35-1, 36-1, or 37-1;

(169) the compound wherein the ring A has a structure of the formula (1-b), absolute configuration of the carbon atom to which $G^4$ binds is S-configuration, $G^1$ is hydrogen atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is methyl group, or ethyl group;

(170) the compound according to (169) which is the compound of Example 1-3, 8-3, 8-4, 18-3, 19-3, 19-4, 35-1, 36-1, or 37-1;

(171) the compound wherein the ring A has a structure of the formula (1-b), absolute configuration of the carbon atom to which $G^4$ binds is S-configuration, $G^1$ is hydrogen atom, or hydroxyl group, $G^2$ is a halogen atom, an alkyl group which may be substituted, an alkenyl group which may be substituted, or an alkynyl group which may be substituted, $G^3$ (172) the compound according to (171) which is the compound of Example 1-3, 8-3, 18-3, 19-3, 35-1, 36-1, or 37-1;
(173) the compound wherein the ring A has a structure of the formula (1-b), absolute configuration of the carbon atom to which $G^4$ binds is S-configuration, $G^1$ is hydrogen atom, or hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is an aralkyl group which may be substituted;
(174) the compound according to (173) which is the compound of Example 10-7;
(175) the compound wherein the ring A has a structure of the formula (1-b), absolute configuration of the carbon atom to which $G^4$ binds is S-configuration, $G^1$ is hydrogen atom, or hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is a saturated heterocyclic group which may be substituted;
(176) the compound wherein the ring A has a structure of the formula (1-b), absolute configuration of the carbon atom to which $G^4$ binds is S-configuration, $G^1$ is hydrogen atom, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;
(177) the compound according to (176) which is the compound of Example 1-1, 1-3, 1-11, 1-14, 1-18, 1-30, 4-1, 8-1, 8-3, 8-4, 8-5, 8-6, 8-7, 8-8, 8-12, 8-13, 8-21, 8-26, 9-1, 10-1, 10-7, 11-1, 18-1, 18-3, 18-7, 18-8, 18-31, 19-1, 19-2, 19-3, 19-4, 19-8, 19-31, 19-40, or 23-1;
(178) the compound wherein the ring A has a structure of the formula (1-b), absolute configuration of the carbon atom to which $G^4$ binds is S-configuration, $G^1$ is hydrogen atom, $G^2$ is a halogen atom, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;
(179) the compound according to (178) which is the compound of Example 1-1, 1-3, 1-11, 1-14, 1-18, 1-30, 4-1, 18-1, 18-3, 18-7, 18-8, 18-31, 19-1, 19-3, 19-4, 19-8, 19-31, or 19-40;
(180) the compound wherein the ring A has a structure of the formula (1-b), absolute configuration of the carbon atom to which $G^4$ binds is S-configuration, $G^1$ is hydrogen atom, $G^2$ is an alkyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;
(181) the compound according to (180) which is the compound of Example 8-1, 8-3, 8-4, 8-5, 8-6, 8-7, 8-8, 8-12, 8-13, 8-21, 8-26, 11-1, or 23-1;
(182) the compound wherein the ring A has a structure of the formula (1-b), absolute configuration of the carbon atom to which $G^4$ binds is S-configuration, $G^1$ is hydrogen atom, $G^2$ is an alkenyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;
(183) the compound wherein the ring A has a structure of the formula (1-b), absolute configuration of the carbon atom to which $G^4$ binds is S-configuration, $G^1$ is hydrogen atom, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;
(184) the compound according to (183) which is the compound of Example 10-1, or 10-7;
(185) the compound wherein the ring A has a structure of the formula (1-b), absolute configuration of the carbon atom to which $G^4$ binds is S-configuration, $G^1$ is hydrogen atom, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), and $R^1$ and $R^2$ are both hydrogen atoms;
(186) the compound according to (185) which is the compound of Example 1-1, 8-1, 9-1, 10-1, 11-1, 18-1, 19-1, or 23-1;
(187) the compound wherein the ring A has a structure of the formula (1-b), absolute configuration of the carbon atom to which $G^4$ binds is S-configuration, $G^1$ is hydrogen atom, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is an alkyl group which may be substituted, an aralkyl group which may be substituted, or a saturated heterocyclic group which may be substituted;
(188) the compound according to (187) which is the compound of Example 1-3, 1-11, 1-14, 1-18, 1-30, 4-1, 8-3, 8-4, 8-5, 8-6, 8-7, 8-8, 8-12, 8-13, 8-21, 8-26, 10-7, 18-3, 18-7, 18-8, 18-31, 19-3, 19-4, 19-8, 19-31, or 19-40;
(189) the compound wherein the ring A has a structure of the formula (1-b), absolute configuration of the carbon atom to which $G^4$ binds is S-configuration, $G^1$ is hydrogen atom, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is an alkyl group which may be substituted;
(190) the compound wherein the ring A has a structure of the formula (1-b), absolute configuration of the carbon atom to which $G^4$ binds is S-configuration, $G^1$ is hydrogen atom, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is a lower alkyl group compound wherein
(191) the compound according to (190) which is the compound of Example 1-3, 8-3, 8-4, 8-5, 8-26, 18-3, 19-3, or 19-4;
(192) the compound wherein the ring A has a structure of the formula (1-b), absolute configuration of the carbon atom to which $G^4$ binds is S-configuration, $G^1$ is hydrogen atom, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is methyl group, or ethyl group;

(193) the compound according to (192) which is the compound of Example 1-3, 8-3, 8-4, 18-3, 19-3, or 19-4;

(194) the compound wherein the ring A has a structure of the formula (1-b), absolute configuration of the carbon atom to which $G^4$ binds is S-configuration, $G^1$ is hydrogen atom, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is methyl group;

(195) the compound according to (194) which is the compound of Example 1-3, 8-3, 18-3, or 19-3;

(196) the compound wherein the ring A has a structure of the formula (1-b), absolute configuration of the carbon atom to which $G^4$ binds is S-configuration, $G^1$ is hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(197) the compound according to (196) which is the compound of Example 7-1, 25-1, 29-1, 30-1, 35-1, 36-1, 37-1, or 38-1;

(198) the compound wherein the ring A has a structure of the formula (1-b), absolute configuration of the carbon atom to which $G^4$ binds is S-configuration, $G^1$ is hydroxyl group, $G^2$ is a halogen atom, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(199) the compound according to (198) which is the compound of Example 7-1, 29-1, 30-1, 35-1, 36-1, 37-1, or 38-1;

(200) the compound wherein the ring A has a structure of the formula (1-b), absolute configuration of the carbon atom to which $G^4$ binds is S-configuration, $G^1$ is hydroxyl group, $G^2$ is an alkyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(201) the compound wherein the ring A has a structure of the formula (1-b), absolute configuration of the carbon atom to which $G^4$ binds is S-configuration, $G^1$ is hydroxyl group, $G^2$ is an alkenyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(202) the compound wherein the ring A has a structure of the formula (1-b), absolute configuration of the carbon atom to which $G^4$ binds is S-configuration, $G^1$ is hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(203) the compound wherein the ring A has a structure of the formula (1-b), absolute configuration of the carbon atom to which $G^4$ binds is S-configuration, $G^1$ is hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), and $R^1$ and $R^2$ are both hydrogen atoms;

(204) the compound according to (203) which is the compound of Example 7-1, 25-1, 29-1, or 30-1;

(205) the compound wherein the ring A has a structure of the formula (1-b), absolute configuration of the carbon atom to which $G^4$ binds is S-configuration, $G^1$ is hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is an alkyl group which may be substituted;

(206) the compound wherein the ring A has a structure of the formula (1-b), absolute configuration of the carbon atom to which $G^4$ binds is S-configuration, $G^1$ is hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is a lower alkyl group;

(207) the compound wherein the ring A has a structure of the formula (1-b), absolute configuration of the carbon atom to which $G^4$ binds is S-configuration, $G^1$ is hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is methyl group, or ethyl group;

(208) the compound wherein the ring A has a structure of the formula (1-b), absolute configuration of the carbon atom to which $G^4$ binds is S-configuration, $G^1$ is hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is methyl group;

(209) the compound according to (208) which is the compound of Example 35-1, 36-1, 37-1, or 38-1;

(210) the compound wherein the ring A has a structure of the formula (1-b), absolute configuration of the carbon atom to which $G^4$ binds is S-configuration, $G^1$ is hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is an aralkyl group which may be substituted;

(211) the compound wherein the ring A has a structure of the formula (1-b), absolute configuration of the carbon atom to which $G^4$ binds is S-configuration, $G^1$ is hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is a saturated heterocyclic group which may be substituted;

(212) the compound wherein the ring A has a structure of the formula (1-b), absolute configuration of the carbon atom to which $G^4$ binds is R-configuration, $G^1$ is hydrogen atom, chlorine atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(213) the compound wherein the ring A has a structure of the formula (1-b), absolute configuration of the carbon atom to which $G^4$ binds is R-configuration, $G^1$ is hydrogen atom, chlorine atom, or hydroxyl group, $G^2$ is a halogen atom, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(214) the compound wherein the ring A has a structure of the formula (1-b), absolute configuration of the carbon atom to which $G^4$ binds is R-configuration, $G^1$ is hydrogen atom, chlorine atom, or hydroxyl group, $G^2$ is an alkyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(215) the compound wherein the ring A has a structure of the formula (1-b), absolute configuration of the carbon atom to which $G^4$ binds is R-configuration, $G^1$ is hydrogen atom, chlorine atom, or hydroxyl group, $G^2$ is an alkenyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(216) the compound wherein the ring A has a structure of the formula (1-b), absolute configuration of the carbon atom to which $G^4$ binds is R-configuration, $G^1$ is hydrogen atom, chlorine atom, or hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(217) the compound wherein the ring A has a structure of the formula (1-b), absolute configuration of the carbon atom to which $G^4$ binds is R-configuration, $G^1$ is hydrogen atom, chlorine atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), and $R^1$ and $R^2$ are both hydrogen atoms;

(218) the compound wherein the ring A has a structure of the formula (1-b), absolute configuration of the carbon atom to which $G^4$ binds is R-configuration, $G^1$ is hydrogen atom, chlorine atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is an alkyl group which may be substituted;

(219) the compound wherein the ring A has a structure of the formula (1-b), absolute configuration of the carbon atom to which $G^4$ binds is R-configuration, $G^1$ is hydrogen atom, chlorine atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is a lower alkyl group;

(220) the compound wherein the ring A has a structure of the formula (1-b), absolute configuration of the carbon atom to which $G^4$ binds is R-configuration, $G^1$ is hydrogen atom, chlorine atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is methyl group, or ethyl group;

(221) the compound wherein the ring A has a structure of the formula (1-b), absolute configuration of the carbon atom to which $G^4$ binds is R-configuration, $G^1$ is hydrogen atom, chlorine atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is methyl group;

(222) the compound wherein the ring A has a structure of the formula (1-b), absolute configuration of the carbon atom to which $G^4$ binds is R-configuration, $G^1$ is hydrogen atom, chlorine atom, or hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is an aralkyl group which may be substituted;

(223) the compound wherein the ring A has a structure of the formula (1-b), absolute configuration of the carbon atom to which $G^4$ binds is R-configuration, $G^1$ is hydrogen atom, chlorine atom, or hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is a saturated heterocyclic group which may be substituted;

(224) the compound wherein the ring A has a structure of the formula (1-b), absolute configuration of the carbon atom to which $G^4$ binds is R-configuration, $G^1$ is hydrogen atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(225) the compound according to (224) which is the compound of Example 1-2, 4-2, 7-2, 8-2, 9-2, 10-2, 11-2, 18-2, 19-2, 23-2, 25-2, 27, 29-2, 30-2, 31-2, 32-2, 33-2, 34-2, 35-2, 36-2, 37-2, or 38-2;

(226) the compound wherein the ring A has a structure of the formula (1-b), absolute configuration of the carbon atom to which $G^4$ binds is R-configuration, $G^1$ is hydrogen atom, or hydroxyl group, $G^2$ is a halogen atom, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(227) the compound according to (226) which is the compound of Example 1-2, 4-2, 7-2, 18-2, 19-2, 29-2, 30-2, 31-2, 32-2, 33-2, 35-2, 36-2, 37-2, or 38-2;

(228) the compound wherein the ring A has a structure of the formula (1-b), absolute configuration of the carbon atom to which $G^4$ binds is R-configuration, $G^1$ is hydrogen atom, or hydroxyl group, $G^2$ is an alkyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(229) the compound according to (228) which is the compound of Example 8-2, 11-2, 23-2, 25-2, 27, or 34-2;

(230) the compound wherein the ring A has a structure of the formula (1-b), absolute configuration of the carbon atom to which $G^4$ binds is R-configuration, $G^1$ is hydrogen atom, or hydroxyl group, $G^2$ is an alkenyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(231) the compound wherein the ring A has a structure of the formula (1-b), absolute configuration of the carbon atom to which $G^4$ binds is R-configuration, $G^1$ is hydrogen atom, or hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(232) the compound wherein the ring A has a structure of the formula (1-b), absolute configuration of the carbon atom to which $G^4$ binds is R-configuration, $G^1$ is hydrogen atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), and $R^1$ and $R^2$ are both hydrogen atoms;

(233) the compound according to (232) which is the compound of Example 1-2, 7-2, 8-2, 9-2, 10-2, 11-2, 18-2, 19-2, 23-2, 25-2, 29-2, or 30-2;

(234) the compound wherein the ring A has a structure of the formula (1-b), absolute configuration of the carbon atom to which $G^4$ binds is R-configuration, $G^1$ is hydrogen atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is an alkyl group which may be substituted;

(235) the compound wherein the ring A has a structure of the formula (1-b), absolute configuration of the carbon atom to which $G^4$ binds is R-configuration, $G^1$ is hydrogen atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is a lower alkyl group;

(236) the compound according to (235) which is the compound of Example 27, 31-2, 32-2, 33-2, 34-2, 35-2, 36-2, 37-2, or 38-2;

(237) the compound wherein the ring A has a structure of the formula (1-b), absolute configuration of the carbon atom to which $G^4$ binds is R-configuration, $G^1$ is hydrogen atom, or hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is an aralkyl group which may be substituted;

(238) the compound according to (237) which is the compound of Example 4-2, or 38-2;

(239) the compound wherein the ring A has a structure of the formula (1-b), absolute configuration of the carbon atom to which $G^4$ binds is R-configuration, $G^1$ is hydrogen atom, or hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is a saturated heterocyclic group which may be substituted;

(240) the compound wherein the ring A has a structure of the formula (1-b), absolute configuration of the carbon atom to which $G^4$ binds is R-configuration, $G^1$ is hydrogen atom, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(241) the compound according to (240) which is the compound of Example 1-2, 4-2, 8-2, 9-2, 10-2, 11-2, 18-2, 19-2, 23-2, 31-2, 32-2, 33-2, or 34-2;

(242) the compound wherein the ring A has a structure of the formula (1-b), absolute configuration of the carbon atom to which $G^4$ binds is R-configuration, $G^1$ is hydrogen atom, $G^2$ is a halogen atom, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(243) the compound according to (242) which is the compound of Example 1-1, 4-2, 8-2, 18-2, 19-2, 31-2, 32-2, or 33-2;

(244) the compound wherein the ring A has a structure of the formula (1-b), absolute configuration of the carbon atom to which $G^4$ binds is R-configuration, $G^1$ is hydrogen atom, $G^2$ is an alkyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(245) the compound according to (244) which is the compound of Example 8-2, 11-2, 23-2, 27, or 34-2;

(246) the compound wherein the ring A has a structure of the formula (1-b), absolute configuration of the carbon atom to which $G^4$ binds is R-configuration, $G^1$ is hydrogen atom, $G^2$ is an alkenyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(247) the compound wherein the ring A has a structure of the formula (1-b), absolute configuration of the carbon atom to which $G^4$ binds is R-configuration, $G^1$ is hydrogen atom, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(248) the compound wherein the ring A has a structure of the formula (1-b), absolute configuration of the carbon atom to which $G^4$ binds is R-configuration, $G^1$ is hydrogen atom, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), and $R^1$ and $R^2$ are both hydrogen atoms;

(249) the compound according to (248) which is the compound of Example 1-2, 8-2, 9-2, 10-2, 11-2, 18-2, 19-2, or 23-2;

(250) the compound wherein the ring A has a structure of the formula (1-b), absolute configuration of the carbon atom to which $G^4$ binds is R-configuration, $G^1$ is hydrogen atom, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is an alkyl group which may be substituted;

(251) the compound wherein the ring A has a structure of the formula (1-b), absolute configuration of the carbon atom to which $G^4$ binds is R-configuration, $G^1$ is hydrogen atom, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is a lower alkyl group;

(252) the compound according to (251) which is the compound of Example 27, 31-2, 32-2, 33-2, or 34-2;

(253) the compound wherein the ring A has a structure of the formula (1-b), absolute configuration of the carbon atom to which $G^4$ binds is R-configuration, $G^1$ is hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(254) the compound according to (253) which is the compound of Example 7-2, 25-2, 29-2, 30-2, 35-2, 36-2, 37-2, or 38-2;

(255) the compound wherein the ring A has a structure of the formula (1-b), absolute configuration of the carbon atom to which $G^4$ binds is R-configuration, $G^1$ is hydroxyl group, $G^2$ is a halogen atom, $G^3$ and $G^5$ are both hydrogen atoms, $G^4$ is N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(256) the compound according to (255) which is the compound of Example 7-2, 29-2, 30-2, 35-2, 36-2, 37-2, or 38-2;

(257) the compound wherein the ring A has a structure of the formula (1-b), absolute configuration of the carbon atom to which $G^4$ binds is R-configuration, $G^1$ is hydroxyl group, $G^2$ is an alkyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(258) the compound wherein the ring A has a structure of the formula (1-b), absolute configuration of the carbon atom to which $G^4$ binds is R-configuration, $G^1$ is hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), and $R^1$ and $R^2$ are both hydrogen atoms;

(259) the compound according to (258) which is the compound of Example 7-2, 25-2, 29-2, or 30-2;

(260) the compound wherein the ring A has a structure of the formula (1-b), absolute configuration of the carbon atom to which $G^4$ binds is R-configuration, $G^1$ is hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is an alkyl group which may be substituted;

(261) the compound wherein the ring A has a structure of the formula (1-b), absolute configuration of the carbon atom to which $G^4$ binds is R-configuration, $G^1$ is hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is a lower alkyl group;

(262) the compound according to (263) which is the compound of Example 35-2, 36-2, 37-3, or 38-2;

(263) the compound wherein the ring A has a structure of the formula (1-b), absolute configuration of the carbon atom to which $G^4$ binds is R-configuration, $G^1$ is hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is an aralkyl group which may be substituted;

(264) the compound wherein the ring A has a structure of the formula (1-b), absolute configuration of the carbon atom to which $G^4$ binds is R-configuration, $G^1$ is hydroxyl group, $G^2$ is an alkynyl group which may be substituted, $G^3$ and $G^5$ are both hydrogen atoms, $G^4$ is —N($R^1$)($R^2$), one of $R^1$ and $R^2$ is hydrogen atom, and the other is a saturated heterocyclic group which may be substituted;

(265) the compound wherein the ring A has a structure of the formula (1-c), $G^1$ is hydrogen atom, or hydroxyl group, $G^2$ is a halogen atom, an alkyl group which may be substituted, an alkenyl group which may be substituted, or an alkynyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(266) the compound wherein the ring A has a structure of the formula (1-c), $G^1$ is hydrogen atom, or hydroxyl group, $G^2$ is a halogen atom, or an alkyl group which may be substituted, $G^3$ and $G^5$ are both hydrogen atoms, $G^4$ is —N($R^1$)($R^2$), one of $R^1$ and $R^2$ is hydrogen atom, and the other is hydrogen atom, an alkyl group which may be substituted, an aralkyl group which may be substituted, or a saturated heterocyclic group which may be substituted;

(267) the compound wherein the ring A has a structure of the formula (1-c), $G^1$ is hydrogen atom, or hydroxyl group, $G^2$ is a halogen atom, or an alkyl group which may be substituted, $G^3$ and $G^5$ are both hydrogen atoms, $G^4$ is —N($R^1$)($R^2$), and $R^1$ and $R^2$ are both hydrogen atoms;

(268) the compound according to (267) which is the compound of Example 2-1, 2-2, 20-1, 20-2, 21-1, 21-2, 22-1, or 22-2;

(269) the compound wherein the ring A has a structure of the formula (1-c), absolute configuration of the carbon atom to which $G^4$ binds is S-configuration, $G^1$ is hydrogen atom, or hydroxyl group, $G^2$ is a halogen atom, or an alkyl group which may be substituted, $G^3$ and $G^5$ are both hydrogen atoms, $G^4$ is —$N(R^1)(R^2)$, and $R^1$ and $R^2$ are both hydrogen atoms;
(270) the compound according to (269) which is the compound of Example 2-1, 20-1, 21-1, or 22-1;
(271) the compound wherein the ring A has a structure of the formula (1-c), absolute configuration of the carbon atom to which $G^4$ binds is R-configuration, $G^1$ is hydrogen atom, or hydroxyl group, $G^2$ is a halogen atom, or an alkyl group which may be substituted, $G^3$ and $G^5$ are both hydrogen atoms, $G^4$ is —$N(R^1)(R^2)$, and $R^1$ and $R^2$ are both hydrogen atoms;
(272) the compound according to (271) which is the compound of Example 2-2, 20-2, 21-2, or 22-2;
(273) the compound wherein the ring A has a structure of the formula (1-b), absolute configuration of the carbon atom to which $G^4$ binds is S-configuration, $G^1$ is amino group, $G^2$ is a halogen atom, $G^3$ and $G^5$ are both hydrogen atoms, $G^4$ is —$N(R^1)(R^2)$, one of $R^1$ and $R^2$ is hydrogen atom, and the other is hydrogen atom, or an alkyl group;
(274) the compound wherein the ring A has a structure of the formula (1-b), absolute configuration of the carbon atom to which $G^4$ binds is S-configuration, $G^1$ is amino group, $G^2$ is a halogen atom, $G^3$ and $G^5$ are both hydrogen atoms, $G^4$ is —$N(R^1)(R^2)$, one of $R^1$ and $R^2$ is hydrogen atom, and the other is hydrogen atom, or methyl group;
(275) the compound according to (274) which is the compound of Example 39-1, 40-1, 41-1, or 42-1;
(276) a salt of the compound according to any one of (1) to (275); and
(277) a derivative of the compound according to any one of (1) to (275), which is a prodrug.

The compounds of the present invention are novel compounds not described in literatures. The compounds of the present invention represented by the general formula (1) can be prepared by, for example, the following methods. However, the preparation methods of the compounds of the present invention are not limited to the following preparation methods.

In each reaction, reaction time is not particularly limited. Advance of the reactions can be readily monitored by the analysis means described later, and therefore the reactions may be terminated when yields of the target substances reach the maximum.

The compound represented by the general formula (1) can be decomposed into a compound represented by the formula (4) and a compound represented by the formula (5) according to the following reaction route. Therefore, the compounds of the present invention can be prepared by the synthetic route reverse to the following reaction route.

(Preparation Method 1)

[Formula 3]
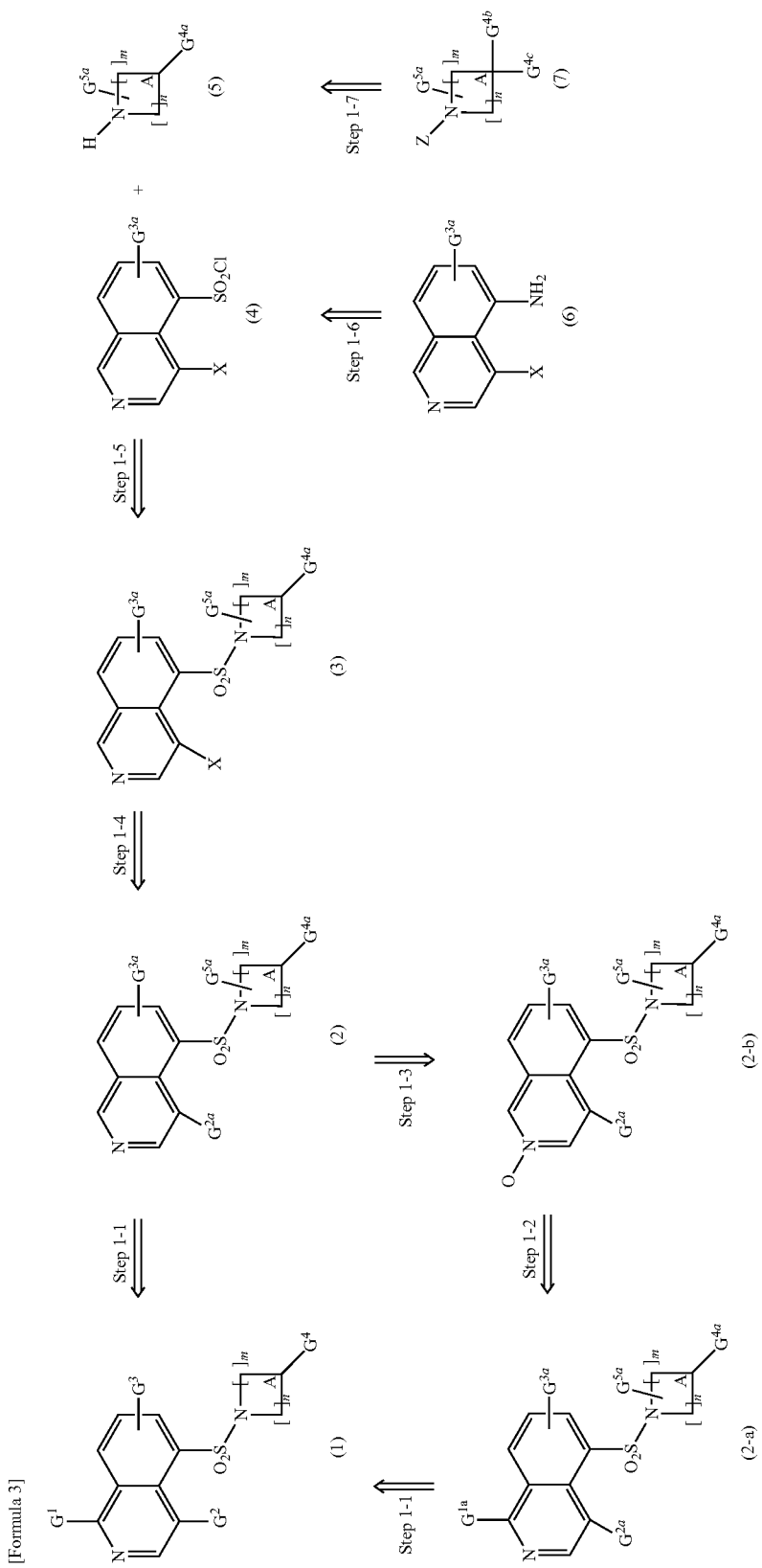

For example, the compounds represented by the general formula (1) can be prepared by simultaneously or successively removing all the protective groups of a compound represented by the general formula (2) [in the formula, A, m, and n have the same meanings as those defined above, $G^{2a}$, $G^{3a}$, $G^{4a}$ and $G^{5a}$ have the same meanings as those of $G^2$, $G^3$, $G^4$ and $G^5$ mentioned above, respectively, and one or more of these groups may be protected], or a compound represented by the general formula (2-a) [in the formula, A, m, n, $G^{2a}$, $G^{3a}$, $G^{4a}$, and $G^{5a}$ have the same meanings as those defined above, $G^{1a}$ is chlorine atom, hydroxyl group, an alkoxy group, or amino group, and these groups may be protected] (Step 1-1).

The deprotection reactions can be carried out according to known methods, for example, the methods described in "Protective Groups in Organic Synthesis", published by John Wiley and Sons (1999), and the like. When $G^{1a}$, $G^{2a}$, $G^{3a}$, $G^{4a}$ and $G^{5a}$ are the same groups as $G^1$, $G^2$, $G^3$, $G^4$ and $G^5$, respectively, the compounds of the formula (2) and the formula (2-a) constitute a part of the compounds of the formula (1), and thus Step 1-1 mentioned above is not required for the preparation.

Further, the compounds of the formula (2) wherein $G^{4a}$ is —N($R^{1a}$)($R^{2a}$) [in the formula, $R^{1a}$ and $R^{2a}$ have the same meanings as those of $R^1$ and $R^2$ mentioned above, respectively, and one or more of these groups may be protected, provided that $R^{2a}$ is not hydrogen atom] can be prepared from a compound of the formula (2) wherein $G^{4a}$ is —NH($R^{1a}$) [$R^{1a}$ has the same meaning as that defined above].

The method can be performed by by subjecting a compound of the formula (2) wherein $G^{4a}$ is —NH($R^{1a}$) to alkylation or reductive amination corresponding to introduction of $R^{2a}$. This method can be performed also for a compound of the formula (2-a) wherein $G^{4a}$ is —NH($R^{1a}$).

Examples of the method for the alkylation include, for example, a method of using a halide of $R^{2a}$ (chloride, bromide, iodide, and the like). The reaction can usually be performed in the presence of a base. As the base, for example, an inorganic base is preferred, and examples include potassium carbonate, sodium carbonate, cesium carbonate, sodium hydrogencarbonate, potassium hydroxide, and sodium hydroxide. Particularly preferred is potassium carbonate. The halide of $R^{2a}$ is preferably used in an amount of 1 fold mole or more, particularly preferably 2 to 10 fold moles, based on the compound of the formula (2) wherein $G^{4a}$ is —NH($R^{1a}$) [$R^{1a}$ has the same meaning as that defined above]. Examples of the reaction solvent include, for example, water, alcohol solvents such as methanol, and ethanol, inert solvents such as N,N-dimethylformamide, tetrahydrofuran, 1,4-dioxane, acetone, 2-butanone, dimethyl sulfoxide, and acetonitrile, and the like, which can be used independently or as a mixed solvent thereof, and preferred are water, N,N-dimethylformamide, and acetone. The reaction temperature is, for example, −10° C. or higher, preferably 0 to 80° C. The reaction time is, for example, usually 0.5 hour or longer, preferably 2 to 20 hours.

As for the reductive amination, the compounds can be prepared by, for example, using an aldehyde or ketone corresponding to $R^{2a}$ according to the method of Step 1-7, i) described later.

Further, the compounds represented by the general formula (2-a) can be prepared by, for example, any one of the following methods.

(i) The compounds of the formula (2-a) wherein $G^{1a}$ is chlorine atom can be prepared by allowing a chlorinating reagent to act on a compound of the general formula (2-b) [in the formula, A, m, n, $G^{2a}$, $G^{3a}$, $G^{4a}$, and $G^{5a}$ have the same meanings as those defined above] to chlorinate it (Step 1-2). Examples of the chlorinating reagent include, for example, phosphorous trichloride, phosphorous pentachloride, and phosphorus oxychloride, and preferred examples include phosphorus oxychloride. The chlorinating reagent is preferably used in an amount of 0.1 fold mole or more, particularly preferably 1 to 10 fold moles, based on the compound of the formula (2-b). As for the solvent, examples of the method include a method of performing the reaction without solvent or in an inert solvent, and preferred examples include a method of performing the reaction without solvent, or using dichloromethane, 1,2-dichloroethane, chloroform, or toluene as the solvent. The reaction is preferably carried out at room temperature or a higher temperature. The reaction time is preferably 0.1 to 48 hours.

(ii) The compounds of the formula (2-a) wherein $G^{1a}$ is hydroxyl group can be prepared by hydroxylating a compound of the formula (2-a) wherein $G^{1a}$ is chlorine atom obtainable as described above. A hydrolysis reaction performed under an acidic condition is preferred, and hydrolysis in a mineral acid is more preferred. Examples of the mineral acid for use include, for example, hydrochloric acid, sulfuric acid, nitric acid, and the like, and hydrochloric acid is particularly preferred. The acid is preferably used in an amount of 0.1 fold mole or more, particularly preferably 1 to 100 fold moles, based on the compound of the formula (2-a) wherein $G^{1a}$ is chlorine atom. As for the solvent, examples of the method include a method of performing the reaction without solvent or in an inert solvent, and preferred examples include a method of performing the reaction without solvent, or using water, or an ether solvent such as tetrahydrofuran, and 1,4-dioxane. The reaction can be performed, for example, at room temperature or a higher temperature. The reaction time is preferably 0.1 to 48 hours.

(iii) The compounds of the formula (2-a) wherein $G^{1a}$ is an alkoxy group can be prepared by alkoxylating a compound of the formula (2-a) wherein $G^{1a}$ is chlorine atom obtainable as described above. An alkoxylation reaction under an acidic condition is preferred, and a reaction with a corresponding alcohol in a mineral acid is more preferred. Examples of the mineral acid for use include, for example, hydrochloric acid, sulfuric acid, nitric acid and the like, and hydrochloric acid is particularly preferred. The acid is preferably used in an amount of 0.1 fold mole or more, particularly preferably 1 to 100 fold moles, based on the compound of the formula (2-a) wherein $G^{1a}$ is chlorine atom. As for the solvent, examples of the method include a method of performing the reaction without solvent or in an inert solvent, and preferred examples include a method of performing the reaction without solvent or using an ether solvent such as tetrahydrofuran and 1,4-dioxane. The alcohol is preferably used in an amount of 0.1 fold mole or more, particularly preferably 1 to 100 fold moles, based on the compound of the formula (2-a) wherein $G^{1a}$ is chlorine atom. The reaction can be performed, for example, at room temperature or a higher temperature. The reaction time is preferably 0.1 to 48 hours.

Further, the compounds of the formula (2-a) wherein $G^{1a}$ is an alkoxy group can be prepared directly from a compound of the aforementioned formula (2-b). For example, a method of allowing a corresponding alcohol to act on a compound of the formula (2-b) in an inert solvent in the presence of chloroformic acid ester and a base is preferred. As for the solvent, examples of the method include a method of performing the reaction without solvent or in an inert solvent, and the reaction can be preferably performed without solvent. Examples of the chloroformic acid ester include, for example, methyl chloroformate, ethyl chloroformate, and the like, and it is usually preferable to use a respective corresponding chloroformic acid ester, for example, methyl chloroformate for methoxylation, ethyl chloroformate for ethoxylation, and the like. Examples of the base include, for example, organic bases such as triethylamine, N,N-diisopropylethylamine, and pyridine, and inorganic bases such as potassium carbonate, and sodium hydrogencarbonate. An organic base is preferred, and triethylamine is particularly preferred. The base and the chloroformic acid ester are usually used in an amount of 1 to 20 fold moles, preferably 1.1 to 5 fold moles, based on the compound of the formula (2-b). The reaction temperature is about −10 to 40° C., preferably about 0 to 30° C. The reaction time is preferably 0.1 to 48 hours.

Further, the compounds of the formula (2-a) wherein $G^{1a}$ is hydroxyl group can be prepared from a compound of the formula (2-a) wherein $G^{1a}$ is an alkoxy group. A solvolysis reaction under an acidic condition is preferred, and solvolysis in a mineral acid is more preferred. Examples of the mineral acid for use include, for example, hydrochloric acid, sulfuric acid, nitric acid, and the like, and hydrochloric acid is particularly preferred. The acid is preferably used in an amount of 0.1 fold mole or more, particularly preferably 1 to 100 fold moles, based on the compound of the formula (2-a) wherein $G^{1a}$ is an alkoxy group (for example, methoxy group, ethoxy group, and the like). As for the solvent, examples include a method of using water, an alcohol such as methanol and ethanol, an ether solvent such as tetrahydrofuran and 1,4-dioxane, and the like, and an alcohol is preferred. The reaction can be performed, for example, at room temperature or a higher temperature. The reaction time is preferably 0.1 to 48 hours.

(iv) The compounds of the formula (2-a) wherein $G^{1a}$ is amino group can be prepared by aminating a compound of the formula (2-a) wherein $G^{1a}$ is chlorine atom obtainable as described above. For the amination, ammonia is preferably used, and aqueous ammonia of a concentration of 5% or higher is more preferably used. As for the amount of ammonia, it is preferably used in an amount of 0.1 fold mole or more, particularly preferably 1 to 100 fold moles, in terms of the $NH_3$ content. As for the reaction solvent, examples of the method include a method of performing the reaction without solvent or in an inert solvent, and preferred examples include a method of performing the reaction without solvent or using an ether solvent such as tetrahydrofuran and 1,4-dioxane. The reaction can be performed, for example, at room temperature or a higher temperature. The reaction time is preferably 0.1 to 48 hours.

The compounds represented by the general formula (2-b) can be prepared by oxidizing a compound represented by the general formula (2) (Step 1-3). Examples of the oxidizing agent include aqueous hydrogen peroxide, sodium periodate, sodium perborate, 3-chloroperbenzoic acid, ruthenium trichloride, dimethyldioxirane, and the like, and 3-chloroperbenzoic acid is preferred. The oxidizing agent is preferably used in an amount of 0.1 fold mole or more, particularly preferably 1 to 20 fold moles, based on the compound of the formula (2). Examples of the solvent include, for example, acetic acid, trifluoroacetic acid, dichloromethane, 1,2-dichloroethane, chloroform, acetonitrile, acetone, trichlorofluoromethane, benzene, 1,4-dioxane, tert-butanol, water, and a mixed solvent thereof, and preferred examples include acetic acid. The reaction is preferably carried out at room temperature or a higher temperature.

The compounds represented by the general formula (2) can be prepared from a compound represented by the general formula (3) [in the formula, A, m, n, $G^{3a}$, $G^{4a}$, and $G^{5a}$ have the same meanings as those defined above, and X represents a halogen atom] (Step 1-4). In the implementation of Step 1-4, X in the formula (3) represents a halogen atom, and X is preferably chlorine atom, or bromine atom, particularly preferably bromine atom. When $G^{2a}$ is the same group as X, the compounds of the formula (3) constitute a part of the compounds of the formula (2), and therefore Step 1-4 mentioned above is not required for the preparation.

Step 1-4 can be performed by any one of the following methods.

(i) The compounds of the formula (2) wherein $G^{2a}$ is an alkyl group which may be substituted, an alkenyl group which may be substituted, an alkynyl group which may be substituted, or an aryl group which may be substituted, and these groups may be protected can be prepared from a compound of the formula (3). More specifically, it is preferable to alkylate, alkenylate, alkynylate, or arylate a compound of the formula (3) in an inert solvent. Examples of the inert solvent include, for example, ether solvents such as diethyl ether, tetrahydrofuran, and 1,2-dimethoxyethane, acetonitrile, N,N-dimethylformamide, water, and mixed solvents thereof. The alkylation, alkenylation, alkynylation, and arylation can be preferably performed, for example, by reacting an alkylating reagent, an alkenylating reagent, an alkynylating reagent, or an arylating reagent in the presence of a nickel catalyst or palladium catalyst.

Examples of the nickel catalyst include, for example, dichloro(1,1'-bis(diphenylphosphino)ferrocene)nickel(II), dichloro(1,3-bis(diphenylphosphino)propane)nickel(II), and bis(acetylacetonato)nickel(II), and examples of the palladium catalyst include, for example, dichloro(1,1'-bis(diphenylphosphino)ferrocene)palladium(II), tetrakis(triphenylphosphine)palladium(0), dichloro(bis(triphenylphosphine))palladium(II), and dichloro(bis(benzonitrile))palladium(II). Examples of the alkylating reagent, alkenylating reagent, alkynylating reagent, and arylating reagent include, for example, Grignard reagents such as magnesium methyl iodide and magnesium methyl bromide, organic zinc reagents such as (ethoxycarbonylethyl)zinc bromide and (ethoxycarbonylmethyl)zinc bromide, organic tin reagents such as allyltributyltin and vinyltributyltin, organic aluminum reagents such as vinyldiisobutylaluminum, organic boron reagents such as an alkylboronic acid, an alkenylboronic acid, and an arylboronic acid, organic lithium reagents such as methyllithium and vinyllithium, organic copper reagents such as an alkylcopper and an alkenylcopper, organic silicon reagents such as vinyltrimethylsilane and trimethylsylilacetylene, and the like. The alkylating reagent, alkenylating reagent, alkynylating reagent, and arylating reagent are preferably used in an amount of 1 to 20 fold moles, and the catalyst is preferably used in an amount of 0.0001 to 1 fold mole, based on the compound of the formula (3).

The reaction is performed, for example, at 0 to 150° C., preferably room temperature to 120° C., and the reaction time is preferably 0.1 to 48 hours. For example, by using tetramethyltin as the aforementioned alkylating reagent, the compounds of the formula (2) wherein $G^{2a}$ is methyl group can be prepared. By using allyltributyltin, the compounds wherein $G^{2a}$ is allyl group can be prepared. By using (ethoxycarbonylethyl)zinc bromide, the compounds wherein $G^{2a}$ is ethoxycarbonylethyl group can be prepared. By using (ethoxycarbonylmethyl)zinc bromide, the compounds wherein $G^{2a}$ is ethoxycarbonylmethyl group can be prepared. By using vinyltributyltin, the compounds wherein $G^{2a}$ is vinyl group can be prepared. Further, by using an arylboronic acid, the compounds wherein $G^{2a}$ is a corresponding aryl group can be prepared.

Further, the target compounds can also be prepared by reacting an alkenyl compound or alkynyl compound including acrylic acid esters, acrylonitrile, propargyl alcohol derivatives, end acetylene derivatives, and the like in the presence of a palladium catalyst, base, copper(I) iodide, or the like. As for these reactions, Heck R. F. et al., J. Org. Chem., 2947 (1978); Sonogashira, K. et al., Tetrahedron, 2303 (1984), and the like can be referred to. Examples of the palladium catalyst include tetrakis(triphenylphosphine)palladium(0), dichlorobis(triphenylphosphine)palladium(II), those of palladium(II)acetate/triphenylphosphine type, tris(dibenzylideneacetone)dipalladium(0)/tri(tert-butyl)phosphine type, dichlorobis(benzonitrile)palladium(0)/tri(tert-butyl)phosphine type, and the like. Examples of the base include triethylamine, diethylamine, diisopropylamine, sodium acetate, sodium hydroxide, lithium hydroxide, potassium fluoride, potassium carbonate, cesium carbonate, cesium fluoride, sodium tert-butoxide, and the like. When protection with a protective group and following deprotection are required in the aforementioned synthesis, the reaction can be properly carried out by utilizing the aforementioned methods of Greene and Wuts, and Kocienski.

(ii) The compounds of the formula (2) wherein $G^{2a}$ is an amino group which may be substituted (and may contain a protective group) can be prepared from a compound of the formula (3). Examples include, for example, a method of aminating a compound of the formula (3) in an inert solvent. The amination referred to here include not only conversion into unsubstituted —$NH_2$, but also conversion into an amino group which may have one or more substituents. Examples of the inert solvent include, for example, ether solvents such as tetrahydrofuran, 1,4-dioxane, and 1,2-dimethoxyethane, N,N-dimethylformamide, N-methylpyrrolidone, dimethyl sulfoxide, sulfolane, alcohol solvents such as methanol and ethanol, water, and mixed solvents thereof. Examples of the aminating reagent include, ammonia, primary amines such as methylamine, and secondary amines such as dimethylamine. The aminating reagent is preferably used in an amount of 1 fold mole or more to a large excess amount based on the compound of the formula (3). The reaction is preferably performed at room temperature or under a heating condition up to about 200° C., and the reaction time is preferably 0.5 to 72 hours.

As an alternative method, the coupling of a compound of the formula (3) and an aminating agent can be performed in an inert solvent in the presence of a palladium catalyst, phosphorus compound, and base (according to, for example, Buchwald, S. L., J. Org. Chem., 1158 (2000); Buchwald, S. L., Organic Letters, 1101 (2000)). Examples of the inert solvent include ether solvents such as tetrahydrofuran, 1,4-dioxane and 1,2-dimethoxyethane, toluene, and N,N-dimethylformamide, and examples of the palladium catalyst include, for example, tris(dibenzylideneacetone)dipalladium(0), palladium(II)acetate, and the like. Examples of the phosphorus compound include, for example, 2-(di-tert-butylphosphino)biphenyl, 2-(dicyclohexylphosphino)biphenyl, 2,2'-bis(diphenylphosphino)-1,1'-binaphthyl, xanthophos, and tri(tert-butyl)phosphine. Examples of the base include, for example, sodium tert-butoxide, cesium carbonate, potassium phosphate, and the like. Examples of the aminating agent include, for example, lithium hexamethyldisilazide, primary amines such as methylamine, secondary amines such as dimethylamine, and the like. By using lithium hexamethyldisilazide, the compounds of the formula (2) wherein amino group is introduced as $G^{2a}$ can be prepared. Further, by using methylamine, methylamino group can be introduced, and by using dimethylamine, dimethylamino group can be introduced.

(iii) The compounds of the formula (2) wherein $G^{2a}$ is an alkoxy group which may be substituted (and may contain a protective group) can be prepared from a compound of the formula (3). Preferred examples of the method include a method of etherifying a compound of the formula (3) in an inert solvent. Examples of the inert solvent include, for example, ether solvents such as tetrahydrofuran, 1,4-dioxane, and 1,2-dimethoxyethane, solvents such as N,N-dimethylformamide, N-methylpyrrolidone, dimethyl sulfoxide, and sulfolane, water, and mixed solvents thereof. Examples of the etherifying reagent include, for example, metal alcoholates such as those of lithium, sodium, and potassium (including, for example, $C_{1-6}$ alkoxides such as methylate, and ethylate, 2-hydroxyethylate, 2-methoxyethylate, 2-methanesulfonylethylate, and the like). The reaction is preferably carried out in the presence of a copper catalyst, and the reaction temperature is room temperature to about 180° C. The etherifying agent is preferably used in an amount of 1 to 20 fold moles. For example, if a methylate is used as the metal alcoholate, the compounds of the formula (2) wherein methoxy group is introduced as $G^{2a}$ can be obtained. By using an ethylate, ethoxy group can be introduced, by using 2-hydroxyethylate, 2-hydroxyethoxy group can be introduced, by using 2-methoxyethylate, 2-methoxyethoxy group can be introduced, and by using 2-methanesulfonylethylate, 2-methanesulfonylethoxy group can be introduced. The reaction time is preferably 0.1 to 72 hours.

As an alternative method, the compounds of the formula (2) wherein $G^{2a}$ is an alkoxy group which may be substituted (and may contain a protective group) can be prepared by reacting a compound of the formula (3) with an etherifying agent in an inert solvent in the presence of a palladium catalyst, phosphorus compound, and base (according to, for example, Buchwald, S. L., J. Org. Chem., 1158 (2000); Buchwald, S. L., Organic Letters, 1101 (2000)). Examples of the inert solvent include, for example, ether solvents such as tetrahydrofuran, 1,4-dioxane, and 1,2-dimethoxyethane, and toluene. Examples of the palladium catalyst include, for example, palladium(II)acetate, tris(dibenzylideneacetone)dipalladium(0), palladium(II)acetate and the like. Examples of the phosphorus compound include, for example, 2-(di-tert-butylphosphino)biphenyl, 2-(di-tert-butylphosphino)-1,1'-binaphthyl, and 2-(di-tert-butylphosphino)-2'-dimethylamino-1,1'-binaphthyl. Examples of the base include, for example, sodium tert-butoxide, potassium tert-butoxide, cesium carbonate, potassium phosphate, and the like. Examples of the etherifying agent include, for example, alcohols including methanol, ethanol, ethylene glycol, methanesulfonylethanol, and the like. Depending on the type of the alcohol used, the compounds of the formula (2) wherein $G^{2a}$ is converted into a corresponding alkoxy group are obtained. Further, when the alkyl moiety of the alkoxy group is a protective group, the compounds can be converted into the compounds wherein $G^{2a}$ is hydroxyl group by performing a deprotection reaction. When protection with a protective group and following deprotection are required, the reactions can be properly performed by utilizing the methods described by Greene and Wuts, and Kocienski.

(iv) The compounds of the formula (2) wherein $G^{2a}$ is an alkylthio group which may be substituted (and may contain a protective group) can be prepared from a compound of the formula (3). Preferred examples of the method include a method of alkylthiolating a compound of the formula (3) in an inert solvent. Examples of the inert solvent include, for example, solvents such as tetrahydrofuran, 1,4-dioxane, 1,2-dimethoxyethane, N,N-dimethylformamide, N-methylpyrrolidone, dimethyl sulfoxide, sulfolane, methanol, ethanol, and propanol, water, and mixed solvents thereof. Examples of the alkylthiolating reagent include, for example, metal thiolates such as those of lithium, sodium, and potassium (for example, $C_{1-6}$ alkylthiolates including methylthiolate, ethylthiolate, and the like). The alkylthiolating reagent is preferably used in an amount of 1 to 20 fold moles, and the reaction is preferably carried out at room temperature to about 180° C. The reaction time is preferably 0.1 to 72 hours.

The compounds of the formula (2) wherein $G^{2a}$ is an alkylsulfinyl group which may be substituted (and may contain a protective group) can be prepared from a compound of the formula (2) wherein $G^{2a}$ is an alkylthio group which may be substituted (and may contain a protective group). Preferred examples of the method include a method of oxidizing a compound of the formula (2) wherein $G^{2a}$ is an alkylthio group which may be substituted (and may contain a protective group) in an inert solvent. Examples of the inert solvent include, for example, dichloromethane, chloroform, tetrahydrofuran, 1,4-dioxane, acetonitrile, tert-butanol, acetic acid, trifluoroacetic acid, water, and mixed solvents thereof. Examples of the oxidizing agent include, for example, sodium metaperiodate, 3-chloroperbenzoic acid, and hydrogen peroxide. The oxidizing agent is preferably used in an amount of 0.3 to 2 fold moles based on the starting compound, and the reaction time is preferably 0.1 to 48 hours.

The compounds of the formula (2) wherein $G^{2a}$ is an alkylsulfonyl group which may be substituted (and may contain a protective group) can be prepared from a compound of the formula (2) wherein $G^{2a}$ is an alkylthio group which may be substituted (and may contain a protective group). Preferred examples of the method include a method of oxidizing a compound of the formula (2) wherein $G^{2a}$ is an alkylthio group which may be substituted (and may contain a protective group) in an inert solvent. The reaction can be performed by using an inert solvent and an oxidizing agent similar to those used for the aforementioned oxidation step, and the oxidizing agent is preferably used in an amount of 2 fold moles or more based on the starting compound. As an alternative method, the compounds of the formula (2) wherein $G^{2a}$ is an alkylsulfonyl group which may be substituted (and may contain a protective group) can be prepared from a compound of the formula (3). Preferred examples of the method include a method of sulfonylating a compound of the formula (3) in an inert solvent. Examples of the inert solvent include, for example, solvents such as tetrahydrofuran, 1,4-dioxane, 1,2-dimethoxyethane, N,N-dimethylformamide, N-methylpyrrolidone, dimethyl sulfoxide, sulfolane, methanol, ethanol, and propanol, water, and mixed solvents thereof. Examples of the sulfonylating reagent include, for example, sodium or potassium alkylsulfinates, and they enables conversion into a compounds of the formula (2) wherein $G^{2a}$ is a corresponding alkylsulfonyl group. The reaction is preferably performed at room temperature to about 180° C. The reaction time is preferably 0.1 to 48 hours. When protection with a protective group and following deprotection are required, the reaction can be properly carried out by utilizing the aforementioned methods described by Greene and Wuts, and Kocienski.

(v) The compounds of the formula (2) wherein $G^{2a}$ is cyano group can be prepared from a compound of the formula (3). Preferred examples of the method include a method of cyanating a compound of the formula (3) in an inert solvent by using a suitable cyanating agent (according to, for example, Newman, M. S. et al., J. Org. Chem., 2525 (1961)). Examples of the inert solvent include, for example, solvents such as tetrahydrofuran, 1,4-dioxane, 1,2-dimethoxyethane, N,N-dimethylformamide, N-methylpyrrolidone, dimethyl sulfoxide, sulfolane, methanol, ethanol, and propanol, water, and mixed solvents thereof. Examples of the cyanating agent include, for example, copper(I) cyanide, sodium cyanide, potassium cyanide, zinc cyanide, silver cyanide, potassium ferrocyanide, and the like. The cyanating agent is preferably used in an amount of 1 to 20 fold moles, and the reaction is preferably carried out at room temperature to about 180° C.

As an alternative method, the coupling of a compound of the formula (2) and the aforementioned cyanating agent can be performed in an inert solvent in the presence of a catalyst and a phosphorus compound (according to, for example, Weissman, S. A. et al., J. Org. Chem., 2005, 70, 1508). Examples of the catalyst include dichloro(1,1'-bis(diphenylphosphino)ferrocene)palladium(II), tetrakis(triphenylphosphine)palladium(0), dichloro(bis(triphenylphosphine))palladium(II), dichlorothis(benzonitrilapalladium(II), tris(dibenzylideneacetone)dipalladium(0), palladium(II)acetate, dichloro(1,1'-bis(diphenylphosphino)ferrocene) nickel(II), dichloro(1,3-bis(diphenylphosphino)propane) nickel(II), dibromo(bis(triphenylphosphine))nickel(II), bis (acetylacetonato)nickel(II), and the like. Examples of the phosphorus compound include, for example, 2-(di-tert-butylphosphino)biphenyl, 2-(dicyclohexylphosphino)biphenyl, 2,2'-bis(diphenylphosphino)-1,1'-binaphthyl, 1,1'-bis(diphenylphosphino)ferrocene, xanthophos, and tri(tert-butyl) phosphine. When protection with a protective group and following deprotection are required in the aforementioned synthesis, the reaction can be properly carried out by utilizing the aforementioned methods described by Greene and Wuts, and Kocienski. In addition, the compounds of the formula (2) wherein $G^{2a}$ is carboxy group can be prepared from a compound of the formula (2) wherein $G^{2a}$ is cyano group. Preferred examples of the method include a method of hydrolyzing a compound of the formula (3) in an inert solvent under a known appropriate acidic condition, or basic condition (according to, for example, Marvel, C. S. et al., J. Am. Chem. Soc., 1945, 67, 2250).

The compounds represented by the aforementioned formula (3) can be prepared by coupling a compound represented by the general formula (4) [in the general formula (4), X and $G^{3a}$ have the same meanings as those defined above] and a compound represented by the general formula (5) [in the general formula (5), A, m, n, $G^{4a}$, and $G^{5a}$ have the same meanings as those defined above] in an inert solvent in the presence of a base (Step 1-5). Examples of the inert solvent include, for example, halogenated hydrocarbons such as dichloromethane, chloroform, and 1,2-dichloroethane, and acetonitrile. Examples of the base include, for example, organic bases such as triethylamine, N,N-diisopropylethylamine, and pyridine, and inorganic bases such as potassium carbonate, and sodium hydrogencarbonate. The base and the compound of the formula (5) are usually used in an amount of 1 to 6 fold moles, preferably 1.1 to 3.3 fold moles, based on the compound of the formula (4), and the reaction temperature is about −10 to 40° C., preferably about 0 to 30° C. The reaction time is preferably 0.1 to 48 hours.

The compounds represented by the aforementioned formula (4) can be prepared form a compound represented by the general formula (6) [in the formula, X and $G^{3a}$ have the same meanings as those defined above] by a known method (Japanese Patent No. 2763791), or a similar method (Step 1-6).

The compounds represented by the aforementioned formula (5) can be prepared from a compound represented by the general formula (7) [in the formula, A, m, n, and $G^{5a}$ have the same meanings as those defined above, $G^{4b}$ and $G^{4c}$ together represent oxo group, or one of $G^{4b}$ or $G^{4c}$ represents hydrogen atom, and the other represents hydroxyl group, or amino group, these hydroxyl group and amino group may be protected with a protective group; and Z represents hydrogen atom, or an amino protective group] by the following various methods (Step 1-7). As for the combination of $G^{4b}$ and $G^{4c}$, the compounds of the formula (7) except for the compounds wherein $G^{4b}$ and $G^{4c}$ together form oxo group constitute a part of the compounds of the formula (5), and therefore Step 1-7 mentioned above is not required in such a case.

i) The compounds of the formula (5) wherein $G^{4a}$ is —N($R^1$)($R^2$) (which may contain a protective group) can be prepared by coupling a compound of the formula (7) wherein $G^{4b}$ and $G^{4c}$ together represent oxo group, and a compound represented by the following formula (8):

H—N($R^1$)($R^2$)     (8)

[in the formula, $R^1$ and $R^2$ have the same meanings as those defined above, and one ore more of these group may be protected]. A method of performing the coupling by allowing a reducing agent to act on the compound in a solvent is preferred. Examples of the reducing agent include, for example, metal hydride reducing agents such as sodium borohydride, zinc borohydride, sodium triacetoxyborohydride, borane/dimethyl sulfide complex, borane/pyridine complex, borane/triethylamine complex, borane/tetrahydrofuran complex, lithium triethylboride, and the like, and preferred examples include sodium borohydride and sodium triacetoxyborohydride. The reducing agent is used in an amount of, for example, 0.1 fold mole or more, preferably 1 to 20 fold moles, based on the compound of the formula (7). Examples of the solvent include, for example, alcohols such as methanol, ethanol, and isopropanol, ethers such as tetrahydrofuran, 1,2-dimethoxyethane, and 1,4-dioxane, halogenated hydrocarbons such as dichloromethane, chloroform, and 1,2-dichloroethane, N,N-dimethylformamide and the like, and preferred examples include methanol, tetrahydrofuran, and 1,2-dichloroethane. The reaction temperature is, for example 0° C. or higher, preferably 10° C. to the reflux temperature of the solvent. The reaction time is, for example, 0.1 hour or longer, preferably 0.5 to 30 hours.

ii) The compounds of the formula (7) wherein $G^{4b}$ and $G^{4c}$ together represent oxo group can be prepared by oxidizing a compound of the formula (7) wherein one of $G^{4b}$ and $G^{4c}$ is hydrogen atom, and the other is hydroxyl group. As the method for the oxidization, a usually used known method of converting a secondary alcohol into a ketone is widely known, and the preparation can be easily attained by those skilled in the art (according to, for example, Finney, N. S. et al., Org. Lett., 2002.4.3001).

Among the compounds of the formula (7) wherein one of $G^{4b}$ and $G^{4c}$ is hydrogen atom, and the other is hydroxyl group or amino group, those compounds wherein these hydroxyl group and amino group may be protected with a protective group are known as cyclic amine compounds, and many commercial products are provided. Therefore, those skilled in the art can easily perform the aforementioned preparation method.

Further, the compounds of the formula (8) are known as primary or secondary amines, and many commercial products are provided. Therefore, those skilled in the art can easily perform the aforementioned preparation method.

(Preparation Method 2)

[Formula 4]

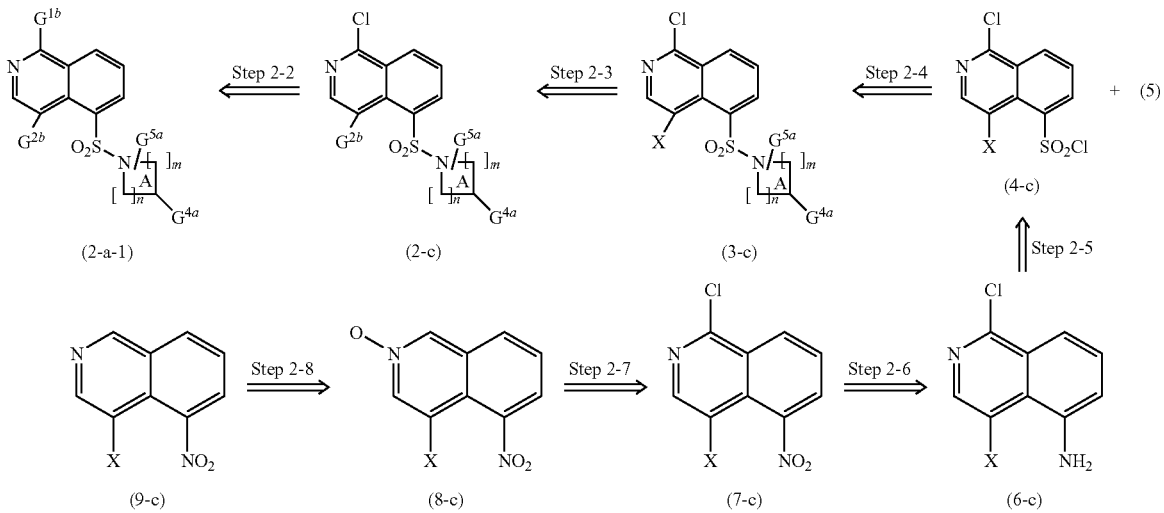

For example, the compounds of the general formula (1) wherein $G^1$ is chlorine atom, hydroxyl group, an alkoxy group, or amino group, $G^2$ is a halogen atom, or an alkyl group which may be substituted, and $G^3$ is hydrogen atom can be prepared by simultaneously or successively removing all protective groups of a compound represented by the general formula (2-a-1) when protective groups are present [in the formula, $G^{1b}$ is chlorine atom, hydroxyl group, an alkoxy group, or amino group, $G^{2b}$ is a halogen atom, or an alkyl group which may be substituted, and A, m, n, $G^{4a}$, and $G^{5a}$ have the same meanings as those defined above] according to the method of Step 1-1 mentioned above. When $G^{4a}$ and $G^{5a}$ are the same groups as $G^4$ and $G^5$, the compounds of the formula (2-a-1) constitute a part of the compounds of the formula (1), and therefore Step 1-1 is not required for the preparation.

Further, the compounds of the formula (2-a-1) wherein $G^{4a}$ is —N($R^{1a}$)($R^{2a}$) [in the formula, $R^{1a}$ and $R^{2a}$ have the same meanings as those of $R^1$ and $R^2$ mentioned above, respectively, and one or more of these groups may be protected, provided that $R^{2a}$ is not hydrogen atom] can be prepared from a compound of the formula (2-a-1) wherein $G^{4a}$ is —$NH(R^{1a})$ [$R^{1a}$ has the same meanings as that defined above] in the same manner as that of Preparation method 1.

The compounds of the general formula (2-a-1) can be prepared by using a compound represented by the general formula (2-c) [in the formula, A, m, n, $G^{2b}$, $G^{4a}$, and $G^{5a}$ have the same meanings as those defined above] in Step 2-2 described below. When $G^1$ in the general formula (2-a-1) is chlorine atom, the compounds of the formula (2-c) constitute a part of the compounds of the formula (2-a-1), and therefore Step 2-2 is not required for the preparation.

[Step 2-2]
(i) When $G^{1b}$ is hydroxyl group, the target compounds can be prepared according to the method of converting a compound of the formula (2-a) wherein $G^{1a}$ is chlorine atom into a compound of the formula (2-a) wherein $G^{1a}$ is hydroxyl group mentioned in Preparation method 1.
(ii) When $G^{1b}$ is an alkoxy group, the target compounds can be prepared according to the method of converting a compound of the formula (2-a) wherein $G^{1a}$ is chlorine atom into a compound of the formula (2-a) wherein $G^{1a}$ is an alkoxy group mentioned in Preparation method 1.
(iii) When $G^{1b}$ is amino group, the target compounds can be prepared according to the method of converting a compound of the formula (2-a) wherein $G^{1a}$ is chlorine atom into a compound of the formula (2-a) wherein $G^{1a}$ is amino group mentioned in Preparation method 1.

[Step 2-3]
The compounds represented by the general formula (2-c) can be prepared from a compound represented by the general formula (3-c) [in the formula, X represents a halogen atom, and A, m, n, $G^{4a}$, and $G^{5a}$ have the same meanings as those defined above]. Among the compounds of the formula (2-c), those wherein $G^{2b}$ is an alkyl group which may be substituted can be prepared according to the method of Preparation method 1, Step 1-4, (i) (in this case, X in the formula (3-c) is preferably chlorine atom or bromine atom, particularly preferably bromine atom). When $G^{2b}$ is a halogen atom, the compounds of the formula (3-c) constitute a part of the compounds of the formula (2-c), and therefore Step 2-3 is not required for the preparation.

[Step 2-4]
The compounds represented by the general formula (3-c) can be prepared from a compound represented by the general formula (4-c) [in the formula, X is a halogen atom] and a compound of the aforementioned formula (5) according to the method of Preparation method 1, Step 1-5.

[Step 2-5]
The compounds represented by the general formula (4-c) can be prepared from a compound represented by the general formula (6-c) [in the formula, X is a halogen atom] according to the method of Preparation method 1, Step 6.

[Step 2-6]
The compounds represented by the general formula (6-c) can be prepared by reducing a compound represented by the general formula (7-c) (for the nitro group moiety) [in the formula, X is a halogen atom]. This reduction is preferably carried out in an acidic solvent. Examples of the acidic solvent include hydrochloric acid, and acetic acid, and preferred examples include hydrochloric acid. Examples of the method of the reduction include a method of using a tin (divalent) reagent as the reducing agent. Preferred examples of the tin (divalent) reagent include stannous chloride, and hydrates thereof. The reaction temperature is −20° C. or higher, preferably 80 to 150° C. The reaction time is, for example, 2 hours or longer, preferably 4 to 15 hours.

As an alternative method, the compounds represented by the general formula (6-c) can be prepared from a compound of the general formula (7-c) by hydrogenation in an inert solvent in the presence of a platinum catalyst. Examples of the inert solvent include, for example, alcohols such as methanol, ethanol, and isopropanol, ethers such as tetrahydrofuran, and 1,2-dimethoxyethane, which can be used independently or as a mixed solvent thereof, and a mixed solvent of ethanol and tetrahydrofuran is preferred. Examples of the platinum catalyst include platinum/activated carbon, and platinum-sulfur/activated carbon, and platinum-sulfur/activated carbon is preferred.

The reaction temperature is −20° C. or higher, preferably 10 to 30° C. The reaction time is, for example, 1 hour or longer, preferably 10 to 20 hours.

[Step 2-7]
The compounds represented by the general formula (7-c) can be prepared by chlorinating a compound represented by the general formula (8-c) [in the formula, X is a halogen atom]. The preparation of this step can be performed according to the method of Preparation method 1, Step 1-2, (i).

[Step 2-8]
The compounds represented by the general formula (8-c) can be prepared by oxidizing a compound represented by the general formula (9-c) [in the formula, X is a halogen atom]. The preparation of this step can be performed according to the method of Preparation method 1, Step 1-3.

The compounds represented by formula (9-c) [in the formula, X is a halogen atom] can be prepared according to the method described in Reference Example 1, Reference Example 5, or Example 1.

The compounds of the invention obtainable as described above, respective starting compounds and preparation intermediates can be isolated and purified by conventional isolation and purification methods such as extraction, distillation and chromatography. Products obtained in the reactions can also be used as starting materials of the following steps without purification as the case may be.

Salts can be prepared from the compounds represented by general formula (1). While the method for preparing the salts are not particularly limited, an acid addition salt of the compound represented by general formula (1) can be obtained by dissolving the compound in an alcohol such as methanol and ethanol, and adding an acid component to the solution in an equivalent amount or an amount of several times in excess. The acid component for use may be an acid component corresponding to the acid addition salts described later, and preferable examples include physiologically acceptable inorganic or organic acids such as hydrochloric acid, hydrobromic acid, sulfuric acid, hydrogen sulfuric acid, phosphoric acid, dihydrogen phosphoric acid, hydrogen phosphoric acid, citric acid, maleic acid, tartaric acid, fumaric acid, glucuronic acid and methanesulfonic acid. As for the method of preparing a base addition salt, a base addition salt can be prepared by, for example, dissolving the compound in an alcohol such as methanol and ethanol, and adding a base component to the solution in an equivalent amount or an amount of several times in excess. The base component for use may be a base component corresponding to the base addition salts described below, and preferred examples thereof include physiologically acceptable inorganic and organic bases such as sodium hydroxide, potassium hydroxide, sodium carbonate, potassium carbonate, ammonia, and methylamine.

Type of the salt of the compound represented by general formula (1) is not particularly limited in the present invention, and may be either an acid addition salt or a base addition salt, or may be in the form of an intramolecular counter ion pair. Examples of the acid addition salt include hydrochloride, hydrobromide, sulfate, hydrogen sulfate, phosphate, dihydrogen phosphate, hydrogen phosphate, citrate, maleate, tartrate, fumarate, gluconate and methanesulfonate, or acid addition salts with optically active acids such as camphorsulfonic acid, mandelic acid, or a substituted mandelic acid. Examples of the base addition salt include metal salts such as sodium salt and potassium salt, and base addition salts of organic bases such as N-methyl-D-glucamine, N,N'-dibenzylethylenediamine, 2-aminoethanol, tris(hydroxymethyl)aminomethane, arginine and lysine. However, the type of the salt is of course not limited to those described above, and it may be appropriately selected by those skilled in the art. Among these salts, physiologically acceptable salts are preferred. The compounds of the invention may exist as a hydrate or solvate, and these substances also fall within the scope of the invention.

Prodrugs can be prepared from the compounds represented by the aforementioned general formula (1) or salts thereof. In the specification, "prodrug of a compound represented by the general formula (1) or a salt thereof" means a compound or a salt thereof that is oxidized, hydrolyzed, or the like in living bodies, preferably in blood, after oral or parenteral administration to mammals to produce a compound of the aforementioned general formula (1) or a salt thereof. For example, many means are known for making medicaments having carboxyl group, amino group, hydroxyl group or the like into prodrugs, and an appropriate means can be chosen by those skilled in the art. For example, a prodrug can be prepared by appropriately binding a group constituting prodrug (for example, an acyl group, an alkoxycarbonyl group, an alkyl group, and the like) to one or more arbitrary groups selected from hydroxyl group and amino group in a compound represented by the general formula (1) in a conventional manner using a corresponding prodrug forming reagent such as halides, and performing isolation and purification as required.

Although type of the prodrug of the compound of general formula (1) of the present invention is not particularly limited, examples include a compound in which a group constituting prodrug is introduced into at least one group selected from hydroxy group, and amino group of the compound represented by general formula (1). Examples of the group constituting prodrug include, for example, an acyl group and an alkoxycarbonyl group. Preferred example includes acetyl group, propionyl group, methoxycarbonyl group, and ethoxycarbonyl group, and ethoxycarbonyl group is particularly preferred. There are other embodiments in which acetyl group is preferred, propionyl group is preferred, or methoxycarbonyl group is preferred.

The compounds of the present invention represented by the aforementioned formula (1) and physiologically acceptable salts thereof have cell movement inhibitory actions on the basis of the Rho kinase inhibitory action in the cells, and are useful as active ingredients of medicaments.

Among the cell movement inhibitory actions of the compounds of the present invention, the cell contraction inhibitory action can be confirmed by measuring vasoconstriction inhibitory activity, bronchus relaxation activity, intraocular pressure reducing activity, respiratory tract constriction inhibitory activity, or the like. The action to regulate change of cell morphology can be confirmed by, for example, measuring neurite outgrowth of retinal ganglion cells of eyes, or the like. The inhibitory action on cell migration (the action will be abbreviated as "cell migration inhibitory action") can be confirmed by measuring neutrophil migration inhibitory activity, respiratory tract inflammation suppressing activity, or the like. The cell release inhibitory action can be confirmed by measuring the chemical mediator releasing amount from neutrophils. The cell aggregation inhibitory action can be confirmed by measuring platelet aggregation inhibitory activity, or the like. Further, the apoptosis inhibitory action can be confirmed by, for example, giving stimulation to induce apoptosis to cells and then measuring cell viability or occurring frequencies of morphological changes of cells characteristic to apoptosis such as nuclear condensation, nuclear fragmentation, and blebbing of cells. However, since the cell movement inhibitory actions on the basis of the Rho kinase inhibitory action in the cells are known to be associated with various biological actions as described in the section of background art in the specification, the aforementioned cell contraction inhibitory action, action to regulate change of cell morphology, cell migration inhibitory action, cell release inhibitory action, cell aggregation inhibitory action, and apoptosis inhibitory action should be construed to constitute a part of the actions of the medicament of the present invention.

More specifically, the compounds of the present invention represented by the aforementioned formula (1) and physiologically acceptable salts thereof have actions including the Rho kinase inhibitory action (see, Test Example 1 of the specification), intraocular pressure reducing activity (see, Test Example 3 in the specification), and the like. Further, it can be confirmed that the compounds of the present invention represented by the aforementioned formula (1) and physiologically acceptable salts thereof have an action for inhibiting the phosphorylation of myosin regulatory light chain (see, Test Example 2 of the specification), vasoconstriction inhibitory activity, activity for suppressing respiratory tract constriction induced by antigen stimulation, neutrophil migration inhibitory activity (see, Test Example 4 in the specification), respiratory tract inflammation suppressing activity, pulmonary inflammation suppressing activity, trachea relaxation activity, activity for suppressing respiratory tract constriction induced by a constriction elicitor, and the like. Therefore, the compounds represented by the aforementioned formula (1) and physiologically acceptable salts thereof as well as derivatives thereof useful as prodrugs are useful as active ingredients of medicaments for prophylactic and/or therapeutic treatment of diseases relating to contraction of various cells, diseases relating to morphological change of various cells, diseases relating to migration of various cells, diseases relating to release of various cells, diseases relating to aggregation of various cells, diseases relating to apoptosis of various cells, and the like.

Examples of the method for confirming that the compounds of the present invention represented by the aforementioned formula (1) and physiologically acceptable salts thereof have the Rho kinase inhibitory action include, for example, the following methods. However, the method is not limited to these methods.

Method 1: The activity of Rho kinase can be measured by, for example, the method disclosed in WO01/56988. More specifically, ATP ($\gamma^{32}$P-ATP) is added to a substrate (Ribosomal S6 kinase substrate) together with a commercially available Rho kinase (Upstate) to start the enzymatic reaction and phosphorylate the substrate. The substrate is adsorbed on filter paper, and ATP is washed off with the phosphate buffer. Then, the amount of the phosphorylated substrate is measured by using a liquid scintillation counter. The inhibitory activity of the compounds of the present invention represented by the aforementioned formula (1) for the Rho kinase activity can be determined by adding the compounds before starting the enzymatic reaction, and measuring suppression of the phosphorylation amount of the substrate. The phosphorylation reaction of myosin phosphatase can be measured by, for example, using an antibody specifically recognizing the phosphorylated myosin phosphatase (Feng, J. et al., J. Biol. Chem., 274, pp. 37385-37390, 1999). More specifically, proteins including myosin phosphatase are extracted from a tissue, subjected to electrophoresis on acrylamide gel, and transferred to a nitrocellulose membrane. The proteins are reacted with antibodies specifically recognizing phosphorylated myosin phosphatase to detect the amount of phosphorylated myosin phosphatase. The inhibitory activity of the compounds of the present invention on the phosphorylation reaction of myosin phosphatase can be determined by adding the compounds before starting the extraction from the tissue, and measuring suppression of the phosphorylation amount of the myosin phosphatase.

Method 2: It is known that increase of the amount of phosphorylated myosin regulatory light chain activates the actomyosin system, which is a movement apparatus of cytoskeleton, and activates cell movements. Therefore, it is considered that the phosphorylation reaction of myosin regulatory light chain is important for cell movements (Kamm, K., et al., Annu. Rev. Physiol., 51, pp. 299-313, 1989; Niggli, V., FEBS Lett., 445, pp. 69-72, 1999; Itoh, K., et al., Biochim. Biophys. Acta., 1136, pp. 52-56, 1992; Kitani, S., et al., Biochem. Biophys. Res. Commun., 183, pp. 48-54, 1992). By measuring the amount of phosphorylated myosin regulatory light chain in the cells according to, for example, the method described in Test Example 2 of the specification, it can be confirmed that the compounds represented by the aforementioned formula (1) and salts thereof decrease the amount of phosphorylated myosin regulatory light chain in the cells.

It is known that the amount of phosphorylated myosin regulatory light chain in the cells is determined by activated states of two reaction routes including Reaction route 1 and Reaction route 2 described below (Fukata, Y., et al., Trends Pharmacol. Sci., 22, pp. 32-39, 2001).

<Reaction Route 1>
Increase of intracellular calcium concentration→Activation of myosin light chain kinase→Increase of amount of phosphorylated myosin regulatory light chain <Reaction Route 2>
Activation of low molecular weight G protein Rho→Activation of Rho kinase→Phosphorylation (inactivation) of myosin phosphatase→Increase of amount of phosphorylated myosin regulatory light chain It is considered that a compound that inhibits Reaction route 1 and/or Reaction route 2 mentioned above has an activity for decreasing the amount of phosphorylated myosin regulatory light chain. In order to estimate whether either or both of Reaction route 1 and Reaction route 2 mentioned above are the target site for the compounds of the present invention represented by the aforementioned formula (1) and salts thereof, effects of the compounds of the present invention represented by the aforementioned formula (1) and salts thereof on increase of intracellular calcium concentration and activity of myosin light chain kinase can be examined according to, for example, the methods described in Test Examples 5 and 6 of the specification. If it can be confirmed, as a result, that the compounds of the present invention and salts thereof give no influence on the increase of intracellular calcium concentration, and do not inhibit the myosin light chain kinase activity, it is readily presumed that the compounds of the formula (1) according to the present invention inhibit Rho kinase of Reaction route 2 mentioned above to decrease the amount of phosphorylated myosin regulatory light chain.

The compounds of the present invention represented by the aforementioned formula (1) and salts thereof inhibit Rho kinase. It is known that Rho kinase plays an important role for cell contraction and cell migration. Other than the above, it has been reported that Rho kinase controls a variety of cellular functions such as morphological change, aggregation, release, production, division, apoptosis, and regulation of gene expression in various cell lines (Fukata, Y., et al., Trends in Pharmacological Sciences, 22, pp. 32-39, 2001; Murata T., et al., J. Hepatotol., 35, pp. 474-481, 2001; Ohnaka, K., et al., Biochem. Biophys. Res. Commun., 287, pp. 337-342, 2001; Yuhong, S., et al., Exp. Cell Res., 278, pp. 45-52, 2002; Arakawa, Y. et al., BIO Clinica, 17(13), pp. 26-28, 2002; Inoue, M. et al., Nat. Med., 10 pp. 712-718, 2004). Therefore, the compounds of the present invention which inhibit Rho kinase exhibit, based on that effect, potent cell contraction inhibitory activity (it can be confirmed by, for example, Test Example 3 etc.), cell morphology change regulating activity, cell migration inhibitory activity (it can be confirmed by, for example, Test Example 4 etc.), cell release inhibitory activity, cell aggregation inhibitory activity, apoptosis inhibitory activity, and activity of regulating gene expression, and are useful as active ingredients of medicaments for prophylactic and/or therapeutic treatment of diseases relating to contraction of various cells, diseases relating to morphological change of various cells, diseases relating to migration of various cells, diseases relating to release from various cells, diseases relating to aggregation of various cells, diseases relating to apoptosis of various cells, and/or diseases relating to abnormal gene expression in various cells.

Examples of the diseases relating to contraction of various cells include, for example, as those relating to vascular smooth muscles, hypertension, arteriosclerosis, cerebral circulatory disturbance, brain function disorder with the aforementioned disease (mental disorder, memory disorder, dementia, delirium, poriomania, dyskinesia and the like), dizziness, auditory disorder, cardiac diseases, pokkuri-byou (sudden death), disturbances of peripheral circulation, disturbances of retinal circulation, renal failure and the like, as those relating to airway smooth muscles, asthma, acute respiratory distress syndrome, pulmonary emphysema, peripheral respiratory tract disease, chronic bronchitis, chronic obstructive pulmonary disease (COPD), and the like (Ueki, J. et al., Gendai Iryo (Contemporary Medical Care), Vol. 34, No. 9, pp. 87-92, 2002), as those relating to digestive tract smooth muscles, vomiting, chronic gastritis, reflux esophagitis, irritable bowel syndrome, and the like, as those relating to smooth muscle cells existing in eyes, glaucoma, and the like, as those relating to vitreum of eyes, vitreoretinal diseases, and the like (Hirayama, K., et al., Preliminary Published Abstracts of the 42nd Congress of the Vitreoretina Society of Japan), as those relating to smooth muscles of bladder and urethra, dysuria, pollakiuria, incontinence and the like, as those relating to smooth muscles of uterus, gestational toxicosis, threatened premature delivery, abortion and the like, and as those relating to smooth muscles of penis, erectile dysfunction. However, the diseases are not limited to the aforementioned examples.

In more detail, examples of hypertension include, for example, essential hypertension, renal hypertension, renovascular hypertension, hypertension during pregnancy, endocrine hypertension, cardiovascular hypertension, neurogenic hypertension, iatrogenic hypertension, pulmonary hypertension and the like, and examples of arteriosclerosis include those in which pathological change is observed in major arteries in whole body such as coronary artery, aorta abdominalis, renal artery, carotid artery, ophthalmic artery, and cerebral artery. Examples of cerebral circulatory disturbance include cerebral thrombosis, cerebral infarction, cerebral hemorrhage, transient brain ischemic attack, hypertensive encephalopathy, cerebral arteriosclerosis, subdural hemorrhage, epidural hemorrhage, subarachnoid hemorrhage, brain hypoxia, cerebral edema, encephalitis, brain abscess, head injury, mental disorder, metabolic intoxication, drug intoxication, transient asphyxia, deep anesthesia in operation and the like. The cardiac diseases include congestive heart failure, acute myocardial infarction, previous myocardial infarction, subendocardial infarction, right ventricular infarction, atypical myocardial infarction, ischemic cardiomyopathy, variant angina pectoris, stable angina, effort angina, coronary vasospasm, postinfarction angina, unstable angina pectoris, arrhythmia, acute cardiac death, and the like.

The peripheral circulatory disturbances include aortic diseases such as Buerger's disease, arteriosclerotic obliteration, and Raynaud's syndrome, venous diseases such as venous thrombosis and thrombophlebitis, hyperviscosity syndrome, frostbite and chilblain, psychoesthesia and hypnagogic disturbance due to feeling of cold, bedsore, cleft, capped skin, and alopecia. Examples of the retinal circulatory disturbances include retinal vascular obstruction, arteriosclerotic retinopathy, vasospastic retinopathy, hypertonic fundus, hypertensive retinopathy, renal retinopathy, hypertensive neuroretinopathy, diabetic retinopathy and the like. Glaucoma includes primary glaucoma, secondary glaucoma, developmental glaucoma, childhood secondary glaucoma and the like. Primary glaucoma is classified into primary open-angle glaucoma (broad sense), primary angle-closure glaucoma, and mixed-type glaucoma, and primary open-angle glaucoma (broad sense) includes primary open-angle glaucoma, normal ocular pressure glaucoma, and ocular hypertension. Secondary glaucoma is classified into secondary open-angle glaucoma, and secondary angle-closure glaucoma (Japanese Journal of Ophthalmology, vol. 107, No. 3, 2003). Further, examples of the vitreoretinal diseases include retinal detachment, retinoschisis, vitreoretinal interface syndrome, retinal pigment epitheliosis, macular hole, phacomatosis, vitreous hemorrhage, retinal circulatory disturbances, and the like (the vitreoretinal diseases mentioned herein include more narrowly classified diseases belonging to each of the categories according to the pathological typology described in Shin Zusetsu Rinsho Ganka Koza (Illustrative Lecture of Clinical Ophthalmology, New Edition), Ed. By Tano, Y., Araie, M., et al, Vol. 5, Vitreoretinal Diseases, MEDICAL VIEW, 2003). The urinary disturbances include dysuria, bladder neck contracture, bladder neck occlusion, urethral syndrome, detrusor sphincter dyssynergia, unstable bladder, chronic prostatitis, chronic cystitis, prostate pain, Hinman's syndrome, Fowler's syndrome, psychogenic dysuria, drug-induced dysuria, dysuria with aging and the like. The erectile dysfunction include organic erectile dysfunction accompanying diseases of diabetes mellitus, arteriosclerosis, hypertension, multiple-sclerotic cardiac diseases, hyperlipidemia, depression and the like, functional erectile dysfunction, erectile dysfunction with aging, erectile dysfunction after radical prostatectomy, and the like.

Examples of the diseases relating to morphological change of various cells include, for example, as those relating to ocular nerve cells, neurodegenerative diseases such as diabetic retinopathy, and glaucoma. Glaucoma refers to the same as that mentioned above.

Examples of the diseases relating to migration of various cells include, for example, as those relating to cancer cells, infiltration and metastasis of cancer. Examples of those relating to vascular endothelial cells include angiogenesis, neovascular maculopathy, macular edema, and the like (the macular diseases mentioned herein include more narrowly classified diseases belonging to each of the categories according to the pathological typology described in Shin Zusetsu Rinsho Ganka Koza (Illustrative Lecture of Clinical Ophthalmology, New Edition), Ed. By Tano, Y., Araie, M., et al, Vol. 5, Vitreoretinal Diseases, MEDICAL VIEW, 2003). Examples of those relating to leukocytes include bacterial infection, allergic hypersensitive diseases (e.g., bronchial asthma, atopic dermatitis, pollinosis, anaphylactic shock and the like), collagen diseases (e.g., systemic lupus erythematodes, multiple sclerosis, Sjogren's disease and the like), angiitis, inflammatory bowel diseases (e.g., ulcerative colitis, Crohn's disease and the like), ischemic reperfusion injury of visceral organs, pneumonia, hepatitis, nephritis, pancreatitis, otitis media, sinusitis, fibrosis, AIDS, adult T-cell leukemia, rejection after organ transplantation (graft versus host reaction), vascular restenosis, and endotoxin shock. Example of the cancer include myelocytic leukemia, lymphatic leukemia, gastric cancer, carcinoma of the colon and rectum, lung cancer, pancreatic carcinoma, hepatic carcinoma, carcinoma of the esophagus, ovarian cancer, breast cancer, skin cancer, head and neck cancer, cancer of the testicles, neuroblastoma, urinary tract epithelial cancer, multiple myeloma, carcinoma uteri, melanoma, brain tumor and the like. Examples of hepatitis include hepatitis by virus infection (e.g., hepatitis B, hepatitis C and the like), and alcoholic hepatitis. Examples of the pneumonia include chronic obstructive pulmonary disease (COPD) and interstitial pneumonia, which may shift to fibrosis. Examples of nephritis include chronic nephritic syndrome, asymptomatic proteinuria, acute nephritic syndrome, nephrotic syndrome, IgA nephropathy, pyelonephritis, glomerulonephritis and the like. Fibrosis include chronic pathological changes characterized by excess deposition of connective tissue proteins in lung, skin, heart, liver, pancreas, kidney and the like. The major pathological conditions are pulmonary fibrosis, hepatic fibrosis, and skin fibrosis. However, fibrosis is not limited to these examples. In hepatic fibrosis, viral hepatitis progresses by infection of, in particular, hepatitis B virus or hepatitis C virus, thus hepatic cells cause necrosis, and thereby fibrosis progresses, which means macronodular hepatic cirrhosis. Further, hepatic fibrosis also includes micronodular hepatic cirrhosis caused by progress of alcoholic hepatitis.

Examples of diseases relating to release of various cells include, as those relating to leukocytes, for example, allergic diseases.

Examples of the allergic diseases include asthma, atopic dermatitis, allergic conjunctivitis, allergic arthritis, allergic rhinitis, allergic pharyngitis and the like.

Examples of the diseases relating to aggregation of various cells include, as those relating to platelets, for example, thrombosis.

Thrombosis include the aforementioned circulatory disturbances of major arteries, major veins and peripheral arteries and veins in whole body, as well as shock caused by hemorrhage, drug intoxication, or endotoxin, disseminated intravascular coagulation (DIC) following it, and multiple organ failure (MOF).

Examples of the diseases relating to apoptosis of various cells include, as those relating to nerves, for example, neurodegenerative diseases such as Alzheimer's disease, Parkinson's disease, diabetic peripheral neuropathy, retinopathy, amyotrophic lateral sclerosis due to cerebral ischemia, pigmented retinitis, and cerebellar degeneration, and glaucoma. Examples of glaucoma are mentioned above. AIDS, and fulminant hepatitis are examples of disease relating to viruses, chronic heart failure due to myocardial ischemia is an example of diseases relating to smooth muscles, and myelodysplasia, aplastic anemia, sideroblastic anemia, and graft-versus-host disease (GVHD) after organ transplantation are examples of diseases relating to blood.

Examples of the diseases relating to abnormal gene expression of various cells include, for example, AIDS as one relating to virus, and cancers as those relating to cancer cells.

Examples of AIDS include acquired immunodeficiency syndrome caused by human immunodeficiency virus (HIV) infection. Examples of the cancers include gastric cancer, carcinoma of the colon and rectum, hepatocellular carcinoma, pancreatic carcinoma, lung cancer, leukemia, malignant lymphoma, carcinoma uteri, ovarian cancer, breast cancer, skin cancer and the like.

Usefulness of the compounds of the present invention represented by the aforementioned formula (1) and salts thereof as well as derivatives thereof useful as prodrugs as active ingredients of medicaments for prophylactic and/or therapeutic treatment of hypertension can be confirmed by, for example, administering the compound to various hypertension model animals or the like. Examples of hypertension animal models include spontaneous hypertensive rat (SHR), renal hypertensive rat, DOCA-salt hypertensive rat and the like (Uehata, M. et al., Nature, 389, 990-994, 1997). A compound is orally, intravenously or intraperitoneally administered to a hypertension model animal at a dose of 0.1 to 1,000 mg/kg, preferably 0.1 to 100 mg/kg, and the diastolic blood pressure is measured. The usefulness as a medicament for hypertension can be confirmed based on an action of reducing the diastolic blood pressure.

Usefulness of the compounds of the present invention represented by the aforementioned formula (1) and salts thereof as well as derivatives thereof useful as prodrugs as active ingredients of medicaments for prophylactic and/or therapeutic treatment of pulmonary hypertension can be confirmed by using, for example, a rat model of pulmonary hypertension created by administering monocrotaline to a rat for 2 to 3 weeks (Ito, K. M. et al., Am. J. Physiol., 279, H1786-H1795, 2000). A compound is orally, intravenously or intraperitoneally administered to a model animal of pulmonary hypertension at a dose of 0.1 to 1,000 mg/kg, preferably 0.1 to 100 mg/kg, and the intrapulmonary pressure is measured. The usefulness as a medicament for pulmonary hypertension can be confirmed based on an action of decreasing the intrapulmonary pressure.

Usefulness of the compounds of the present invention represented by the aforementioned formula (1) and salts thereof as well as derivatives thereof useful as prodrugs as active ingredients of medicaments for prophylactic and/or therapeutic treatment of arteriosclerosis can be confirmed by using, for example, a rat model of L-NAME-induced arteriosclerosis (Cir. Res. 89(5):415-21, 2001), a rat model of balloon-induced neointimal formation (Sawada N. et al., Circulation 101 (17):2030-3, 2000) or the like. A compound is orally, intravenously or intraperitoneally administered to a model animal of arteriosclerosis at a dose of 0.1 to 1,000 mg/kg, preferably 0.1 to 100 mg/kg, and thickening of arteries is observed. The usefulness as a medicament for arteriosclerosis can be confirmed based on an action of suppressing neointimal formation in arteries.

Usefulness of the compounds of the present invention represented by the aforementioned formula (1) and salts thereof as well as derivatives thereof useful as prodrugs as active ingredients of medicaments for prophylactic and/or therapeutic treatment of cerebral circulatory dysfunction can be confirmed by using, for example, a gerbil model of hippocampal neuronal death (Kirino et al., Brain Res., 239, 57-69, 1982) or the like. A compound is orally, intravenously or intraperitoneally administered to the model animal at a dose of 0.1 to 1,000 mg/kg, preferably 0.1 to 100 mg/kg, and the amount of energy-related substances and survival period of gerbil, or inhibition of late-onset of neuronal death is measured. The usefulness as a medicament for cerebral circulatory dysfunction can be confirmed based on actions for maintaining, improving and activating cerebral metabolic ability, brain and nerve protective action, and action for suppressing formation of cerebral infarction.

Usefulness of the compounds of the present invention represented by the aforementioned formula (1) and salts thereof as well as derivatives thereof useful as prodrugs as active ingredients of medicaments for prophylactic and/or therapeutic treatment of cardiac diseases can be confirmed by using, for example, a rat model of myocardial infarction based on the ligation of artery (Xia Q. G. et al., Cardiovasc. Res., 49(1): 110-7, 2001) or the like. Effectiveness as a medicament for cardiac diseases can be confirmed by orally, intravenously or intraperitoneally administering a compound to the model animal at a dose of 0.1 to 1,000 mg/kg, preferably 0.1 to 100 mg/kg, and observing a cardiac tissue fixed by formalin perfusion after ischemic reperfusion.

Usefulness of the compounds of the present invention represented by the aforementioned formula (1) and salts thereof as well as derivatives thereof useful as prodrugs as active ingredients of medicaments for prophylactic and/or therapeutic treatment of disturbances of peripheral circulation can be confirmed by using, for example, a rat model of bedsore (Pierce S. M. et al., Am. J. Physiol. Heart Circ. Physiol., 281(1):H67-74, 2001) or the like. Effectiveness as a medicament for bedsore (peripheral circulatory disturbance) can be confirmed by orally, intravenously or intraperitoneally administering a compound to the model animal at a dose of 0.1 to 1,000 mg/kg, preferably 0.1 to 100 mg/kg, compressing the hind leg skin at a pressure of 50 mmHg, and then observing a tissue of necrotic area of the lesion or measuring epithelial blood flow of the same.

Usefulness of the compounds of the present invention represented by the aforementioned formula (1) and salts thereof as well as derivatives thereof useful as prodrugs as active ingredients of medicaments for prophylactic and/or therapeutic treatment of disturbances of retinal circulation can be confirmed by using, for example, rabbit model of rose bengal-mediated argon laser retinal vein photothrombosis (Jpn. J. Ophthalmol., 45(4):359-62, 2001), or the like. Effectiveness as a medicament for retinal circulatory disturbance can be confirmed by ocular instillation, orally, intravenously, intraperitoneally or intraocularly (direct administration to vitreum, retina and the like) administering a compound to the model animal at a dose of 0.1 to 1,000 mg/kg, preferably 0.1 to 100 mg/kg, comparing the degree of retinal circulatory disturbance with that of a control based on count of laser spots.

Usefulness of the compounds of the present invention represented by the aforementioned formula (1) and salts thereof as well as derivatives thereof useful as prodrugs as active ingredients of medicaments for prophylactic and/or therapeutic treatment of renal failure can be confirmed by using, for example, a rat model of one-kidney, one-clip renal hypertension (Kiso to Rinsho, 30, 511-524, 1996). Effectiveness as a medicament for renal failure can be confirmed by orally, intravenously or intraperitoneally administering a compound to the model animal at a dose of 0.1 to 1,000 mg/kg, preferably 0.1 to 100 mg/kg, and measuring the diuretic effect.

Usefulness of the compounds of the present invention represented by the aforementioned formula (1) and salts thereof as well as derivatives thereof useful as prodrugs as active ingredients of medicaments for prophylactic and/or therapeutic treatment of asthma such as bronchial asthma can be confirmed by using, for example, suppression of constriction of a trachea isolated from an animal (Kunihiko Iizuka, Allergy, 47:943, 1998; Kunihiko Iizuka, Akihiro Yoshii, Jpn. J. Respirol. Soc., 37:196, 1999.), antigen-stimulation induced respiratory tract constriction model, antigen-stimulation induced chronic respiratory tract inflammation model (Henderson, W. R., et al., Am. J. Respir. Cric. Care Med., 165(1), pp. 108-116, 2002), constriction elicitor-induced respiratory tract constriction model (histamine, acetylcholine and the like are generally used, Daniela, S. et al., J. Pharmacol. Exp. Ther., 297(1), pp. 280-290, 2001), LPS-induced acute respiratory tract inflammation model, inhibition of human peripheral blood leucocyte migration and the like. The usefulness as a medicament for bronchial asthma can be confirmed by orally, intravenously or intraperitoneally administering a compound to the model animal at a dose of 0.1 to 1,000 mg/kg, preferably 0.1 to 100 mg/kg, and measuring elevation of airway resistance caused by tracheal constriction or relaxation, antigen stimulation, histamine inhalation, or acetylcholine inhalation, migrating leucocyte count in bronchoalveolar lavage fluid and the like, or performing analysis of histological inflammatory findings.

Usefulness of the compounds of the present invention represented by the aforementioned formula (1) and salts thereof as well as derivatives thereof useful as prodrugs as active ingredients of medicaments for prophylactic and/or therapeutic treatment of irritable bowel syndrome can be confirmed by administering the compounds to a stress burden model animal, or the like. Examples of the stress burden model animal include, for example, a rat model of arresting stress (Miyata, K. et al., J. Pharmacol. Exp. Ther., 259, pp. 815-819, 1991), a CRH-administered rat model (Miyata, K. et al., Am. J. Physiol., 274, G827-831, 1998), and the like. A compound is orally, intravenously or intraperitoneally administered to a stress burden model animal at a dose of 0.1 to 1,000 mg/kg, preferably 0.1 to 100 mg/kg, and counting the number of fecal pellets. The usefulness as a medicament for curative medicine of irritable bowel syndrome can be confirmed based on effect for reducing the number of fecal pellets.

Usefulness of the compounds of the present invention represented by the aforementioned formula (1) and salts thereof as well as derivatives thereof useful as prodrugs as active ingredients of medicaments for prophylactic and/or therapeutic treatment of glaucoma can be confirmed by, for example, measuring intraocular-pressure of a rabbit, cat or monkey after administration of the medicaments by instillation (Surv. Ophthalmol. 41:S9-S18, 1996). The usefulness as a medicament for glaucoma can be confirmed by ocular instillation, or orally, intravenously, intraperitoneally or intraocularly (direct administration to anterior chamber, vitreum and the like) administering a compound to a locally anesthetized rabbit or monkey model animal at a dose of 0.1 to 1,000 mg/kg, preferably 0.1 to 100 mg/kg, and measuring the intraocular pressure over time using a tonometer to evaluate degree of intraocular pressure reducing activity, or sustained intraocular pressure reducing activity.

Usefulness of the compounds of the present invention represented by the aforementioned formula (1) and salts thereof as well as derivatives thereof useful as prodrugs as active ingredients of medicaments for prophylactic and/or therapeutic treatment of vitreoretinal diseases can be confirmed by a known method, for example, the methods described in Oshima, Y. et al., Gene Ther., 9(18), pp. 1214-20, 2002; and Ito, S., et al., Graefes Arch. Clin. Exp. Ophthalmol., 237(8), pp. 691-6., 1999. The usefulness as a medicament for vitreoretinal diseases can be confirmed by ocular instillation, orally, intravenously, intraperitoneally or intraocularly administering (direct administration to vitreum or retina) a compound to a rabbit in which retinal detachment is induced by cell transfer to the vitreoretinal interface, vitrectomy, or the like at a dose of 0.1 to 1,000 mg/kg, preferably 0.1 to 100 mg/kg, and evaluating amelioration of the pathological conditions on the basis of histological analysis.

Usefulness of the compounds of the present invention represented by the aforementioned formula (1) and salts thereof as well as derivatives thereof useful as prodrugs as active ingredients of medicaments for prophylactic and/or therapeutic treatment of dysuria can be confirmed by using, for example, a model of rhythmic bladder contraction (Kaneko S. et al., Folia Pharmacol. Japon, Vol. 93(2), 55-60, 1989; Nomura N. et al., Folia Pharmacol. Japon, Vol. 94(3), 173, 1989) or the like. The usefulness as a medicament for urinary disturbance can be confirmed by orally, intravenously or intraperitoneally administering a compound to an anesthetized rat or dog at a dose of 0.1 to 1,000 mg/kg, preferably 0.1 to 100 mg/kg, and measuring the number of rhythmic contraction of filled bladder (micturition).

Usefulness of the compounds of the present invention represented by the aforementioned formula (1) and salts thereof as well as derivatives thereof useful as prodrugs as active ingredients of medicaments for prophylactic and/or therapeutic treatment of erectile dysfunction can be confirmed by a known method, for example, the method described in J. Uro., 151, 797-800, 1994. A compound is dissolved in a hydrophilic ointment, 30 mg of the ointment was applied to a rat penis, and the rat is held in an acrylic cylinder for 10 minutes so that the rat was not able to lick the penis. The rat is moved to an acrylic cage of 30 cm×30 cm, and videotaped for 60 minutes from the side and the bottom of the cage. Then, the number of erection of the penis per 30 minutes can be counted to confirm the usefulness as a medicament for erectile dysfunction.

Usefulness of the compounds of the present invention represented by the aforementioned formula (1) and salts thereof as well as derivatives thereof useful as prodrugs as active ingredients of medicaments for suppressing cancer metastasis and invasion can be confirmed by, for example, the method described in Cancer Res., 55:3551-3557 (1995). The usefulness as a medicament for cancer metastasis and invasion can be confirmed by orally, intravenously or intraperitoneally administering a compound at a dose of 0.1 to 1,000 mg/kg, preferably 0.1 to 100 mg/kg, to a nude mouse transplanted with human cancer cell suspension transplantable to immunodeficient mice at the same site (spontaneous metastasis model), and measuring the metastasized lesion.

Usefulness of the compounds of the present invention represented by the aforementioned formula (1) and salts thereof as well as derivatives thereof useful as prodrugs as active ingredients of medicaments for prophylactic and/or therapeutic treatment of collagen disease can be confirmed by using, for example, collagen-induced arthritis model of a rat or mouse (Griffith, M. M. et al., Arthritis Rheumatism, 24:781, 1981; Wooley, P. H. et al., J. Exp. Med., 154:688, 1981). The usefulness as a medicament for collagen disease can be confirmed by orally, intravenously or intraperitoneally administering a compound to the model mouse or rat at a dose of 0.1 to 1,000 mg/kg, preferably 0.1 to 100 mg/kg, and measuring footpad volume or progression of bone destruction.

Usefulness of the compounds of the present invention represented by the aforementioned formula (1) and salts thereof as well as derivatives thereof useful as prodrugs as active ingredients of medicaments for prophylactic and/or therapeutic treatment of inflammatory bowel disease can be confirmed by using a rat model of idiopathic ulcerative colitis induced by subserosal injection of acetic acid, a model of sodium dextransulfate-induced colitis, a model of trinitrobenzenesulfonic acid-induced colitis (Kojima et al., Folia. Pharmacol. Jpn., 118, 123-130, 2001), or the like. The usefulness as a medicament for inflammatory bowel disease can be confirmed by, for example, orally, intravenously or intraperitoneally administering a compound at a dose of 0.1 to 1,000 mg/kg, preferably 0.1 to 100 mg/kg, to a rat in which colitis is induced by intraintestinal injection of acetic acid, dissecting the rat after several days to two weeks, then observing and measuring the ulcer area of the intestinal epithelium, and amount of leucotriene B4 in a colon homogenate.

Usefulness of the compounds of the present invention represented by the aforementioned formula (1) and salts thereof as well as derivatives thereof useful as prodrugs as active ingredients of medicaments for prophylactic and/or therapeutic treatment of pneumonia can be confirmed by using, for example, a mouse model of OVA-induced chronic pneumonia (Henderson W. R. et al., Am. J. Respir. Crit. Care Med., 165(1):108-16, 2002), a mouse model of LPS-induced acute pneumonia (Gonzales de Moraes, V L., et al., Br. J. Pharmacol., 123, pp. 631-6, 1998), or the like. Effectiveness as a medicament for pneumonia can be confirmed by orally, intravenously or intraperitoneally administering a compound to the model animal at a dose of 0.1 to 1,000 mg/kg, preferably 0.1 to 100 mg/kg, and evaluating change in number of eosinophils or monocytes in the pulmonary cavity, and histological findings of inflammation.

Usefulness of the compounds of the present invention represented by the aforementioned formula (1) and salts thereof as well as derivatives thereof useful as prodrugs as active ingredients of medicaments for prophylactic and/or therapeutic treatment of hepatitis can be confirmed by using a mouse model of endotoxin-induced liver injury according to, for example, the method described in J. Immunol., 159, 3961-3967, 1997. The usefulness as a medicament for hepatitis can be confirmed by orally, intravenously or intraperitoneally administering a compound to the mouse model of endotoxin-induced liver injury at a dose of 0.1 to 1,000 mg/kg, preferably 0.1 to 100 mg/kg, and measuring the plasmic transaminase level or amount of hydroxyproline in a hepatic tissue, which are indicators of liver function, or performing histological analysis.

Usefulness of the compounds of the present invention represented by the aforementioned formula (1) and salts thereof as well as derivatives thereof useful as prodrugs as active ingredients of medicaments for prophylactic and/or therapeutic treatment of pancreatitis can be confirmed by using, for example, a mouse model of caerulein-inducted acute pancreatitis (Niedirau, C. et al., Gastroenterology 88 (5 Pt 1):1192-204, 1985) or the like. Effectiveness as a medicament for pancreatitis can be confirmed by orally, intravenously or intraperitoneally administering a compound to the model animal at a dose of 0.1 to 1,000 mg/kg, preferably 0.1 to 100 mg/kg, and measuring the serum amylase activity, or weight of pancreas.

Usefulness of the compounds of the present invention represented by the aforementioned formula (1) and salts thereof as well as derivatives thereof useful as prodrugs as active ingredients of medicaments for prophylactic and/or therapeutic treatment of nephritis can be confirmed by using, for example, a nephritis rat model prepared by administering anti-GBM antibodies obtained by immunizing a rabbit with a GBM fraction derived from a rat to a rat (WO01/56988), or the like. A compound is orally, intravenously or intraperitoneally administered to the nephritis rat model at a dose of 0.1 to 1,000 mg/kg, preferably 0.1 to 100 mg/kg, and the urinary proteins are measured. The usefulness as a medicament for nephritis can be confirmed based on an action of reducing the urinary protein level.

Usefulness of the compounds of the present invention represented by the aforementioned formula (1) and salts thereof as well as derivatives thereof useful as prodrugs as active ingredients for suppressing allograft rejection at the time of organ transplantation can be confirmed by using, for example, a rat model of skin transplantation, rat model of heart transplantation (Ochiai T. et al., Transplant. Proc., 19, 1284-1286, 1987), or the like. Effectiveness as a medicament for suppressing rejection at the time of organ transplantation can be confirmed by orally, intravenously or intraperitoneally administering a compound to a model animal at a dose of 0.1 to 1,000 mg/kg, preferably 0.1 to 100 mg/kg, and estimating the graft survival ratio.

Usefulness of the compounds of the present invention represented by the aforementioned formula (1) and salts thereof as well as derivatives thereof useful as prodrugs as active ingredients of medicaments for prophylactic and/or therapeutic treatment of chronic obstructive pulmonary disease (COPD) can be confirmed by using, for example, suppression of constriction of a trachea isolated from an animal, an antigen stimulation-induced respiratory tract constriction model, a constriction elicitor-induced respiratory tract constriction model (histamine, acetylcholine and the like are generally used), antigen stimulation-induced chronic respiratory tract inflammation model, a mouse model of LPS-induced acute respiratory tract inflammation, a tobacco smoke exposition model (Fuchigami J. et al., 73rd Meeting of Japanese Pharmacological Society, Collection of Abstracts, 2000), inhibition of chemotaxis of human peripheral leucocytes, or the like. The usefulness as a medicament for COPD can be confirmed by orally, intravenously or intraperitoneally administering a compound to any of the model animals mentioned above at a dose of 1 to 1,000 mg/kg, preferably 1 to 100 mg/kg, and measuring tracheal constriction or relaxation, change in airway resistance, migrating leucocyte count in bronchoalveolar lavage fluid, change in number of number of eosinophils or monocytes in the pulmonary cavity, histological findings of inflammation, or the like.

Usefulness of the compounds of the present invention represented by the aforementioned formula (1) and salts thereof as well as derivatives thereof useful as prodrugs as active ingredients of medicaments for prophylactic and/or therapeutic treatment of hepatic fibrosis can be confirmed by using a carbon tetrachloride-induced hepatic fibrosis model according to, for example, the method described in J. Hepatol., 35(4), 474-81, 2001. The usefulness as a medicament for hepatic fibrosis can be confirmed by orally, intravenously or intraperitoneally administering a compound to the hepatic fibrosis model at a dose of 0.1 to 1,000 mg/kg, preferably 0.1 to 100 mg/kg, and measuring the plasmic transaminase level, or amount of hydroxyproline in a hepatic tissue, which are indicators of liver function, or performing histological analysis.

Usefulness of the compounds of the present invention represented by the aforementioned formula (1) and salts thereof as well as derivatives thereof useful as prodrugs as active ingredients of medicaments for prophylactic and/or therapeutic treatment of pulmonary fibrosis can be confirmed by using an animal model of Bleomycin-induced pulmonary fibrosis according to the method described in, for example, Am. J. Respir. Crit. Care Med., 163(1), pp. 210-217, 2001. The usefulness as a medicament for pulmonary fibrosis can be confirmed by orally, intravenously or intraperitoneally administering a compound to the pulmonary fibrosis mouse model at a dose of 0.1 to 1,000 mg/kg, preferably 0.1 to 100 mg/kg, and measuring respiratory function, or amount of hydroxyproline in a pulmonary tissue.

Usefulness of the compounds of the present invention represented by the aforementioned formula (1) and salts thereof as well as derivatives thereof useful as prodrugs as active ingredients of medicaments for prophylactic and/or therapeutic treatment of allergy can be confirmed by using an atopic dermatitis mouse model or the like according to the method described in, for example, Allergy, 50 (12) 1152-1162, 2001. The usefulness as a medicament for allergy can be confirmed by orally, intravenously or intraperitoneally administering a compound to an NC/Nga mouse pretreated with a surfactant or an organic solvent at a dose of 0.1 to 1,000 mg/kg, preferably 0.1 to 100 mg/kg, when eruption is induced in the mouse by using housedust mite antigens, and measuring the plasmic IgE level, number of eosinophils and the like.

Usefulness of the compounds of the present invention represented by the aforementioned formula (1) and salts thereof as well as derivatives thereof useful as prodrugs as active ingredients of medicaments for prophylactic and/or therapeutic treatment of thrombosis can be confirmed by using, for example, a rabbit model of experimentally-induced venous thrombus (Maekawa, T. et al., Trombos. Diathes. Haemorrh., 60, pp. 363-370, 1974), or the like. Effectiveness as a medicament for thrombosis can be confirmed by orally, intravenously or intraperitoneally administering a compound to the model animal at a dose of 0.1 to 1,000 mg/kg, preferably 0.1 to 100 mg/kg, and estimating the incidence of thrombus.

Usefulness of the compounds of the present invention represented by the aforementioned formula (1) and salts thereof as well as derivatives thereof useful as prodrugs as active ingredients of medicaments for prophylactic and/or therapeutic treatment of Alzheimer's disease can be confirmed by using, for example, an in vitro culture system of nerve cells derived from rat embryos (Yankner, B. A. et al., Science, 250, pp. 279-282, 1990), or the like. Effectiveness as a medicament for Alzheimer's disease can be confirmed by adding 0.1 to 1 mM, preferably 0.1 to 100 µM, of a compound, and measuring suppression ratio for cell death induced by beta-amyloid proteins.

Usefulness of the compounds of the present invention represented by the aforementioned formula (1) and salts thereof as well as derivatives thereof useful as prodrugs as active ingredients of medicaments for prophylactic and/or therapeutic treatment of AIDS can be confirmed by using, for example, a rhesus monkey model of SIV-infection (Crub S. et al., Acta Neuropathol., 101(2), pp. 85-91, 2001) or the like. Effectiveness as a medicament for AIDS can be confirmed by orally, intravenously or intraperitoneally administering a compound to the model animal at a dose of 0.1 to 1,000 mg/kg, preferably 0.1 to 100 mg/kg, and quantifying the SIV mRNA level in blood.

Usefulness of the compounds of the present invention represented by the aforementioned formula (1) and salts thereof as well as derivatives thereof useful as prodrugs as active ingredients of medicaments for prophylactic and/or therapeutic treatment of cancer can be confirmed by using, for example, a mouse model of ultraviolet ray irradiation-induced skin cancer, a nude mouse model of tumor xenograft (Orengo I. F. et al., Arch Dermatol., 138(6), pp. 823-4, 2002; Ki D. W. et al., Anticancer Res., 22(2A), pp. 777-88, 2002) or the like. Effectiveness as a medicament for cancer can be confirmed by orally, intravenously or intraperitoneally administering a compound to a model animal at a dose of 0.1 to 1,000 mg/kg, preferably 0.1 to 100 mg/kg, and observing progression or reduction of the grafted cancer tissues on the body surface.

Further, when the compounds of the present invention or salts thereof were orally administered to mice every day at a dose of 1 mg/kg for 5 days, death was not observed. Furthermore, even when the compounds of the present invention or salts thereof were continuously instilled to rabbit eyes in a volume of 50 µl at 3 mM, severe eye irritation was not observed. In a general genotoxicity test utilizing salmonella and skin irritation test, they gave negative results. On the basis of the results of these tests, the compounds the present invention or salts thereof have no particular problem also in safety or toxicity. Furthermore, the compounds of the present invention and salts thereof show superior solubility. The compounds of the present invention and salts thereof also have only weak inhibition to the P-450 enzymes.

Furthermore, the compounds of the present invention and salts thereof as well as derivatives thereof useful as prodrugs are excellent in safety (various toxicities and safety pharmacology), pharmacokinetic performance, and the like, and thus usefulness thereof as active ingredients of medicaments can be confirmed.

Examples of tests concerning safety include, for example, those listed below. However, they are not limited to these examples. Examples include cytotoxic tests (tests using HL60 cells, hepatocytes and the like), genotoxicity tests (Ames test, mouse lymphoma TK test, chromosomal aberration test, micronucleus test and the like), skin sensitization tests (Buehler method, GPMT method, APT method, LLNA test and the like), skin photosensitization tests (adjuvant and strip method and the like), eye irritation tests (single instillation, short-term continuation instillation, repetitive instillation and the like), safety pharmacology tests for the cardiovascular system (telemetry method, APD method, hERG inhibition assay and the like), safety pharmacology tests for the central nervous system (FOB method, modified version of Irwin method and the like), safety pharmacology tests for the respiratory system (measurement method utilizing a respiratory function measuring apparatus, measurement method utilizing a blood gas analyzer and the like), general toxicity tests, reproductive and developmental toxicity tests, and the like.

Examples tests concerning pharmacokinetic performance include, for example, those listed below. However, they are not limited to these examples. Examples include cytochrome P450 enzyme inhibition or induction tests, cell permeability tests (tests using CaCO-2 cells, MDCK cells and the like), drug transporter ATPase assay, oral absorption tests, blood concentration transition measurement tests, metabolism tests (stability test, metabolite molecular species test, reactivity test and the like), solubility tests (solubility test based on turbidity method and the like), and the like.

Usefulness of the compounds of the present invention represented by the aforementioned formula (1) and salts thereof as well as derivatives thereof useful as prodrugs as active ingredients of medicaments can be confirmed by performing, for example, a cytotoxic test. Examples of the cytotoxic test include methods utilizing various cultured cells, for example, HL-60 cells, which are human preleukemia cells, primary isolated cultured cells of hepatocytes, a neutrophil fraction prepared from human peripheral blood, and the like. Although the test can be carried out by the method described below, the method is not limited only to the following description. Cells are prepared as a suspension of $10^5$ to $10^7$ cells/ml, and the suspension is added to microtubes or microplate in a volume of 0.01 to 1 mL. To the suspension, a solution dissolving a compound is added in a volume of 1/100 to 1 fold volume of the cell suspension, and the cells were cultured in a cell culture medium having a final concentration of the compound of 0.001 to 1000 μM for 30 minutes to several days at 37° C. under 5% $CO_2$. After terminating the culture, survival rate of the cells is evaluated by using the MTT method, WST-1 method (Ishiyama, M., et al., In Vitro Toxicology, 8, p. 187, 1995), or the like. By measuring cytotoxicity of the compound to cells, usefulness as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a genotoxicity test. Examples of the genotoxicity test include, the Ames test, mouse lymphoma TK test, chromosomal aberration test, micronucleus test, and the like. The Ames test is a method of determining reverse mutation by culturing *Salmonella* or *Escherichia* bacteria of designated species on a culture dish or the like added with a compound (refer to IYAKUSHIN (Notification by the chief of Evaluation and Licensing Division, Pharmaceutical and Medical Safety Bureau, Ministry of Health, Labor and Welfare, Japan), No. 1604, 1999, "Guideline for Genotoxicity Test", II-1. Genotoxicity Test, and the like). The mouse lymphoma TK test is a genetic mutation ability detection test targeting the thymidine kinase gene of the mouse lymphoma L5178Y cell (refer to IYAKUSHIN No. 1604, 1999, "Guideline for Genotoxicity Test", II-3. Mouse Lymphoma TK Test; Clive, D. et al., Mutat. Res., 31, pp. 17-29, 1975; Cole, J., et al., Mutat. Res., 111, pp. 371-386, 1983, and the like). The chromosomal aberration test is a method for determining activity of causing chromosomal aberration by culturing mammalian cultured cells in the presence of a compound, then after fixation of the cells, staining and observing chromosomes of the cells (refer to IYAKUSHIN No. 1604, 1999, "Guideline for Genotoxicity Test", II-2. Chromosomal Aberration Test Utilizing Mammalian Cultured Cells, and the like). The micronucleus test is a method of evaluating micronucleus forming ability caused by chromosomal aberration, and a method of using a rodent (in vivo test) (IYAKUSHIN No. 1604, 1999, "Guideline for Genotoxicity Test", II-4. Micronucleus Test Using Rodent; Hayashi M. et al., Mutat. Res., 312, pp. 293-304, 1994; Hayashi, M. et al., Environ. Mol. Mutagen., 35, pp. 234-252, 2000), a method of using cultured cells (in vitro test) (Fenech M., et al., Mutat. Res., 147, pp. 29-36, 1985; Miller, B., et al., Mutat. Res., 392, pp. 45-59, 1997, and the like) are available. By elucidating genotoxicity of the compounds based on one or more of these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a skin sensitization test. As the skin sensitization test using guinea pig, the Buehler method (Buehler, E. V., Arch. Dermatol., 91, pp. 171-177, 1965), GPMT method (maximization method, Magnusson B., et al., J. Invest. Dermatol., 52, pp. 268-276, 1969), APT method (adjuvant and patching method (Sato, Y. et al., Contact Dermatitis, 7, pp. 225-237, 1981)) and the like are available. Further, as the skin sensitization test using mouse, the LLNA (local lymph node assay) method (OECD Guideline for the testing of chemicals 429, skin sensitization 2002; Takeyoshi, M. et al., Toxicol. Lett., 119 (3), pp. 203-8, 2001; Takeyoshi, M. et al., J. Appl. Toxicol., 25 (2), pp. 129-34, 2005) and the like are available. By elucidating skin sensitization property of the compounds based on one or more of these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a skin photosensitization test. Examples of the skin photosensitization test include a skin photosensitization test using guinea pig (refer to "Drug Nonclinical Test Guideline Commentary 2002", Yakuji Nippo, published on 2002, 1-9: Skin Photosensitization Test, and the like), and the like, and examples of the method include the adjuvant and strip method (Ichikawa, H. et al., J. Invest. Dermatol., 76, pp. 498-501, 1981), Harber method (Harber, L. C., Arch. Dermatol., 96, pp. 646-653, 1967), Horio method (Horio, T., J. Invest. Dermatol., 67, pp. 591-593, 1976), Jordan method (Jordan, W. P., Contact Dermatitis, 8, pp. 109-116, 1982), Kochever method (Kochever, I. E. et al., J. Invest. Dermatol., 73, pp. 144-146, 1979), Maurer method (Maurer, T. et al., Br. J. Dermatol., 63, pp. 593-605, 1980), Morikawa method (Morikawa, F. et al., "Sunlight and Man", Tokyo Univ. Press, Tokyo, pp. 529-557, 1974), Vinson method (Vinson, L. J., J. Soc. Cosm. Chem., 17, pp. 123-130, 1966), and the like. By elucidating skin photosensitization property of the compounds based on one or more of these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, an eye irritation test. Examples of the eye irritation test include the single instillation test method using rabbit eyes, monkey eyes, and the like (instillation of one time), short term continuous instillation test method (instillation of multiple times in a short period of time with equal intervals), repetitive instillation test method (repetitive intermittent instillation over several days to 10 days), and the like, and a method of evaluating eye irritation symptoms during a certain period of time after instillation according to the improved Draize scores (Fukui, N. et al., Gendai no Rinsho, 4 (7), pp. 277-289, 1970) and the like are available. By elucidating eye irritation of the compounds based on one or more of these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a safety pharmacology test for the cardiovascular system. Examples of the safety pharmacology test for the cardiovascular system include the telemetry method (method for measuring influence of administration of a compound under no anesthetization on electrocardiogram, heart rate, blood pressure, blood stream, and the like (Electrocardiographic, Echocardiographic, Blood Pressure and Pathological Tests of Animals for Fundamental and Clinical Medicine, edited by Sugano S., Tsubone H., Nakada Y., published on 2003, Maruzen), APD method (method for measuring cardiac muscle cell action potential retention time (Muraki, K. et al., AM. J. Physiol., 269, H524-532, 1995; Ducic, I. et al., J. Cardiovasc. Pharmacol., 30 (1), pp. 42-54, 1997)), hERG inhibition evaluation method (patch clamping method (Chachin, M. et al., Nippon Yakurigaku Zasshi, 119, pp. 345-351, 2002), binding assay method (Gilbert, J. D. et al., J. Pharm. Tox. Methods, 50, pp. 187-199, 2004), Rb$^+$ efflex assay method (Cheng, C. S. et al., Drug Develop. Indust. Pharm., 28, pp. 177-191, 2002), Membrane potential assay method (Dorn, A. et al., J. Biomol. Screen., 10, pp. 339-347, 2005), and the like. By elucidating influence on the cardiovascular system of the compounds based on one or more of these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a safety pharmacology test for the central nervous system. Examples of the safety pharmacology test for the central nervous system include the FOB method (Functional Observational Battery, Mattson, J. L. et al., J. American College of Technology, 15 (3), pp. 239-254, 1996)), modified version of Irwin method (method for evaluating observation of general symptoms and behavior (Irwin, S., Comprehensive Observational Assessment (Berl.) 13, pp. 222-257, 1968)), and the like. By elucidating action on the central nervous system of the compounds based on one or more of these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a safety pharmacology test for the respiratory system. Examples of the safety pharmacology test for the respiratory system include the measurement method using a respiratory function measuring apparatus (method of measuring respiration rate, single ventilation volume, minute ventilation and the like, Drorbaugh, J. E. et al., Pediatrics, 16, pp. 81-87, 1955; Epstein, M. A. et al., Respir. Physiol., 32, pp. 105-120, 1978), measurement method of using a blood gas analyzer (method of measuring blood gas, hemoglobin oxygen saturation and the like, Matsuo, S., Medicina, 40, pp. 188-, 2003), and the like. By elucidating action on the respiratory system of the compounds based on one or more of these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a general toxicity test. The general toxicity test is a method of orally or intravenously administering a compound dissolved or suspended in an appropriate solvent once or repetitively (over several days) to a rodent such as rat and mouse or non-rodent such as monkey and dog, and evaluating observation of general conditions, clinicochemical changes, pathohistological changes, and the like of the administered animal. By elucidating general toxicity of a compound based on these methods, usefulness of the compound as an active ingredient of medicament can be confirmed.

Usefulness of the compounds of the present invention represented by the aforementioned formula (1) and salts thereof as well as derivatives thereof useful as prodrugs as active ingredients of medicaments can be confirmed by performing, for example, a reproductive and developmental toxicity test. The reproductive and developmental toxicity test is a test for examining induction of harmful effect by a compound on the reproductive and developmental processes by using a rodent such as rat and mouse or non-rodent such as monkey and dog (refer to "Drug Nonclinical Test Guideline Commentary 2002", Yakuji Nippo, published on 2002, 1-6: Reproductive and Developmental Toxicity Test and the like). Examples of the reproductive and developmental toxicity test include tests concerning fertility and early embryogenesis up to nidation, tests concerning development and maternal functions before and after birth, tests concerning embryogenesis and fetal development (refer to IYAKUSHIN No. 1834, 2000, Appendix, "Guideline for Drug Toxicity Test", [3] Reproductive and Developmental Toxicity Test and the like), and the like. By elucidating reproductive and developmental toxicity of a compound based on these methods, usefulness of the compound as an active ingredient of medicament can be confirmed.

Usefulness of the compounds of the present invention represented by the aforementioned formula (1) and salts thereof as well as derivatives thereof useful as prodrugs as active ingredients of medicaments can be confirmed by performing, for example, a cytochrome P450 enzyme inhibition or induction test (Gomez-Lechon, M. J. et al., Curr. Drug Metab., 5 (5), pp. 443-462, 2004). Examples of the cytochrome P450 enzyme inhibition or induction test include, for example, the method of determining in vitro whether a compound inhibits activity of a cytochrome P450 enzyme by using a cytochrome P450 enzyme of each molecular species purified from cells or prepared by using a genetic recombinant, or a human P450 expression system microsome (Miller, V. P. et al., Ann. N.Y. Acad. Sci., 919, pp. 26-32, 2000), method of measuring changes of expression of cytochrome P450 enzyme of each molecular species and enzyme activity by using human liver microsomes or disrupted cell suspension (Hengstler, J. G. et al., Drug Metab. Rev., 32, pp. 81-118, 2000), method of extracting RNA from human hepatocytes exposed to a compound, and comparing mRNA expression amount with that of a control to investigate enzyme induction ability of the compound (Kato, M. et al., Drug Metab. Pharmacokinet., 20 (4), pp. 236-243, 2005), and the like. By elucidating action of the compounds on inhibition or induction of cytochrome P450 enzyme based on one or more of these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a cell permeability test. Examples of the cell permeability test include, for example, the method of measuring cell membrane permeability of a compound in an in vitro cell culture system using CaCO-2 cells (Delie, F. et al., Crit. Rev. Ther. Drug Carrier Syst., 14, pp. 221-286, 1997; Yamashita, S. et al., Eur. J. Pham. Sci., 10, pp. 195-204, 2000; Ingels, F. M. et al., J. Pham. Sci., 92, pp. 1545-1558, 2003), method of measuring cell membrane permeability of a compound in an in vitro cell culture system using MDCK cells (Irvine, J. D. et al., J. Pham. Sci., 88, pp. 28-33, 1999), and the like. By elucidating cell permeability of the compounds based on one or more of these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a drug transporter ATPase assay. Examples of the drug transporter ATPase assay include the method of examining whether a compound is a substrate of P-glycoprotein (P-gp) by using a P-gp baculovirus expression system (Germann, U. A., Methods Enzymol., 292, pp. 427-41, 1998), and the like. By elucidating action of the compounds on P-gp based on these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, an oral absorption test. Examples of the oral absorption test include a method of orally administering a compound of a certain amount dissolved or suspended in an appropriate solvent to a rodent, monkey, dog or the like, and measuring blood level of the compound after the oral administration over time to evaluate blood transition of the compound by oral administration using the LC-MS/MS method ("Newest Mass Spectrometry for Life Science", Kodansha Scientific, 2002, edited by Harada K. et al, and the like), and the like. By elucidating oral absorption of the compounds based on these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a blood concentration transition measurement test. Examples of the blood concentration transition measurement test include a method of orally or parenterally (e.g., intravenously, intramuscularly, intraperitoneally, subcutaneously, transdermally, by instillation, transnasally, and the like) administering a compound to a rodent, monkey, dog or the like, and measuring change of the blood level of the compound over time after the administration using the LC-MS/MS method ("Newest Mass Spectrometry for Life Science", Kodansha Scientific, 2002, edited by Harada K. et al, and the like), and the like. By elucidating blood concentration transition of the compounds based on these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a metabolic test. Examples of the metabolic test include the blood stability test method (method of predicting metabolic clearance in vivo based on metabolic rate of a compound in hepatic microsomes of human or other animal species (refer to Shou, W. Z. et al., J. Mass Spectrom., 40 (10) pp. 1347-1356, 2005; Li, C. et al., Drug Metab. Dispos., 34 (6), 901-905, 2006, and the like), metabolite molecular species test method, reactive metabolite test method, and the like. By elucidating metabolic profile of the compounds based on one or more of these methods, usefulness of the compounds as active ingredients of medicaments can be confirmed.

Usefulness of the compounds of the present invention represented by the aforementioned formula (1) and salts thereof as well as derivatives thereof useful as prodrugs as active ingredients of medicaments can be confirmed by performing, for example, a solubility test. Examples of the solubility test include the solubility test based on the turbidity method (Lipinski, C. A. et al., Adv. Drug Deliv. Rev., 23, pp. 3-26, 1997; Bevan, C. D. et al., Anal. Chem., 72, pp. 1781-1787, 2000), and the like. By elucidating solubility of the compounds based on these methods, usefulness of the compounds as active ingredients of medicaments can be confirmed.

As the active ingredients of the medicaments of the present invention, the compounds represented by the aforementioned formula (1), physiologically acceptable salts thereof, and derivatives thereof useful as prodrugs are preferred.

The aforementioned substance, per se, may be administrated as the medicament of the present invention. A pharmaceutical composition containing one or more kinds of the aforementioned substances as the active ingredients and one or more kinds of pharmaceutical additives can be generally prepared and administrated orally or parenterally (e.g., intravenous administration, intramuscular administration, subcutaneous administration, transdermal administration, intrapulmonary administration, intranasal administration, instillation, intraurethral administration, intravaginal administration, sublingual administration, intrarectal administration, and the like) to human or an animal other than human. The aforementioned pharmaceutical composition can be prepared in a dosage form suitable for an intended administration route. More specifically, examples of the pharmaceutical composition suitable for oral administration include oral drug products (tablets, film-coated tablets, intraoral collapsing tablets, hard capsules, soft capsules, powders, fine granules, granules, dry syrups, syrups, pills, troches and the like), and examples of the pharmaceutical composition suitable for parenteral administration include injections (liquid dosage forms, lyophilized dosage forms, suspensions and the like), inhalants, suppositories, transdermally absorbed agents (e.g., tapes), ointments, ophthalmic solutions, ophthalmic ointments, ophthalmic membrane adherent agents and the like. For glaucoma, preferred examples of the dosage form include oral drug products, ophthalmic solutions, ophthalmic ointments, and ophthalmic membrane adherent agents. Further, preferred dosage forms for bronchial asthma or chronic obstructive pulmonary disease include oral drug products, inhalants (for example, a method of inhaling powder of the pharmaceutical composition or a liquid dosage form prepared by dissolving or suspending the pharmaceutical composition in a solvent as it is, or inhaling mist thereof by using a sprayer called atomizer or nebulizer), and transdermal preparations.

These pharmaceutical compositions can be prepared in a conventional manner by using pharmaceutical additives usually used in this field (e.g., excipients, disintegrants, binders, lubricants, colorants, buffering agents, coating agents, flavors, fragrances, emulsifying agents, isotonic agents, solubilizing agents, preservatives, viscosity improvers, pH adjusters and the like). Examples of the excipients include saccharides such as lactose, sucrose, and trehalose, sugar alcohols such as D-mannitol, erythritol, xylitol, and sorbitol, starches such as maize starch, crystalline cellulose, calcium hydrogenphosphate and the like, examples of the disintegrants include starches, partially pregelatinized starch, carmellose and metal salts thereof, croscarmellose sodium, sodium carboxymethyl starch, agar powder, crospovidone, low substituted hydroxypropylcellulose and the like, examples of the binders include hydroxypropylmethylcellulose, hydroxypropylcellulose, polyvinyl alcohol, methylcellulose, ethylcellulose, popidone, acacia powder, pullulan, pregelatinized starch and the like, and examples of the lubricants include stearic acid and metal salts thereof, talc, silicic acid and metal salts thereof, salt-hardened oil, sucrose fatty acid esters, sodium laurylsulfate, sodium stearyl fumarate and the like When solid pharmaceutical compositions are prepared, there are used pharmaceutical additives including, for example, sucrose, lactose, glucose, fructose, trehalose, D-mannitol, sorbitol, erythritol, xylitol, maltitol, maize starch, potato starch, wheat starch, rice starch, crystalline cellulose, carmellose, carmellose calcium, low substituted hydroxypropylcellulose, croscarmellose sodium, crospovidone, dextrin, cyclodextrin, dextran, agar, xanthane gum, guar gum, rosin, acacia, hydroxypropylcellulose, hydroxypropylmethylcellulose, methylcellulose, ethylcellulose, polyvinyl alcohol, povidone, pregelatinized starch, partly pregelatinized starch, pullulan, pectin, polysorbate, polyethylene glycol, propylene glycol, glycerol, magnesium stearate, talc, light anhydrous silicic acid, hydrated silicon dioxide, kaolin, sucrose fatty acid esters, sodium laurylsulfate, silicic acid, aluminum silicate, magnesium aluminometasilicate, calcium carbonate, sodium hydrogencarbonate, sodium chloride, sodium citrate, citric acid, succinic acid, tartaric acid, hydrogenated castor oil, hydrogenated tallow, stearic acid, cetanol, olive oil, orange oil, soybean oil, cacao butter, carnauba wax, paraffin, vaseline, triacetin, triethyl citrate, iron oxide, caramel, tartrazine, vanillin, carmellose sodium, cellulose derivatives such as hydroxypropylmethylcellulose phthalate, hydroxypropylmethylcellulose acetate succinate, carboxymethylethylcellulose, carboxyvinyl polymer, cellulose acetate phthalate, cellulose acetate trimellitate, ethylcellulose, and cellulose acetate, polyethylene glycol, gelatin, shellac, methacrylic acid and derivatives thereof as well as copolymers thereof, ethylcellulose aqueous dispersion (Aquacoat), silicone oil, triacetin and the like. The tablets can be tablets having usual surfaces of the tablets as required, and examples include sugar-coated tablets, enteric coating tablets, film-coated tablets, bilayer tablets, and multilayer tablets.

When semi-solid pharmaceutical compositions are prepared, there are used pharmaceutical additives including, for example, animal fats and oils (olive oil, maize oil, castor oil and the like), mineral fats and oils (vaseline, white petrolatum, solid paraffin and the like), waxes (jojoba oil, carnauba wax, beeswax and the like), partially or totally synthesized glycerol fatty acid esters. Examples of commercial products include Witepsol (Dynamit Nobel), Pharmasol (Nippon Oil & Fats) and the like. When liquid pharmaceutical compositions are prepared, pharmaceutical additives including, for example, sodium chloride, glucose, sorbitol, glycerol, olive oil, propylene glycol, ethyl alcohol and the like can be used. When injections are prepared, sterile liquid media, for example, physiological saline, isotonic solutions, oily liquids such as sesame oil and soybean oil are used. Further, if necessary, suitable suspending agents such as carboxymethylcellulose sodium, nonionic surfactants, solubilizing agents such as benzyl benzoate and benzyl alcohol and the like may be used together. When eye drops are prepared, they can be prepared as aqueous liquids or aqueous solutions. For example, aqueous solutions can be prepared by using a sterile aqueous solution for injections. To these liquids for instillation, various additives such as buffers (borate buffers, acetate buffers, carbonate buffers and the like are preferred in view of reduction of stimulus), isotonic agents (for example, sodium chloride, potassium chloride and the like can be mentioned), preservatives (for example, methyl paraoxybenzoate, ethyl paraoxybenzoate, benzyl alcohol, chlorobutanol and the like can be mentioned), viscosity improvers (for example, methylcellulose, sodium carboxymethylcellulose and the like can be mentioned) and the like may be optionally added. As for preparation of inhalants, when the composition is inhaled as powder, for example, preparation of the aforementioned solid pharmaceutical composition can be referred to, and the obtained powder is preferably further pulverized. Further, when the composition is inhaled as a liquid, preferable methods include a method of preparing the pharmaceutical composition by referring to the aforementioned preparation of solid pharmaceutical composition to prepare a solid composition and dissolving the solid in distilled water or a suitable solvent to obtain a medicament solution upon use, or a method of preparing the pharmaceutical composition by referring to the aforementioned preparation of liquid pharmaceutical composition to obtain a medicament solution. The size of particles in the aforementioned powder or medicament solution to be inhaled is preferably a particle size suitable for inhalation, and the upper limit of the size is, for example, preferably 100 µm or less, more preferably 50 µm or less, particularly preferably 10 µm or less. The lower limit of the particle size is not particularly limited, and a smaller particle size is more preferred.

A content of the active ingredient in the aforementioned pharmaceutical composition can be suitably chosen depending on a dosage form. Although the lower limit of the content of the active ingredient is not particularly limited so long as the desired pharmacological efficacy of the medicament of the present invention can be exhibited, the content is, for example, 0.00001% by weight or more, preferably 0.0001% by weight or more, more preferably 0.001% by weight or more, based on the total weight of the pharmaceutical composition. Further, the content may be 0.01% by weight or more, 0.1% by weight or more, or 1% by weight or more, based on the total weight of the composition. Although the upper limit of the content of the active ingredient is not also particularly limited so long as the desired pharmacological efficacy of the medicament of the present invention can be exhibited, the content is, for example, 100% by weight or less, preferably 80% by weight or less, more preferably 50% by weight or less, still more preferably 10% by weight or less, based on the total weight of the pharmaceutical composition. Further, it may also be 5% by weight or less, 1% by weight or less, or 0.1% by weight or less.

Dose of the medicament of the present invention can be suitably determined for each case in consideration of age, body weight, sexuality of patients, type of disease, severity of pathological condition, and the like. The lower limit is, for example, 0.001 mg or more, preferably 0.01 mg or more, more preferably 0.1 mg or more, still more preferably 1 mg or more, per day for adults. The upper limit may be 1000 mg or less, preferably 500 mg or less, more preferably 100 mg or less, still more preferably 30 mg or less, per day for adults. These doses can be administered once in a day or several times a day as divided portions.

A drug used for the combination with the compounds of the present invention represented by the aforementioned formula (1) and salts thereof as well as derivatives thereof useful as prodrugs is hereinafter referred to as a drug for combination use. As the drug for combination use, for example, drugs in various molecular forms such as low molecular weight compounds, low molecular peptides, polypeptides, nucleic acid oligomers, peptide-nucleic acid (PNA) oligomers, and antibodies can be used, and the drug can be chosen depending on administration object, administration route, objective disease and the like from various drugs of which objective diseases are diseases relating to contraction of various cells, diseases relating to morphological change of various cells, diseases relating to migration of various cells, diseases relating to release of various cells, diseases relating to aggregation of various cells, diseases relating to apoptosis of various cells, and/or diseases relating to abnormal gene expression in various cells, and the like.

A medicament characterized by comprising, in combination, the compound of the present invention represented by the aforementioned formula (1), a salt thereof, or a derivative thereof useful as a prodrug and a drug for combination use may sometimes be more preferred compared with a pharmaceutical composition comprising the compound of the present invention represented by the aforementioned formula (1), a salt thereof, or a derivative thereof useful as a prodrug alone as an active ingredient. Such characteristic feature can be understood by any kind of more preferred result provided by a medicament comprising, in combination, the compound of the present invention represented by the aforementioned formula (1), a salt thereof, or a derivative thereof useful as a prodrug and a drug for combination use compared with a pharmaceutical composition comprising solely the compound of the present invention represented by the aforementioned formula (1), a salt thereof, or a derivative thereof useful as a prodrug, for example, in any of the test methods described below.

The following test methods are examples for indicating that usefulness of medicaments based on the aforementioned combination can be demonstrated on the basis of the prophylactic and/or therapeutic effect on, for example, glaucoma, and the methods are not intended to indicate that the usefulness of the medicaments based on the combination is limited to the application. Glaucoma referred to in the present invention is as exemplified and explained above in detail in relation to the diseases relating to contraction of various cells.

For example, it can be concluded that a medicament based on the aforementioned combination is useful as a medicament for prophylactic and/or therapeutic treatment of glaucoma as follows. First, usefulness of the compounds of the present invention represented by the aforementioned formula (1) and salts thereof as well as derivatives thereof useful as prodrugs can be confirmed by a result obtained by evaluation of the compounds of the present invention represented by the aforementioned formula (1) and salts thereof as well as derivatives thereof useful as prodrugs in the aforementioned test methods. Further, usefulness of a medicament based on the combination, such as enhancement of an intraocular pressure reducing action, and extension of duration of an intraocular pressure reducing action, can be confirmed by a result obtained by evaluating each compound combined with each drug for combination use, for example, a prostaglandin-relating agent such as isopropylunoprostone and latanoprost, a carbonic anhydrase inhibitor such as dorzolamide hydrochloride, brinzolamide hydrochloride, and acetazolamide hydrochloride, an adrenergic receptor blocker such as bunazosin hydrochloride, timolol maleate, carteolol hydrochloride, befunolol hydrochloride, betaxolol hydrochloride and nipradilol hydrochloride.

The aforementioned medicament based on the combination include, for example, a medicament for simultaneous administration of the compound of the present invention represented by the aforementioned formula (1), a salt thereof, or a derivative thereof useful as a prodrug, and a drug for combination use, a medicament for administering the compound of the present invention represented by the aforementioned formula (1), a salt thereof, or a derivative thereof useful as a prodrug, and a drug for combination use with an interval within which efficacy of each substance can be expected, and the like. Further, a medicament prepared in a single form in which the compound of the present invention represented by the aforementioned formula (1), a salt thereof, or a derivative thereof useful as a prodrug and a drug for combination use are mixed, and a medicament comprising the compound of the present invention represented by the aforementioned formula (1), a salt thereof, or a derivative thereof useful as a prodrug and a drug for combination use, which are prepared in separate forms are also included. Furthermore, a medicament for administering the compound of the present invention represented by the aforementioned formula (1), a salt thereof, or a derivative thereof useful as a prodrug and a drug for combination use via the same route, a medicament for administering the compound of the present invention represented by the aforementioned formula (1), a salt thereof, or a derivative thereof useful as a prodrug and a drug for combination use via different routes, and the like are also included.

In the aforementioned medicament based on the combination, a mixing ratio of the compound of the present invention represented by the aforementioned formula (1), a salt thereof, or a derivative thereof useful as a prodrug and a drug for combination use, a form of the compound of the present invention represented by the aforementioned formula (1), a salt thereof, or a derivative thereof useful as a prodrug and a drug for combination use after mixing when the compound of the present invention represented by the aforementioned formula (1), a salt thereof, or a derivative thereof useful as a prodrug and the drug for combination use are prepared in a single form, and the like can be suitably determined depending on object of administration, administration route, disease to be treated, symptoms, physicochemical properties of the medicament, ease of administration, and the like, and the dose thereof can be suitably chosen on the basis of, for example, clinically used doses of the compound of the present invention represented by the aforementioned formula (1), a salt thereof, or a derivative thereof useful as a prodrug and the drug for combination use.

When the compound of the present invention represented by the aforementioned formula (1), a salt thereof, or a derivative thereof useful as a prodrug and a drug for combination use are prepared in a single form, the aforementioned pharmaceutical additives may be used in addition to the compound of the present invention represented by the aforementioned formula (1), a salt thereof, or a derivative thereof useful as a prodrug and the drug for combination use to prepare a pharmaceutical composition, and a preferred form such as oral agents, injections (solution, suspension and the like), fusion drips, inhalants, suppositories, transdermally absorbed agents (e.g., tapes), ointments, ophthalmic solutions, ophthalmic ointments, ophthalmic membrane adherent agents and the like can be prepared and used.

When the compound of the present invention represented by the aforementioned formula (1), a salt thereof, or a derivative thereof useful as a prodrug and a drug for combination use are prepared in separate forms, each of the compound of the present invention represented by the aforementioned formula (1), a salt thereof, or a derivative thereof useful as a prodrug and the drug for combination use can be prepared in a preferred from in the same manner as mentioned above and used.

The medicament characterized by comprising, in combination, the compound of the present invention represented by the aforementioned formula (1), a salt thereof, or a derivative thereof useful as a prodrug and a drug for combination use can be used as an agent for prophylactic and/or therapeutic treatment of various diseases. The diseases are preferably those relating to contraction of various cells, and among the diseases relating to contraction of various cells, glaucoma is preferred.

The following [1] to [10] are encompassed within the scope of the present invention.

[1] A medicament comprising the compound of the present invention represented by the aforementioned formula (1), a salt thereof, or a derivative thereof useful as a prodrug and a drug having an intraocular pressure reducing action and/or a drug having an optic nerve protective action in combination.

[2] A medicament comprising the compound of the present invention represented by the aforementioned formula (1), a salt thereof, or a derivative thereof useful as a prodrug and any one or more of an adrenergic receptor stimulant, a prostaglandin-related agent, a carbonic anhydrase inhibitor, an adrenergic receptor blocker, a cholinesterase inhibitor, a calcium antagonist, a Rho kinase inhibitor, an angiotensin II receptor antagonist, and an NMDA receptor blocker in combination.

[3] A medicament comprising the compound of the present invention represented by the aforementioned formula (1), a salt thereof, or a derivative thereof useful as a prodrug and a drug having an intraocular pressure reducing action in combination.

[4] A medicament comprising the compound of the present invention represented by the aforementioned formula (1), a salt thereof, or a derivative thereof useful as a prodrug and any one or more of a prostaglandin-related agent, a carbonic anhydrase inhibitor, and an adrenergic receptor blocker.

[5] The medicament according to [4], which is an agent for prophylactic and/or therapeutic treatment of glaucoma.

[6] A medicament comprising the compound of the present invention represented by the aforementioned formula (1), a salt thereof, or a derivative thereof useful as a prodrug and a drug having an optic nerve protective action in combination.

[7] The medicament according to [4] wherein the prostaglandin-related agent mentioned in [4] is any one of latanoprost, bimatoprost, travoprost, isopropylunoprostone, and tafluprost.

[8] The medicament according to [4] wherein the carbonic anhydrase inhibitor mentioned in [4] is any one of dorzolamide hydrochloride, brinzolamide hydrochloride, and acetazolamide hydrochloride.

[9] The medicament according to [4] wherein the adrenergic receptor blocker mentioned in [4] is any one of bunazosin hydrochloride, timolol maleate, carteolol hydrochloride, levobunolol hydrochloride, betaxolol hydrochloride, nipradilol hydrochloride, and befunolol hydrochloride.

[10] A method for therapeutic and/or prophylactic treatment of glaucoma, which uses the medicament according to any one of [1] to [9].

The compounds of the present invention represented by the aforementioned formula (1), and salt thereof, as well as derivatives thereof useful as prodrugs have an intraocular pressure reducing action as demonstrated in Test Example 3, and it was confirmed that the medicaments of [1], [2], and [3] mentioned above exhibited enhancement of the intraocular pressure reducing action, extension of duration of the intraocular pressure reducing action and the like compared with a pharmaceutical composition containing the compound of the present invention represented by the aforementioned formula (1), a salt thereof, or a derivative thereof useful as a prodrug alone as an active ingredient as demonstrated in Test Examples 7 and 8. Thus, they are preferred as agents for therapeutic and/or prophylactic treatment of glaucoma.

Further, a medicament comprising the compound of the present invention represented by the aforementioned formula (1), a salt thereof, or a derivative thereof useful as a prodrug and an agent for therapeutic and/or prophylactic treatment of glaucoma in combination is also preferred. As the agent for therapeutic and/or prophylactic treatment of glaucoma, for example, drugs having an intraocular pressure reducing action, drugs having an optic nerve protective action, drugs having an intraocular pressure reducing action, and/or an optic nerve protective action and the like are also known.

Among the drugs for combination use used for the present invention, the drug having an intraocular pressure reducing action is not particularly limited so long as the drug has an intraocular pressure reducing action. Examples include adrenergic receptor stimulants, prostaglandin-related agents, carbonic anhydrase inhibitors (also abbreviated as CAI), adrenergic receptor blockers, cholinesterase inhibitors, Rho kinase inhibitors (Honjo, M. et al., Invest. Ophthalmol. Vis. Sci., 42 (1), pp. 137-44 (2001); Honjo, M. et al., Arch. Ophthalmol. 119 (8), pp. 1171-8 (2001)), angiotensin II receptor antagonists (Inoue, T. et al., Current Eye Res., 23 (2), pp. 133-8 (2001)) and the like, and any one or more of these drugs can be used. When two or more kinds of drugs for combination use are selected, two or more kinds of the drugs may be selected from drugs belonging to the same classification, or one or more kind of the drugs may be selected from drugs belonging to each of different classifications. The drugs are preferably selected from those belonging to different classifications. Further, as the drug having an intraocular pressure reducing action, one or more kinds of drugs among a prostaglandin-related agent, a carbonic anhydrase inhibitor, and an adrenergic receptor blocker are preferred. This medicament is preferred as an agent for therapeutic and/or prophylactic treatment of glaucoma.

Among the drugs for combination use used in the present invention, the drug having an optic nerve cell protective action means a drug having an action of protecting optic nerves, and examples include drugs having an action of protecting optic nerve cells based on an action of suppressing cell death as well as an action of improving eyeground vascular flow. The action of suppressing cell death of optic nerve cells can be confirmed as, for example, an action of suppressing cell death induced via a glutamate receptor in an exo vivo culture system using retinal nerve cells extracted from a rat or the like by adding NMDA (Hahn et al., Proc. Natl. Acad. Sci. USA, 85, 6556. (1998)), and the action of improving the eyeground vascular flow can be confirmed by, for example, quantitatively analyzing change of the eyeground vascular flow in human, rabbit, monkey, or the like administered with the drug using the laser speckle method (Tamaki, Y. et al., Surv. Ophthalmol., 42 (Suppl. 1), S52-S63. (1997)).

Examples of the drug having an optic nerve protective action include adrenergic receptor stimulants (Wheeler, L A. et al., Eur. J. Ophthalmol., 11 (Suppl. 2) 403-11. (2001)), adrenergic receptor blockers (Wood, J P., et al., Exp. Eye Res. 76 (4), 505-16. (2003) and the like), calcium antagonists (Toriu, N. et al., Exp. Eye Res., 70 (4)), 475-84. (2000)), NMDA receptor blockers (Kim, T W. et al., Korean J. Ophthalmol., 16 (1), 1-7. (2002)), prostaglandin-related agents (Tamaki, Y. et al., and J. Ocul. Pharmacol. Ther., 17 (5), 403-11. (2001) and the like), carbonic anhydrase inhibitors (Harris, A. et al., J. Ocul. Pharmacol. Ther., 15, 189-197. (1999)), angiotensin II receptor antagonists (Inoue, T. et al., Ophthalmic Res., 35, pp. 351-4. (2003)) and the like, and any one or more of these drugs can be used.

Besides drugs having either of the intraocular pressure reducing action and the optic nerve protective action, drugs having both the intraocular pressure reducing action and the optic nerve protective action as a single agent are also known. Examples of such drugs include, for example, adrenergic receptor stimulants, prostaglandin-related agents, carbonic anhydrase inhibitors, adrenergic receptor blockers, calcium antagonists and the like, and any one or more these drugs may be used.

Specifically, among the drugs for combination use used for the present invention, the drugs having an intraocular pressure reducing action and/or drugs having an optic nerve protective action can be divided into the aforementioned drugs having an intraocular pressure reducing action, drugs having an optic nerve protective action, and drugs having both of an intraocular pressure reducing action and an optic nerve protective action as a single agent. Examples of the drugs having an intraocular pressure reducing action and/or drugs having an optic nerve protective action include, for example, one or more of adrenergic receptor stimulants, prostaglandin-related agents, carbonic anhydrase inhibitors, adrenergic receptor blockers, cholinesterase inhibitors, calcium antagonists, Rho kinase inhibitors, angiotensin II receptor antagonists, NMDA receptor blockers and the like. Furthermore, preferred examples include one or more of prostaglandin-related agents, carbonic anhydrase inhibitors, adrenergic receptor blockers, and the like.

In this specification, the adrenergic receptors include, for example, those of $\alpha$1A-subtype, $\alpha$1B-subtype, $\alpha$1D-subtype, $\alpha$2A-subtype, $\alpha$2B-subtype, $\alpha$2C-subtype, $\beta$1-subtype, $\beta$2-subtype, and $\beta$3-subtype, which considered to be involved in control of constriction and relaxation of various smooth muscles. (Kurose et al., Protein Nucleic Acid Enzyme, Vol. 42, No. 3, pp. 316-26. (1997)).

In this specification, the adrenergic receptor stimulants means a medicament that acts as an agonist against at least one of the aforementioned adrenergic receptors and has an regulatory action on various smooth muscles. Examples of the regulatory action on various smooth muscles include, for example, an intraocular pressure reducing action, and a tracheal dilational action. The medicaments herein referred to mean those exhibiting an intraocular pressure reducing action. Depending on the degree of selectivity for the adrenergic receptors, for example, those selectively acting on $\alpha$-receptors may be described as $\alpha$-stimulants, and those selectively acting on $\alpha$2-receptors may be described as $\alpha$2-stimulants.

In the present invention, examples of the adrenergic receptor stimulants include, for example, non-selective sympathetic nerve stimulants, $\alpha$1-stimulants, and $\alpha$2-stimulants. Epinephrine, dipivefrin (U.S. Pat. No. 3,809,714), apraclonidine (U.S. Pat. No. 4,517,199), brimonidine (U.S. Pat. No. 4,517,199), and physiologically acceptable salts thereof are preferred, and epinephrine hydrochloride, dipivefrin hydrochloride, apraclonidine, and brimonidine tartrate are preferred. Any one of these drugs is preferred, and any two or more of them are also preferred.

The prostaglandin-related agents are roughly classified into prostaglandin receptor (FP receptor) binding prostaglandins (Richard, M B. et al., Annu. Rev. Pharmacol. Toxicol., 41, pp. 661-90. (2001)), and metabolic type prostaglandins. In addition, isopropylunoprostone and the like as derivatives thereof can also be exemplified. The prostaglandin receptor (FP receptor) binding prostaglandins are prostaglandins having an ability to bind to an FP receptor, and they are generally naturally occurring prostaglandins or compounds having similar structures in many cases. The prostaglandin-related agents preferably further exhibit an intraocular pressure reducing action, and preferably have a curative effect for glaucoma. Examples of the naturally occurring prostaglandins include, for example, prostaglandin F2$\alpha$ and the like. Examples of the FP receptor binding prostaglandins having a structure similar to that of naturally occurring prostaglandins include, for example, latanoprost, travoprost, bimatoprost, tafluprost and the like.

The metabolic type prostaglandins mean compounds produced by metabolism of the FP receptor binding prostaglandins in the living bodies.

Therefore, in the present invention, as the prostaglandin-related agents, isopropylunoprostone (U.S. Pat. No. 5,627, 209), latanoprost (U.S. Pat. No. 5,296,504), travoprost (U.S. Pat. No. 5,510,383), bimatoprost (U.S. Pat. No. 6,403,649), tafluprost (Japanese Patent Unexamined Publication (Kokai) No. 2003-321442), and physiologically acceptable salts thereof are preferred, and isopropylunoprostone, latanoprost, travoprost, bimatoprost, and tafluprost are preferred. Any one of these is preferred, and any two or more of them are also preferred.

In this specification, the carbonic anhydrase inhibitors mean isozymes of carbonic anhydrase having at least type II and/or type IV enzyme inhibitory action. Examples of the carbonic anhydrase inhibitors include, for example, dorzolamide (European Patent Publication No. 296879), brinzolamide (U.S. Pat. No. 5,378,703), acetazolamide (U.S. Pat. No. 2,554,816), and physiologically acceptable salts thereof, and dorzolamide hydrochloride, brinzolamide hydrochloride, and acetazolamide hydrochloride are preferred. Any one of these is preferred, or any two or more of them are also preferred.

In this specification, the adrenergic receptors are the same as those mentioned above. The adrenergic receptor blockers means drugs that act as an antagonist against at least one type of adrenergic receptor, and have an action of regulating various smooth muscles. The action of regulating various smooth muscles preferably means an action exhibiting an intraocular pressure reducing action. Depending on the degree of selectivity for adrenergic receptors, they may be described as $\alpha$-blockers, $\beta$-blockers, or $\alpha\beta$-blockers. Examples of the adrenergic receptor blockers include, for example, $\alpha$-blockers, $\beta$-blockers, and $\alpha\beta$-blockers. Bunazosin (British Patent Application Publication No. 1398455), timolol (U.S. Pat. No. 5,354,860), carteolol (U.S. Pat. No. 3,953,456), befunolol (U.S. Pat. No. 4,515,977), betaxolol (U.S. Pat. No. 4,252, 984), nipradilol (Japanese Patent Publication (Kokoku) No. 60-54317), levobunolol (U.S. Pat. No. 5,426,227), and physiologically acceptable salts thereof are preferred, and bunazosin hydrochloride, timolol maleate, carteolol hydrochloride, befunolol hydrochloride, betaxolol hydrochloride, and nipradilol hydrochloride are also preferred. Any one of these is preferred, and any two or more of them are also preferred.

Examples of the cholinesterase inhibitors include, for example, demecarium, physostigmine (U.S. Pat. No. 4,791, 107), echothiophate, and physiologically acceptable salts thereof, and physostigmine sulfate and the like are preferred. Any one of these is preferred, and any two or more of them are also preferred.

Examples of the calcium antagonists include, iganidipine (U.S. Pat. No. 2,554,816), lomerizine (Japanese Patent Unexamined Publication No. 60-222472), and physiologically acceptable salts thereof, and iganidipine hydrochloride, and lomerizine hydrochloride are also preferred. Any one of these is preferred, and any two or more of them are also preferred.

Examples of other Rho kinase inhibitors that can be used with the compounds of the present invention represented by the aforementioned formula (1) and salts thereof as well as derivatives thereof useful as prodrugs include, for example, (+)-trans-4-(1-aminoethyl)-1-(4-pyridylcarbamoyl)cyclohexane, (+)-trans-N-(pyrrolo[1H[2,3-b]pyridin-4-yl)-4-(1-aminoethyl)cyclohexanecarboxamide, (R)-(+)-N-(4-pyridyl)-4-(1-aminoethyl)benzamide, (R)-(+)-N-(1H-pyrrolo[2,3-b]pyridin-4-yl)-4-(1-aminoethyl)benzamide (International Patent Publication WO02/083175), HA-1077 (Nagumo, H. et al., Am. J. Physiol. Cell Physiol., 278 (1) pp. C57-65. (2000)), physiologically acceptable salts thereof, and pharmaceutical compositions comprising these compounds. Any one of these is preferred, and any two or more of them are also preferred.

In this specification, the angiotensin II receptors include those of $AT_{1A}$, $AT_{1B}$, $AT_2$, $AT_3$, and $AT_4$ subtypes, which bind to angiotensin II to be involved in blood pressure regulating action, and the like, and the angiotensin II receptor antagonists mean drugs having a binding activity at least to an $AT_1$ receptor for antagonizing against angiotensin II, and attenuating the action of angiotensin II. Examples of the angiotensin II receptor antagonists include, for example, olmesartan (CS-088) (U.S. Pat. No. 5,616,599), and physiologically acceptable salts thereof, and olmesartan is preferred. Any one of these is preferred, and any two or more of them are also preferred.

Examples of the NMDA receptor antagonists include, for example, memantine (U.S. Pat. No. 4,122,193), and physiologically acceptable salts thereof, and memantine hydrochloride is preferred. Any one of these is preferred, and any two or more are also preferred.

A method for therapeutic and/or prophylactic treatment of glaucoma, which uses any of the medicaments mentioned above is also preferred.

When the aforementioned medicaments are used as an eye drop, for example, one to ten drops, preferably one or two drops (volume of one drop is about 50 μL), as a single dose for administration, can be preferably administered about 1 to 6 times a day.

When the object of the administration is human, for example, the drug for combination use is generally preferably used in an amount of 0.001 to 1000 parts by weight with 1 weight part of the compound of the present invention represented by the aforementioned formula (1), a salt thereof, or a derivative thereof useful as a prodrug. More specifically, although the lower limit of the amount of the drug for combination use is not particularly limited so long as the effect of the present invention is exhibited, the drug for combination use is used in an amount of, for example, 0.00001 part by weight or more, preferably 0.0001 part by weight or more, more preferably 0.001 part by weight or more, further preferably 0.01 part by weight or more, with 1 weight part of the compound of the present invention represented by the aforementioned formula (1), a salt thereof, or a derivative thereof useful as a prodrug. Although the upper limit of the amount of the drug for combination use is not also particularly limited, for example, the drug for combination use is generally used in an amount of 1000 parts by weight or less, preferably 500 parts by weight or less, more preferably 250 parts by weight or less, or 100 parts by weight or less.

Examples

The present invention will be further specifically explained with reference to the following examples. However, the present invention is not limited to these examples.

For thin layer chromatography (TLC), Precoated Silica Gel 60 F254 (produced by Merck) was used. After development with chloroform:methanol (100:1 to 4:1), or n-hexane:ethyl acetate (100:1 to 1:10), spots were observed by UV irradiation (254 nm) or coloration with ninhydrin or phosphomolybdic acid. For drying organic solvent, anhydrous magnesium sulfate or anhydrous sodium sulfate was used. For flash column chromatography, Silica gel 60N (spherical shape, neutral, 40 to 100 μm, produced by Kanto Chemicals) was used. For preparative thin layer chromatography (PTLC), Precoated Silica Gel 60 F254 (20×20 cm, thickness: 2 mm, produced by Merck) was used. For the measurement of nuclear magnetic resonance (NMR) spectra, the measurement was performed by using Gemini-300 (FT-NMR, produced by Varian), or AL-300 (FT-NMR, produced by JOEL).

As a solvent, deuterated chloroform was used, unless otherwise indicated. Chemical shifts were measured by using tetramethylsilane (TMS) as an internal standard, and indicated with δ (ppm), and binding constant was indicated with J (Hz). Mass spectrum (MS) was measured by liquid chromatography-mass spectrometry (LC-MS). Platform-LC type mass spectrometry apparatus (produced by Micromass) was used as the mass spectrometer, and the measurement was performed by the electrospray ionization (ESI) method. As the liquid chromatography apparatus, an apparatus produced by GILSON was used. As the separation column, Mightysil RP-18 GP 50-4.6 (produced by Kanto Chemicals) was used. Elution was generally performed at a flow rate of 2 ml/minute using a linear gradient of 5 to 100% (v/v) Solution B [acetonitrile containing 0.1% (v/v) acetic acid] in Solution A [water containing 0.1% (v/v) acetic acid] from 0 minute to 5 minutes as the solvent.

Reference Example 1

4-Fluoroisoquinoline

A solution of n-butyllithium in n-hexane (1.58 M, 60.1 ml, Kanto Chemicals) was added with tetrahydrofuran (345 ml), and the mixture was sufficiently cooled on a dry ice-acetone bath. The mixture was added dropwise with a solution of 4-bromoisoquinoline (9.0 g, Tokyo Kasei Kogyo) in tetrahydrofuran (65 ml) over 1 hour so that the temperature of the reaction mixture should not exceed −65° C. The mixture was stirred at the same temperature for 30 minutes, and then added dropwise with a solution of N-fluorobenzenesulfonimide (30 g, Tokyo Kasei Kogyo) in tetrahydrofuran (100 ml) over 1 hour so that the temperature of the reaction mixture should not exceed −65° C. Subsequently, the mixture was stirred at the same temperature for 1 hour, then the cooling bath was removed, and the mixture was gradually warmed to room temperature. The reaction mixture was added with saturated aqueous sodium hydrogencarbonate (300 ml) and ethyl acetate (300 ml), and stirred at room temperature for 12 hours. The organic layer was separated, and the aqueous layer was extracted with ethyl acetate 3 times (200 ml for each time). The combined organic layer was washed with saturated brine (500 ml), and dried over anhydrous magnesium sulfate. The solvent was evaporated under reduced pressure, the residue was added with chloroform (250 ml), and the insoluble solids were removed by filtration. The solvent was evaporated under reduced pressure, and the residue was purified by silica gel chromatography (n-hexane:ethyl acetate=5:1) to obtain the title compound (3.6 g).

MS (m/z): 148 (MH+)

$^1$H-NMR (CDCl$_3$) δ (ppm): 7.26-7.71 (1H, m), 7.75-7.82 (1H, m), 8.03 (1H, dd, J=1.2 Hz, J=8.4 Hz), 8.10 (1H, d, J=8.4 Hz), 8.38 (1H, s), 9.08 (1H, s)

Reference Example 2

4-Fluoro-5-nitroisoquinoline

4-Fluoroisoquinoline (3.6 g) obtained in Reference Example 1 was dissolved in concentrated sulfuric acid (20 ml), and the solution was added dropwise with a solution of potassium nitrate (3.25 g, Wako Pure Chemical Industries) in concentrated sulfuric acid (28 ml) under cooling at −5° C. so that the temperature of the reaction mixture should not exceed 5° C. The reaction mixture was stirred at 0° C. for 1 hour, poured into ice water, neutralized with 28% aqueous ammonia (pH 8), and extracted 3 times with ethyl acetate (150 ml for each time). The combined organic layer was washed with saturated aqueous sodium hydrogencarbonate (300 ml), and dried over anhydrous magnesium sulfate. The solvent was evaporated under reduced pressure, and the residue was purified by silica gel chromatography (n-hexane:ethyl acetate=3:1) to obtain the title compound (2.2 g).

Reference Example 3

5-Amino-4-fluoroisoquinoline

4-Fluoro-5-nitroisoquinoline (2.2 g) obtained in Reference Example 2 was added with concentrated hydrochloric acid (40 ml), and added with stannous chloride dihydrate (13 g, Wako Pure Chemical Industries) at 0° C., and the mixture was refluxed for 12 hours by heating. The reaction mixture was cooled to room temperature, and the solvent was evaporated under reduced pressure. The residue was neutralized with 5 N aqueous sodium hydroxide, and extracted 4 times with chloroform (50 ml for each time). The combined organic layer was washed with saturated brine (200 ml), and dried over anhydrous magnesium sulfate. The solvent was evaporated under reduced pressure, and the residue was purified by silica gel chromatography (chloroform:acetone=15:1) to obtain the title compound (1.45 g).

MS (m/z): 163 (MH+)

$^1$H-NMR (CDCl$_3$) δ (ppm): 6.85 (1H, dd, J=1.2 Hz, J=7.5 Hz), 7.31-7.35 (1H, m), 7.42 (1H, t, J=7.8 Hz), 8.19 (1H, d, J=5.1 Hz), 8.91 (1H, s)

Reference Example 4

4-Fluoro-5-isoquinolinesulfonyl chloride

The title compound was obtained from 5-amino-4-fluoroisoquinoline obtained in Reference Example 3 according to a known method (Japanese Patent No. 2763791).

Reference Example 5

4-Chloro-5-nitroisoquinoline

According to the method described in Reference Example 2, the title compound was obtained from 4-chloroisoquinoline obtained according to the method described in a known literature (Vaughan et al., J. Org. Chem., 1961, 26, 468).

MS (m/z): 209 (MH+)

$^1$H-NMR (CDCl$_3$) δ (ppm): 7.75 (1H, t, J=7.8 Hz), 7.94 (1H, dd, J=1.2 Hz, J=7.8 Hz), 8.22 (1H, dd, J=1.2 Hz, J=7.8 Hz), 8.71 (1H, s), 9.26 (1H, s)

Reference Example 6

5-Amino-4-chloroisoquinoline

The title compound was obtained from 4-chloro-5-nitroisoquinoline obtained in Reference Example 5 according to the method described in Reference Example 2.

MS (m/z): 179 (MH+)

$^1$H-NMR (CDCl$_3$) δ (ppm): 6.89 (1H, dd, J=1.3 Hz, J=7.4 Hz), 7.25-7.44 (2H, m), 8.32 (1H, s), 8.96 (1H, s)

Reference Example 7

4-Chloro-5-isoquinolinesulfonyl chloride

The title compound was obtained from 5-amino-4-chloroisoquinoline obtained in Reference Example 6 according to the method described in Japanese Patent No. 2763791.

Example 1

(R/S)-3-Amino-1-(4-bromo-5-isoquinolinesulfonyl)pyrrolidine (R/S)-3-(tert-Butoxycarbonylamino)-1-(4-bromo-5-isoquinolinesulfonyl)-piperidine (Intermediate 1), which can be synthesized in the same manner as that of Example 1-1, Step B, can be used in the method of Step B in a similar manner to obtain the title compound.

Example 1-1

(S)-3-Amino-1-(4-bromo-5-isoquinolinesulfonyl)pyrrolidine

Step A (S)-3-(tert-Butoxycarbonylamino)-1-(4-bromo-5-isoquinolinesulfonyl)pyrrolidine (Intermediate 1a)

A solution of 4-bromo-5-isoquinolinesulfonyl chloride (0.50 g) prepared according to a known method (described in Japanese Patent No. 2763791), and (S)-3-(tert-butoxycarbonylamino)pyrrolidine (0.33 g, Tokyo Kasei Kogyo) in methylene chloride (5 ml) was added with triethylamine (0.68 ml, Wako Pure Chemical Industries) at 0° C., and the mixture was stirred at the same temperature for 30 minutes, and then further stirred at room temperature for 5 hours. The reaction mixture was washed with saturated brine (10 ml), and then dried over anhydrous magnesium sulfate. The solvent was evaporated under reduced pressure, and then the residue was purified by silica gel chromatography (n-hexane:ethyl acetate=1:1) to obtain the title compound (0.62 g).

MS (m/z): 456 (MH+)

$^1$H-NMR (CDCl$_3$) δ (ppm): 1.44 (9H, s), 1.96-2.06 (1H, m), 2.26-2.37 (1H, m), 3.36-3.41 (1H, m), 3.52-3.56 (1H, m), 3.62-3.71 (2H, m), 4.36 (1H, m), 4.82 (1H, m), 7.70 (1H, t, J=7.8 Hz), 8.20 (1H, dd, J=1.3, 7.8 Hz), 8.41 (1H, dd, J=1.3, 7.8 Hz), 9.01 (1H, s), 9.22 (1H, s)

Step B (S)-3-Amino-1-(4-bromo-5-isoquinoline sulfonyl)pyrrolidine

Intermediate 1a (120 mg) prepared in Step A mentioned above was added with 10% hydrogen chloride/methanol (2 ml, Tokyo Kasei Kogyo), and the mixture was stirred at room temperature for 12 hours. The solvent was concentrated under reduced pressure, and the obtained solid was collected by filtration to obtain the title compound as hydrochloride (84 mg).

MS (m/z): 356 (MH+)

$^1$H-NMR (DMSO) δ (ppm): 2.15-2.25 (1H, m), 2.37-2.48 (1H, m), 3.49-3.58 (2H, m), 3.66-3.80 (2H, m), 4.00-4.08 (1H, m), 7.90 (1H, t, J=7.8 Hz), 8.42 (1H, d, J=7.8 Hz), 8.52 (1H, d, J=8.1 Hz), 8.96 (1H, s), 9.45 (1H, s)

Example 1-2

(R)-3-Amino-1-(4-bromo-5-isoquinolinesulfonyl)pyrrolidine (R)-3-(tert-Butoxycarbonylamino)-1-(4-bromo-5-isoquinolinesulfonyl)-pyrrolidine (Intermediate 1b) was prepared by using (R)-3-(tert-butoxycarbonylamino)pyrrolidine (Tokyo Kasei Kogyo) in the method of Example 1-1, Step A instead of (S)-3-(tert-butoxycarbonylamino)pyrrolidine, and then used in the method of Step B in a similar manner to obtain the title compound as hydrochloride.

MS (m/z): 356 (MH+)
$^1$H-NMR (DMSO) δ (ppm): 2.15-2.25 (1H, m), 2.37-2.48 (1H, m), 3.49-3.58 (2H, m), 3.66-3.80 (2H, m), 4.00-4.08 (1H, m), 7.90 (1H, t, J=7.8 Hz), 8.42 (1H, d, J=7.8 Hz), 8.52 (1H, d, J=8.1 Hz), 8.96 (1H, s), 9.45 (1H, s)

Example 2

(R/S)-3-Amino-1-(4-bromo-5-isoquinolinesulfonyl)piperidine (R/S)-3-(tert-Butoxycarbonylamino)-1-(4-bromo-5-isoquinolinesulfonyl)-piperidine (Intermediate 2) can be prepared from 4-bromo-5-isoquinolinesulfonyl chloride and 3-(tert-butoxycarbonylamino)piperidine (AstaTech) according to the method described in Example 1-1, Step A, and then used in the method of Example 1-1, Step B in a similar manner to obtain the title compound as hydrochloride.

Example 2-1

(S)-3-Amino-1-(4-bromo-5-isoquinolinesulfonyl)piperidine (S)-3-(tert-Butoxycarbonylamino)-1-(4-bromo-5-isoquinolinesulfonyl)-piperidine (Intermediate 2a) can be prepared by using (S)-3-(tert-butoxycarbonyl-amino)piperidine (AstaTech) in the method of Example 1-1, Step A instead of (S)-3-(tert-butoxycarbonylamino)pyrrolidine, and then used in the method of Example 1-1, Step B in a similar manner to obtain the title compound as hydrochloride.

Example 2-2

(R)-3-Amino-1-(4-bromo-5-isoquinolinesulfonyl)piperidine (R)-3-(tert-Butoxycarbonylamino)-1-(4-bromo-5-isoquinolinesulfonyl)-piperidine (Intermediate 2b) can be prepared by using (R)-3-(tert-butoxycarbonylamino)piperidine (AstaTech) in the method of Example 1-1, Step A instead of (S)-3-(tert-butoxycarbonylamino)pyrrolidine, and then used in the method of Example 1-1, Step B in a similar manner to obtain the title compound as hydrochloride.

Example 3

3-Amino-1-(4-bromo-5-isoquinolinesulfonyl)azetidine

The title compound can be obtained as hydrochloride from 4-bromo-5-isoquinolinesulfonyl chloride and 3-(tert-butoxycarbonylamino)azetidine (AstaTech) according to the method described in Example 1-1, Step A and Step B.

Example 4

(R/S)-3-(2-Furylmethyl)amino-1-(4-bromo-5-isoquinolinesulfonyl)pyrrolidine (R/S)-3-Amino-1-(4-bromo-5-isoquinolinesulfonyl)pyrrolidine hydrochloride can be used in the method of Example 4-1 instead of (S)-3-amino-1-(4-bromo-5-isoquinolinesulfonyl)pyrrolidine hydrochloride to obtain the title compound as hydrochloride.

Example 4-1

(S)-3-(2-Furylmethyl)amino-1-(4-bromo-5-isoquinolinesulfonyl)pyrrolidine

A suspension of (S)-3-amino-1-(4-bromo-5-isoquinolinesulfonyl)pyrrolidine hydrochloride (172 mg) obtained in Example 1-1 in 1,2-dichloroethane (10 ml) was added with triethylamine (0.28 ml, Wako Pure Chemical Industries), and then with furfural (42 mg, Aldrich), and the mixture was stirred at room temperature for 30 minutes, then added with sodium triacetoxyborohydride (170 mg, Aldrich), and further stirred at room temperature for 30 hours. The reaction mixture was added with saturated aqueous sodium hydrogencarbonate (15 ml), and the organic layer was separated. The aqueous layer was extracted 3 times with chloroform (10 ml for each time), and the combined organic layer was washed with saturated brine (30 ml). The organic layer was dried over anhydrous magnesium sulfate, and then the solvent was evaporated under reduced pressure. The residue was purified by silica gel chromatography (chloroform:methanol=30:1) to obtain the title compound (52 mg).

MS (m/z): 436 (MH+)
$^1$H-NMR (DMSO) δ (ppm): 2.29-2.55 (2H, m), 3.47-3.73 (3H, m), 3.79-3.85 (1H, m), 3.98-4.08 (1H, m), 4.32 (2H, m), 6.55 (1H, dd, J=1.8, J=3.3 Hz), 6.70 (1H, d, J=3.3 Hz), 7.81 (1H, d, J=1.8 Hz), 7.90 (1H, t, J=7.8 Hz), 8.42 (1H, d, J=7.8 Hz), 8.53 (1H, d, J=7.8 Hz), 8.95 (1H, s), 9.46 (1H, s)

Example 4-2

(R)-3-(2-Furylmethyl)amino-1-(4-bromo-5-isoquinolinesulfonyl)pyrrolidine (R)-3-Amino-1-(4-bromo-5-isoquinolinesulfonyl)pyrrolidine hydrochloride can be used in the method of Example 4-1 instead of (S)-3-amino-1-(4-bromo-5-isoquinolinesulfonyl)pyrrolidine hydrochloride to obtain the title compound.

Example 5

(R/S)-3-(Allylamino)-1-(4-bromo-5-isoquinolinesulfony)pyrrolidine

3-Amino-1-(4-bromo-5-isoquinolinesulfonyl)pyrrolidine hydrochloride can be used in the method of Example 5-1 instead of (S)-3-amino-1-(4-bromo-5-isoquinolinesulfonyl)pyrrolidine hydrochloride to obtain the title compound.

Example 5-1

(S)-3-(Allylamino)-1-(4-bromo-5-isoquinolinesulfonyl)pyrrolidine

The title compound can be obtained by adding allyl bromide (Tokyo Kasei Kogyo) to a suspension of (S)-3-amino- 1-(4-bromo-5-isoquinolinesulfonyl)pyrrolidine hydrochloride obtained in Example 1-1 and potassium carbonate in N,N-dimethylformamide to perform the reaction, and then performing purification of the product by silica gel chromatography.

Example 5-2

(R)-3-(Allylamino)-1-(4-bromo-5-isoquinolinesulfonyl)pyrrolidine (R)-3-Amino-1-(4-bromo-5-isoquinolinesulfonyl)pyrrolidine hydrochloride can be used in the method of Example 5-1 instead of (S)-3-amino-1-(4-bromo-5-isoquinolinesulfonyl)pyrrolidine hydrochloride to obtain the title compound.

Example 6

(R/S)-3-Amino-1-(4-bromo-1-methoxy-5-isoquinolinesulfonyl)pyrrolidine 3-(tert-Butoxycarbonylamino)-1-(2-oxy-4-bromo-5-isoquinolinesulfonyl)pyrrolidine (Intermediate 3) can be obtained by using Intermediate 1 in the method of Example 6-1, Step A instead of Intermediate 1a, and then used in the method of Step B to obtain 3-(tert-butoxycarbonylamino)-1-(4-bromo-1-methoxy-5-isoquinolinesulfonyl)pyrrolidine (Intermediate 4), and then Intermediate 4 can be used in the method of Step C to obtain the title compound.

Example 6-1

(S)-3-Amino-1-(4-bromo-1-methoxy-5-isoquinolinesulfonyl)pyrrolidine

Step A

(S)-3-(tert-Butoxycarbonylamino)-1-(2-oxy-4-bromo-5-isoquinolinesulfonyl)pyrrolidine (Intermediate 3a)

A suspension of Intermediate 1a (455 mg) obtained in Example 1-1, Step A and sodium acetate (164 mg) in methylene chloride (20 ml) was cooled on an ice bath, and added with 3-chloroperbenzoic acid (70%, 493 mg, Tokyo Kasei Kogyo) as several portions, and the mixture was stirred at the same temperature for 30 minutes. The mixture was further stirred at room temperature for 15 hours, and then added with saturated aqueous sodium hydrogencarbonate (25 ml), and the organic layer was separated. The organic layer was washed with saturated brine (20 ml), and dried over anhydrous magnesium sulfate, and then the solvent was evaporated under reduced pressure. The residue was purified by silica gel chromatography (ethyl acetate:methanol=10:1) to obtain the title compound (312 mg).

MS (m/z): 472 (MH+)

Step B

(S)-3-(tert-Butoxycarbonylamino)-1-(4-bromo-1-methoxy-5-isoquinolinesulfonyl)-pyrrolidine (Intermediate 4a)

A solution of Intermediate 3a (236 mg) obtained in Step A mentioned above in methanol (3.5 ml) was cooled on an ice bath, and added dropwise with methyl chloroformate (0.08 ml, Tokyo Kasei Kogyo), and then triethylamine (0.18 ml, Wako Pure Chemical Industries). The reaction mixture was stirred at room temperature for 3 hours, then cooled again on an ice bath, added with triethylamine (0.18 ml), and then methyl chloroformate (0.08 ml), and stirred at room temperature for 12 hours. The solvent was evaporated under reduced pressure, and the residue was added with saturated aqueous sodium hydrogencarbonate (10 ml) and methylene chloride (10 ml). The organic layer was separated, washed with saturated brine, and then dried over anhydrous magnesium sulfate. The solvent was evaporated under reduced pressure, and the residue was purified by silica gel chromatography (ethyl acetate:methanol=20:1) to obtain the title compound (120 mg).

MS (m/z): 486 (MH+)

Step C

(S)-3-Amino-1-(1-methoxy-4-bromo-5-isoquinolinesulfonyl)pyrrolidine

The protective group of Intermediate 4a obtained in Step B mentioned above can be removed according to the method described in Example 1-1, Step B to obtain the title compound as hydrochloride.

Example 6-2

(R)-3-Amino-1-(4-bromo-1-methoxy-5-isoquinolinesulfonyl)pyrrolidine

Intermediate 1b can be used in the method of Example 6-1 instead of Intermediate 1a to obtain the title compound as hydrochloride.

Example 7

(R/S)-3-Amino-1-(1-hydroxy-4-bromo-5-isoquinolinesulfonyl)pyrrolidine Intermediate 4 can be used in the method of Example 7-1 instead of Intermediate 4a to obtain the title compound as hydrochloride.

Example 7-1

(S)-3-Amino-1-(1-hydroxy-4-bromo-5-isoquinolinesulfonyl)pyrrolidine

Intermediate 4a (25 mg) obtained in Example 6-1, Step B was added with 10% hydrogen chloride/methanol (10 ml), and the mixture was stirred at 50° C. for 50 hours. The solvent was evaporated under reduced pressure to obtain the title compound as hydrochloride (13 mg).

MS (m/z): 372 (MH+)

$^1$H-NMR (DMSO) δ (ppm): 2.05-2.17 (1H, m), 2.33-2.45 (1H, m), 3.37-3.51 (2H, m), 3.59-3.70 (2H, m), 3.95-4.03 (1H, m), 7.68 (1H, s), 7.69 (1H, t, J=7.9 Hz), 8.18 (1H, dd, J=1.1, 7.9 Hz), 8.56 (1H, dd, J=1.1, 7.9 Hz)

Example 7-2

(R)-3-Amino-1-(1-hydroxy-4-bromo-5-isoquinolinesulfonyl)pyrrolidine

Intermediate 1b can be used in the method of Example 6-1, Step A instead of Intermediate 1a, then the resultant can be used in the method of Example 6-1, Step B in a similar manner, and then the title compound can be obtained as hydrochloride according to the method of Example 7-1.

Example 8

(R/S)-3-Amino-1-(4-methyl-5-isoquinolinesulfonyl)pyrrolidine

By using 4-methyl-5-isoquinolinesulfonyl chloride obtained according to the method described in WO09728130 instead of 4-bromo-5-isoquinolinesulfonyl chloride, and 3-(tert-butoxycarbonylamino)pyrrolidine instead of (S)-3-(tert-butoxycarbonylamino)pyrrolidine in the method of Example 1-1, (R/S)-3-(tert-butoxycarbonylamino)-1-(4-methyl-5 isoquinoline sulfonyl)pyrrolidine (Intermediate 5) can be prepared, and then the protective group of Intermediate 5 can be removed according to the method described in Example 1-1, Step B to obtain the title compound as hydrochloride.

Example 8-1

(S)-3-Amino-1-(4-methyl-5-isoquinolinesulfonyl)pyrrolidine

Step A (S)-3-(tert-Butoxycarbonylamino)-1-(4-methyl-5-isoquinolinesulfonyl)pyrrolidine (Intermediate 5a)

4-Methyl-5-isoquinolinesulfonyl chloride was used in the method of Example 1-1 instead of 4-bromo-5-isoquinolinesulfonyl chloride to obtain the title compound.

MS (m/z): 392 (MH+)

Step B (S)-3-Amino-1-(4-methyl-5-isoquinolinesulfonyl)pyrrolidine

The protective group of Intermediate 5a obtained in Step A mentioned above was removed according to the method described in Example 1-1, Step B to obtain the title compound as hydrochloride.

MS (m/z): 292 (MH+)

$^1$H-NMR (DMSO) δ (ppm): 2.17-2.28 (1H, m), 2.44-2.55 (1H, m), 3.03 (3H, s), 3.56-3.64 (2H, m), 3.72-3.87 (2H, m), 4.04-4.12 (1H, m), 7.97 (1H, t, J=7.8 Hz), 8.45 (1H, d, J=7.8 Hz), 8.64 (1H, d, J=7.8 Hz), 8.67 (1H, s), 9.64 (1H, s)

Example 8-2

(R)-3-Amino-1-(4-methyl-5-isoquinolinesulfonyl)pyrrolidine

By using 4-methyl-5-isoquinolinesulfonyl chloride instead of 4-bromo-5-isoquinolinesulfonyl chloride, and (R)-3-(tert-butoxycarbonylamino)pyrrolidine instead of (S)-3-(tert-butoxycarbonylamino)pyrrolidine in the method of Example 1-1, (R)-3-(tert-butoxycarbonylamino)-1-(4-methyl-5-isoquinolinesulfonyl)pyrrolidine (Intermediate 513) can be prepared, and then the protective group of Intermediate 5b can be removed according to the method described in Example 1-1, Step B to obtain the title compound as hydrochloride.

Example 9

(R/S)-3-Amino-1-(4-vinyl-5-isoquinolinesulfonyl)pyrrolidine 3-(tert-Butoxycarbonylamino)-1-(4-vinyl-5-isoquinolinesulfonyl)pyrrolidine (Intermediate 6) can be prepared by using Intermediate 1 in the method of Example 9-1, Step A instead of Intermediate 1a, and then used in the method of Step B in a similar manner to obtain the title compound as hydrochloride.

Example 9-1

(S)-3-Amino-1-(4-vinyl-5-isoquinolinesulfonyl)pyrrolidine

Step A (S)-3-(tert-Butoxycarbonylamino)-1-(4-vinyl-5-isoquinolinesulfonyl)pyrrolidine (Intermediate 6a)

A solution of Intermediate 1a (250 mg) obtained in Example 1-1, Step A, 2,6-di(tert-butyl)-4-methylphenol (0.5 mg, Tokyo Kasei Kogyo), and tri(n-butyl)vinyltin (0.25 ml, Tokyo Kasei Kogyo) in toluene (8 ml) was added with tetrakis(triphenylphosphine)palladium(0) (13 mg, Kanto Chemicals) under a nitrogen gas atmosphere, and the mixture was refluxed by heating for 12 hours. The reaction mixture was cooled to room temperature, and then the solvent was evaporated under reduced pressure. The residue was purified by silica gel chromatography (n-hexane:ethyl acetate=2:1) to obtain the title compound (195 mg).

MS (m/z): 404 (MH+)

Step B (S)-3-Amino-1-(4-vinyl-5-isoquinolinesulfonyl)pyrrolidine

The protective group of Intermediate 6a obtained in Step A mentioned above was removed according to the method described in Example 1-1, Step B to obtain the title compound as hydrochloride.

MS (m/z): 304 (MH+)

$^1$H-NMR (DMSO) δ (ppm): 2.09-2.20 (1H, m), 2.34-2.45 (1H, m), 3.41-3.53 (2H, m), 3.62-3.75 (2H, m), 3.95-4.03 (1H, m), 5.43 (1H, AB$_q$, J=1.2, 10.8 Hz), 5.69 (1H, AB$_q$, J=1.2, 17.0 Hz), 7.84 (1H, AB$_q$, J=10.8, 17.0 Hz), 7.89 (1H, t, J=7.8 Hz), 8.55 (1H, d), J=7.8 Hz), 8.71 (1H, s), 9.51 (1H, s)

Example 9-2

(R)-3-Amino-1-(4-vinyl-5-isoquinolinesulfonyl)pyrrolidine (R)-3-(tert-butoxycarbonylamino)-1-(4-vinyl-5-isoquinolinesulfonyl)pyrrolidine (Intermediate 6b) can be prepared by using Intermediate 1b in the method of Example 9-1, Step A instead of Intermediate 1a, and then used in the method of Step B in a similar manner to obtain the title compound as hydrochloride.

Example 10

(R/S)-3-Amino-1-(4-ethynyl-5-isoquinolinesulfonyl)pyrrolidine

Intermediate 1 can be used in the method of Example 10-1 instead of Intermediate 1a to obtain the title compound as hydrochloride.

Example 10-1

(S)-3-Amino-1-(4-ethynyl-5-isoquinolinesulfonyl)pyrrolidine

Step A (S)-3-(tert-Butoxycarbonylamino)-1-[4-(2-trimethylsilyl)ethynyl-5-isoquinolinesulfonyl]pyrrolidine (Intermediate 7a)

A suspension of Intermediate 1a (160 mg) obtained in Example 1-1, Step A, dichlorobisbenzonitrile)palladium(II) (31 mg, Tokyo Kasei Kogyo), tri(tert-butyl)phosphonium tetrafluoroborate (49 mg, Aldrich), and copper iodide (9 mg, Wako Pure Chemical Industries) in 1,4-dioxane (2 ml) was added with trimethylsilylacetylene (0.146 ml, Tokyo Kasei Kogyo) and diisopropylamine (0.148 ml, Wako Pure Chemical Industries) under a nitrogen gas atmosphere, and the mixture was stirred at room temperature for 18 hours. The reaction mixture was added with ethyl acetate (20 ml), and filtered through silica gel. The solvent was evaporated under reduced pressure, and then the residue was purified by silica gel chromatography (n-hexane:ethyl acetate=2:1) to obtain the title compound (98 mg).
MS (m/z): 474 (MH+)
Step B (S)-3-(tert-Butoxycarbonylamino)-1-[4-ethynyl-5-isoquinolinesulfonyl]pyrrolidine (Intermediate 8a)

A solution of Intermediate 7a (92 mg) obtained in Step A mentioned above in methanol (2 ml) was added with potassium carbonate (2.7 mg), and the mixture was stirred at room temperature for 3 hours. The solvent was evaporated under reduced pressure, and then the residue was added with methylene chloride (2 ml) and water (2 ml). The organic layer was separated, and dried over anhydrous magnesium sulfate, and then the solvent was evaporated under reduced pressure. The residue was purified by silica gel chromatography (n-hexane:ethyl acetate=1:1) to obtain the title compound (74 mg).
MS (m/z): 402 (MH+)
Step C (S)-3-Amino-1-(4-ethynyl-5-isoquinolinesulfonyl)pyrrolidine The protective group of Intermediate 8a obtained in Step B mentioned above was removed according to the method described in Example 1-1, Step B to obtain the title compound as hydrochloride (50 mg).
MS (m/z): 302 (MH+)
$^1$H-NMR (DMSO) δ (ppm): 2.11-2.22 (1H, m), 2.35-2.45 (1H, m), 3.46-3.56 (2H, m), 3.63-3.79 (2H, m), 3.93-4.10 (1H, m), 4.59 (1H, s), 7.89 (1H, t, J=7.8 Hz), 8.40 (1H, d, J=7.8 Hz), 8.51 (1H, d, J=7.8 Hz), 8.87 (1H, s), 9.50 (1H, s)
Example 10-2: (R)-3-Amino-1-(4-ethynyl-5-isoquinolinesulfonyl)pyrrolidine Intermediate 1b can be used in the method of Example 10-1 instead of Intermediate 1a to obtain the title compound as hydrochloride.

Example 11

(R/S)-3-Amino-1-(4-cyclopropyl-5-isoquinolinesulfonyl)pyrrolidine

Intermediate 1 can be used in the method of Example 11-1 instead of Intermediate 1a to obtain the title compound as hydrochloride.

Example 11-1

(S)-3-Amino-1-(4-cyclopropyl-5-isoquinolinesulfonyl)pyrrolidine

Step A (S)-3-(tert-Butoxycarbonylamino)-1-(4-cyclopropyl-5-isoquinolinesulfonyl)pyrrolidine (Intermediate 9a)

A suspension of Intermediate 1a (200 mg) obtained in Example 1-1, Step A, cyclopropylboronic acid (57 mg, Aldrich), anhydrous potassium phosphate (372 mg, Aldrich), and tricyclohexylphosphonium tetrafluoroborate (33 mg, Aldrich) in toluene (2 ml) was added with palladium acetate (10 mg, Wako Pure Chemical Industries), and the mixture was stirred at 80° C. with heating for 14 hours under a nitrogen gas atmosphere. The reaction mixture was cooled to room temperature, and then added with ethyl acetate (5 ml), and the insoluble solids were removed by filtration through Celite. The solvent was evaporated under reduced pressure, and the residue was purified by silica gel chromatography (n-hexane:ethyl acetate=1:1) to obtain the title compound (53 mg).
MS (m/z): 418 (MH+)
Step B (S)-3-Amino-1-(4-cyclopropyl-5-isoquinolinesulfonyl)pyrrolidine The protective group of Intermediate 9a obtained in Step A mentioned above was removed according to the method described in Example 1-1, Step B to obtain the title compound as hydrochloride (38 mg).
MS (m/z): 318 (MH+)
$^1$H-NMR (DMSO) δ (ppm): 0.86-0.92 (2H, m), 1.07-1.16 (2H, m), 2.13-2.24 (1H, m), 2.41-2.51 (1H, m), 3.07-3.16 (1H, m), 3.37-3.60 (2H, m), 3.68-3.80 (2H, m), 4.02-4.08 (1H, m), 7.91 (1H, t, J=7.8 Hz), 8.39 (1H, d, J=7.8 Hz), 8.49 (1H, s), 8.56 (1H, d, J=7.8 Hz), 9.50 (1H, s)

Example 11-2

(R)-3-Amino-1-(4-cyclopropyl-5-isoquinolinesulfonyl)pyrrolidine

Intermediate 1b can be used in the method of Example 11-1 instead of Intermediate 1a to obtain the title compound as hydrochloride.

Example 12

(R/S)-3-Amino-1-(4-amino-5-isoquinolinesulfonyl)pyrrolidine

Intermediate 1 can be used in the method of Example 12-1 instead of Intermediate 1a to obtain the title compound as hydrochloride.

Example 12-1

(S)-3-Amino-1-(4-amino-5-isoquinolinesulfonyl)pyrrolidine

Step A (S)-3-(tert-Butoxycarbonylamino)-1-[4-(tert-butoxycarbonylamino)-5-isoquinolinesulfonyl]pyrrolidine (Intermediate 10a)

A suspension of Intermediate 1a (137 mg) obtained in Example 1-1, Step A, tris(dibenzylideneacetone)dipalladium(0) (55 mg, Aldrich), (±)-2,2'-bis(diphenylphosphino)-1,1'-binaphthyl (37 mg, Aldrich), tert-butyl carbamate (70 mg, Aldrich), and cesium carbonate (196 mg, Aldrich) in toluene (5 ml) was stirred at 100° C. for 15 hours. The reaction mixture was cooled to room temperature, and then added with ethyl acetate (5 ml), and the insoluble solids were removed by filtration through Celite. The solvent was evaporated under reduced pressure, and the residue was purified by silica gel chromatography (n-hexane:ethyl acetate=1:1) to obtain the title compound (48 mg).

Step B (S)-3-Amino-1-(4-amino-5-isoquinolinesulfonyl)pyrrolidine

The protective group of Intermediate 10a obtained in Step A mentioned above was removed according to the method described in Example 1-1, Step B to obtain the title compound as hydrochloride (36 mg).

MS (m/z): 293 (MH+)

$^1$H-NMR (DMSO) δ (ppm): 2.06-2.17 (1H, m), 2.31-2.43 (1H, m), 3.45-3.76 (6H, m), 3.94-4.02 (1H, m), 7.90 (1H, t, J=7.8 Hz), 8.16 (1H, s), 8.40 (1H, d, J=7.8 Hz), 8.49 (1H, d, J=7.8 Hz), 8.93 (1H, s)

Example 12-2

(R)-3-Amino-1-(4-amino-5-isoquinolinesulfonyl)pyrrolidine

Intermediate 1b can be used in the method of Example 12-1 instead of Intermediate 1a to obtain the title compound as hydrochloride.

Example 13

(R/S)-3-Amino-1-(4-cyano-5-isoquinolinesulfonyl)pyrrolidine

Intermediate 1 can be used in the method of Example 13-1 instead of Intermediate 1a to obtain the title compound as hydrochloride.

Example 13-1

(S)-3-Amino-1-(4-cyano-5-isoquinolinesulfonyl)pyrrolidine

Step A (S)-3-(tert-Butoxycarbonylamino)-1-(4-cyano-5-isoquinolinesulfonyl)pyrrolidine (Intermediate 11a)

The title compound was obtained from Intermediate 1a obtained in Example 1-1, Step A according to the method described in a known literature (Weissman S. A. et al., J. Org. Chem., 2005, 70, 1508).

Step B

The protective group of Intermediate 11a obtained in Step A mentioned above was removed according to the method described in Example 1-1, Step B to obtain the title compound as hydrochloride.

MS (m/z): 303 (MH+)

$^1$H NMR (DMSO) δ (ppm): 2.01-2.12 (1H, m), 2.31-2.42 (1H, m), 3.40-3.78 (4H, m), 3.92-3.98 (1H, m), 8.04 (1H, t, J=7.8 Hz), 8.60 (1H, dd, J=1.3, 7.8 Hz), 8.68 (1H, dd, J=1.3, 7.8 Hz), 9.23 (1H, s), 9.80 (1H, s)

Example 13-2

(R)-3-Amino-1-(4-cyano-5-isoquinolinesulfonyl)pyrrolidine

Intermediate 1b can be used in the method of Example 13-1 instead of Intermediate 1a to obtain the title compound as hydrochloride.

Example 14

(R/S)-3-Amino-1-(4-phenyl-5-isoquinolinesulfonyl)pyrrolidine

Intermediate 1 can be used in the method of Example 14-1 instead of Intermediate 1a to obtain the title compound as hydrochloride.

Example 14-1

(S)-3-Amino-1-(4-phenyl-5-isoquinolinesulfonyl)pyrrolidine

Step A (S)-3-(tert-Butoxycarbonylamino)-1-[4-phenyl-5-isoquinolinesulfonyl]pyrrolidine (Intermediate 12a)

Intermediate 1a (228 mg) obtained in Example 1-1, Step A was added with phenylboronic acid (122 mg, Aldrich), tetrakis(triphenylphosphine)palladium(0) (116 mg), 1,2-dimethoxyethane (5 ml) and 2 N aqueous sodium carbonate (2 ml), and the mixture was refluxed by heating for 5 hours under a nitrogen gas atmosphere. The reaction mixture was cooled to room temperature, then added with water (25 ml), and extracted 3 times with ethyl acetate (20 ml for each time), and the combined organic layer was washed with saturated brine (30 ml), and dried over anhydrous magnesium sulfate. The solvent was evaporated under reduced pressure, and the residue was purified by silica gel chromatography (n-hexane: ethyl acetate=2:1) to obtain the title compound (158 mg).

MS (m/z): 454 (MH+)

Step B (S)-3-Amino-1-(4-phenyl-5-isoquinolinesulfonyl)pyrrolidine

The protective group of Intermediate 12a obtained in Step A mentioned above was removed according to the method described in Example 1-1, Step B to obtain the title compound as hydrochloride.
MS (m/z): 354 (MH+)

Example 14-2

(R)-3-Amino-1-(4-phenyl-5-isoquinolinesulfonyl)pyrrolidine

Intermediate 1b can be used in the method of Example 14-1 instead of Intermediate 1a to obtain the title compound as hydrochloride.

Example 15

(R/S)-3-Amino-1-(4-methoxy-5-isoquinolinesulfonyl)pyrrolidine (R/S)-3-(tert-Butoxycarbonylamino)-1-(4-methoxy-5-isoquinolinesulfonyl)pyrrolidine (Intermediate 13) can be prepared by using Intermediate 1 in the method of Example 15-1, Step A instead of Intermediate 1a, and then used in the method of Example 15-1, Step B in a similar manner to obtain the title compound as hydrochloride.

Example 15-1

(S)-3-Amino-1-(4-methoxy-5-isoquinolinesulfonyl)pyrrolidine

Step A (S)-3-(tert-Butoxycarbonylamino)-1-(4-methoxy-5-isoquinolinesulfonyl)pyrrolidine (Intermediate 13a)

A solution of Intermediate 1a (337 mg) obtained in Example 1-1, Step A in methanol (2.7 ml) and pyridine (2.7 ml) was added with a solution of 28% sodium methylate (847 mg) in methanol, and then with copper iodide (70 mg), and the mixture was stirred at 65° C. for 30 hours. The reaction mixture was cooled to room temperature, and added with water (30 ml) and ethyl acetate (30 ml), and the insoluble solids were removed by filtration through Celite. The organic layer of the filtrate was separated, and the aqueous layer was extracted 3 times with ethyl acetate (20 ml for each time). The combined organic layer was washed 3 times with saturated brine (30 ml for each time), and dried over anhydrous magnesium sulfate. The solvent was evaporated under reduced pressure, and the residue was purified by silica gel chromatography (chloroform:methanol=30:1) to obtain the title compound (98 mg).
MS (m/z): 408 (MH+)
Step B (S)-3-Amino-1-(4-methoxy-5-isoquinolinesulfonyl)pyrrolidine The protective group of Intermediate 13a obtained in Step A mentioned above was removed according to the method described in Example 1-1, Step B to obtain the title compound as hydrochloride
MS (m/z): 308 (MH+).

Example 15-2

(R)-3-Amino-1-(4-methoxy-5-isoquinolinesulfonyl)pyrrolidine (R)-3-(tert-Butoxycarbonylamino)-1-(4-methoxy-5-isoquinolinesulfonyl)pyrrolidine (Intermediate 13b) can be prepared by using Intermediate 1b in the method of Example 15-1, Step A instead of Intermediate 1a, and then used in the method of Example 15-1, Step B in a similar manner to obtain the title compound as hydrochloride.

Example 16

(R/S)-3-Amino-1-(4-hydroxy-5-isoquinolinesulfonyl)pyrrolidine

Intermediate 13 can be used in the method of Example 16-1 instead of Intermediate 13a to obtain the title compound as hydrobromide.

Example 16-1

(S)-3-Amino-1-(4-hydroxy-5-isoquinolinesulfonyl)pyrrolidine

The title compound can be obtained by adding Intermediate 13a obtained in Example 15-1, Step A to 30% hydrogen bromide/acetic acid and performing the reaction.

Example 16-2

(R)-3-Amino-1-(4-hydroxy-5-isoquinolinesulfonyl)pyrrolidine

Intermediate 13b can be used in the method of Example 16-1 instead of Intermediate 13a to obtain the title compound as hydrobromide.

Example 17

(R/S)-3-Amino-1-[4-(1-butylthio)-5-isoquinolinesulfonyl]pyrrolidine

Intermediate 1 can be used in the method of Example 17-1 instead of Intermediate 1a to obtain the title compound as hydrochloride.

Example 17-1

(S)-3-Amino-1-[4-(1-butylthio)-5-isoquinolinesulfonyl]pyrrolidine

Step A (S)-3-(tert-Butoxycarbonylamino)-1-[4-(1-butylthio)-5-isoquinolinesulfonyl]pyrrolidine (Intermediate 14a)

The title compound can be obtained from Intermediate 1a obtained in Example 1-1, Step A according to the method described in a known literature (Itoh et al., Org. Lett., 2004, 6, 4587).

Step B

The protective group of Intermediate 14a obtained in Step A mentioned above can be removed according to the method described in Example 1-1, Step B to obtain the title compound as hydrochloride.

Example 17-2

(R)-3-Amino-1-[4-(1-butylthio)-5-isoquinolinesulfonyl]pyrrolidine

Intermediate 1b can be used in the method of Example 17-1 instead of Intermediate 1a to obtain the title compound as hydrochloride.

Example 18

(R/S)-3-Amino-1-(4-fluoro-5-isoquinolinesulfonyl)pyrrolidine 3-(tert-Butoxycarbonylamino)-1-(4-fluoro-5-isoquinolinesulfonyl)pyrrolidine (Intermediate 15) can be prepared by using 3-(tert-butoxycarbonylamino)pyrrolidine in the method of Example 18-1, Step A instead of (S)-3-(tert-butoxycarbonylamino)pyrrolidine, and then used in the method of Step B in a similar manner to obtain the title compound as hydrochloride.

Example 18-1

(S)-3-Amino-1-(4-fluoro-5-isoquinolinesulfonyl)pyrrolidine

Step A (S)-3 (tert-Butoxycarbonylamino)-1-(4-fluoro-5-isoquinolinesulfonyl)pyrrolidine (Intermediate 15a)

4-Fluoro-5-isoquinolinesulfonyl chloride (147 mg) obtained in Reference Example 4 was used in the method of Example 1-1, Step A instead of 4-bromo-5-isoquinolinesulfonyl chloride, and reacted with (S)-3-(tert-butoxycarbonylamino)pyrrolidine (134 mg) to obtain the title compound (190 mg).

MS (m/z): 396 (MH+)

$^1$H-NMR (CDCl$_3$) δ (ppm): 1.42 (9H, s), 1.88-1.99 (1H, m), 2.19-2.30 (1H, m), 3.34-3.39 (1H, m), 3.46-3.70 (3H, m), 4.22-4.32 (1H, m), 7.73 (1H, t, J=7.8 Hz), 8.25 (1H, ddd, J=1.2, 1.9, 7.8 Hz), 8.54 (1H, dd, J=1.2, 7.8 Hz), 8.57 (1H, d, J=4.5 Hz), 9.16 (1H, s), Step B (S)-3-Amino-1-(4-fluoro-5-isoquinolinesulfonyl)pyrrolidine The title compound was obtained as hydrochloride (106 mg) from Intermediate 15a (158 mg) according to the method of Example 1-1, Step B.

MS (m/z): 296 (MH+)

$^1$H-NMR (DMSO) δ (ppm): 2.12-2.23 (1H, m), 2.34-2.45 (1H, m), 3.49-3.58 (2H, m), 3.64-3.72 (1H, m), 3.77-3.83 (1H, m), 3.95-4.03 (1H, m), 7.93 (1H, t, J=7.8 Hz), 8.46 (1H, d, J=7.8 Hz), 8.58 (1H, d, J=7.8 Hz), 8.72 (1H, d, J=4.8 Hz), 9.41 (1H, s)

Example 18-2

(R)-3-Amino-1-(4-fluoro-5-isoquinolinesulfonyl)pyrrolidine (R)-3-(tert-Butoxycarbonylamino)-1-(4-fluoro-5-isoquinolinesulfonyl)-pyrrolidine (Intermediate 15b) can be prepared by using (R)-3-(tert-butoxycarbonylamino)pyrrolidine in the method of Example 18-1, Step A instead of (S)-3-(tert-butoxycarbonylamino)pyrrolidine, and then used in the method of Step B in a similar manner to obtain the title compound as hydrochloride.

Example 19

(R/S)-3-Amino-1-(4-chloro-5-isoquinolinesulfonyl)pyrrolidine 3-(tert-Butoxycarbonylamino)-1-(4-chloro-5-isoquinolinesulfonyl)pyrrolidine (Intermediate 16) can be prepared by using 3-(tert-butoxycarbonylamino)pyrrolidine in the method of Example 19-1, Step A instead of (S)-3-(tert-butoxycarbonylamino)pyrrolidine, and then used in the method of Step B in a similar manner to obtain the title compound as hydrochloride.

Example 19-1

(S)-3-Amino-1-(4-chloro-5-isoquinolinesulfonyl)pyrrolidine

Step A (S)-3-(tert-Butoxycarbonylamino)-1-(4-chloro-5-isoquinolinesulfonyl)pyrrolidine (Intermediate 16a)

4-Chloro-5-isoquinolinesulfonyl chloride (157 mg) obtained in Reference Example 7 was used in the method of Example 1-1, Step A instead of 4-bromo-5-isoquinolinesulfonyl chloride, and reacted with (S)-3-(tert-butoxycarbonylamino)pyrrolidine (134 mg) to obtain the title compound (198 mg).

MS (m/z): 412 (MH+)

$^1$H-NMR (CDCl$_3$) δ (ppm): 1.44 (9H, s), 1.97-2.05 (1H, m), 2.25-2.36 (1H, m), 3.36-3.41 (1H, m), 3.48-3.56 (1H, m), 3.63-3.67 (2H, m), 4.35 (1H, m), 4.78 (1H, m), 7.71 (1H, t, J=7.8 Hz), 8.22 (1H, dd, J=1.3, 7.8 Hz), 8.45 (1H, dd, J=1.3, 7.8 Hz), 8.78 (1H, s), 9.19 (1H, s)

Step B (S)-3-Amino-1-(4-chloro-5-isoquinoline sulfonyl)pyrrolidine

The title compound was obtained as hydrochloride (148 mg) from Intermediate 16a (165 mg) in the same manner as Example 1-1, Step B.

MS (m/z): 312 (MH+)

$^1$H-NMR (DMSO) δ (ppm): 2.13-2.21 (1H, m), 2.39-2.50 (1H, m), 3.47-3.56 (2H, m), 3.65-3.80 (2H, m), 4.00-4.08 (1H, m), 7.90 (1H, t, J=7.8 Hz), 8.37 (1H, d, J=7.8 Hz), 8.54 (1H, d, J=7.8 Hz), 8.78 (1H, s), 9.44 (1H, s)

Example 19-2

(R)-3-Amino-1-(4-chloro-5-isoquinolinesulfonyl) pyrrolidine (R)-3-(tert-Butoxycarbonylamino)-1-(4-chloro-5-isoquinolinesulfonyl)-pyrrolidine (Intermediate 16b) was prepared by using (R)-3-(tert-butoxycarbonylamino)pyrrolidine in the method of Example 19-1, Step A instead of (S)-3-(tert-butoxycarbonylamino)pyrrolidine, and then used in the method of Step B in a similar manner to obtain the title compound as hydrochloride.

MS (m/z): 312 (MH+)

$^1$H-NMR (DMSO) δ (ppm): 2.13-2.21 (1H, m), 2.39-2.50 (1H, m), 3.47-3.56 (2H, m), 3.65-3.80 (2H, m), 4.00-4.08 (1H, m), 7.90 (1H, t, J=7.8 Hz), 8.37 (1H, d, J=7.8 Hz), 8.54 (1H, d, J=7.8 Hz), 8.78 (1H, s), 9.44 (1H, s)

Example 20

(R/S)-3-Amino-1-(4-fluoro-5-isoquinolinesulfonyl) piperidine 3-(tert-Butoxycarbonylamino)-1-(4-fluoro-5-isoquinolinesulfonyl)piperidine (Intermediate 17) can be prepared by using 3-(tert-butoxycarbonylamino)piperidine in the method of Example 20-1, Step A instead of (S)-3-(tert-butoxycarbonylamino)piperidine, and used in the method of Step B in a similar manner to obtain the title compound as hydrochloride.

Example 20-1

(S)-3-Amino-1-(4-fluoro-5-isoquinolinesulfonyl) piperidine (S)-3-(tert-Butoxycarbonylamino)-1-(4-fluoro-5-isoquinolinesulfonyl)-piperidine (Intermediate 17a) was prepared from 4-fluoro-5-isoquinolinesulfonyl chloride (172 mg) and 3-(tert-butoxycarbonylamino)piperidine (168 mg) according to the method of Example 1-1, Step A, and then used in the method of Example 1-1, Step B in a similar manner to obtain the title compound as hydrochloride (156 mg).

MS (m/z): 310 (MH+)

Example 20-2

(R)-3-Amino-1-(4-fluoro-5-isoquinolinesulfonyl) piperidine (R)-3-(tert-Butoxycarbonylamino)-1-(4-fluoro-5-isoquinolinesulfonyl)-piperidine (Intermediate 17b) can be prepared by using (R)-3-(tert-butoxycarbonylamino)piperidine in the method of Example 20-1, Step A instead of (S)-3-(tert-butoxycarbonylamino)piperidine, and then used in the method of Step B in a similar manner to obtain the title compound as hydrochloride.

Example 21

(R/S)-3-Amino-1-(4-chloro-5-isoquinolinesulfonyl) piperidine 3-(tert-Butoxycarbonylamino)-1-(4-chloro-5-isoquinolinesulfonyl)piperidine (Intermediate 18) can be prepared by using 3-(tert-butoxycarbonylamino)piperidine in the method of Example 21-1, Step A instead of (S)-3-(tert-butoxycarbonylamino)piperidine, and then used in the method of Step B in a similar manner to obtain the title compound as hydrochloride.

Example 21-1

(S)-3-Amino-1-(4-chloro-5-isoquinolinesulfonyl) piperidine (S)-3-(tert-Butoxycarbonylamino)-1-(4-chloro-5-isoquinolinesulfonyl)-piperidine (Intermediate 18a) was prepared from 4-chloro-5-isoquinolinesulfonyl chloride (183 mg) and (S)-3-(tert-butoxycarbonylamino)piperidine (168 mg) according to the method described in Example 1-1, Step A, and then used in the method of Example 1-1, Step B in a similar manner to obtain the title compound as hydrochloride (164 mg).

MS (m/z): 326 (MH+)

Example 21-2

(R)-3-Amino-1-(4-chloro-5-isoquinolinesulfonyl) piperidine (R)-3-(tert-Butoxycarbonylamino)-1-(4-chloro-5-isoquinolinesulfonyl)-piperidine (Intermediate 18b) was prepared by using (R)-3-(tert-butoxycarbonylamino)piperidine in the method of Example 21-1, Step A instead of (S)-3-(tert-butoxycarbonylamino)piperidine, and then used in the method of Step B in a similar manner to obtain the title compound as hydrochloride.

MS (m/z): 326 (MH+)

Example 22

(R/S)-3-Amino-1-(4-methyl-5-isoquinolinesulfonyl) piperidine (R/S)-3-(tert-Butoxycarbonylamino)-1-(4-methyl-5-isoquinolinesulfonyl)-piperidine can be prepared by using 4-methyl-5-isoquinolinesulfonyl chloride instead of 4-bromo-5-isoquinolinesulfonyl chloride, and 3-(tert-butoxycarbonylamino)pyrrolidine instead of (S)-3-(tert-butoxycarbonylamino)pyrrolidine in the method of Example 1-1, and then the protective group of the resultant can be removed according to the method described in Example 1-1, Step B to obtain the title compound as hydrochloride.

Example 22-1

(S)-3-Amino-1-(4-methyl-5-isoquinolinesulfonyl) piperidine (S)-3-(tert-Butoxycarbonylamino)-1-(4-methyl-5-isoquinolinesulfonyl)-piperidine was prepared by using 4-methyl-5-isoquinolinesulfonyl chloride instead of 4-bromo-5-isoquinolinesulfonyl chloride, and (S)-3-(tert-butoxycarbonylamino)piperidine instead of (S)-3-(tert-butoxycarbonylamino)pyrrolidine in the method of Example 1-1, and then the protective group of the resultant was removed according to the method described in Example 1-1, Step B to obtain the title compound as hydrochloride.

MS (m/z): 306 (MH+)

$^1$H-NMR (DMSO) δ (ppm): 1.55-2.20 (4H, m), 3.04 (3H, s), 3.16-3.36 (3H, m), 3.65-3.71 (1H, m), 3.93-3.99 (1H, m), 7.97 (1H, dd, J=6.6 Hz, J=8.1 Hz), 8.38 (1H, d,

Example 22-2

(R)-3-Amino-1-(4-methyl-5-isoquinolinesulfonyl)piperidine (R)-3-(tert-Butoxycarbonylamino)-1-(4-methyl-5-isoquinolinesulfonyl)-piperidine was prepared by using 4-methyl-5-isoquinolinesulfonyl chloride instead of 4-bromo-5-isoquinolinesulfonyl chloride, and (R)-3-(tert-butoxycarbonylamino)piperidine instead of (S)-3-(tert-butoxycarbonylamino)pyrrolidine in the method of Example 1-1, and then the protective group of the resultant was removed according to the method described in Example 1-1, Step B to obtain the title compound as hydrochloride.

MS (m/z): 306 (MH+)
$^1$H-NMR (DMSO) δ (ppm): 1.55-2.20 (4H, m), 3.04 (3H, s), 3.16-3.36 (3H, m), 3.65-3.71 (1H, m), 3.93-3.99 (1H, m), 7.97 (1H, dd, J=6.6 Hz, J=8.1 Hz), 8.38 (1H, d, J=6.6 Hz), 8.51 (3, br.s), 8.65 (1H, d, J=8.1 Hz), 8.69 (1H, s), 9.67 (1H, s)

Example 23

(R/S)-3-Amino-1-(4-ethyl-5-isoquinolinesulfonyl)pyrrolidine

Intermediate 6 can be used in the method of Example 23-1 instead of Intermediate 6a to obtain the title compound as hydrochloride.

Example 23-1

(S)-3-Amino-1-(4-ethyl-5-isoquinolinesulfonyl)pyrrolidine

Step A (S)-3-(tert-Butoxycarbonylamino)-1-(4-ethyl-5-isoquinolinesulfonyl)pyrrolidine (Intermediate 19a)

A solution of Intermediate 6a (120 mg) obtained in Example 9-1, Step A in ethanol (2 ml) was added with 10% palladium/activated carbon (90 mg, Wako Pure Chemical Industries), and the mixture was stirred at room temperature for 72 hours under a hydrogen gas atmosphere. The atmosphere was replaced with nitrogen gas, and then the insoluble solids were removed by filtration through Celite. The solvent was evaporated under reduced pressure, and the residue was purified by silica gel chromatography (n-hexane:ethyl acetate=2:1) to obtain the title compound (195 mg).

MS (m/z): 406 (MH+)

Step B (S)-3-Amino-1-(4-ethyl-5-isoquinolinesulfonyl)pyrrolidine

The protective group of Intermediate 19a obtained in Step A mentioned above was removed according to the method described in Example 1-1, Step B to obtain the title compound as hydrochloride.

MS (m/z): 406 (MH+)

Example 23-2

(R)-3-Amino-1-(4-ethyl-5-isoquinolinesulfonyl)pyrrolidine

Intermediate 6b can be used in the method of Example 23-1 instead of Intermediate 6a to obtain the title compound as hydrochloride.

Example 24

(R/S)-3-Amino-1-[4-(4-isoxazolyl)-5-isoquinolinesulfonyl]pyrrolidine

Intermediate 1 can be used in the method of Example 24-1 instead of Intermediate 1a to obtain the title compound as hydrochloride. Example 24-1: (S)-3-Amino-1-[4-(4-isoxazolyl)-5 isoquinolinesulfonyl]pyrrolidine The title compound was obtained from Intermediate 1a as hydrochloride by using 4-isoxazoleboronic acid pinacol ester (Fronteir Scientific) in the method of Example 14-1 instead of phenylboronic acid.

MS (m/z): 345 (MH+)

Example 24-2

(R)-3-Amino-1-[4-(4-isoxazolyl)-5-isoquinolinesulfonyl]pyrrolidine

Intermediate 1b can be used in the method of Example 24-1 instead of Intermediate 1a to obtain the title compound as hydrochloride.

Example 25

(R/S)-3-Amino-1-(1-hydroxy-4-methyl-5-isoquinolinesulfonyl)pyrrolidine

Intermediate 5 can be used in the method of Example 6-1, Step A instead of Intermediate 1a, then the resultant can be used in the method of Step B in a similar manner, and then the title compound can be obtained as hydrochloride according to the method described in Example 7-1.

Example 25-1

(S)-3-Amino-1-(1-hydroxy-4-methyl-5-isoquinolinesulfonyl)pyrrolidine

Intermediate 5a was used in the method of Example 6-1, Step A instead of Intermediate 1a, then the resultant was used in the method of Step B in a similar manner, and then the title compound was obtained as hydrochloride according to the method described in Example 7-1.

MS (m/z): 308 (MH+)
$^1$H-NMR (DMSO) δ (ppm): 2.13-2.24 (1H, m), 2.37-2.49 (1H, m), 2.56 (3H, s), 3.46-3.57 (2H, m), 3.65-3.79 (2H, m), 4.00-4.07 (1H, m), 7.18 (1H, d, J=5.1 Hz), 7.62 (1H, t, J=7.8 Hz), 8.13 (1H, dd, 7.8 Hz), 8.60 (1H, dd, J=1.5, 7.8 Hz)

Example 25-2

(R)-3-Amino-1-(1-hydroxy-4-methyl-5-isoquinolines

Intermediate 5b can be used in the method of Example 6-1, Step A instead of Intermediate 1a, then the resultant can be used in the method of Step B in a similar manner, and then the title compound can be obtained as hydrochloride according to the method described in Example 7-1.

Example 26

3-Amino-1-(4-methyl-5-isoquinolinesulfonyl)azetidine (S)-3-(tert-Butoxycarbonylamino)-1-(4-methyl-5-isoquinolinesulfonyl)azetidine was prepared by using 4-methyl-5-isoquinolinesulfonyl chloride instead of 4-bromo-5-isoquinolinesulfonyl chloride, and (S)-3-(tert-butoxycarbonylamino)azetidine (AstaTech) instead of (S)-3-(tert-butoxycarbonylamino)pyrrolidine in the method of Example 1-1, and used in the method of Example 1-1, Step B to obtain the title compound as hydrochloride.
MS (m/z): 278 (MH+)
$^1$H-NMR (DMSO) δ (ppm): 3.02 (1H, s), 4.10-4.80 (5H, m), 7.93 (1H, t, J=7.8 Hz), 8.61 (1H, dd, J=0.9 Hz, J=7.8 Hz), 8.65 (1H, s), 8.80 (3H, br.s), 8.97 (1H, dd, J=0.9 Hz, J=7.8 Hz), 9.55 (1H, s)

Example 27

(R)-3-(Methylamino)-1-(4-methyl-5-isoquinolinesulfonyl)pyrrolidine

Hydrochloride of the compound obtained in Example 8-2 and methyl iodide (Tokyo Kasei Kogyo) can be used in the method of Example 5-1 instead of (S)-3-amino-1-(4-bromo-5-isoquinolinesulfonyl)pyrrolidine hydrochloride and allyl bromide, respectively, to obtain the title compound as hydrochloride.

Example 28

(R/S)-3-Amino-1-[4-(2-hydroxymethyl)ethynyl-5-isoquinolinesulfonyl]pyrrolidine Intermediate 1 and 2-propyn-1-ol (Tokyo Kasei Kogyo) can be used in the method of Example 10-1, Step A instead of Intermediate 1a and trimethylsilylacetylene, respectively, and then the resultant can be used in the method of Example 1-1, Step B to obtain the title compound as hydrochloride.

Example 28-1

(S)-3-Amino-1-[4-(2-hydroxymethyl)ethynyl-5-isoquinolinesulfonyl]pyrrolidine 2-Propyn-1-ol was used in the method of Example 10-1, Step A instead of trimethylsilylacetylene, and then the resultant was used in the method of Example 1-1, Step B to obtain the title compound as hydrochloride.
MS (m/z): 332 (MH+)
$^1$H-NMR (DMSO) δ (ppm): 2.11-2.22 (1H, m), 2.38-2.49 (1H, m), 3.45-3.57 (2H, m), 3.65-3.81 (2H, m), 3.95-4.06 (1H, m), 4.39 (2H, s), 7.84-7.89 (1H, m), 8.31-8.33 (1H, m), 8.48-8.51 (1H, m), 8.78 (1H, s), 9.45 (1H, s)

Example 28-2

(R)-3-Amino-1-[4-(2-hydroxymethypethynyl-5-isoquinolinesulfonyl]pyrrolidine Intermediate 1b and 2-propyn-1-ol can be used in the method of Example 10-1, Step A instead of Intermediate 1a and trimethylsilylacetylene, respectively, and then the resultant can be used in the method of Example 1-1, Step B, to obtain the title compound as hydrochloride.

Example 29

(R/S)-3-Amino-1-(1-hydroxy-4-fluoro-5-isoquinolinesulfonyl)pyrrolidine

Intermediate 15 can be used in the method of Example 6-1, Step A instead of Intermediate 1a, then the resultant can be used in the method of Step B in a similar manner, and then the title compound can be obtained as hydrochloride according to the method described in Example 7-1.

Example 29-1

(S)-3-Amino-1-(1-hydroxy-4-fluoro-5-isoquinolinesulfonyl)pyrrolidine

Intermediate 15a was used in the method of Example 6-1, Step A instead of Intermediate 1a, then the resultant was used in the method of Step B in a similar manner, and then the title compound was obtained as hydrochloride according to the method described in Example 7-1.
MS (m/z): 312 (MH+)
$^1$H-NMR (DMSO) δ (ppm): 2.02-2.12 (1H, m), 2.31-2.42 (1H, m), 3.37-3.51 (2H, m), 3.58-3.74 (2H, m), 3.92-4.00 (1H, m), 7.58 (1H, d, J=8.1 Hz), 7.72 (1H, t, J=7.8 Hz), 8.25 (1H, dd, J=1.2, 7.8 Hz), 8.54 (1H, ddd, J=1.2, 2.3, 7.8 Hz)

Example 29-2

(R)-3-Amino-1-(1-hydroxy-4-fluoro-5-isoquinolinesulfonyl)pyrrolidine

Intermediate 15b can be used in the method of Example 6-1, Step A instead of Intermediate 1a, then the resultant can be used in the method of Step B in a similar manner, and then the title compound can be obtained as hydrochloride according to the method described in Example 7-1.

Example 30

(R/S)-3-Amino-1-(1-hydroxy-4-chloro-5-isoquinolinesulfonyl)pyrrolidine

Intermediate 16 can be used in the method of Example 6-1, Step A instead of Intermediate 1a, then the resultant can be used in the method of Step B in a similar manner, and then the title compound can be obtained as hydrochloride according to the method described in Example 7-1.

Example 30-1

(S)-3-Amino-1-(1-hydroxy-4-chloro-5-isoquinolinesulfonyl

Intermediate 16a was used in the method of Example 6-1, Step A instead of Intermediate 1a, then the resultant was used in the method of Step B in a similar manner, and then the title compound was obtained as hydrochloride according to the method described in Example 7-1.
MS (m/z): 328 (MH+)
$^1$H-NMR (DMSO) δ (ppm): 2.09-2.19 (1H, m), 2.35-2.46 (1H, m), 3.42-3.53 (2H, m), 3.61-3.74 (2H, m), 3.96-4.04

(1H, m), 7.58 (1H, s), 7.71 (1H, t, J=7.9 Hz), 8.20 (1H, dt, J=1.2, 7.9 Hz), 8.57 (1H, dd, J=1.2, 7.9 Hz)

Example 30-2

(R)-3-Amino-1-(1-hydroxy-4-chloro-5-isoquinolines

Intermediate 16b can be used in the method of Example 6-1, Step A instead of Intermediate 1a, then the resultant can be used in the method of Step B in a similar manner, and then the title compound can be obtained as hydrochloride according to the method described in Example 7-1.

<Examples 1-6, 1-7, 1-11 to 1-14, 1-18 to 1-19, 1-30, 1-33, 1-38, 8-4 to 8-9, 8-12, 8-13, 8-16, 8-18, 8-21, 8-26 to 8-34, 8-36, 10-7, 10-14, 10-29, 10-31, 18-7, 18-8, 18-14, 18-16, 18-21, 18-31, 19-4, 19-7, 19-8, 19-12, 19-14, 19-17, 19-21, 19-31, 19-33, 19-36 and 19-40>

Synthesis of the compounds of Examples 1-6, 1-7, 1-11 to 1-14, 1-18 to 1-19, 1-30, 1-33, 1-38, 8-4 to 8-9, 8-12, 8-13, 8-16, 8-18, 8-21, 8-26 to 8-34, 8-36, 10-7, 10-14, 10-29, 10-31, 18-7, 18-8, 18-14, 18-16, 18-21, 18-31, 19-4, 19-7, 19-8, 19-12, 19-14, 19-17, 19-21, 19-31, 19-33, 19-36 and 19-40 was performed according to the method of Example 4 or 5.

The details of the compounds of Examples 1-6, 1-7, 1-11 to 1-14, 1-18 to 1-19, 1-30, 1-33, 1-38, 8-4 to 8-9, 8-12, 8-13, 8-16, 8-18, 8-21, 8-26 to 8-34, 8-36, 10-7, 10-14, 10-29, 10-31, 18-7, 18-8, 18-14, 18-16, 18-21, 18-31, 19-4, 19-7, 19-8, 19-12, 19-14, 19-17, 19-21, 19-31, 19-33, 19-36 and 19-40 are shown in Table 1-1.

<Examples 1-4, 1-5, 1-8 to 1-10, 1-15 to 1-17, 1-20 to 1-29, 1-31, 1-32, 1-34 to 1-37, 2-4 to 2-40, 8-10, 8-11, 8-14, 8-15, 8-17, 8-19, 8-20, 8-22 to 8-25, 8-35, 8-37 to 8-78, 9-4 to 9-78, 10-4 to 10-6, 10-8 to 10-13, 10-15 to 10-28, 10-30, 10-32 to 10-78, 18-4 to 18-6, 18-9 to 18-13, 18-15, 18-17 to 18-20, 18-22 to 18-30, 18-32 to 18-40, 19-5, 19-6, 19-9 to 19-11, 19-13, 19-15, 19-16, 19-18 to 19-20, 19-22 to 19-30, 19-32, 19-34, 19-35, 19-37 to 19-39, 20-4 to 20-40 and 21-4 to 21-40>

Synthesis of the compounds of Examples 1-4, 1-5, 1-8 to 1-10, 1-15 to 1-17, 1-20 to 1-29, 1-31, 1-32, 1-34 to 1-37, 2-4 to 2-40, 8-10, 8-11, 8-14, 8-15, 8-17, 8-19, 8-20, 8-22 to 8-25, 8-35, 8-37 to 8-78, 9-4 to 9-78, 10-4 to 10-6, 10-8 to 10-13, 10-15 to 10-28, 10-30, 10-32 to 10-78, 18-4 to 18-6, 18-9 to 18-13, 18-15, 18-17 to 18-20, 18-22 to 18-30, 18-32 to 18-40, 19-5, 19-6, 19-9 to 19-11, 19-13, 19-15, 19-16, 19-18 to 19-20, 19-22 to 19-30, 19-32, 19-34, 19-35, 19-37 to 19-39, 20-4 to 20-40 and 21-4 to 21-40 can be performed according to the method of Example 4 or 5.

The details of the compounds of Examples 1-4, 1-5, 1-8 to 1-10, 1-15 to 1-17, 1-20 to 1-29, 1-31, 1-32, 1-34 to 1-37, 2-4 to 2-40, 8-10, 8-11, 8-14, 8-15, 8-17, 8-19, 8-20, 8-22 to 8-25, 8-35, 8-37 to 8-78, 9-4 to 9-78, 10-4 to 10-6, 10-8 to 10-13, 10-15 to 10-28, 10-30, 10-32 to 10-78, 18-4 to 18-6, 18-9 to 18-13, 18-15, 18-17 to 18-20, 18-22 to 18-30, 18-32 to 18-40, 19-5, 19-6, 19-9 to 19-11, 19-13, 19-15, 19-16, 19-18 to 19-20, 19-22 to 19-30, 19-32, 19-34, 19-35, 19-37 to 19-39, 20-4 to 20-40 and 21-4 to 21-40 are shown in Table 1-2.

Meanings of the symbols used in Tables 1-1 and 1-2 are as follows.
$CH_2=CH$: Vinyl group
HCC: Ethynyl group,
Exp.: Example number,
Str.: Structure represented by either one of the following general formulas

[Formula 5]

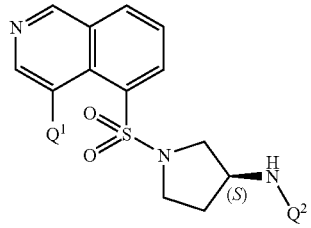

(Q$_a$)

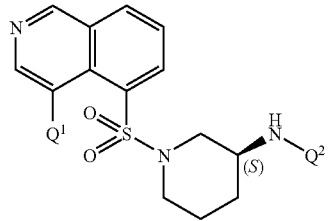

(Q$_b$)

$Q^1$: Group $Q^1$ in the structural formulas mentioned for Str.

$Q^2$: Group $Q^2$ in the structural formulas mentioned for Str., which may be $CH_3$, $CH_2CH_3$, $CH_2CH_2CH_3$, or a group indicated with the numbers of the groups shown in Formula 6, below SM: Example number or intermediate number of starting substance (example numbers are shown only with numbers, and intermediate numbers are shown as "IM-Intermediate number" (for example, "IM-2a" means Intermediate 2a))

MS: Mass spectrum data obtained in LCMS

Ref.: Corresponding preparation method of intermediate. The symbols used in the columns of "Ref." mean preparation methods of intermediates as follows, and two or more symbols mean that the preparation methods were performed from the left. EA: preparation method shown in Example 4-1, EB: preparation method shown in Example 5-1, EC: preparation method shown in Example 8-1, ED: preparation method shown in Example 9-1, and EE: preparation method shown in Example 10-1.

MS: Mass spectrum data obtained in LCMS

[Formula 6]

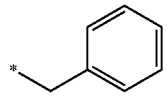

(q-1)

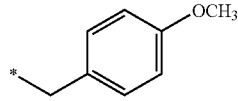

(q-2)

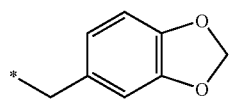

(q-3)

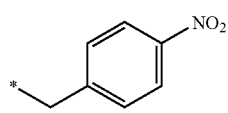

(q-4)

-continued
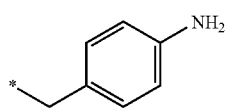 (q-5)
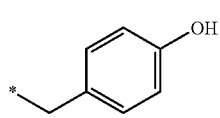 (q-6)
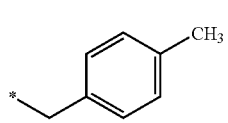 (q-7)
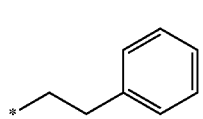 (q-8)
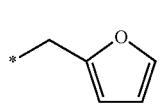 (q-9)
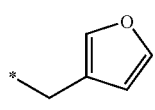 (q-10)
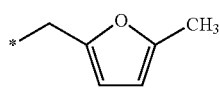 (q-11)
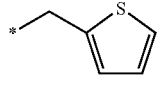 (q-12)
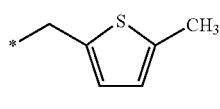 (q-13)
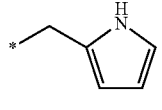 (q-14)
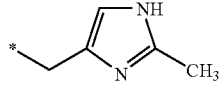 (q-15)
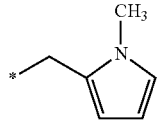 (q-16)
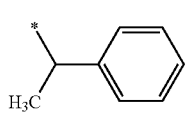 (q-17)
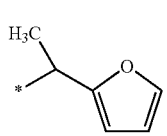 (q-18)
-continued
 (q-19)
 (q-20)
 (q-21)
 (q-22)
 (q-23)
 (q-24)
 (q-25)
 (q-26)
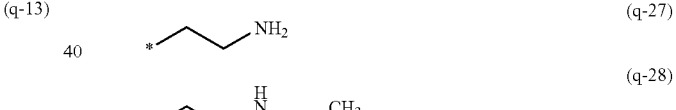 (q-27)
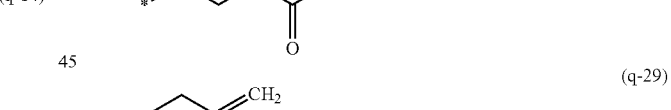 (q-28)
 (q-29)
 (q-30)
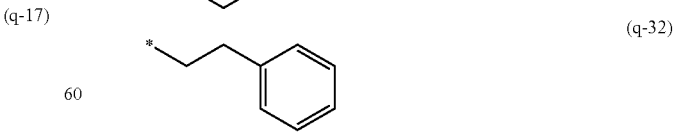 (q-31)
 (q-32)
(q-33)
(q-34)

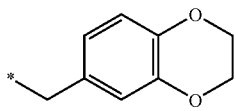

(q-35)

TABLE 1-1

| Exp. | Str. | Q¹ | Q² | SM | Mass (MH+) | Ref. |
|---|---|---|---|---|---|---|
| 1-6 | Qa | Br | q-1 | 1-1 | 446 | EA |
| 1-7 | Qa | Br | q-2 | 1-1 | 476 | EA |
| 1-11 | Qa | Br | q-6 | 1-1 | 462 | EA |
| 1-12 | Qa | Br | q-7 | 1-1 | 460 | EA |
| 1-13 | Qa | Br | q-8 | 1-1 | 460 | EA |
| 1-14 | Qa | Br | q-10 | 1-1 | 436 | EA |
| 1-18 | Qa | Br | q-14 | 1-1 | 435 | EA |
| 1-19 | Qa | Br | q-15 | 1-1 | 450 | EA |
| 1-30 | Qa | Br | q-26 | 1-1 | 440 | EA |
| 1-33 | Qa | Br | q-30 | 1-1 | 454 | EA |
| 1-38 | Qa | Br | q-35 | 1-1 | 504 | EA |
| 8-4 | Qa | $CH_3$ | $CH_2CH_3$ | 8-1 | 320 | EB |
| 8-5 | Qa | $CH_3$ | $CH_2CH_2CH_3$ | 8-1 | 334 | EA |
| 8-6 | Qa | $CH_3$ | q-1 | 8-1 | 382 | EA |
| 8-7 | Qa | $CH_3$ | q-2 | 8-1 | 412 | EA |
| 8-8 | Qa | $CH_3$ | q-3 | 8-1 | 426 | EA |
| 8-9 | Qa | $CH_3$ | q-4 | 8-1 | 427 | EA |
| 8-12 | Qa | $CH_3$ | q-7 | 8-1 | 396 | EA |
| 8-13 | Qa | $CH_3$ | q-8 | 8-1 | 396 | EA |
| 8-16 | Qa | $CH_3$ | q-11 | 8-1 | 386 | EA |
| 8-18 | Qa | $CH_3$ | q-13 | 8-1 | 402 | EA |
| 8-21 | Qa | $CH_3$ | q-16 | 8-1 | 385 | EA |
| 8-26 | Qa | $CH_3$ | q-21 | 8-1 | 346 | EA |
| 8-27 | Qa | $CH_3$ | q-22 | 8-1 | 334 | EA |
| 8-28 | Qa | $CH_3$ | q-23 | 8-1 | 346 | EA |
| 8-29 | Qa | $CH_3$ | q-24 | 8-1 | 360 | EA |
| 8-30 | Qa | $CH_3$ | q-25 | 8-1 | 374 | EA |
| 8-31 | Qa | $CH_3$ | q-26 | 8-1 | 376 | EA |
| 8-32 | Qa | $CH_3$ | q-27 | 8-1 | 335 | EA |
| 8-33 | Qa | $CH_3$ | q-28 | 8-1 | 377 | EA |
| 8-34 | Qa | $CH_3$ | q-29 | 8-1 | 332 | EB |
| 8-36 | Qa | $CH_3$ | q-31 | 8-1 | 375 | EA |
| 10-7 | Qa | HCC | q-2 | 10-1 | 422 | EA |
| 10-14 | Qa | HCC | q-9 | 10-1 | 382 | EA |
| 10-29 | Qa | HCC | q-24 | 10-1 | 370 | EA |
| 10-31 | Qa | HCC | q-26 | 10-1 | 386 | EA |
| 18-7 | Qa | F | q-2 | 18-1 | 416 | EA |
| 18-8 | Qa | F | q-3 | 18-1 | 430 | EA |
| 18-14 | Qa | F | q-9 | 18-1 | 376 | EA |
| 18-16 | Qa | F | q-11 | 18-1 | 390 | EA |
| 18-21 | Qa | F | q-16 | 18-1 | 389 | EA |
| 18-31 | Qa | F | q-26 | 18-1 | 380 | EA |
| 19-4 | Qa | Cl | $CH_2CH_3$ | 19-1 | 340 | EB |
| 19-7 | Qa | Cl | q-2 | 19-1 | 432 | EA |
| 19-8 | Qa | Cl | q-3 | 19-1 | 446 | EA |
| 19-12 | Qa | Cl | q-7 | 19-1 | 416 | EA |
| 19-14 | Qa | Cl | q-9 | 19-1 | 392 | EA |
| 19-17 | Qa | Cl | q-12 | 19-1 | 408 | EA |
| 19-21 | Qa | Cl | q-16 | 19-1 | 405 | EA |
| 19-31 | Qa | Cl | q-26 | 19-1 | 396 | EA |
| 19-33 | Qa | Cl | q-28 | 19-1 | 397 | EA |
| 19-36 | Qa | Cl | q-31 | 19-1 | 395 | EA |
| 19-40 | Qa | Cl | q-35 | 19-1 | 460 | EA |

TABLE 1-2

| Exp. | Str. | Q¹ | Q² | SM | Mass (MH+) | Ref. |
|---|---|---|---|---|---|---|
| 1-4 | Qa | Br | $CH_2CH_3$ | 1-1 | | EB |
| 1-5 | Qa | Br | $CH_2CH_2CH_3$ | 1-1 | | EA |
| 1-8 | Qa | Br | q-3 | 1-1 | | EA |
| 1-9 | Qa | Br | q-4 | 1-1 | | EA |
| 1-10 | Qa | Br | q-5 | 1-1 | | EA |
| 1-15 | Qa | Br | q-11 | 1-1 | | EA |
| 1-16 | Qa | Br | q-12 | 1-1 | | EA |
| 1-17 | Qa | Br | q-13 | 1-1 | | EA |
| 1-20 | Qa | Br | q-16 | 1-1 | | EA |
| 1-21 | Qa | Br | q-17 | 1-1 | | EA |
| 1-22 | Qa | Br | q-18 | 1-1 | | EA |
| 1-23 | Qa | Br | q-19 | 1-1 | | EA |
| 1-24 | Qa | Br | q-20 | 1-1 | | EA |
| 1-25 | Qa | Br | q-21 | 1-1 | | EA |
| 1-26 | Qa | Br | q-22 | 1-1 | | EA |
| 1-27 | Qa | Br | q-23 | 1-1 | | EA |
| 1-28 | Qa | Br | q-24 | 1-1 | | EA |
| 1-29 | Qa | Br | q-25 | 1-1 | | EA |
| 1-31 | Qa | Br | q-27 | 1-1 | | EA |
| 1-32 | Qa | Br | q-28 | 1-1 | | EA |
| 1-34 | Qa | Br | q-31 | 1-1 | | EA |
| 1-35 | Qa | Br | q-32 | 1-1 | | EA |
| 1-36 | Qa | Br | q-33 | 1-1 | | EB |
| 1-37 | Qa | Br | q-34 | 1-1 | | EB |
| 2-4 | Qb | Br | $CH_2CH_3$ | 2-1 | | EB |
| 2-5 | Qb | Br | $CH_2CH_2CH_3$ | 2-1 | | EA |
| 2-6 | Qb | Br | q-1 | 2-1 | | EA |
| 2-7 | Qb | Br | q-2 | 2-1 | | EA |
| 2-8 | Qb | Br | q-3 | 2-1 | | EA |
| 2-9 | Qb | Br | q-4 | 2-1 | | EA |
| 2-10 | Qb | Br | q-5 | 2-1 | | EA |
| 2-11 | Qb | Br | q-6 | 2-1 | | EA |
| 2-12 | Qb | Br | q-7 | 2-1 | | EA |
| 2-13 | Qb | Br | q-8 | 2-1 | | EA |
| 2-14 | Qb | Br | q-9 | 2-1 | | EA |
| 2-15 | Qb | Br | q-10 | 2-1 | | EA |
| 2-16 | Qb | Br | q-11 | 2-1 | | EA |
| 2-17 | Qb | Br | q-12 | 2-1 | | EA |
| 2-18 | Qb | Br | q-13 | 2-1 | | EA |
| 2-19 | Qb | Br | q-14 | 2-1 | | EA |
| 2-20 | Qb | Br | q-15 | 2-1 | | EA |
| 2-21 | Qb | Br | q-16 | 2-1 | | EA |
| 2-22 | Qb | Br | q-17 | 2-1 | | EA |
| 2-23 | Qb | Br | q-18 | 2-1 | | EA |
| 2-24 | Qb | Br | q-19 | 2-1 | | EA |
| 2-25 | Qb | Br | q-20 | 2-1 | | EA |
| 2-26 | Qb | Br | q-21 | 2-1 | | EA |
| 2-27 | Qb | Br | q-22 | 2-1 | | EA |
| 2-28 | Qb | Br | q-23 | 2-1 | | EA |
| 2-29 | Qb | Br | q-24 | 2-1 | | EA |
| 2-30 | Qb | Br | q-25 | 2-1 | | EA |
| 2-31 | Qb | Br | q-26 | 2-1 | | EA |
| 2-32 | Qb | Br | q-27 | 2-1 | | EA |
| 2-33 | Qb | Br | q-28 | 2-1 | | EA |
| 2-34 | Qb | Br | q-29 | 2-1 | | EB |
| 2-35 | Qb | Br | q-30 | 2-1 | | EA |
| 2-36 | Qb | Br | q-31 | 2-1 | | EA |
| 2-37 | Qb | Br | q-32 | 2-1 | | EA |
| 2-38 | Qb | Br | q-33 | 2-1 | | EB |
| 2-39 | Qb | Br | q-34 | 2-1 | | EB |
| 2-40 | Qb | Br | q-35 | 2-1 | | EA |
| 8-3 | Qa | $CH_3$ | $CH_3$ | 8-1 | | EB |
| 8-10 | Qa | $CH_3$ | q-5 | 8-1 | | EA |
| 8-11 | Qa | $CH_3$ | q-6 | 8-1 | | EA |
| 8-14 | Qa | $CH_3$ | q-9 | 8-1 | | EA |
| 8-15 | Qa | $CH_3$ | q-10 | 8-1 | | EA |
| 8-17 | Qa | $CH_3$ | q-12 | 8-1 | | EA |
| 8-19 | Qa | $CH_3$ | q-14 | 8-1 | | EA |
| 8-20 | Qa | $CH_3$ | q-15 | 8-1 | | EA |
| 8-22 | Qa | $CH_3$ | q-17 | 8-1 | | EA |
| 8-23 | Qa | $CH_3$ | q-18 | 8-1 | | EA |
| 8-24 | Qa | $CH_3$ | q-19 | 8-1 | | EA |
| 8-25 | Qa | $CH_3$ | q-20 | 8-1 | | EA |
| 8-35 | Qa | $CH_3$ | q-30 | 8-1 | | EA |
| 8-37 | Qa | $CH_3$ | q-32 | 8-1 | | EA |
| 8-38 | Qb | $CH_3$ | $CH_3$ | IM-2a | | EC, EB |
| 8-39 | Qb | $CH_3$ | $CH_2CH_3$ | IM-2a | | EC, EB |
| 8-40 | Qb | $CH_3$ | $CH_2CH_2CH_3$ | IM-2a | | EC, EA |
| 8-41 | Qb | $CH_3$ | q-1 | IM-2a | | EC, EA |
| 8-42 | Qb | $CH_3$ | q-2 | IM-2a | | EC, EA |
| 8-43 | Qb | $CH_3$ | q-3 | IM-2a | | EC, EA |
| 8-44 | Qb | $CH_3$ | q-4 | IM-2a | | EC, EA |

TABLE 1-2-continued

| Exp. | Str. | $Q^1$ | $Q^2$ | SM | Mass (MH+) | Ref. |
|---|---|---|---|---|---|---|
| 8-45 | Qb | $CH_3$ | q-5 | IM-2a | | EC, EA |
| 8-46 | Qb | $CH_3$ | q-6 | IM-2a | | EC, EA |
| 8-47 | Qb | $CH_3$ | q-7 | IM-2a | | EC, EA |
| 8-48 | Qb | $CH_3$ | q-8 | IM-2a | | EC, EA |
| 8-49 | Qb | $CH_3$ | q-9 | IM-2a | | EC, EA |
| 8-50 | Qb | $CH_3$ | q-10 | IM-2a | | EC, EA |
| 8-51 | Qb | $CH_3$ | q-11 | IM-2a | | EC, EA |
| 8-52 | Qb | $CH_3$ | q-12 | IM-2a | | EC, EA |
| 8-53 | Qb | $CH_3$ | q-13 | IM-2a | | EC, EA |
| 8-54 | Qb | $CH_3$ | q-14 | IM-2a | | EC, EA |
| 8-55 | Qb | $CH_3$ | q-15 | IM-2a | | EC, EA |
| 8-56 | Qb | $CH_3$ | q-16 | IM-2a | | EC, EA |
| 8-57 | Qb | $CH_3$ | q-17 | IM-2a | | EC, EA |
| 8-58 | Qb | $CH_3$ | q-18 | IM-2a | | EC, EA |
| 8-59 | Qb | $CH_3$ | q-19 | IM-2a | | EC, EA |
| 8-60 | Qb | $CH_3$ | q-20 | IM-2a | | EC, EA |
| 8-61 | Qb | $CH_3$ | q-21 | IM-2a | | EC, EA |
| 8-62 | Qb | $CH_3$ | q-22 | IM-2a | | EC, EA |
| 8-63 | Qb | $CH_3$ | q-23 | IM-2a | | EC, EA |
| 8-64 | Qb | $CH_3$ | q-24 | IM-2a | | EC, EA |
| 8-65 | Qb | $CH_3$ | q-25 | IM-2a | | EC, EA |
| 8-66 | Qb | $CH_3$ | q-26 | IM-2a | | EC, EA |
| 8-67 | Qb | $CH_3$ | q-27 | IM-2a | | EC, EA |
| 8-68 | Qb | $CH_3$ | q-28 | IM-2a | | EC, EA |
| 8-69 | Qb | $CH_3$ | q-29 | IM-2a | | EC, EB |
| 8-70 | Qb | $CH_3$ | q-30 | IM-2a | | EC, EA |
| 8-71 | Qb | $CH_3$ | q-31 | IM-2a | | EC, EA |
| 8-72 | Qb | $CH_3$ | q-32 | IM-2a | | EC, EA |
| 8-73 | Qa | $CH_3$ | q-33 | 8-1 | | EB |
| 8-74 | Qa | $CH_3$ | q-34 | 8-1 | | EB |
| 8-75 | Qa | $CH_3$ | q-35 | 8-1 | | EA |
| 8-76 | Qb | $CH_3$ | q-33 | IM-2a | | EC, EB |
| 8-77 | Qb | $CH_3$ | q-34 | IM-2a | | EC, EB |
| 8-78 | Qb | $CH_3$ | q-35 | IM-2a | | EC, EA |
| 9-4 | Qa | $CH_2{=}CH$ | $CH_2CH_3$ | 9-1 | | EB |
| 9-5 | Qa | $CH_2{=}CH$ | $CH_2CH_2CH_3$ | 9-1 | | EA |
| 9-6 | Qa | $CH_2{=}CH$ | q-1 | 9-1 | | EA |
| 9-7 | Qa | $CH_2{=}CH$ | q-2 | 9-1 | | EA |
| 9-8 | Qa | $CH_2{=}CH$ | q-3 | 9-1 | | EA |
| 9-9 | Qa | $CH_2{=}CH$ | q-4 | 9-1 | | EA |
| 9-10 | Qa | $CH_2{=}CH$ | q-5 | 9-1 | | EA |
| 9-11 | Qa | $CH_2{=}CH$ | q-6 | 9-1 | | EA |
| 9-12 | Qa | $CH_2{=}CH$ | q-7 | 9-1 | | EA |
| 9-13 | Qa | $CH_2{=}CH$ | q-8 | 9-1 | | EA |
| 9-14 | Qa | $CH_2{=}CH$ | q-9 | 9-1 | | EA |
| 9-15 | Qa | $CH_2{=}CH$ | q-10 | 9-1 | | EA |
| 9-16 | Qa | $CH_2{=}CH$ | q-11 | 9-1 | | EA |
| 9-17 | Qa | $CH_2{=}CH$ | q-12 | 9-1 | | EA |
| 9-18 | Qa | $CH_2{=}CH$ | q-13 | 9-1 | | EA |
| 9-19 | Qa | $CH_2{=}CH$ | q-14 | 9-1 | | EA |
| 9-20 | Qa | $CH_2{=}CH$ | q-15 | 9-1 | | EA |
| 9-21 | Qa | $CH_2{=}CH$ | q-16 | 9-1 | | EA |
| 9-22 | Qa | $CH_2{=}CH$ | q-17 | 9-1 | | EA |
| 9-23 | Qa | $CH_2{=}CH$ | q-18 | 9-1 | | EA |
| 9-24 | Qa | $CH_2{=}CH$ | q-19 | 9-1 | | EA |
| 9-25 | Qa | $CH_2{=}CH$ | q-20 | 9-1 | | EA |
| 9-26 | Qa | $CH_2{=}CH$ | q-21 | 9-1 | | EA |
| 9-27 | Qa | $CH_2{=}CH$ | q-22 | 9-1 | | EA |
| 9-28 | Qa | $CH_2{=}CH$ | q-23 | 9-1 | | EA |
| 9-29 | Qa | $CH_2{=}CH$ | q-24 | 9-1 | | EA |
| 9-30 | Qa | $CH_2{=}CH$ | q-25 | 9-1 | | EA |
| 9-31 | Qa | $CH_2{=}CH$ | q-26 | 9-1 | | EA |
| 9-32 | Qa | $CH_2{=}CH$ | q-27 | 9-1 | | EA |
| 9-33 | Qa | $CH_2{=}CH$ | q-28 | 9-1 | | EA |
| 9-34 | Qa | $CH_2{=}CH$ | q-29 | 9-1 | | EB |
| 9-35 | Qa | $CH_2{=}CH$ | q-30 | 9-1 | | EA |
| 9-36 | Qb | $CH_2{=}CH$ | $CH_3$ | IM-2a | | ED, EB |
| 9-37 | Qb | $CH_2{=}CH$ | $CH_2CH_3$ | IM-2a | | ED, EB |
| 9-38 | Qb | $CH_2{=}CH$ | $CH_2CH_2CH_3$ | IM-2a | | ED, EA |
| 9-39 | Qb | $CH_2{=}CH$ | q-1 | IM-2a | | ED, EA |
| 9-40 | Qb | $CH_2{=}CH$ | q-2 | IM-2a | | ED, EA |
| 9-41 | Qb | $CH_2{=}CH$ | q-3 | IM-2a | | ED, EA |
| 9-42 | Qb | $CH_2{=}CH$ | q-4 | IM-2a | | ED, EA |
| 9-43 | Qb | $CH_2{=}CH$ | q-5 | IM-2a | | ED, EA |
| 9-44 | Qb | $CH_2{=}CH$ | q-6 | IM-2a | | ED, EA |
| 9-45 | Qb | $CH_2{=}CH$ | q-7 | IM-2a | | ED, EA |
| 9-46 | Qb | $CH_2{=}CH$ | q-8 | IM-2a | | ED, EA |
| 9-47 | Qb | $CH_2{=}CH$ | q-9 | IM-2a | | ED, EA |
| 9-48 | Qb | $CH_2{=}CH$ | q-10 | IM-2a | | ED, EA |
| 9-49 | Qb | $CH_2{=}CH$ | q-11 | IM-2a | | ED, EA |
| 9-50 | Qb | $CH_2{=}CH$ | q-12 | IM-2a | | ED, EA |
| 9-51 | Qb | $CH_2{=}CH$ | q-13 | IM-2a | | ED, EA |
| 9-52 | Qb | $CH_2{=}CH$ | q-14 | IM-2a | | ED, EA |
| 9-53 | Qb | $CH_2{=}CH$ | q-15 | IM-2a | | ED, EA |
| 9-54 | Qb | $CH_2{=}CH$ | q-16 | IM-2a | | ED, EA |
| 9-55 | Qb | $CH_2{=}CH$ | q-17 | IM-2a | | ED, EA |
| 9-56 | Qb | $CH_2{=}CH$ | q-18 | IM-2a | | ED, EA |
| 9-57 | Qb | $CH_2{=}CH$ | q-19 | IM-2a | | ED, EA |
| 9-58 | Qb | $CH_2{=}CH$ | q-20 | IM-2a | | ED, EA |
| 9-59 | Qb | $CH_2{=}CH$ | q-21 | IM-2a | | ED, EA |
| 9-60 | Qb | $CH_2{=}CH$ | q-22 | IM-2a | | ED, EA |
| 9-61 | Qb | $CH_2{=}CH$ | q-23 | IM-2a | | ED, EA |
| 9-62 | Qb | $CH_2{=}CH$ | q-24 | IM-2a | | ED, EA |
| 9-63 | Qb | $CH_2{=}CH$ | q-25 | IM-2a | | ED, EA |
| 9-64 | Qb | $CH_2{=}CH$ | q-26 | IM-2a | | ED, EA |
| 9-65 | Qb | $CH_2{=}CH$ | q-27 | IM-2a | | ED, EA |
| 9-66 | Qb | $CH_2{=}CH$ | q-28 | IM-2a | | ED, EA |
| 9-67 | Qb | $CH_2{=}CH$ | q-29 | IM-2a | | ED, EB |
| 9-68 | Qb | $CH_2{=}CH$ | q-30 | IM-2a | | ED, EA |
| 9-69 | Qa | $CH_2{=}CH$ | q-31 | 9-1 | | EA |
| 9-70 | Qa | $CH_2{=}CH$ | q-32 | 9-1 | | EA |
| 9-71 | Qa | $CH_2{=}CH$ | q-33 | 9-1 | | EB |
| 9-72 | Qa | $CH_2{=}CH$ | q-34 | 9-1 | | EB |
| 9-73 | Qa | $CH_2{=}CH$ | q-35 | 9-1 | | EA |
| 9-74 | Qb | $CH_2{=}CH$ | q-31 | IM-2a | | ED, EA |
| 9-75 | Qb | $CH_2{=}CH$ | q-32 | IM-2a | | ED, EA |
| 9-76 | Qb | $CH_2{=}CH$ | q-33 | IM-2a | | ED, EB |
| 9-77 | Qb | $CH_2{=}CH$ | q-34 | IM-2a | | ED, EB |
| 9-78 | Qb | $CH_2{=}CH$ | q-35 | IM-2a | | ED, EA |
| 10-4 | Qa | HCC | $CH_2CH_3$ | 10-1 | | EB |
| 10-5 | Qa | HCC | $CH_2CH_2CH_3$ | 10-1 | | EA |
| 10-6 | Qa | HCC | q-1 | 10-1 | | EA |
| 10-8 | Qa | HCC | q-3 | 10-1 | | EA |
| 10-9 | Qa | HCC | q-4 | 10-1 | | EA |
| 10-10 | Qa | HCC | q-5 | 10-1 | | EA |
| 10-11 | Qa | HCC | q-6 | 10-1 | | EA |
| 10-12 | Qa | HCC | q-7 | 10-1 | | EA |
| 10-13 | Qa | HCC | q-8 | 10-1 | | EA |
| 10-15 | Qa | HCC | q-10 | 10-1 | | EA |
| 10-16 | Qa | HCC | q-11 | 10-1 | | EA |
| 10-17 | Qa | HCC | q-12 | 10-1 | | EA |
| 10-18 | Qa | HCC | q-13 | 10-1 | | EA |
| 10-19 | Qa | HCC | q-14 | 10-1 | | EA |
| 10-20 | Qa | HCC | q-15 | 10-1 | | EA |
| 10-21 | Qa | HCC | q-16 | 10-1 | | EA |
| 10-22 | Qa | HCC | q-17 | 10-1 | | EA |
| 10-23 | Qa | HCC | q-18 | 10-1 | | EA |
| 10-24 | Qa | HCC | q-19 | 10-1 | | EA |
| 10-25 | Qa | HCC | q-20 | 10-1 | | EA |
| 10-26 | Qa | HCC | q-21 | 10-1 | | EA |
| 10-27 | Qa | HCC | q-22 | 10-1 | | EA |
| 10-28 | Qa | HCC | q-23 | 10-1 | | EA |
| 10-30 | Qa | HCC | q-25 | 10-1 | | EA |
| 10-32 | Qa | HCC | q-27 | 10-1 | | EA |
| 10-33 | Qa | HCC | q-28 | 10-1 | | EA |
| 10-34 | Qa | HCC | q-29 | 10-1 | | EB |
| 10-35 | Qa | HCC | q-30 | 10-1 | | EA |
| 10-36 | Qb | HCC | $CH_3$ | IM-2a | | EE, EB |
| 10-37 | Qb | HCC | $CH_2CH_3$ | IM-2a | | EE, EB |
| 10-38 | Qb | HCC | $CH_2CH_2CH_3$ | IM-2a | | EE, EA |
| 10-39 | Qb | HCC | q-1 | IM-2a | | EE, EA |
| 10-40 | Qb | HCC | q-2 | IM-2a | | EE, EA |
| 10-41 | Qb | HCC | q-3 | IM-2a | | EE, EA |
| 10-42 | Qb | HCC | q-4 | IM-2a | | EE, EA |
| 10-43 | Qb | HCC | q-5 | IM-2a | | EE, EA |
| 10-44 | Qb | HCC | q-6 | IM-2a | | EE, EA |
| 10-45 | Qb | HCC | q-7 | IM-2a | | EE, EA |
| 10-46 | Qb | HCC | q-8 | IM-2a | | EE, EA |
| 10-47 | Qb | HCC | q-9 | IM-2a | | EE, EA |
| 10-48 | Qb | HCC | q-10 | IM-2a | | EE, EA |
| 10-49 | Qb | HCC | q-11 | IM-2a | | EE, EA |
| 10-50 | Qb | HCC | q-12 | IM-2a | | EE, EA |
| 10-51 | Qb | HCC | q-13 | IM-2a | | EE, EA |
| 10-52 | Qb | HCC | q-14 | IM-2a | | EE, EA |

TABLE 1-2-continued

| Exp. | Str. | Q¹ | Q² | SM | Mass (MH+) | Ref. |
|---|---|---|---|---|---|---|
| 10-53 | Qb | HCC | q-15 | IM-2a | | EE, EA |
| 10-54 | Qb | HCC | q-16 | IM-2a | | EE, EA |
| 10-55 | Qb | HCC | q-17 | IM-2a | | EE, EA |
| 10-56 | Qb | HCC | q-18 | IM-2a | | EE, EA |
| 10-57 | Qb | HCC | q-19 | IM-2a | | EE, EA |
| 10-58 | Qb | HCC | q-20 | IM-2a | | EE, EA |
| 10-59 | Qb | HCC | q-21 | IM-2a | | EE, EA |
| 10-60 | Qb | HCC | q-22 | IM-2a | | EE, EA |
| 10-61 | Qb | HCC | q-23 | IM-2a | | EE, EA |
| 10-62 | Qb | HCC | q-24 | IM-2a | | EE, EA |
| 10-63 | Qb | HCC | q-25 | IM-2a | | EE, EA |
| 10-64 | Qb | HCC | q-26 | IM-2a | | EE, EA |
| 10-65 | Qb | HCC | q-27 | IM-2a | | EE, EA |
| 10-66 | Qb | HCC | q-28 | IM-2a | | EE, EA |
| 10-67 | Qb | HCC | q-29 | IM-2a | | EE, EB |
| 10-68 | Qb | HCC | q-30 | IM-2a | | EE, EA |
| 10-69 | Qa | HCC | q-31 | 10-1 | | EA |
| 10-70 | Qa | HCC | q-32 | 10-1 | | EA |
| 10-71 | Qa | HCC | q-33 | 10-1 | | EB |
| 10-72 | Qa | HCC | q-34 | 10-1 | | EB |
| 10-73 | Qa | HCC | q-35 | 10-1 | | EA |
| 10-74 | Qb | HCC | q-31 | IM-2a | | ED, EA |
| 10-75 | Qb | HCC | q-32 | IM-2a | | ED, EA |
| 10-76 | Qb | HCC | q-33 | IM-2a | | ED, EB |
| 10-77 | Qb | HCC | q-34 | IM-2a | | ED, EB |
| 10-78 | Qb | HCC | q-35 | IM-2a | | ED, EA |
| 18-4 | Qa | F | $CH_2CH_3$ | 18-1 | | EB |
| 18-5 | Qa | F | $CH_2CH_2CH_3$ | 18-1 | | EA |
| 18-6 | Qa | F | q-1 | 18-1 | | EA |
| 18-9 | Qa | F | q-4 | 18-1 | | EA |
| 18-10 | Qa | F | q-5 | 18-1 | | EA |
| 18-11 | Qa | F | q-6 | 18-1 | | EA |
| 18-12 | Qa | F | q-7 | 18-1 | | EA |
| 18-13 | Qa | F | q-8 | 18-1 | | EA |
| 18-15 | Qa | F | q-10 | 18-1 | | EA |
| 18-17 | Qa | F | q-12 | 18-1 | | EA |
| 18-18 | Qa | F | q-13 | 18-1 | | EA |
| 18-19 | Qa | F | q-14 | 18-1 | | EA |
| 18-20 | Qa | F | q-15 | 18-1 | | EA |
| 18-22 | Qa | F | q-17 | 18-1 | | EA |
| 18-23 | Qa | F | q-18 | 18-1 | | EA |
| 18-24 | Qa | F | q-19 | 18-1 | | EA |
| 18-25 | Qa | F | q-20 | 18-1 | | EA |
| 18-26 | Qa | F | q-21 | 18-1 | | EA |
| 18-27 | Qa | F | q-22 | 18-1 | | EA |
| 18-28 | Qa | F | q-23 | 18-1 | | EA |
| 18-29 | Qa | F | q-24 | 18-1 | | EA |
| 18-30 | Qa | F | q-25 | 18-1 | | EA |
| 18-32 | Qa | F | q-27 | 18-1 | | EA |
| 18-33 | Qa | F | q-28 | 18-1 | | EA |
| 18-34 | Qa | F | q-29 | 18-1 | | EB |
| 18-35 | Qa | F | q-30 | 18-1 | | EA |
| 18-36 | Qa | F | q-31 | 18-1 | | EA |
| 18-37 | Qa | F | q-32 | 18-1 | | EA |
| 18-38 | Qa | F | q-33 | 18-1 | | EB |
| 18-39 | Qa | F | q-34 | 18-1 | | EB |
| 18-40 | Qa | F | q-35 | 18-1 | | EA |
| 19-5 | Qa | Cl | $CH_2CH_2CH_3$ | 19-1 | | EA |
| 19-6 | Qa | Cl | q-1 | 19-1 | | EA |
| 19-9 | Qa | Cl | q-4 | 19-1 | | EA |
| 19-10 | Qa | Cl | q-5 | 19-1 | | EA |
| 19-11 | Qa | Cl | q-6 | 19-1 | | EA |
| 19-13 | Qa | Cl | q-8 | 19-1 | | EA |
| 19-15 | Qa | Cl | q-10 | 19-1 | | EA |
| 19-16 | Qa | Cl | q-11 | 19-1 | | EA |
| 19-18 | Qa | Cl | q-13 | 19-1 | | EA |
| 19-19 | Qa | Cl | q-14 | 19-1 | | EA |
| 19-20 | Qa | Cl | q-15 | 19-1 | | EA |
| 19-22 | Qa | Cl | q-17 | 19-1 | | EA |
| 19-23 | Qa | Cl | q-18 | 19-1 | | EA |
| 19-24 | Qa | Cl | q-19 | 19-1 | | EA |
| 19-25 | Qa | Cl | q-20 | 19-1 | | EA |
| 19-26 | Qa | Cl | q-21 | 19-1 | | EA |
| 19-27 | Qa | Cl | q-22 | 19-1 | | EA |
| 19-28 | Qa | Cl | q-23 | 19-1 | | EA |
| 19-29 | Qa | Cl | q-24 | 19-1 | | EA |
| 19-30 | Qa | Cl | q-25 | 19-1 | | EA |
| 19-32 | Qa | Cl | q-27 | 19-1 | | EA |
| 19-34 | Qa | Cl | q-29 | 19-1 | | EB |
| 19-35 | Qa | Cl | q-30 | 19-1 | | EA |
| 19-37 | Qa | Cl | q-32 | 19-1 | | EA |
| 19-38 | Qa | Cl | q-33 | 19-1 | | EB |
| 19-39 | Qa | Cl | q-34 | 19-1 | | EB |
| 20-4 | Qb | F | $CH_2CH_3$ | 20-1 | | EB |
| 20-5 | Qb | F | $CH_2CH_2CH_3$ | 20-1 | | EA |
| 20-6 | Qb | F | q-1 | 20-1 | | EA |
| 20-7 | Qb | F | q-2 | 20-1 | | EA |
| 20-8 | Qb | F | q-3 | 20-1 | | EA |
| 20-9 | Qb | F | q-4 | 20-1 | | EA |
| 20-10 | Qb | F | q-5 | 20-1 | | EA |
| 20-11 | Qb | F | q-6 | 20-1 | | EA |
| 20-12 | Qb | F | q-7 | 20-1 | | EA |
| 20-13 | Qb | F | q-8 | 20-1 | | EA |
| 20-14 | Qb | F | q-9 | 20-1 | | EA |
| 20-15 | Qb | F | q-10 | 20-1 | | EA |
| 20-16 | Qb | F | q-11 | 20-1 | | EA |
| 20-17 | Qb | F | q-12 | 20-1 | | EA |
| 20-18 | Qb | F | q-13 | 20-1 | | EA |
| 20-19 | Qb | F | q-14 | 20-1 | | EA |
| 20-20 | Qb | F | q-15 | 20-1 | | EA |
| 20-21 | Qb | F | q-16 | 20-1 | | EA |
| 20-22 | Qb | F | q-17 | 20-1 | | EA |
| 20-23 | Qb | F | q-18 | 20-1 | | EA |
| 20-24 | Qb | F | q-19 | 20-1 | | EA |
| 20-25 | Qb | F | q-20 | 20-1 | | EA |
| 20-26 | Qb | F | q-21 | 20-1 | | EA |
| 20-27 | Qb | F | q-22 | 20-1 | | EA |
| 20-28 | Qb | F | q-23 | 20-1 | | EA |
| 20-29 | Qb | F | q-24 | 20-1 | | EA |
| 20-30 | Qb | F | q-25 | 20-1 | | EA |
| 20-31 | Qb | F | q-26 | 20-1 | | EA |
| 20-32 | Qb | F | q-27 | 20-1 | | EA |
| 20-33 | Qb | F | q-28 | 20-1 | | EA |
| 20-34 | Qb | F | q-29 | 20-1 | | EB |
| 20-35 | Qb | F | q-30 | 20-1 | | EA |
| 20-36 | Qb | F | q-31 | 20-1 | | EA |
| 20-37 | Qb | F | q-32 | 20-1 | | EA |
| 20-38 | Qb | F | q-33 | 20-1 | | EB |
| 20-39 | Qb | F | q-34 | 20-1 | | EB |
| 20-40 | Qb | F | q-35 | 20-1 | | EA |
| 21-4 | Qb | Cl | $CH_2CH_3$ | 21-1 | | EB |
| 21-5 | Qb | Cl | $CH_2CH_2CH_3$ | 21-1 | | EA |
| 21-6 | Qb | Cl | q-1 | 21-1 | | EA |
| 21-7 | Qb | Cl | q-2 | 21-1 | | EA |
| 21-8 | Qb | Cl | q-3 | 21-1 | | EA |
| 21-9 | Qb | Cl | q-4 | 21-1 | | EA |
| 21-10 | Qb | Cl | q-5 | 21-1 | | EA |
| 21-11 | Qb | Cl | q-6 | 21-1 | | EA |
| 21-12 | Qb | Cl | q-7 | 21-1 | | EA |
| 21-13 | Qb | Cl | q-8 | 21-1 | | EA |
| 21-14 | Qb | Cl | q-9 | 21-1 | | EA |
| 21-15 | Qb | Cl | q-10 | 21-1 | | EA |
| 21-16 | Qb | Cl | q-11 | 21-1 | | EA |
| 21-17 | Qb | Cl | q-12 | 21-1 | | EA |
| 21-18 | Qb | Cl | q-13 | 21-1 | | EA |
| 21-19 | Qb | Cl | q-14 | 21-1 | | EA |
| 21-20 | Qb | Cl | q-15 | 21-1 | | EA |
| 21-21 | Qb | Cl | q-16 | 21-1 | | EA |
| 21-22 | Qb | Cl | q-17 | 21-1 | | EA |
| 21-23 | Qb | Cl | q-18 | 21-1 | | EA |
| 21-24 | Qb | Cl | q-19 | 21-1 | | EA |
| 21-25 | Qb | Cl | q-20 | 21-1 | | EA |
| 21-26 | Qb | Cl | q-21 | 21-1 | | EA |
| 21-27 | Qb | Cl | q-22 | 21-1 | | EA |
| 21-28 | Qb | Cl | q-23 | 21-1 | | EA |
| 21-29 | Qb | Cl | q-24 | 21-1 | | EA |
| 21-30 | Qb | Cl | q-25 | 21-1 | | EA |
| 21-31 | Qb | Cl | q-26 | 21-1 | | EA |
| 21-32 | Qb | Cl | q-27 | 21-1 | | EA |
| 21-33 | Qb | Cl | q-28 | 21-1 | | EA |
| 21-34 | Qb | Cl | q-29 | 21-1 | | EB |
| 21-35 | Qb | Cl | q-30 | 21-1 | | EA |
| 21-36 | Qb | Cl | q-31 | 21-1 | | EA |
| 21-37 | Qb | Cl | q-32 | 21-1 | | EA |

TABLE 1-2-continued

| Exp. | Str. | Q¹ | Q² | SM | Mass (MH+) | Ref. |
|---|---|---|---|---|---|---|
| 21-38 | Qb | Cl | q-33 | 21-1 | | EB |
| 21-39 | Qb | Cl | q-34 | 21-1 | | EB |
| 21-40 | Qb | Cl | q-35 | 21-1 | | EA |

Reference Example 8

5-Amino-1-chloro-4-bromoisoquinoline

A solution of 4-bromo-1-chloro-5-nitroisoquinoline (14.0 g) prepared according to the method described in a known literature (Nair et al., Indian J. Chem., 1967, 5, 403) in ethanol (75 ml) and tetrahydrofuran (75 ml) was added with 3% platinum-sulfur/activated carbon (3% Pt—S/C, NE Chemcat, CM101, 14.0 g), and the mixture was stirred at room temperature for 15 hours under a hydrogen gas atmosphere. The atmosphere was replaced with nitrogen gas, and then the insoluble solids were removed by filtration through Celite, and the solvent was evaporated under reduced pressure to obtain the title compound (12.8 g).
MS (m/z): 257 (MH+)
$^1$H-NMR (CDCl$_3$) δ (ppm): 6.95 (1H, dd, J=1.2, 8.1 Hz), 7.46 (1H, t, J=8.1 Hz), 7.75 (1H, dd, J=1.2, 8.1 Hz), 8.25 (1H, s)

Reference Example 9

1-Chloro-4-bromo-5-isoquinolinesulfonyl chloride (Solution A)
A suspension of 5-amino-1-chloro-4-bromoisoquinoline (4.83 g) obtained in Reference Example 8 in concentrated hydrochloric acid (40 ml) was slowly added with an aqueous solution (8 ml) of sodium nitrite (1.82 g, Wako Pure Chemical Industries) so that the temperature of the solution should be maintained around −15° C., and the mixture was stirred at the same temperature for 1 hour.
(Solution B)
A suspension of cupric chloride dihydrate (960 mg, Wako Pure Chemical Industries) in water (8 ml) and glacial acetic acid (50 ml) was bubbled with sulfur dioxide gas at 0° C. for 1.5 hours with stirring.
Solution B was cooled to 0° C., and slowly added with Solution A mentioned above so that the temperature of the mixture should be maintained to be 5° C. or lower, and the mixture was stirred at room temperature for 2 hours. The reaction mixture was poured into ice water, and the mixture was extracted 3 times with methylene chloride (100 ml for each time). The combined organic layer was washed twice with water (200 ml for each time), and dried over anhydrous magnesium sulfate. The solvent was evaporated under reduced pressure to obtain the title compound (5.0 g).
MS (m/z): 374 (MH+)

Reference Example 10

2-Oxy-4-chloro-5-nitroisoquinoline

A solution of 4-chloro-5-nitroisoquinoline (35.2 g) obtained in Reference Example 5 in chloroform (500 ml) was cooled on an ice bath, and added with 3-chloroperbenzoic acid (70%, 67.0 g, Tokyo Kasei Kogyo) as several portions, and the mixture was stirred at the same temperature for 30 minutes. The mixture was further stirred at room temperature for 24 hours, and then added with saturated aqueous sodium hydrogencarbonate (1,000 ml), and the organic layer was separated. The aqueous layer was extracted 3 times with chloroform (300 ml for each time), and the combined organic layer was washed with saturated brine (1,000 ml). The organic layer was dried over anhydrous magnesium sulfate, and then the solvent was evaporated under reduced pressure to obtain the title compound (31.2 g).
MS (m/z): 225 (MH+)

Reference Example 11

1,4-Dichloro-5-nitroisoquinoline

A suspension of 2-oxy-4-chloro-5-nitroisoquinoline (37.9 g) obtained in Reference Example 10 in chloroform (735 ml) was added with phosphorus oxychloride (77.8 g, Wako Pure Chemical Industries) under ice cooling, and the mixture was stirred at 60° C. with heating for 24 hours. The reaction mixture was cooled to room temperature, and poured into ice water (500 ml), and the mixture was extracted 3 times with chloroform (for each time 400 ml). The combined organic layer was washed twice with saturated aqueous sodium hydrogencarbonate (800 ml for each time), and dried over anhydrous magnesium sulfate. The solvent was evaporated under reduced pressure, and the obtained solid was recrystallized (n-hexane/ethyl acetate) to obtain the title compound (15.5 g).
MS (m/z): 243 (MH+)
$^1$H-NMR (CDCl$_3$) δ (ppm): 7.83 (1H, t, J=8.0 Hz), 7.97 (1H, dd, J=0.9, 8.0 Hz), 8.46 (1H, s), 8.62 (1H, dd, J=0.9, 8.0 Hz)

Reference Example 12

5-Amino-1,4-dichloroisoquinoline 1,4-Dichloro-5-nitroisoquinoline (11.2 g) obtained in Reference Example 11 was used in the method of Reference Example 8 instead of 4-bromo-1-chloro-5-nitroisoquinoline to obtain the title compound (7.5 g).
MS (m/z): 213 (MH+)
$^1$H-NMR (CDCl$_3$) δ (ppm): 6.92 (1H, dd, J=1.1, 8.1 Hz), 7.47 (1H, t, J=8.1 Hz), 7.73 (1H, dd, J=1.1, 8.1 Hz), 8.09 (1H, s)

Reference Example 13

1,4-Dichloro-5-isoquinolinesulfonyl chloride

5-Amino-1,4-dichloroisoquinoline (4.0 g) obtained in Reference Example 12 was used in the method of Reference Example 9 instead of 5-amino-1-chloro-4-bromoisoquinoline to obtain the title compound (4.34 g).
MS (m/z): 329 (MH+)

Reference Example 14

2-Oxy-4-fluoro-5-nitroisoquinoline

4-Fluoro-5-nitroisoquinoline (12.8 g) obtained in Reference Example 2 was used in the method of Reference Example 10 instead of 4-chloro-5-nitroisoquinoline to obtain the title compound (13.5 g).
MS (m/z): 209 (MH+)

Reference Example 15

1-Chloro-4-fluoro-5-nitroisoquinoline

2-Oxy-4-fluoro-5-nitroisoquinoline (10.5 g) obtained in Reference Example 14 was used in the method of Reference Example 11 instead of 2-oxy-4-chloro-5-nitroisoquinoline to obtain the title compound (4.2 g).
MS (m/z): 227 (MH+)

Reference Example 16

5-Amino-1-chloro-4-fluoroisoquinoline

1-Chloro-4-fluoro-5-nitroisoquinoline (3.8 g) obtained in Reference Example 15 was used in the method of Reference Example 8 instead of 4-bromo-1-chloro-5-nitroisoquinoline to obtain the title compound (3.1 g).
MS (m/z): 197 (MH+)

Reference Example 17

1-Chloro-4-fluoro-5-isoquinolinesulfonyl chloride

5-Amino-1-chloro-4-fluoroisoquinoline (3.69 g) obtained in Reference Example 15 was used in the method of Reference Example 9 instead of 5-amino-1-chloro-4-bromoisoquinoline to obtain the title compound (2.89 g).
MS (m/z): 313 (MH+)

Example 1-3

(S)-1-(4-Bromo-5-isoquinolinesulfonyl)-3-(methylamino)pyrrolidine

Step A (S)-3-[N-(tert-Butoxycarbonyl)-N-methylamino]-1-(4-bromo-5-isoquinolinesulfonyl)pyrrolidine (Intermediate 20a)

A solution of (S)-3-N-(tert-butoxycarbonyl)-N-methylamino]pyrrolidine (0.110 g) obtained from 4-bromo-5-isoquinolinesulfonyl chloride (0.153 g) and (S)-1-benzyl-3-(methylamino)pyrrolidine (Tokyo Kasei Kogyo) according to the method described in a known literature (Barlocco et al., Tetrahedron, 1995, 51, 11547) in methylene chloride (3 ml) was added with triethylamine (0.140 ml) at 0° C., and the mixture was stirred at the same temperature for 30 minutes, and then further stirred at room temperature for 5 hours. The reaction mixture was washed with saturated brine (6 ml), and then dried over anhydrous magnesium sulfate. The solvent was evaporated under reduced pressure, and then the residue was purified by silica gel chromatography (n-hexane:ethyl acetate=2:1) to obtain the title compound (0.200 g).
MS (m/z): 470 (MH+)
$^1$H-NMR (CDCl$_3$) δ (ppm): 1.35 (9H, s), 2.00-2.14 (2H, m), 2.72 (3H, s), 3.22-3.26 (1H, m), 3.31-3.38 (1H, m), 3.51-3.55 (1, m), 3.59-3.64 (1H, m), 4.76 (1H, m), 7.57 (1H, t, J=7.6 Hz), 8.06 (1H, dd, J=1.2, 7.6 Hz), 8.21 (1H, dd, J=1.2, 7.6 Hz), 8.83 (1H, s), 9.06 (1H, s)

Step B (S)-1-(4-Bromo-5-isoquinolinesulfonyl)-3-(methylamino)pyrrolidine

Intermediate 20a (0.157 g) prepared in Step A mentioned above was added with 10% hydrogen chloride/methanol (2 ml), and the mixture was stirred at room temperature for 12 hours. The solvent was evaporated under reduced pressure to obtain the title compound as hydrochloride (125 mg).
MS (m/z): 370 (MH+)
$^1$H-NMR (DMSO) δ (ppm): 2.26-2.35 (1H, m), 2.39-2.51 (1H, m), 2.60 (3H, s), 3.48-3.73 (3H, m), 3.80-3.86 (1H, m), 3.94-4.00 (1H, m), 7.90 (1H, t, J=7.5 Hz), 8.42 (1H, dd, J=0.9, 7.5 Hz), 8.51 (1H, dd, J=0.9, 7.5 Hz), 8.96 (1H, s), 9.46 (1H, s)

Example 31

(R/S)-1-(4-Bromo-5-isoquinolinesulfonyl)-3-(methylamino)pyrrolidine

3-[N-(tert-Butoxycarbonyl)-N-methylamino]-1-(4-bromo-5-isoquinolinesulfonyl)pyrrolidine (Intermediate 20) can be prepared by using 3-[N-(tert-butoxycarbonyl)-N-methylamino]pyrrolidine (Tokyo Kasei Kogyo) instead of (S)-3-[N-(tert-butoxycarbonyl)-N-methylamino]pyrrolidine, and used in the method of Example 1-3, Step B in a similar manner to obtain the title compound as hydrochloride.

Example 31-2

(R)-1-(4-Bromo-5-isoquinolinesulfonyl)-3-(methylamino)pyrrolidine (R)-3-[N-(tert-Butoxycarbonyl)-N-methylamino]-1-(4-bromo-5-isoquinolinesulfonyl)pyrrolidine (Intermediate 20b) can be prepared by using (R)-3-[N-(tert-butoxycarbonyl)-N-methylamino]pyrrolidine obtained from (R)-1-benzyl-3-(methylamino)pyrrolidine (Tokyo Kasei Kogyo) instead of (S)-3-[N-(tert-butoxycarbonyl)-N-methylamino]pyrrolidine according to the method described in a known literature (Barlocco et al., Tetrahedron, 1995, 51, 11547) in Example 1-3, Step A, and used in the method of Example 1-3, Step B in a similar manner to obtain the title compound as hydrochloride.

Example 19-3

(S)-1-(4-Chloro-5-isoquinolinesulfonyl)-3-(methylamino)pyrrolidine (S)-3-[N-(tert-Butoxycarbonyl)-N-methylamino]-1-(4-chloro-5-isoquinoline-sulfonyl)pyrrolidine (Intermediate 21a) was prepared by using 4-chloro-5-isoquinolinesulfonyl chloride in the method of Example 1-3, Step A instead of 4-bromo-5-isoquinolinesulfonyl chloride, and then used in the method of Example 1-3, Step B in a similar manner to obtain the title compound as hydrochloride.
MS (m/z): 326 (MH+)
$^1$H-NMR (DMSO) δ (ppm): 2.25-2.37 (1H, m), 2.40-2.50 (1H, m), 2.60 (3H, s), 3.51-3.75 (3H, m), 3.82-3.88 (1H, m), 3.94-4.03 (1H, m), 7.91 (1H, t, J=7.8 Hz), 8.43 (1H, dd, J=0.9, 7.8 Hz), 8.53 (1H, dd, J=0.9, 7.8 Hz), 8.78 (1H, s), 9.44 (1H, s)

Example 32

(R/S)-1-(4-Chloro-5-isoquinolinesulfonyl)-3-(methylamino)pyrrolidine

3-[N-(tert-Butoxycarbonyl)-N-methylamino]-1-(4-chloro-5-isoquinolinesulfonyl)pyrrolidine (Intermediate 21) can be prepared by using 4-chloro-5-isoquinolinesulfonyl chloride and 3-[N-(tert-butoxycarbonyl)-N-methylamino]pyrrolidine in the method of Example 1-3, Step A instead of 4-bromo-5-isoquinolinesulfonyl chloride and (S)-3-[N-(tert-butoxycarbonyl)-N-methyl-amino]pyrrolidine, respectively, and then used in the method of Example 1-3, Step B in a similar manner to obtain the title compound as hydrochloride.

Example 32-2

(R)-1-(4-Chloro-5-isoquinolinesulfonyl)-3-(methylamino)pyrrolidine (R)-3-[N-(tert-Butoxycarbonyl)-N-methylamino]-1-(4-chloro-5-isoquinolinesulfonyl)pyrrolidine (Intermediate 21b) was prepared by using 4-chloro-5-isoquinolinesulfonyl chloride and (R)-31N-(tert-butoxycarbonyl)-N-methylamino]pyrrolidine in the method of Example 1-3, Step A instead of 4-bromo-5-isoquinolinesulfonyl chloride and (S)-3-[N-(tert-butoxycarbonyl)-N-methylamino]pyrrolidine, respectively, and then used in the method of Example 1-3, Step B in a similar manner to obtain the title compound as hydrochloride.

MS (m/z): 326 (MH+)

$^1$H-NMR (DMSO) δ (ppm): 2.25-2.37 (1H, m), 2.40-2.50 (1H, m), 2.60 (3H, s), 3.51-3.75 (3H, m), 3.82-3.88 (1H, m), 3.94-4.03 (1H, m), 7.91 (1H, t, J=7.8 Hz), 8.43 (1H, dd, J=0.9, 7.8 Hz), 8.53 (1H, dd, J=0.9, 7.8 Hz), 8.78 (1H, s), 9.44 (1H, s)

Example 18-3

(S)-1-(4-Fluoro-5-isoquinolinesulfonyl)-3-(methylamino)pyrrolidine (S)-3-[N-(tert-Butoxycarbonyl)-N-methylamino]-1-(4-fluoro-5-isoquinoline-sulfonyl)pyrrolidine (Intermediate 22a) was prepared by using 4-fluoro-5-isoquinolinesulfonyl chloride in the method of Example 1-3, Step A instead of 4-bromo-5-isoquinolinesulfonyl chloride, and then used in the method of Example 1-3, Step B in a similar manner to obtain the title compound as hydrochloride.

MS (m/z): 310 (MH+)

$^1$H-NMR (DMSO) δ (ppm): 2.21-2.32 (1H, m), 2.35-2.46 (1H, m), 2.57 (3H, s), 3.48-3.71 (3H, m), 3.81-3.98 (2H, m), 7.92 (1H, t, J=7.8 Hz), 8.45 (1H, dd, J=0.9, 7.8 Hz), 8.56 (1H, dd, J=0.9, 7.8 Hz), 8.70 (1H, d, J=4.8 Hz), 9.39 (1H, s)

Example 33

(R/S)-1-(4-Fluoro-5-isoquinolinesulfonyl)-3-(methylamino)pyrrolidine

3-[N-(tert-Butoxycarbonyl)-N-methylamino]-1-(4-fluoro-5-isoquinolinesulfonyl)pyrrolidine (Intermediate 22) can be prepared by using 4-fluoro-5-isoquinolinesulfonyl chloride and 3-[N-(tert-butoxycarbonyl)-N-methyl-amino]pyrrolidine in the method of Example 1-3, Step A instead of 4-bromo-5-isoquinolinesulfonyl chloride and (S)-3-[N-(tert-butoxycarbonyl)-N-methyl-amino]pyrrolidine, respectively, and then used in the method of Example 1-3, Step B in a similar manner to obtain the title compound as hydrochloride.

Example 33-2

(R)-1-(4-Fluoro-5-isoquinolinesulfonyl)-3-(methylamino)pyrrolidine (R)-3-[N-(tert-Butoxycarbonyl)-N-methylamino]-1-(4-fluoro-5-isoquinolinesulfonyl)pyrrolidine (Intermediate 22b) can be prepared by using 4-fluoro-5-isoquinolinesulfonyl chloride and (R)-3-[N-(tert-butoxycarbonyl)-N-methyl-amino]pyrrolidine in the method of Example 1-3, Step A instead of 4-bromo-5-isoquinolinesulfonyl chloride and (S)-3-[N-(tert-butoxycarbonyl)-N-methyl-amino]pyrrolidine, respectively, and then used in the method of Example 1-3, Step B in a similar manner to obtain the title compound as hydrochloride.

Example 34

(R/S)-1-(4-Methyl-5-isoquinolinesulfonyl)-3-(methylamino)pyrrolidine

3-[N-(tert-Butoxycarbonyl)-N-methylamino]-1-(4-methyl-5-isoquinoline sulfonyl)pyrrolidine (Intermediate 23) can be prepared by using 4-methyl-5-isoquinolinesulfonyl chloride and 3-[N-(tert-butoxycarbonyl)-N-methyl-amino]pyrrolidine in the method of Example 1-3, Step A instead of 4-bromo-5-isoquinolinesulfonyl chloride and (S)-3-[N-(tert-butoxycarbonyl)-N-methyl-amino]pyrrolidine, respectively, and then used in the method of Step B in a similar manner to obtain the title compound as hydrochloride.

Although the compound of Example 8-3 can be prepared by the aforementioned method, it can also be prepared by the following method as an alternative method.

More specifically, Intermediate 23 was prepared by using 4-methyl-5-isoquinolinesulfonyl chloride in the method of Example 1-3, Step A instead of 4-bromo-5-isoquinolinesulfonyl chloride, and then used in the method of Step B in a similar manner to obtain the title compound as hydrochloride.

MS (m/z): 306 (MH+)

$^1$H-NMR (DMSO) δ (ppm): 2.30-2.43 (1H, m), 2.46-2.51 (1H, m), 2.62 (1H, s), 3.01 (1H, s), 3.55-3.97 (5H, m), 7.92 (1H, t, J=7.8 Hz), 8.45 (1H, d, J=7.8 Hz), 8.57 (1H, d, J=7.8 Hz), 8.64 (1H, s), 8.64 (1H, s)

Example 34-2

(R)-1-(4-Methyl-5-isoquinolinesulfonyl)-3-(methylamino)pyrrolidine

3-[N-(tert-Butoxycarbonyl)-N-methylamino]-1-(4-methyl-5-isoquinoline-sulfonyl)pyrrolidine (Intermediate 23b) can be prepared by using 4-methyl-5-isoquinolinesulfonyl chloride and (R)-3-[N-(tert-butoxycarbonyl)-N-methylamino]pyrrolidine in the method of Example 1-3, Step A instead of 4-bromo-5-isoquinolinesulfonyl chloride and (S)-3-[N-(tert-butoxycarbonyl)-N-methyl-amino]pyrrolidine, respectively, and then used in the method of Step B in a similar manner to obtain the title compound as hydrochloride.

Example 35

(R/S)-1-(1-Hydroxy-4-bromo-5-isoquinolinesulfonyl)-3-(methylamino)pyrrolidine

3-[N-(tert-Butoxycarbonyl)-N-methylamino]-1-(1-chloro-4-bromo-5-isoquinolinesulfonyl)pyrrolidine (Intermediate 24) can be prepared by using 3-[N-(tert-butoxycarbonyl)-N-methylamino]pyrrolidine in the method of Example 35-1, Step A instead of (S)-3-[N-(tert-butoxycarbonyl)-N-methylamino]pyrrolidine, and then used in the method of Example 35-1, Step B in a similar manner to obtain the title compound as hydrochloride.

Example 35-1

(S)-1-(1-Hydroxy-4-bromo-5-isoquinolinesulfonyl)-3-(methylamino)pyrrolidine

Step A (S)-3-[N-(tert-Butoxycarbonyl)-N-methylamino]-1-(1-chloro-4-bromo-5-isoquinoline-sulfonyl)pyrrolidine (Intermediate 24a)

A solution of 1-chloro-4-bromo-5-isoquinolinesulfonyl chloride (6.49 g) obtained in Reference Example 9 in tetrahydrofuran (50 ml) was slowly added with a solution of (S)-3-[N-(tert-butoxycarbonyl)-N-methylamino]pyrrolidine (2.93 g) in tetrahydrofuran (20 ml), so that the temperature of the mixture should be kept at −5° C. or lower. Then, the mixture was slowly added with triethylamine (2.66 ml) at the same temperature, and the mixture was stirred at −5° C. for 1 hour. The reaction mixture was poured into cooled saturated brine (70 ml), and extracted 3 times with ethyl acetate (50 ml for each time). The combined organic layer was washed twice with saturated brine (for each time 100 ml), and dried over anhydrous magnesium sulfate. The solvent was evaporated under reduced pressure, and the residue was purified by silica gel chromatography (n-hexane:ethyl acetate=3:1) to obtain the title compound (4.43 g).

MS (m/z): 504 (MH+)
$^1$H-NMR (CDCl$_3$) δ (ppm): 1.48 (9H, s), 2.14-2.31 (2H, m), 2.85 (3H, s), 3.34-3.52 (2H, m), 3.61-3.79 (2H, m), 4.85-4.91 (1H, m), 7.79 (1H, t, J=8.1 Hz), 8.34 (1H, dd, J=0.8, 8.1 Hz), 8.67 (1H, dd, J=0.8, 8.1 Hz), 8.71 (1H, s)

Step B (S)-1-(1-Hydroxy-4-bromo-5-isoquinolinesulfonyl)-3-(methylamino)pyrrolidine Intermediate 24a (168 mg) obtained in Step A mentioned above was added with 10% hydrogen chloride/methanol (4 ml), and the mixture was stirred at 60° C. for 30 hours. The solvent was evaporated under reduced pressure to obtain the title compound as hydrochloride (123 mg).

MS (m/z): 386 (MH+)
$^1$H-NMR (DMSO) δ (ppm): 2.17-2.23 (1H, m), 2.39-2.45 (1H, m), 2.62 (1H, s), 3.46-3.53 (2H, m), 3.59-3.67 (1H, m), 3.73-3.79 (1H, m), 3.92-3.96 (1H, m), 7.58 (1H, s), 7.71 (1, t, J=7.9 Hz), 8.18 (1H, dd, J=1.2, 7.9 Hz), 8.57 (1H, dd, J=1.2, 7.9 Hz)

Example 35-2

(R)-1-(1-Hydroxy-4-bromo-5-isoquinolinesulfonyl)-3-(methylamino)pyrrolidine (R)-3-[N-(tert-Butoxycarbonyl)-N-methylamino]-1-(1-chloro-4-bromo-5-isoquinolinesulfonyl)pyrrolidine (Intermediate 24b) can be prepared by using (R)-3-[N-(tert-butoxycarbonyl)-N-methylamino]pyrrolidine in the method of Example 35-1, Step A mentioned above instead of (S)-3-[N-(tert-butoxycarbonyl)-N-methyl-amino]pyrrolidine, and then used in the method of Example 35-1, Step B in a similar manner to obtain the title compound as hydrochloride.

Example 36

(R/S)-1-(1-Hydroxy-4-chloro-5-isoquinolinesulfonyl)-3-(methylamino)pyrrolidine 3-[N-(tert-Butoxycarbonyl)-N-methylamino]-1-(1,4-dichloro-5-isoquinolinesulfonyl)pyrrolidine (Intermediate 25) can be prepared by using 1,4-dichloro-5-isoquinolinesulfonyl chloride and 3-[N-(tert-butoxycarbonyl)-N-methylamino]pyrrolidine in the method of Example 35-1, Step A instead of 1-chloro-4-bromo-5-isoquinolinesulfonyl chloride and (S)-3-[N-(tert-butoxycarbonyl)-N-methylamino]pyrrolidine, respectively, and then used in the method of Example 35-1, Step B in a similar manner to obtain the title compound as hydrochloride.

Example 36-1

(S)-1-(1-Hydroxy-4-chloro-5-isoquinolinesulfonyl)-3-(methylamino)pyrrolidine (S)-3-[N-(tert-Butoxycarbonyl)-N-methylamino]-1-(1,4-dichloro-5-isoquinolinesulfonyl)pyrrolidine (Intermediate 25a) was prepared by using 1,4-dichloro-5-isoquinolinesulfonyl chloride obtained in Reference Example 13 in the method of Example 35-1, Step A instead of 1-chloro-4-bromo-5-isoquinolinesulfonyl chloride, and then used in the method of Step B in a similar manner to obtain the title compound as hydrochloride.

MS (m/z): 342 (MH+)
$^1$H-NMR (DMSO) δ (ppm): 2.21-2.32 (1H, m), 2.36-2.48 (1H, m), 2.60 (3H, s), 3.44-3.58 (2H, m), 3.61-3.69 (1H, m), 3.76-3.82 (1H, m), 3.91-4.00 (1H, m), 7.58 (1H, s), 7.71 (1H, t, J=7.8 Hz), 8.25 (1H, dd, J=1.1, 7.8 Hz), 8.57 (1H, dd, J=1.1, 7.8 Hz)

Example 36-2

(R)-1-(1-Hydroxy-4-chloro-5-isoquinolinesulfonyl)-3-(methylamino)pyrrolidine (R)-3-[N-(tert-Butoxycarbonyl)-N-methylamino]-1-(1,4-dichloro-5-isoquinolinesulfonyl)pyrrolidine (Intermediate 25b) was prepared by using 1,4-dichloro-5-isoquinolinesulfonyl chloride and (R)-3-[N(tert-butoxycarbonyl)-N-methylamino]pyrrolidine in the method of Example 35-1, Step A instead of 1-chloro-4-bromo-5-isoquinolinesulfonyl chloride and (S)-3-[N-(tert-butoxycarbonyl)-N-methylamino]pyrrolidine, respectively, and then used in the method of Example 35-1, Step B in a similar manner to obtain the title compound as hydrochloride.

MS (m/z): 342 (MH+)
$^1$H-NMR (DMSO) δ (ppm): 2.21-2.32 (1H, m), 2.36-2.48 (1H, m), 2.60 (3H, s), 3.44-3.58 (2H, m), 3.61-3.69 (1H, m), 3.76-3.82 (1H, m), 3.91-4.00 (1H, m), 7.58 (1H, s), 7.71 (1H, t, J=7.8 Hz), 8.25 (1H, dd, J=1.1, 7.8 Hz), 8.57 (1H, dd, J=1.1, 7.8 Hz)

Although the compound of Example 30 can be prepared by the aforementioned method, it can also be prepared by the following method as an alternative method.

More specifically, (R/S)-3-(tert-butoxycarbonyl)amino-1-(1,4-dichloro-5-isoquinolinesulfonyl)pyrrolidine (Intermediate 26) can be obtained by using 1,4-dichloro-5-isoquinolinesulfonyl chloride and 3-(tert-butoxycarbonylamino)pyrrolidine in the method of Example 35-1, Step A instead of 1-chloro-4-bromo-5-isoquinolinesulfonyl chloride and (S)-3-[N-(tert-butoxycarbonyl)-N-methyl-amino]pyrrolidine, respectively, and used in the method of Step B in a similar manner to obtain the compound of Example 30 as hydrochloride.

Although the compound of Example 30-1 can be prepared by the aforementioned method, it can also be prepared by the following method as an alternative method.

More specifically, (S)-3-(tert-butoxycarbonyl)amino-1-(1,4-dichloro-5-isoquinolinesulfonyl)pyrrolidine (Intermediate 26a) was obtained by using 1,4-dichloro-5-isoquinolinesulfonyl chloride in the method of Example 35-1, Step A instead of 1-chloro-4-bromo-5-isoquinolinesulfonyl chloride. Then, the resultant was used in the method of Step B in a similar manner to obtain the compound of Example 30-1 as hydrochloride.

MS (m/z): 328 (MH+)

$^1$H-NMR (DMSO) δ (ppm): 2.09-2.19 (1H, m), 2.35-2.46 (1H, m), 3.42-3.53 (2H, m), 3.61-3.74 (2H, m), 3.96-4.04 (1H, m), 7.58 (1H, s), 7.71 (1H, t, J=7.9 Hz), 8.20 (1H, dt, J=1.2, 7.9 Hz), 8.57 (1H, dd, J=1.2, 7.9 Hz)

Although the compound of Example 30-2 can be prepared by the aforementioned method, it can also be prepared by the following method as an alternative method.

More specifically, (R)-3-(tert-butoxycarbonyl)amino-1-(1,4-dichloro-5-isoquinolinesulfonyl)pyrrolidine (Intermediate 26b) can be prepared by using 1,4-dichloro-5-isoquinolinesulfonyl chloride and (R)-3-(tert-butoxycarbonyl-amino)pyrrolidine in the method of Example 35-1, Step A instead of 1-chloro-4-bromo-5-isoquinolinesulfonyl chloride and (S)-3-[N-(tert-butoxycarbonyl)-N-methylamino]pyrrolidine, respectively, and used in the method of Step B in a similar manner to obtain the compound of Example 30-2 as hydrochloride.

Example 37

(R/S)-1-(1-Hydroxy-4-fluoro-5-isoquinolinesulfonyl)-3-(methylamino)pyrrolidine

3-[N-(tert-Butoxycarbonyl)-N-methylamino]-1-(1-chloro-4-fluoro-5-isoquinolinesulfonyl)pyrrolidine (Intermediate 27) can be prepared by using 1-chloro-4-fluoro-5-isoquinolinesulfonyl chloride and 3-[N-(tert-butoxycarbonyl)-N-methylamino]pyrrolidine in the method of Example 35-1, Step A instead of 1-chloro-4-bromo-5-isoquinolinesulfonyl chloride and (S)-3-[N-(tert-butoxycarbonyl)-N-methylamino]pyrrolidine, respectively, and then used in the method of Example 35-1, Step B in a similar manner to obtain the title compound as hydrochloride.

Example 37-1

(S)-1-(1-Hydroxy-4-fluoro-5-isoquinolinesulfonyl)-3-(methylamino)pyrrolidine (S)-3-[N-(tert-Butoxycarbonyl)-N-methylamino]-1-(1-chloro-4-fluoro-5-isoquinolinesulfonyl)pyrrolidine (Intermediate 27a) can be prepared by using 1-chloro-4-fluoro-5-isoquinolinesulfonyl chloride in the method of Example 35-1, Step A instead of 1-chloro-4-bromo-5-isoquinolinesulfonyl chloride, and then used in the method of Step B in a similar manner to obtain the title compound as hydrochloride.

Example 37-2

(R)-1-(1-Hydroxy-4-fluoro-5-isoquinolinesulfonyl)-3-(methylamino)pyrrolidine (R)-3-[N-(tert-Butoxycarbonyl)-N-methylamino]-1-(1-chloro-4-fluoro-5-isoquinolinesulfonyl)pyrrolidine (Intermediate 27b) can be prepared by using 1-chloro-4-fluoro-5-isoquinolinesulfonyl chloride and (R)-3-[N-(tert-butoxycarbonyl)-N-methylamino]pyrrolidine in the method of Example 35-1, Step A instead of 1-chloro-4-bromo-5-isoquinolinesulfonyl chloride and (S)-3-[N-(tert-butoxycarbonyl)-N-methylamino]pyrrolidine, respectively, and then used in the method of Example 35-1, Step B in a similar manner to obtain the title compound as hydrochloride.

Example 38

(R/S)-1-(1-Hydroxy-4-bromo-5-isoquinolinesulfonyl)-3-(2-furylmethylamino)pyrrolidine The compound of Example 7 can be used in the method of Example 38-1 instead of the compound of Example 7-1 to obtain the title compound as hydrochloride.

Example 38-1

(S)-1-(1-Hydroxy-4-bromo-5-isoquinolinesulfonyl)-3-(2-furylmethylamino)pyrrolidine A suspension of hydrochloride of the compound of Example 7-1 (186 mg), triethylamine (209 μl), furfural (124 μl), and powdery molecular sieves 3A (220 mg, Aldrich) in methanol (7 ml) was stirred at room temperature for 20 hours. The reaction mixture was cooled to 0° C., and added with sodium borohydride (95 mg), and the mixture was stirred at the same temperature for 1 hour, and then poured into cooled saturated brine (10 ml). The reaction mixture was filtered through Celite, and then extracted 3 times with chloroform (10 ml for each time), and the combined organic layer was washed twice with water (20 ml for each time), and dried over anhydrous magnesium sulfate. The solvent was evaporated under reduced pressure, and the residue was purified by silica gel chromatography (chloroform:acetonitrile=2:1) to obtain the title compound (195 mg).

MS (m/z): 452 (MH+)

$^1$H-NMR (hydrochloride, DMSO) δ (ppm): 2.22-2.34 (1H, m), 2.38-2.47 (1H, m), 3.35-3.55 (2H, m), 3.59-3.66 (1H, m), 3.74 (1H, dd, J=7.2, 10.5 Hz), 3.98 (1H, m), 4.31 (2H, s), 6.53-6.55 (1, m), 6.85 (1H, d, J=3.0 Hz), 7.68 (1H, s), 7.70 (1H, t, J=7.8 Hz), 7.80 (1H, m), 8.22 (1H, dd, J=1.1, 7.8 Hz), 8.56 (1H, dd, J=1.1, 7.8 Hz)

Example 38-2

(R)-1-(1-Hydroxy-4-bromo-5-isoquinolinesulfonyl)-3-(2-furylmethylamino)pyrrolidine The compound of Example 7-2 can be used in the method of Example 38-1 instead of the compound of Example 7-1 to obtain the title compound.

Example 39

(R/S)-3-Amino-1-(1-amino-4-chloro-5-isoquinolinesulfonyl)pyrrolidine

Intermediate 26 can be used in the method of Example 39-1 instead of Intermediate 26a to obtain the title compound as hydrochloride.

Example 39-1

(S)-3-Amino-1-(1-amino-4-chloro-5-isoquinoline-sulfonyl)pyrrolidine

Step A (S)-3-(tert-Butoxycarbonyl)amino-1-(1-amino-4-chloro-5-isoquinolinesulfonyl)-pyrrolidine (Intermediate 28a)

A suspension of Intermediate 26a (0.20 g), and potassium carbonate (0.31 g) in 1,3-dimethyl-2-imidazolidinone (3 ml, Tokyo Kasei Kogyo) was added with 25% aqueous ammonia (2 ml), and the mixture was stirred at 80° C. for 24 hours in a sealed tube. The reaction mixture was added with saturated brine (30 ml), and extracted 3 times with chloroform (30 ml for each time). The combined organic layer was washed twice with saturated brine (50 ml for each time), and dried over anhydrous magnesium sulfate. The solvent was evaporated under reduced pressure, and the residue was purified by silica gel chromatography (chloroform:methanol=9:1) to obtain the title compound (64.4 mg).

MS (m/z): 427 (MH+) $^1$H-NMR (CDCl$_3$) δ (ppm): 1.44 (9H, s), 1.96-2.00 (1H, m), 2.24-2.31 (1H, m), 3.32-3.36 (1H, m), 3.48-3.52 (1H, m), 3.60-3.63 (2H, m), 4.96 (1H, m), 7.50 (1H, t, J=8.1 Hz), 8.04 (1H, d, J=8.1 Hz), 8.13 (1H, s), 8.32 (1H, d, J=8.1 Hz)

Step B (S)-3-Amino-1-(1-amino-4-chloro-5-isoquinoline-sulfonyl)pyrrolidine

Intermediate 28s (30 mg) obtained in Step A mentioned above was added with 10% hydrogen chloride/methanol (4 ml), and the mixture was stirred at room temperature for 20 hours. The solvent was evaporated under reduced pressure to obtain the title compound as hydrochloride (25 mg).

MS (m/z): 327 (MH+)
$^1$H-NMR (DMSO) δ (ppm): 2.14-2.23 (1H, m), 2.38-2.45 (1H, m), 3.45-3.55 (2H, m), 3.64-3.76 (2H, m), 4.01 (1H, m), 7.84 (1H, t, J=7.8 Hz), 8.07 (1H, s), 8.36 (1H, d, J=7.8 Hz), 8.77 (1H, d, J=7.8 Hz)

Example 39-2

(R)-3-Amino-1-(1-amino-4-chloro-5-isoquinoline-sulfonyl)pyrrolidine

Intermediate 26b can be used in the method of Example 39-1 instead of Intermediate 26a to obtain the title compound as hydrochloride.

Example 40

(R/S)-1-(1-Amino-4-chloro-5-isoquinolinesulfonyl)-3-(methylamino)pyrrolidine

Intermediate 25 can be used in the method of Example 39-1 instead of Intermediate 26a to obtain the title compound as hydrochloride.

Example 40-1

(S)-1-(1-Amino-4-chloro-5-isoquinolinesulfonyl)-3-(methylamino)pyrrolidine

Intermediate 25a was used in the method of Example 39-1 instead of Intermediate 26a to obtain the title compound as hydrochloride.

MS (m/z): 341 (MH+)
$^1$H-NMR (DMSO) δ (ppm): 2.23-2.30 (1H, m), 2.40-2.46 (1H, m), 2.60 (3H, s), 3.61-3.69 (2H, m), 3.77-3.83 (2H, m), 3.93-3.95 (1H, m), 7.78 (1H, t, J=7.9 Hz), 8.04 (1H, s), 8.35 (1H, d, J=7.9 Hz), 8.68 (1H, d, J=7.9 Hz)

Example 40-2

(R)-1-(1-Amino-4-chloro-5-isoquinolinesulfonyl)-3-(methylamino)pyrrolidine

Intermediate 25b can be used in the method of Example 39-1 instead of Intermediate 26a to obtain the title compound as hydrochloride.

Example 41

(R/S)-3-Amino-1-(1-amino-4-bromo-5-isoquinoline-sulfonyl)pyrrolidine (R/S)-3-(tert-Butoxycarbonylamino)-1-(1-chloro-4-bromo-5-isoquinoline-sulfonyl)pyrrolidine can be prepared by using 3-(tert-butoxycarbonylamino)-pyrrolidine in the method of Example 35-1, Step A instead of (S)-3-[N-(tert-butoxycarbonyl)-N-methylamino]pyrrolidine, and then the protective group of the obtained compound can be removed according to the method described in Example 39-1, Step B to obtain the title compound as hydrochloride.

Example 41-1

(S)-3-Amino-1-(1-amino-4-bromo-5-isoquinoline-sulfonyl)pyrrolidine

Step A (S)-3-(tert-Butoxycarbonylamino)-1-(1-chloro-4-bromo-5-isoquinolinesulfony)-pyrrolidine (Intermediate 29a)

(S)-3-(tert-Butoxycarbonylamino)pyrrolidine was used in the method of Example 35-1, Step A instead of (S)-3-[N-(tert-butoxycarbonyl)-N-methylamino]pyrrolidine to obtain the title compound.

MS (m/z): 471 (MH+)
$^1$H-NMR (CDCl$_3$) δ (ppm): 1.44 (9H, s), 1.92-2.03 (1H, m), 2.22-2.33 (1H, m), 3.27-3.35 (1H, m), 3.41-3.51 (1H, m), 3.58-3.65 (2H, m), 5.03 (1H, m), 7.47 (1H, t, J=8.1 Hz), 8.04 (1H, d, J=8.1 Hz), 8.25 (1H, d, J=8.1 Hz), 8.30 (1H, s)

Step B (S)-3-Amino-1-(1-amino-4-bromo-5-isoquinoline-sulfonyl)pyrrolidine

Intermediate 29a was used in the method of Example 39-1, Step B instead of Intermediate 28a to obtain the title compound as hydrochloride.

MS (m/z): 371 (MH+)
$^1$H-NMR (DMSO) δ (ppm): 2.15-2.20 (1H, m), 2.33-2.45 (1H, m), 3.42-3.52 (2H, m), 3.61-3.73 (2H, m), 3.98-4.00 (1H, m), 7.81 (1H, t, J=7.8 Hz), 8.17 (1H, s), 8.39 (1H, d, J=7.8 Hz), 8.74 (1H, d, J=7.8 Hz)

Example 41-2

(R)-3-Amino-1-(1-amino-4-bromo-5-isoquinoline-sulfonyl)pyrrolidine (R)-3-(tert-Butoxycarbonylamino)-1-(1-chloro-4-bromo-5-isoquinoline-sulfonyl)pyrrolidine can be prepared by using (R)-3-(tert-butoxycarbonylamino)-pyrrolidine in the method of Example 35-1, Step A instead of (S)-3-[N-(tert-butoxycarbonyl)-N-methylamino]pyrrolidine, and then the protective group of the obtained compound can be removed according to the method described in Example 39-1, Step B to obtain the title compound as hydrochloride.

Example 42

(R/S)-1-(1-Amino-4-bromo-5-isoquinolinesulfonyl)-3-(methylamino)pyrrolidine

Intermediate 24 can be used in the method of Example 39-1 instead of Intermediate 26a to obtain the title compound as hydrochloride.

Example 42-1

(S)-1-(1-Amino-4-bromo-5-isoquinolinesulfonyl)-3-(methylamino)pyrrolidine

Intermediate 24a was used in the method of Example 39-1 instead of Intermediate 26a to obtain the title compound as hydrochloride.

MS (m/z): 385 (MH+)
$^1$H-NMR (DMSO) δ (ppm): 2.20-2.32 (1H, m), 2.36-2.45 (1H, m), 2.60 (3H, s), 3.60-3.68 (2H, m), 3.74-3.80 (2H, m), 3.93-3.97 (1H, m), 7.83 (1H, t, J=7.9 Hz), 8.17 (1H, s), 8.38 (1H, d, J=7.9 Hz), 8.73 (1H, d, J=7.9 Hz)

Example 42-2

(R)-1-(1-Amino-4-bromo-5-isoquinolinesulfonyl)-3-(methylamino)pyrrolidine

Intermediate 24b can be used in the method of Example 39-1 instead of Intermediate 26a to obtain the title compound as hydrochloride.

Test Example 1

Measurement of Rho Kinase Inhibitory Activity

In this test, human ROCK1 was used as Rho kinase, MBS (myosin binding subunit, subunit constituting myosin phosphatase) was used as the substrate of Rho kinase, and an anti-phosphorylated MBS antibody was used for detection of phosphorylation. The activity for inhibiting Rho kinase was determined by measuring phosphorylation of MBS by the Rho kinase by ELISA in the presence of an appropriately diluted test compound. As the Rho kinase used, a recombinant protein (N-terminal His-tagged recombinant human ROCK1 residues (1Met-727Arg)) was used, which was produced in insect cells (Sf9) using a sequence (1-727), of which activity was confirmed in the paper of Ishizaki et al. (Ishizaki, T. et al., FEBS Letters, 404, pp 118-124, 1997), based on the sequence of human ROCK1 (p160 ROCK) described in the report of Ishizaki et al. (Ishizaki, T. et al., EMBO J., 15, pp 1885-1893, 1996). Further, as the MBS protein and anti-phosphorylated MBS antibody, those prepared according to the method described in the paper of Ito et al. (Ito, K et al., J. Physiol., 546, pp823-836, 2003) were used.

A solution of MBS (Asahi Kasei Pharma, lot No, 040814n7-10) diluted with PBS to an appropriate concentration was added to an ELISA plate (Maxisorp, Nunc), and left stand overnight at 4° C., and then the wells were washed twice with a washing solution (WB, washing buffer, 0.1% Tween 20/PBS). To the wells were added 1% bovine serum albumin (Sigma)/PBS, and left for 1 to 3 hours, and then the wells were washed 5 times with WB to prepare a substrate-immobilized plate. Onto this plate, a reaction mixture (5 mM MgSO$_4$/0.1 M NaCl/20 mM HEPES (pH 7.5)/100 μM ATP/5 mM DTT), a test compound, and appropriately diluted human ROCK1 (Asahi Kasei Pharma, lot No, 030126120-22) were added, and then reacted at 30° C. for 10 minutes. Then, 0.2 M EDTA (pH 7.5) was added to terminate the reaction, and the wells were washed 5 times with WB. A rabbit anti-phosphorylated MBS antibody solution (Asahi Kasei Pharma, lot No, 122676431) diluted 10,000 times with WB containing 1% bovine serum albumin was added to the wells, and after the reaction for 1 hour, the wells were washed 5 times with WB. Goat anti-rabbit IgG-HRP (Zymed) diluted 1,000 times with WB containing 1% bovine serum albumin was added to the wells as the secondary detection antibody and the mixture was reacted for 1 hour, and then the wells were washed 5 times with WB. An OPD (o-phenylenediamine) solution (1 mg/ml OPD, Sigma), 5.1 g/l of citric acid monohydrate, and 18.4 g/l of Na$_2$HPO$_4$.12H$_2$O were added to the wells to develop color, 2 N H$_2$SO$_4$ was added 5 minutes later to terminate the color development, and absorbance was measured at 490 nm.

The inhibition ratio was calculated as follows. Inhibition ratio (%)=100−((Absorbance observed with test compound−Absorbance observed for 0% control)/(Absorbance observed for 100% control−Absorbance observed for 0% control))

Further, the inhibition ratio was calculated with changing the concentration of the test compound, and a compound concentration providing an inhibition ratio of 50% was obtained as IC$_{50}$.

Compounds which gave an IC$_{50}$ not lower than 1 μM and not higher than 3 μM (1 μM≦IC$_{50}$≦3 μM) are the compounds of the example numbers of 1-19, 1-30, 1-33, 8-9, 8-16, 8-18, 8-27, 8-29, 8-30, 8-31, 8-73, 10-14, 10-31, 12-1, 15-1, 18-1, 18-16, 19-4, 19-14, 19-17, 19-21, 19-31, 21-1, 21-2, 36-2, 38-1 and 40-1, and compounds which gave an IC$_{50}$ lower than 1 μM (IC$_{50}$≦1 μM) are the compounds of the example numbers of 1-3, 1-6, 1-7, 1-11, 1-12, 1-13, 1-14, 1-18, 1-20, 1-31, 1-38, 1-1, 1-2, 4-1, 7-1, 8-1, 8-2, 8-3, 8-4, 8-5, 8-6, 8-7, 8-8, 8-12, 8-21, 8-26, 8-28, 8-32, 8-34, 8-37, 9-1, 10-7, 11-1, 18-7, 18-8, 19-1, 19-2, 19-3, 19-8, 19-40, 22-1, 22-2, 23-1, 25-1, 26, 27, 29-1, 30-1, 32-2, 35-1, 36-1, 39-1, 41-1 and 42-1.

Thus, it was revealed that the aforementioned compounds of the present invention have an action for inhibiting Rho kinase.

Test Example 2

Inhibitory Action on Phosphorylation of Myosin Regulatory Light Chain

A volume of 50 to 100 ml of peripheral blood collected from healthy volunteers is centrifuged by using Mono-Poly separator solution (Dainippon Pharmaceutical) to prepare a neutrophil containing fraction. The neutrophils are washed with PBS(−) and resuspended in Hanks' Balanced Salt Solution (HBSS+, Gibco) to prepare a cell suspension (8×10$^6$/ml). The cell suspension is diluted to 5×10$^6$/ml, introduced into Eppendorf tubes in a volume of 0.4 ml each, then 0.1 ml each of solutions of a test compound at various concentrations are added to the suspension and allowed to react at 25° C. for 5 minutes. After the reaction, 0.1 ml of trichloroacetic acid solution is added to each reaction mixture, the reaction mixture is gently shaken and centrifuged at 12,000 rpm (4° C., 5 minutes), the supernatant is removed, 3 μl of 1 M Tris solution is added to the residue, and the mixture is further mixed with 50 µl of extraction buffer (8 M urea, 0.02% 2-mercaptoethanol, 0.002% bromophenol blue) and left stand at room temperature for 1 hour. Then, the reaction mixture is loaded on a spin column (0.45 µm, Millipore) to remove the insoluble solids, a sample buffer for SDS polyacrylamide gel electrophoresis (25 mM, Tris-HCl pH 6.8, 2.5% 2-mercaptoethanol, 2% sodium dodecylsulfate, 5% sucrose, 0.002% bromophenol blue as final concentrations) is added, and 10 µl of each sample is subjected to electrophoresis.

The gel after the electrophoresis is blotted on a nitrocellulose membrane (BioRad), blocked with 5% skim milk, and reacted successively with antibodies pLC1 (Sakurada K. et al, Am. J. Physiol., 274, C1563-C1572 (1998)), which specifically recognize the phosphorylated myosin regulatory light chain, and donkey anti-mouse IgG (Chemicon) conjugated with horseradish peroxidase. The band of the phosphorylated myosin regulatory light chain is detected on a film by using ECL Plus Kit (Amersham Pharmacia Biotech). This band is subjected to quantification using a densitometer. By using this value, the inhibitory ratio (%) for phosphorylation of the myosin regulatory light chain is calculated by using the following equation.

Phosphorylation inhibition ratio (%)=1−(Band intensity of phosphorylated myosin regulatory light chain with addition of the test compound/Band intensity of phosphorylated myosin regulatory light chain without addition of the test compound)×100

Further, it is also possible to confirm the effectiveness of the compounds of the present invention by calculating the phosphorylation inhibition ratio with changing the concentration of the test compound, and obtaining a compound concentration providing an inhibition ratio of 50% as $IC_{50}$.

Test Example 3

Intraocular Pressure Reducing Action

A Japanese white rabbit having a body weight of about 2 kg was placed in a positioner and naturalized for one week before the experiment. An ophthalmologic local anesthesant (Benoxil) was administered to both eyes, and then intraocular pressure was measured by using a tonometer (Classic 30, Solan). A 3 mM aqueous solution of a test compound was administered in a volume of 50 µl to the left eye, and the right eye was not treated (control eye). The intraocular pressure values were measured for the left and right eyes immediately before, and 2, 4 and 6 hours after the administration of the aqueous solution of the test compound, and the difference of the measured values for the left and right eyes was considered an intraocular pressure reduction value of the test medicament at each measurement time. The largest difference of the values for the left and right eyes among the measured values at the measurement times (after 2, 4 and 6 hours) was considered the maximum intraocular pressure reduction value (max $\triangle$ IOP) of each test medicament. The intraocular pressure reducing degree representing the intraocular pressure reducing action of each test medicament was calculated according to the following formula. Since rabbits show significant daily variation of intraocular pressure, daily variation is added when change of intraocular pressure is measured over time, and the intraocular pressure reducing action may be overestimated. Therefore, we used this calculation method of intraocular pressure reduction value in order to minimize the influence of the variation.

Intraocular pressure reducing degree(%)=(max $\triangle$ IOP/Intraocular pressure value immediately before administration)×100

Compounds which gave an intraocular pressure reducing degree not lower than 5% and lower than 10% are the compounds of the example numbers of 1-7, 1-14, 1-19, 8-26, 8-28, 8-29, 8-30, 8-32, 8-33, 8-34, 8-36, 8-37, 10-14, 11-1, 13-1, 15-1, 18-7, 18-14, 19-14, 19-17, 19-40, 24-1, 26, 27, 35-1, 38-1, 40-1 and 42-1, and compounds which gave an intraocular pressure reducing degree not lower than 10% and lower than 20% are the compounds of the example numbers of 1-18, 1-20, 1-31, 8-4, 8-21, 8-27, 8-31, 8-74, 10-7, 10-29, 12-1, 18-21, 21-2, 22-1, 22-2, 23-1, 25-1, 29-1, 32-2, 36-1, 36-2 and 39-1. Further, compounds which gave an intraocular pressure reducing degree not lower than 20% are the compounds of the example numbers of 1-3, 1-30, 1-1, 1-2, 4-1, 7-1, 8-1, 8-2, 8-3, 8-12, 9-1, 10-31, 18-1, 18-3, 18-31, 19-1, 19-2, 19-3, 19-4, 19-21, 19-31, 21-1, 28-1 and 30-1. Further, when the same test as that of Test Example 3 was performed with a test compound of 1 mM, compounds which gave an intraocular pressure reducing degree not lower than 20% were the compounds of the example numbers of 1-3, 1-1, 4-1, 8-1, 8-3, 10-1, 18-1, 19-1 and 19-3.

It was demonstrated that the aforementioned compounds of the present invention reduced the rabbit normal intraocular pressure. In addition, even 6 hours after the administration of these compounds, the intraocular pressure reducing action did not disappear, and thus they had a sustained intraocular pressure reducing action.

Thus, it was confirmed that the compounds of the present invention were useful as medicaments for prophylactic and/or therapeutic treatment of glaucoma. The compounds, per se, metabolite thereof after administration, or both may exhibit the intraocular pressure reducing action.

Test Example 4

Neutrophil Migration Inhibitory Action

Neutrophils are isolated from 50 to 100 ml of peripheral blood collected from healthy human donors by the method described in Test Example 2 to obtain a cell suspension ($8 \times 10^6$/ml). Subsequently, solutions of a test compound at various concentrations are introduced into wells of a 96-well plate in a volume of 125 µl per well, the cell suspension of an equivalent volume is added to it and the plate is preincubated at room temperature for 5 minutes. During the preincubation, FMLP (1 µM, Sigma) solution is added to the lower chamber to set Boyden Chamber, the preincubated cell suspension is added to the upper chamber in a volume of 200 µl per well, and the cells are allowed to migrate at 37° C. under 5% carbon dioxide for 30 minutes. The filter after the migration is collected, and the non-migrated cells adhered to the surface that faced the upper chamber are carefully wiped off. Then, the migrated cells on the back surface are stained with DifQuick dye solution (International Reagents), washed with water and dried, and then absorbance is measured at 595 nm. The inhibition ratio against migration (%) of a test compound is calculated by using the following equation:

Migration inhibition ratio(%)=(1−Absorbance of the group with addition of test compound/Absorbance of the group without addition of test compound)×100

Further, it is also possible to confirm the effectiveness of the compounds of the present invention by calculating the phosphorylation inhibition ratio with changing the concentration of the test compound, and obtaining a compound concentration providing an inhibition ratio of 50% as $IC_{50}$.

Test Example 5

Action on Increase of Intracellular Calcium Concentration

According to the method described in Test Example 2, a neutrophil containing fraction is prepared. Fura2-AM (Sigma) at a final concentration of 3 µM is added to the human neutrophil fraction and the mixture is incubated at 37° C. for 1 hour. After centrifugation (250 g for 5 minutes), the supernatant is discarded, and the neutrophils are resuspended in Hanks' Balanced Salt Solution (HBSS, Gibco) to prepare a cell suspension ($8 \times 10^6$/ml) for measurement of intracellular calcium concentration. The cell suspension for measurement of intracellular calcium concentration is left stand at room temperature for 30 minutes. Then, 490 µl of the cell suspension for measurement of intracellular calcium concentration is placed in a cuvette, 10 µl of calcium chloride solution at a final concentration of 1 µM is added to it and the cuvette is set in an intracellular calcium concentration analyzer (CAF110, Nippon Bunko). fMLP (Sigma) solution at a final concentration of 1 µM is added to the cell suspension, and F340 and F380, which are fluorescence intensity at 340 nm and 380 nm, respectively, are measured to obtain an R value (F340/F380) as an index of the intracellular calcium concentration. A test compound (1 µM) is added 3 minutes before the addition of fMLP, and the action on the intracellular calcium concentration is observed. By obtaining ratios of the maximum R value obtained with addition of each test compound relative to the maximum R value obtained without addition of test compound and taken as 100%, effect of the compounds of the present invention on the increase of the intracellular calcium concentration caused by the fMLP stimulation can be confirmed.

Test Example 6

Action on Myosin Light Chain Kinase (MLCK) Activity

A myosin light chain kinase (MLCK) is purified from chicken gizzard smooth muscle by a conventional method (Yoshida, M., et al., J. Biochem., 99, 1027-1036 (1986)). The myosin regulatory light chain as a substrate is purified from the chicken gizzard smooth muscle by a conventional method (Grand, R. J., et al., Biochem. J., 211, 267-272 (1983)). The MLCK activity is measured by ELISA (Sakurada, K., et al., J. Biochem., 115, 18-21 (1994)) using anti-phosphorylated myosin regulatory light chain-recognizing antibodies (Sakurada, K., et al., Am. J. Physiol., 274, C1563-C1572, 1998). The myosin regulatory light chain is diluted in phosphate-buffered saline (PBS, Sigma) to a concentration of 5.0 g/ml, added to 96-well Immunoplate (Nunc) in a volume of 100 µl per well and left stand overnight at 4° C. Each well is washed with PBS, and 25 mM Tris/HCl buffer containing 100 µM ATP, 3 mM $MgCl_2$, 1 mM $CaCl_2$, 100 ng/ml of calmodulin (Sigma) and 100 ng/ml of MLCK (pH 7.4, Buffer A) is added to each well and incubated at 30° C. for 10 minutes. In a volume of 100 µl each of 20% aqueous phosphoric acid solution is added to each well to terminate the enzymatic reaction. Each well is washed with 25 mM Tris/HCl buffer (TTBS) containing 0.1% Tween 20, and then 100 µl of antibodies specifically recognizing phosphorylated myosin regulatory light chain (Sakurada, K., et al., Am. J. Physiol., 274, C1563-C1572, 1998) is added to each well and incubated at room temperature for 90 minutes.

Each well is washed with TTBS, and then 100 µl of the HRP-labeled anti-mouse IgG antibodies (Bio-Rad) are added to each well and incubated at room temperature for 90 minutes. Each well is washed with TTBS, and then 25 mM citrate buffer (pH 5.0) containing orthophenylenediamine (Sigma) as a substrate of HRP and aqueous hydrogen peroxide (0.03%) is added in a volume of 100 µl lper well and incubated at room temperature for 5 minutes. 50 µl of 4 N sulfuric acid is added to each well to terminate the reaction, and then absorbance is measured by using an immunoplate reader (Bio-Rad). By calculating the MLCK activity inhibition ratio after addition of a test compound to Buffer A at various concentrations to obtain a compound concentration providing an inhibitory ratio of 50% as $IC_{50}$, effect of the compounds of the present invention on MLCK activity can be confirmed.

Test Example 7

Rabbit Intraocular Pressure Reduction Enhancing Action

For evaluation of intraocular pressure reduction enhancing action of a combination of the compound of the present invention and a drug for combination use, Japanese white rabbits are used as experimental animals, and the action is demonstrated as follows.

As for a test example, the compound of the example number 19-1 (henceforth referred to as 19-1 compound) was used as a test compound to demonstrate the effect of combination use. However, the effect is not limited to the 19-1 compound, and the ophthalmic solution concentration of the 19-1 compound is not limited to those used in this test example. As for the test compound used for combination use, similar effect can be obtained also with the compounds of the present invention represented with the example numbers mentioned in Test Example 3.

Test Example 7-1

As a test compound, the 19-1 compound was dissolved in physiological saline, and the solution was neutralized by addition of sodium hydroxide (pH 7.0 to 8.0) to prepare a 0.01 weight % aqueous solution (19-1 compound aqueous solution). As the drugs for combination use, isopropyl unoprostone (trade name: Rescula, Santen Pharmaceutical) was used as a prostaglandin-related drug, and brinzolamide hydrochloride (trade name: Azopt, Alcon Japan) was used as a carbonic anhydrase, as the marketed formulations as they were.

A Japanese white rabbit having a body weight of about 2 kg was placed in a positioner and naturalized for one week before the experiment. An ophthalmologic local anesthesant (Benoxil) was administered to both eyes, and then intraocular pressure before instillation was measured by using a tonometer (Classic 30, Solan). A test aqueous solution or the drug for combination use was administered to the left eye, and the right eye was not treated (control eye). The test groups consisted of (1) control group, (2) group instilled only with the 19-1 compound aqueous solution (single drug group 1), (3) group instilled only with the drug for combination use (single drug group 2), and (4) group instilled with the drug for combination use and the 19-1 compound aqueous solution (combination use group), and six rabbits were used for each group. As for the rabbits of these groups, 50 µL of physiological saline was first instilled to the control group, single drug group 1, and single drug group 2, and the drug for combination use was first instilled in the same volume to the combination use group. Then, 5 minutes after the instillation of physiological saline or the drug for combination use, 50 μL of physiological saline was instilled to the control group, the same volume of the 19-1 compound aqueous solution was instilled to the single drug group 1, and the combination use group, and 50 μL of the drug for combination use was instilled to the single drug group 2. The intraocular pressure thereafter was measured for each group 2, 4 and 6 hours after the second administration of the test compound, and the difference of the measured values for the left and right eyes at each measurement time was considered an intraocular pressure reduction value of each group. The largest difference of the intraocular pressure values for the left and right eyes among those of the measured values of the measurement times was considered the maximum intraocular pressure reduction value (max $\triangle$ IOP) of each drug group. The results are shown in Tables 2 and 3.

TABLE 2

|  | Max$\triangle$IOP (mmHg) |
| --- | --- |
| (1) Control group | 0.2 |
| (2) Single drug group 1 (19-1 compound) | 4.3 |
| (3) Single drug group 2 (brinzolamide hydrochloride) | 2.3 |
| (4) Combination use group (19-1 compound + brinzolamide hydrochloride) | 6.3 |

TABLE 3

|  | Max$\triangle$IOP (mmHg) |
| --- | --- |
| (1) Control group | 0.2 |
| (2) Single drug group 1 (19-1 compound) | 4.3 |
| (3) Single drug group 2 (isopropyl unoprostone) | 4.4 |
| (4) Combination use group (19-1 compound + isopropyl unoprostone) | 6.1 |

Test Example 7-2

As a test compound, the 19-1 compound was dissolved in physiological saline, and the solution was neutralized by addition of sodium hydroxide (pH 7.0 to 8.0) to prepare a 0.01 weight % aqueous solution (19-1 compound aqueous solution). As a drug for combination use, timolol maleate (trade name: Timoptol, Santen Pharmaceutical) was used as an adrenergic receptor β blocker, as the marketed formulation as it was.

A Japanese white rabbit having a body weight of about 2 kg was placed in a positioner and naturalized for one week before the experiment. An ophthalmologic local anesthesant (Benoxil) was administered to both eyes, and then intraocular pressure before instillation was measured by using a tonometer (Classic 30, Solan). A test aqueous solution or the drug for combination use was administered to the left eye, and the right eye was not treated (control eye). The test groups consisted of (1) control group, (2) group instilled only with the 19-1 compound aqueous solution (single drug group 1), (3) group instilled only with the drug for combination use (single drug group 2), and (4) group instilled with the drug for combination use and the 19-1 compound aqueous solution (combination use group), and 12 rabbits were used for each group. As for the rabbits of these groups, 50 μL of physiological saline was first instilled to the control group, single drug group 1, and single drug group 2, and the drug for combination use was first instilled in the same volume to the combination use group. Then, 5 minutes after the instillation of physiological saline or the drug for combination use, 50 μL of physiological saline was instilled to the control group, the same volume of the 19-1 compound aqueous solution was instilled to the single drug group 1, and the combination use group, and 50 μL of the drug for combination use was instilled to the single drug group 2. The intraocular pressure thereafter was measured for each group 1, 2 and 4 hours after the second administration of the test compound, and the difference of the measured values at each measurement time for the each group and the control group was considered an intraocular pressure reduction value of each group. The largest difference of the intraocular pressure values relative to the control group among those of the measured values of the measurement times was considered the maximum intraocular pressure reduction value (max $\triangle$ IOP) of each drug group. The results are shown in Table 4.

TABLE 4

|  | Max$\triangle$IOP (mmHg) |
| --- | --- |
| (1) Control group | — |
| (2) Single drug group 1 (19-1 compound) | 4.1 |
| (3) Single drug group 2 (timolol maleate) | 1.9 |
| (4) Combination use group (19-1 compound + timolol maleate) | 6.4 |

In Test Examples 7-1 and 7-2, the compound of the present invention exemplified with the 19-1 compound exhibited the intraocular pressure reducing action in the single drug group 1 in a degree exceeding that of the control group, and the intraocular pressure reducing action in the combination use group in a degree exceeding those of both the single drug group 1 and single drug group 2 (Tables 2, 3, and 4).

From these results, it was confirmed that intraocular pressure reducing action was enhanced in rabbits by combination of the compound of the present invention exemplified with the 19-1 compound and a carbonic anhydrase inhibitor, a prostaglandin-related drug, or an adrenergic receptor β blocker. The compounds of the example numbers 1-3, 4-1, 19-3 and the like can also be evaluated by the same methods as those of Test Examples 7-1 and 7-2 to confirm the effectiveness thereof.

It is also possible to confirm the effectiveness of the compounds of the present invention indicated with the example numbers mentioned in Test Examples 3 other than the 19-1 compound by performing the test using the compounds in combination with a carbonic anhydrase inhibitor, a prostaglandin-related drug, or an adrenergic receptor β blocker.

Furthermore, by performing a test in which the compositions A to C described in Preparation Example 1, the compositions E to G described in Preparation Example 2, and compositions comprising, in combination, the aforementioned example compounds and a drug for combination use are administered as the combination use group instead of successively instilling a solution of the compound of the present invention and a drug for combination use, the effectiveness thereof can be confirmed.

Therefore, it was revealed that medicaments consisting of the compounds of the present invention and drugs for combination use were useful as medicaments for prophylactic and/or therapeutic treatment of glaucoma.

Test Example 8

Intraocular Pressure Reduction Enhancing Action in Monkey

For evaluating the intraocular pressure reduction enhancing action of a combination of the compound of the present invention and latanoprost (trade name: Xalatan, Pfizer) as a prostaglandin related drug, the action can be demonstrated by using a monkey (cynomolgus monkey).

Although the effect of the combination use is demonstrated by using the 19-1 compound for the test example, the effect is not limited to the 19-1 compound, and the ophthalmic solution concentration of the 19-1 compound is not limited to those used in this test example. As for the test compound used for combination use, similar effect can be obtained also with the compounds of the present invention represented with the example numbers mentioned in Test Example 3. The test is performed by using cynomolgus monkeys sufficiently naturalized for the operation of fixation on a monkey chair and intraocular pressure measurement.

As the test compound, the 19-1 compound was dissolved in physiological saline, and the solution is neutralized by addition of sodium hydroxide (pH 7.0 to 8.0) to prepare a 0.01 weight % aqueous solution (19-1 compound aqueous solution). As a drug for combination use, latanoprost (trade name: Xalatan, Pfizer) is used as the marketed formulation per se. The test aqueous solution or the drug for combination use is instilled to the left eye, and the right eye is not treated (control eye). The test groups consist of (1) control group, (2) group instilled only with the 19-1 compound aqueous solution (single drug group 1), (3) group instilled only with the drug for combination use (single drug group 2), and (4) group instilled with the drug for combination use and the 19-1 compound aqueous solution (combination use group). After initial intraocular pressure values of the monkeys are measured for each group, 30 µL of physiological saline is instilled to the control group, single drug group 1, and single drug group 2, and latanoprost is instilled in the same volume to the combination use group. Then, 5 minutes after the instillation of physiological saline or latanoprost, 30 µL of physiological saline is instilled to the control group, the same volume of the 19-1 compound aqueous solution is instilled to the single drug group 1, and the combination use group, and 30 µL of the drug for combination use is instilled to the single drug group 2. Then, the intraocular pressure is measured over time for each group.

In Test Example 8, the 19-1 compound exhibits the intraocular pressure reducing action in the single drug group 1 in a degree exceeding that of the control group, and the intraocular pressure reducing action in the combination use group in a degree exceeding those of both the single drug group 1 and single drug group 2. It is thereby confirmed that the intraocular pressure reducing action is enhanced in monkeys by combining the compound of the present invention and a prostaglandin-related drug. The compounds of the example numbers 1-3, 4-1, and 19-3 can also be evaluated by the same method as that of Test Example 8 to confirm the effectiveness thereof.

It is also possible to confirm the effectiveness of the compounds of the present invention indicated with the example numbers mentioned in Test Examples 2 other than the 19-1 compound by performing the test using the compounds in combination with a prostaglandin-related drug.

Furthermore, by performing a test in which the composition D described in Preparation Example 1, the composition H described in Preparation Example 2, and compositions comprising the aforementioned example compounds and latanoprost in combination are administered as the combination use group instead of successively instilling a solution of the compound of the present invention and latanoprost, the effectiveness thereof can be confirmed.

On the basis of the above procedure, it can be revealed that medicaments consisting of the compounds of the present invention and latanoprost are useful as medicaments for prophylactic and/or therapeutic treatment of glaucoma.

Preparation Example 1

Examples of the preparation of a composition for instillation in which the 19-1 compound and a drug for combination use are combined by dissolving them in physiological saline are mentioned below. However, the present invention is not limited to these examples, and compositions in which a drug for combination use is combined can be prepared with the compounds other than the 19-1 compound. Furthermore, eye drops comprising a desired combination and having desired concentrations can be prepared by appropriately changing type and amount of the drug for combination use, types and amounts of additives, and the like.

A physiological saline solution containing 0.01% by weight of the 19-1 compound, 0.12% by weight of isopropyl unoprostone (Funakoshi), and 0.005% by weight of benzalkonium chloride is designated Composition A.

A physiological saline solution containing 0.01% by weight of the 19-1 compound, 1.0% by weight of brinzolamide hydrochloride (Hydrus Chemical), and 0.005% by weight of benzalkonium chloride is designated Composition B.

A physiological saline solution containing 0.01% by weight of the 19-1 compound, 0.5% by weight of timolol maleate (Sigma Aldrich), and 0.005% by weight of benzalkonium chloride is designated Composition C.

A physiological saline solution containing 0.01% by weight of the 19-1 compound, 0.005% by weight of latanoprost (Funakoshi), and 0.005% by weight of benzalkonium chloride is designated Composition D.

Preparation Example 2

Examples of the preparation of a composition for instillation in which the 19-1 compound and a drug for combination use are combined by dissolving the 19-1 compound in a commercially available eye drop for therapeutic treatment of glaucoma are mentioned below. However, the present invention is not limited to these examples, and compositions in which a drug for combination use is combined can be prepared with the compounds other than the 19-1 compound. Furthermore, eye drops comprising a desired combination and having desired concentrations can be prepared by appropriately changing type and amount of the drug for combination use, types and amounts of additives, and the like.

A solution obtained by dissolving the 19-1 compound at a concentration of 0.01% by weight in the eye drop, Rescula (active ingredient: isopropyl unoprostone, Fujisawa Pharmaceutical), is designated Composition E.

A solution obtained by dissolving the 19-1 compound at a concentration of 0.01% by weight in the eye drop, Azopt (active ingredient: brinzolamide hydrochloride, Alcon Japan), is designated Composition F.

A solution obtained by dissolving the 19-1 compound at a concentration of 0.01% by weight in the eye drop, Timoptol (active ingredient: timolol maleate, Santen Pharmaceutical), is designated Composition G.

A solution obtained by dissolving the 19-1 compound at a concentration of 0.01% by weight in the eye drop, Xalatan (active ingredient: latanoprost, Pfizer), is designated Composition H.

INDUSTRIAL APPLICABILITY

The compounds of the present invention represented by the formula (1), salts thereof and derivatives thereof useful as prodrugs have an action of potently inhibiting Rho kinase. Medicaments comprising a substance selected from the group consisting of the compounds of the present invention represented by the formula (1), salts thereof and derivatives thereof useful as prodrugs as active ingredients are useful as medicaments for prophylactic and/or therapeutic treatment of diseases relating to contraction of cells, diseases relating to morphological change of cells, diseases relating to migration of cells, diseases relating to release of cells, diseases relating to aggregation of cells, and diseases relating to apoptosis of cells, based on the Rho kinase inhibitory action.

What is claimed is:

1. A compound represented by the following general formula (I) or a salt thereof:

[Formula 1]

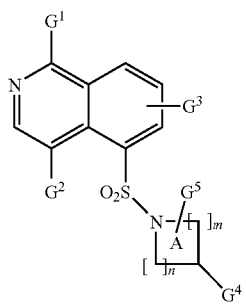

wherein A represents a nitrogen-containing saturated ring;
m represents an integer of 0, 1, or 2;
n represents an integer of 1, 2, 3, or 4;
$G^1$ represents hydrogen atom, chlorine atom, hydroxyl group, an alkoxy group, or amino group;
$G^2$ represents a halogen atom, hydroxyl group, cyano group, carboxy group, an alkyl group which may be substituted, an alkenyl group which may be substituted, an alkynyl group which may be substituted, an alkoxy group which may be substituted, an alkylthio group which may be substituted, an amino group which may be substituted, an alkylsulfinyl group which may be substituted, an alkylsulfonyl group which may be substituted, or an aryl group which may be substituted;
$G^3$ represents hydrogen atom, a halogen atom, hydroxyl group, cyano group, carboxy group, an alkyl group which may be substituted, an alkenyl group which may be substituted, an alkynyl group which may be substituted, an alkoxy group which may be substituted, an alkylthio group which may be substituted, an amino group which may be substituted, an alkoxycarbonyl group which may be substituted, an acyl group which may be substituted, an acyloxy group which may be substituted, an alkylsulfinyl group which may be substituted, an alkylsulfonyl group which may be substituted, or an aryl group which may be substituted (provided that $G^3$ substitutes at the 3-, 6-, 7-, or 8-position of the isoquinoline ring);
$G^4$ represents hydroxyl group, or —N($R^1$)($R^2$) ($R^1$ and $R^2$ may be the same or different, and independently represent hydrogen atom, an alkyl group which may be substituted, an aralkyl group which may be substituted, an alkenyl group which may be substituted, an alkynyl group which may be substituted, or a saturated heterocyclic group which may be substituted); and
$G^5$ represents a substituent on a ring-constituting carbon atom constituting the nitrogen-containing saturated ring represented by A, and represents hydrogen atom, fluorine atom, or an alkyl group.

2. The compound or a salt thereof according to claim 1, wherein m is 1.

3. The compound or a salt thereof according to claim 1, wherein n is 2 or 3.

4. The compound or a salt thereof according to claim 1, wherein $G^3$ is hydrogen atom.

5. The compound or a salt thereof according to claim 1, wherein $G^5$ is hydrogen atom.

6. The compound or a salt thereof according to claim 1, wherein $G^4$ is —N($R^1$)($R^2$).

7. The compound or salt thereof according to claim 1, wherein the carbon atom to which $G^4$ binds has an absolute configuration of S-configuration.

8. The compound or a salt thereof according to claim 1, wherein the compound is (S)-3-amino-1-(1-hydroxy-4-chloro-5-isoquniolinesulfonyl)pyrrolidine.

9. The compound or a salt thereof according to claim 1, wherein the compound is (S)-1-(1-hydroxy-4-chloro-5-isoquniolinesulfonyl)-3-(methlyamino)pyrrolidine.

10. A pharmaceutical composition comprising the compound or a salt thereof according to claim 1 as an active ingredient, and pharmaceutically acceptable carrier.

11. A pharmaceutical composition comprising the compound or a salt thereof according to claim 1 and pharmaceutically acceptable carrier, and a drug having an intraocular pressure reducing action and/or a drug having an optic nerve protective action.

12. A pharmaceutical composition comprising the compound or a salt thereof according to claim 1 and pharmaceutically acceptable carrier and any one or more of an adrenergic receptor stimulant, a prostaglandin-related agent, a carbonic anhydrase inhibitor, an adrenergic receptor blocker, a cholinesterase inhibitor, a calcium antagonist, a Rho kinase inhibitor, an angiotensin II receptor antagonist, and an NMDA receptor blocker.

13. A pharmaceutical composition comprising the compound or a salt thereof according to claim 1 and pharmaceutically acceptable carrier and a drug having an intraocular pressure reducing action.

14. A pharmaceutical composition comprising the compound or a salt thereof according to claim 1 and pharmaceutically acceptable carrier and any one or more of a prostaglandin-related agent, a carbonic anhydrase inhibitor, and an adrenergic receptor blocker.

15. The pharmaceutical composition according to claim 14, which is an agent for prophylactic and/or therapeutic treatment of glaucoma.

16. A pharmaceutical composition comprising the compound or a salt thereof according to claim 1 and pharmaceutically acceptable carrier and a drug having an optic nerve protective action.

17. The pharmaceutical composition according to claim 14, wherein the prostaglandin-related selected from the group consisting of latanoprost, bimatoprost, travoprost, isopropylunoprostone, and tafluprost.

18. The pharmaceutical composition according to claim 14, wherein the carbonic anhydrase inhibitor selected from the group consisting of dorzolamide hydrochloride, brinzolamide, and sodium acetazolamide.

19. The pharmaceutical composition according to claim 14, wherein the adrenergic receptor blocker is selected from the group consisting of bunazosin hydrochloride, timolol maleate, carteolol hydrochloride, levobunolol hydrochloride, betaxolol hydrochloride, nipradilol, and befunolol hydrochloride.

20. A pharmaceutical composition comprising the compound represented by the following formula or salt thereof:

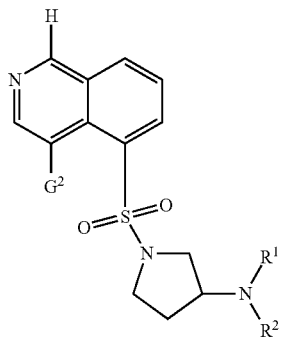

wherein the carbon atom to which —NR$^1$R$^2$ binds has an absolute configuration of S-configuration;

G$^2$ represents a halogen atom, an alkyl group which may be substituted, an alkenyl group which may be substituted, or an alkynyl group which may be substituted, wherein, one of R$_1$ or R$^2$ is a hydrogen atom, and the other is a methyl group, or R$^1$ and R$^2$ are both hydrogen atoms, and pharmaceutically acceptable carrier.

21. A pharmaceutical composition comprising the compound represented by the following formula or salt thereof:

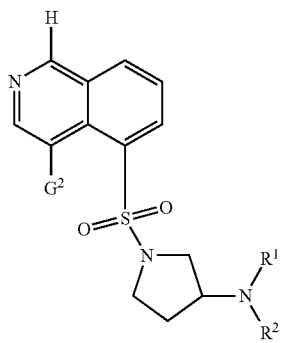

wherein the carbon atom to which —NR$^1$R$^2$ binds has an absolute configuration of S-configuration;

G$^2$ represents a halogen atom, an alkyl group which may be substituted, an alkenyl group which may be substituted, or an alkynyl group which may be substituted, wherein, one of R$^1$ or R$^2$ is a hydrogen atom, and the other is a methyl group, and pharmaceutically acceptable carrier.

22. A pharmaceutical composition according to claim 20, wherein the compound is selected from the group of:

(S)-3-amino-1-(4-bromo-5-isoquinolinesulfonyl)pyrrolidine;

(S)-1-(4-bromo-5-isoquinolinesulfonyl)-3-(methylamino)pyrrolidine;

(S)-3-amino-1-(4-methyl-5-isoquinolinesulfonyl)pyrrolidine;

(S)-1-(4-methyl-5-isoquinolinesulfonyl)-3-(methylamino)pyrrolidine;

(S)-3-amino-1-(4-vinyl-5-isoquinolinesulfonyl)pyrrolidine;

(S)-3-amino-1-(4-ethynyl-5-isoquinolinesulfonyl)pyrrolidine;

(S)-3-amino-1-(4-cyclopropyl-5-isoquinolinesulfonyl)pyrrolidine;

(S)-3-amino-1-(4-fluoro-5-isoquinolinesulfonyl)pyrrolidine;

(S)-1-(4-fluoro-5-isoquinolinesulfonyl)-3-(methylamino)pyrrolidine;

(S)-3-amino-1-(4-chloro-5-isoquinolinesulfonyl)pyrrolidine;

(S)-1-(4-chloro-5-isoquinolinesulfonyl)-3-(methylamino)pyrrolidine; and (S)-3-amino-1-(4-ethyl-5-isoquinolinesulfonyl)pyrrolidine; or a salt of any of the above compounds, and pharmaceutically acceptable carrier.

23. A pharmaceutical composition according to claim 20 or 21, wherein the substituent group on the alkyl group, alkenyl group, alkynyl group which may be substituted is selected from the group consisting of a hydroxyl group, a halogen atom, carboxy group, cyano group, a saturated heterocyclic group, an acylamino group, an alkylsulfonylamino group, an aminocarbonylamino group, an alkylaminocarbonyl amino group, an arylaminocarbonylamino group, and an alkylsulfonylamino group, any of which may be optionally substituted with one or more halogen atoms.

24. A pharmaceutical composition comprising (S)-1-(4-bromo-5-isoquinolinesulfonyl)-3-(methylamino)pyrrolidine or a salt thereof, and pharmaceutically acceptable carrier.

25. A pharmaceutical composition comprising (S)-3-amino-1-(4-fluoro-5-isoquinolinesulfonyl)pyrrolidine or a salt thereof, and pharmaceutically acceptable carrier.

26. A pharmaceutical composition comprising (S)-1-(4-fluoro-5-isoquinolinesulfonyl)-3-(methylamino)pyrrolidine or a salt thereof, and pharmaceutically acceptable carrier.

27. A pharmaceutical composition comprising (S)-3-amino-1-(4-chloro-5-isoquinolinesulfonyl)pyrrolidine or a salt thereof, and pharmaceutically acceptable carrier.

28. A pharmaceutical composition comprising (S)-1-(4-chloro-5-isoquinolinesulfonyl)-3-(methylamino)pyrrolidine or a salt thereof, and pharmaceutically acceptable carrier.

29. A pharmaceutical composition comprising the compound represented by the following formula or a salt thereof:

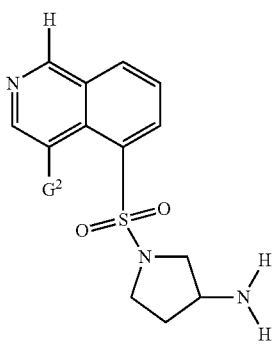

wherein the carbon atom to which —NH$_2$ binds has an absolute configuration of S-configuration and G$^2$ represents a halogen atom, an alkyl group which may be substituted, an alkenyl group which may be substituted or an alkynyl group which may be substituted.

30. A pharmaceutical composition comprising (S)-3-amino-1-(1-hydroxy-4-chloro-5-isoquniolinesulfonyl)pyrrolidine or a salt thereof, and pharmaceutically acceptable carrier.

31. A pharmaceutical composition comprising (S)-1-(1-hydroxy-4-chloro-5-isoquniolinesulfonyl)-3-(methlyamino)pyrrolidine or a salt thereof, and pharmaceutically acceptable carrier.

32. A Rho kinase inhibitor comprising the compound or a salt thereof according to claim 1.

33. A method for the therapeutic or prophylactic treatment of glaucoma, which comprises administering to a patient in need thereof the medicament according to claim 11.

34. A method for the therapeutic or prophylactic treatment of glaucoma, which comprises administering a therapeutically effective amount of the compound according to claim 1 or salt thereof, to a subject in need thereof.

35. A method for therapeutic or prophylactic treatment of glaucoma, which comprises administering a therapeutically effective amount of the medicament according to any one of claims 20 to 22, or 24 to 28, to a subject in need thereof.

36. A method for therapeutic or prophylactic treatment of glaucoma, which comprises administering a therapeutically effective amount of the medicament according to claim 23, to a subject in need thereof.

37. A method of reducing intraocular pressure, which comprises administering a therapeutically effective amount of the compound according to claim 1 or salt thereof, to a subject in need thereof.

38. A method for therapeutic or prophylactic treatment of glaucoma, which comprises administering a therapeutically effective amount of the medicament according to claim 30 or 31, to a subject in need thereof.

* * * * *